US011898190B2

(12) United States Patent
Okita et al.

(10) Patent No.: US 11,898,190 B2
(45) Date of Patent: Feb. 13, 2024

(54) LABYRINTHULID MICROORGANISM CAPABLE OF PRODUCING MICROBIAL OIL, MICROBIAL OIL, METHODS FOR PRODUCING SAID MICROORGANISM AND FOR PRODUCING SAID MICROBIAL OIL, AND USES OF SAID MICROORGANISM AND SAID MICROBIAL OIL

(71) Applicants: KYUSHU UNIVERSITY, NATIONAL UNIVERSITY CORPORATION, Fukuoka (JP); KONAN GAKUEN, Kobe (JP); NIPPON SUISAN KAISHA, LTD., Tokyo (JP)

(72) Inventors: Yuji Okita, Hachioji (JP); Makoto Ito, Fukuoka (JP); Rie Hamaguchi, Fukuoka (JP); Hatsumi Goda, Fukuoka (JP); Seiya Mochinaga, Fukuoka (JP); Daisuke Honda, Kobe (JP)

(73) Assignees: KYUSHU UNIVERSITY, NATIONAL UNIVERSITY CORPORATION, Fukuoka (JP); KONAN GAKUEN, Kobe (JP); NIPPON SUISAN KAISHA, LTD., Tokyo (JP)

( * ) Notice: Subject to any disclaimer, the term of this patent is extended or adjusted under 35 U.S.C. 154(b) by 0 days.

(21) Appl. No.: 17/401,894

(22) Filed: Aug. 13, 2021

(65) Prior Publication Data
US 2022/0042052 A1 Feb. 10, 2022

Related U.S. Application Data

(62) Division of application No. 15/740,969, filed as application No. PCT/JP2016/069825 on Jul. 4, 2016, now abandoned.

(30) Foreign Application Priority Data

Jul. 3, 2015 (JP) ................................. 2015-134715

(51) Int. Cl.
| | | |
|---|---|---|
| *C12P 7/6432* | (2022.01) | |
| *C12N 15/09* | (2006.01) | |
| *C12P 7/64* | (2022.01) | |
| *C12P 1/00* | (2006.01) | |
| *C12N 15/79* | (2006.01) | |
| *C12P 7/6427* | (2022.01) | |
| *C12P 7/6472* | (2022.01) | |
| *C12P 19/34* | (2006.01) | |
| *C12N 1/00* | (2006.01) | |
| *C12N 1/12* | (2006.01) | |
| *C12R 1/00* | (2006.01) | |
| *C12R 1/89* | (2006.01) | |
| *C10G 3/00* | (2006.01) | |
| *C12N 15/52* | (2006.01) | |

(52) U.S. Cl.
CPC ............ *C12P 7/6432* (2022.01); *C12N 15/09* (2013.01); *C12N 15/79* (2013.01); *C12P 1/00* (2013.01); *C12P 7/64* (2013.01); *C12P 7/6427* (2013.01); *C12P 7/6472* (2013.01); *C12P 19/34* (2013.01); *C10G 3/00* (2013.01); *C12N 1/00* (2013.01); *C12N 1/125* (2021.05); *C12N 15/52* (2013.01); *C12R 2001/00* (2021.05); *C12R 2001/89* (2021.05)

(58) Field of Classification Search
None
See application file for complete search history.

(56) References Cited

U.S. PATENT DOCUMENTS

| | | |
|---|---|---|
| 5,130,242 A | 7/1992 | Barclay |
| 5,340,594 A | 8/1994 | Barclay |
| 5,340,742 A | 8/1994 | Barclay |
| 5,518,918 A | 5/1996 | Barclay |

(Continued)

FOREIGN PATENT DOCUMENTS

| | | |
|---|---|---|
| JP | 3127161 B2 | 1/2001 |
| JP | 3669372 B2 | 7/2005 |

(Continued)

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2005).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Cohen, Z . et al. editors, "Single Cell Oils Microbial and Algal Oils", AOCS Press, 2010, 2nd Edition, p. 88; cited in the Specification.
Metz, J. G. et al., "Production of Polyunsaturated Fatty Acids by Polyketide Synthases in Both Prokaryotes and Eukaryotes", Science, Jul. 13, 2001, vol. 293, pp. 290-293; cited in the Specification.
Ratlegde, C., "Omega-3 biotechnology: Erros and omissions", Biotechnology Advances 30, 2012, pp. 1746-1747; cited in the Specification.

(Continued)

*Primary Examiner* — Christian L Fronda
(74) *Attorney, Agent, or Firm* — WHDA, LLP

(57) ABSTRACT

A method for producing a microbial oil includes steps of: genetically modifying a labyrinthulid by disrupting and/or silencing a gene, or by transforming another gene in addition to the disruption and/or gene silencing of the gene, and culturing the labyrinthulid, such that a fatty acid composition accumulated in the labyrinthulid comprises an increased EPA content; and collecting the microbial oil having the increased EPA content from the labyrinthulid. The labyrinthulid before the modification is selected from (A) a labyrinthulid belonging to the genus *Parietichytrium* or genus *Schizochytrium* and having very weak or no activity of producing PUFAs via a PUFA-PKS pathway; and (B) a labyrinthulid belonging to the genus *Thraustochytrium* in which a host PUFA-PKS gene is disrupted or silenced to a very weak level. The increased EPA content is preferably not less than 11.5% of a total fatty acid composition.

4 Claims, 46 Drawing Sheets

Specification includes a Sequence Listing.

(56) References Cited

U.S. PATENT DOCUMENTS

| | | | |
|---|---|---|---|
| 5,656,319 | A | 8/1997 | Barclay |
| 5,688,500 | A | 11/1997 | Barclay |
| 5,698,244 | A | 12/1997 | Barclay |
| 9,062,315 | B2* | 6/2015 | Sakaguchi ..... C12Y 114/19006 |
| 9,150,891 | B2* | 10/2015 | Sakaguchi ............. C12N 15/79 |
| 10,815,505 | B2* | 10/2020 | Sakaguchi ......... C12N 15/8201 |
| 11,203,763 | B2* | 12/2021 | Sakaguchi ........... C12N 9/1029 |
| 2005/0014231 | A1 | 1/2005 | Mukerji et al. |
| 2011/0177031 | A1* | 7/2011 | Apt ........................ A23L 33/40 |
| | | | 435/243 |
| 2012/0322116 | A1* | 12/2012 | Sakaguchi ............ C12P 7/6427 |
| | | | 435/471 |
| 2013/0309772 | A1* | 11/2013 | Sakaguchi ........... C12N 9/0071 |
| | | | 554/1 |

FOREIGN PATENT DOCUMENTS

| | | |
|---|---|---|
| WO | 2011037207 A1 | 3/2011 |
| WO | 2012/043826 A1 | 4/2012 |
| WO | 2013013211 A1 | 1/2013 |

OTHER PUBLICATIONS

Lippmeier, J.C. et al., "Characterization of Both Polyunsaturated Fatty Acid Biosynthetic Pathways in *Schizochytrium* sp.", Lipids, 2009, pp. 621-630; cited in the Specification and ISR.

Matsuda, T. et al., "Analysis of D12-fatty acid desaturase function revealed that two distinct pathways are active for the synthesis of PUFAs in T. aureum TCC 34304", Journal of Lipid Research, 2012, vol. 53, pp. 1210-1222; cited in the Specification and ISR.

Chang, M. L. "Marine microorganisms an unexpected source for anti-inflammatory fatty acids used to treat lipid disorders?", ASBMB Today, Jun. 2012, p. 30; cited in the Specification and ISR.

Sakaguchi, K. et al., "Versatile Transformation System That Is Applicable to both Multiple Transgene Expression and Gene Targeting for Thraustochytrids", Applied and Environmental Microbiology, 2012, pp. 3193-3202; cited in the Specification and ISR.

Yazawa, K. "Production of Eicosapentaenoic Acid from Marine Bacteria", Supplement, 1996, vol. 31, pp. 297-300; cited in the Specification.

"Gene Knockout Construct Production Method by PCR", Journal of the Japan Society for Bioscience, Biotechnology and Agrochem, 2003, pp. 150-153; with English Abstract; cited in the Specification.

"Illustrated Bio Experiments vol. 2 Fundamentals of Gene Analysis", 1995, pp. 63-68; with English Abstract; cited in the Specification.

Sanger, F. et al., "DNA sequencing with chain-terminating inhibitors", Proc. Natl. Acad. Sci., Dec. 1997, vol. 74, No. 12, pp. 5463-5467; cited in the Specification.

Cigan, A. M. et al., "Sequence and structural features associated with translational initiator regions in yeast—a review", Elsevier, 1987, pp. 1-18; cited in the Specification.

Qiu, X. et al., "Identification of a D4 Fatty Acid Desaturase from *Thraustochytrium* sp. Involved in the Biosynthesis of Docosahezanoic Acid by Heterologous Expression in *Saccharomyces cerevisiae* and *Brassica juncea*", The Journal of Biological Chemistry, 2001, vol. 276, No. 34, pp. 31561-31566; cited in the Specification.

Abe, E. et al., "A Novel Phosphatidylcholine Which Contains Pentadecanoic Acid at sn-1 and Docosahexaenoic Acid at sn-2 in *Schizochytrium* sp. F26-b", J. Blochem., 2006, pp. 247-253; cited in the Specification.

Bio-Experiments Illustrated, vol. 2, Illustrated Bio-Expericents vol. 2 Fundamentals of Gene Analysis, 1995, pp. ô€?† 17-128; with English Abstract; cited in the Specification.

"PCR DIG Probe Synthesis Kit", DIG Manual (Japanese Edition) 8th, Roche Applied Science; cited in the Specification.

Ohara, J. et al., "Two Fatty Acid Elongases Processing C18-Delta 6/C18-Delta 9/C20-Delta 5 or C16-Delta 9 Elongase Activity in *Thraustochytrium* sp_ ATCC 26185", Mar. Biotechnol., 2013, vol. 15, pp. 476-486; cited in ISR.

Kobayashi, T. et al., "Increase of Elcosapentaenoic Acid in Thraustochytrids through Thraustochytrid Ubiquitin Promoter-Driven Expression of a Fatty Acid D5 Desaturase Gene", Applied and Environmental Microbiology, Jun. 2011, vol. 77, No. 11, pp. 3870-3876; cited in ISR.

Matsuda, T. et al., "Molecular cloning of a Pinguiochrysis pyriformis oleate-specific microsomal D12-fatty acid desaturase and functional analysis in yeasts and thraustochytrids", J. Biochem., 2011, vol. 150, No. 4, pp. 375-383; cited in ISR.

Matsuda, T. et al., "Species-dependent pathway for production of PUFA in thraustochytrids revealed by analysis of D12 fatty acid desaturase", Chemistry and Physics of Lipids, 2011, vol. 164, p. S24; cited in ISR.

Martinez, M. et al., "The D4-desaturation pathway for DHA biosynthesis is operative in the human species: Differences between normal controls and children with the Zellweger syndrome", Lipids in Health and Disease, 2010, pp. 1-10; cited in ISR.

Martins et al. Mar. Drugs 2013, 11, 2259-2281. (Year: 2013).

Singh et al. Curr Protein Pept Sci. 2017, 18, 1-11 (Year: 2017.

Kizer et al. Appl Environ Microbial. May 2008;74(10):3229-41. (Year: 2008).

Lindblad, V. et al., "Yeast, Chapter 13", Current Protocols in Molecular Biology, 2003. (138 pages).

Romanos, M. A. et al., "Foreign Gene Expression in Yeast: a Review", Yeast, 1992, vol. 8, pp. 423-488; cited in the Specification.

* cited by examiner

| COMPARISON WITH WILD-TYPE STRAIN | C20 -/- | SEK354 | FA |
|---|---|---|---|
| 54.4% | 1.16 | 2.13 | C14:0 |
| 6.5% | 0.02 | 0.36 | C15:0 |
| 66.4% | 17.55 | 26.43 | C16:0 |
| 31.6% | 0.24 | 0.76 | C17:0 |
| 12.0% | 0.05 | 0.42 | C17:1 |
| 29.4% | 4.66 | 15.84 | C18:0 |
| 49.5% | 12.91 | 26.08 | C18:1n-9 |
| — | 0.00 | 0.00 | C18:1n-7 |
| 289.4% | 7.38 | 2.55 | C18:2n-6(LA) |
| 35.3% | 0.02 | 0.06 | C19:0 |
| 366.7% | 1.91 | 0.52 | C18:3n-6(GLA) |
| 99.8% | 0.31 | 0.31 | C19:2 |
| 1673.7% | 8.52 | 0.51 | C20:3n-6(DGLA) |
| 1079.4% | 25.22 | 2.34 | C20:4n-6(ARA) |
| 722.8% | 0.66 | 0.09 | C20:4n-3(ETA) |
| 105.7% | 0.18 | 0.17 | C22:0 |
| 851.2% | 11.56 | 1.36 | C20:5n-3(EPA) |
| 42.2% | 0.67 | 1.59 | C22:4n-6(DTA) |
| 23.1% | 1.64 | 7.07 | C22:5n-6(DPA) |
| 45.4% | 0.26 | 0.58 | C22:5n-3(DPA) |
| 20.0% | 1.28 | 6.38 | C22:6n-3(DHA) |

FIG. 13

| Fatty acid(%) | SEK364 | Δ4 desaturase KO | KO/SKE359 |
|---|---|---|---|
| C14:0 | 2.24 | 2.65 | 118% |
| C16:0 | 20.28 | 29.67 | 146% |
| C18:0 | 16.69 | 15.80 | 95% |
| C18:1n-9 | 33.63 | 27.71 | 82% |
| C18:2n-6(LA) | 2.71 | 4.05 | 150% |
| C18:3n-6(GLA) | 0.19 | 0.38 | 198% |
| C20:3n-6(DGLA) | 0.78 | 0.98 | 125% |
| C20:4n-6(ARA) | 1.30 | 1.59 | 122% |
| C20:4n-3(ETA) | 0.30 | 0.05 | 16% |
| C20:5n-3(EPA) | 1.44 | 0.79 | 55% |
| C22:4n-6(DTA) | 1.17 | 5.91 | 505% |
| C22:5n-6(n-6 DPA) | 4.29 | <0.005 | <0.12% |
| C22:5n-3(n-3 DPA) | 0.85 | 4.02 | 475% |
| C22:6n-3(DHA) | 4.94 | <0.005 | <0.11% |

| C20 elongase KO | SEX358 | FA |
|---|---|---|
| 101.0% | 1.41 | 1.40 | C14:0 |
| 32.0% | 2.44 | 7.63 | C15:0 |
| 62.1% | 13.49 | 21.73 | C16:0 |
| 26.6% | 1.95 | 7.34 | C17:0 |
| 39.6% | 2.95 | 7.46 | C18:0 |
| 22.0% | 3.19 | 14.47 | C18:1n-9 |
| 84.5% | 0.19 | 9.23 | C18:1n-7 |
| 269.4% | 4.28 | 1.59 | C18:2n-6(LA) |
| 247.0% | 2.61 | 1.06 | C18:3n-6(GLA) |
| 201.5% | 0.34 | 0.17 | C19:2 |
| 499.8% | 8.64 | 1.73 | C20:3n-6(DGLA) |
| 654.8% | 21.35 | 3.26 | C20:4n-6(ARA) |
|  | 2.14 | 0.00 | C20:4n-3(ETA) |
|  | 0.30 | 0.00 | C22:0 |
| 1069.6% | 23.83 | 2.23 | C20:5n3(EPA) |
| 8.0% | 0.26 | 3.28 | C22:4n-6(DTA) |
| 6.4% | 0.46 | 7.10 | C22:5n-6(DPA) |
| 21.6% | 0.23 | 1.06 | C22:5n-3(DPA) |
| 12.3% | 0.94 | 7.61 | C22:6n-3(DHA) |

| Fatty acid(%) | SKE 358 | Δ4 desaturase KO | KO/SKE358 |
|---|---|---|---|
| C14:0 | 2.37 | 2.94 | 124% |
| C16:0 | 26.42 | 23.57 | 89% |
| C18:0 | 13.58 | 6.70 | 49% |
| C18:1n-9 | 17.26 | 34.57 | 200% |
| C18:2n-6(LA) | 1.66 | 4.60 | 276% |
| C18:3n-6(GLA) | 0.51 | 0.78 | 152% |
| C20:3n-6(DGLA) | 2.21 | 1.35 | 61% |
| C20:4n-6(ARA) | 4.59 | 3.03 | 66% |
| C20:4n-3(ETA) | 0.16 | 0.03 | 20% |
| C20:5n-3(EPA) | 2.40 | 1.10 | 46% |
| C22:4n-6(DTA) | 3.72 | 7.88 | 212% |
| C22:5n-6(n-6 DPA) | 7.32 | <0.005 | <0.07% |
| C22:5n-3(n-3 DPA) | 1.67 | 5.10 | 305% |
| C22:6n-3(DHA) | 7.13 | <0.005 | <0.07% |

| C20 elongase xO | SEX571 | FA |
|---|---|---|
| 43.3% | 0.98 | 2.23 | C14:0 |
| 197.0% | 4.88 | 2.47 | C15:0 |
| 40.6% | 14.13 | 34.78 | C16:0 |
| 152.7% | 4.80 | 3.14 | C17:0 |
| 43.4% | 4.71 | 10.86 | C18:0 |
| 85.5% | 3.66 | 4.28 | C18:1n-9 |
| 234.6% | 0.37 | 0.16 | C18:1n-7 |
| 251.6% | 1.70 | 0.67 | C18:2n-6(LA) |
| 228.8% | 1.07 | 0.47 | C18:3n-6(GLA) |
| 156.8% | 0.24 | 0.16 | C18:2 |
| 450.2% | 1.93 | 0.43 | C20:3n-6(DGLA) |
| 388.5% | 13.24 | 3.41 | C20:4n-6(ARA) |
| 1046.9% | 1.14 | 0.11 | C20:4n-3(ETA) |
| 182.8% | 0.43 | 0.24 | C22:0 |
| 796.8% | 29.58 | 3.71 | C20:5n-3(EPA) |
| 9.0% | 0.15 | 1.61 | C22:4n-6(DTA) |
| 8.2% | 0.96 | 11.69 | C22:5n-6(DPA) |
| 34.0% | 0.25 | 0.73 | C22:5n-3(DPA) |
| 8.6% | 1.17 | 13.62 | C22:6n-3(DHA) |

FIG. 34

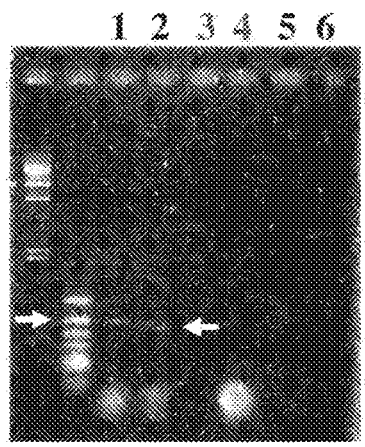
FIG. 35
FIG. 36A
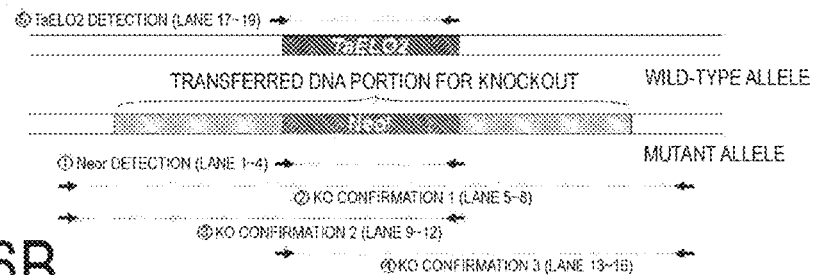
FIG. 36B
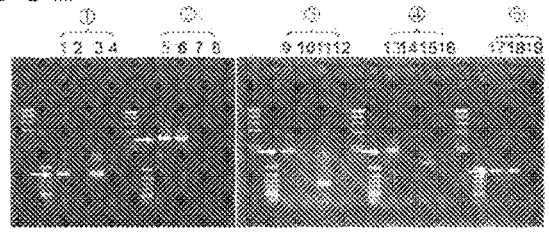
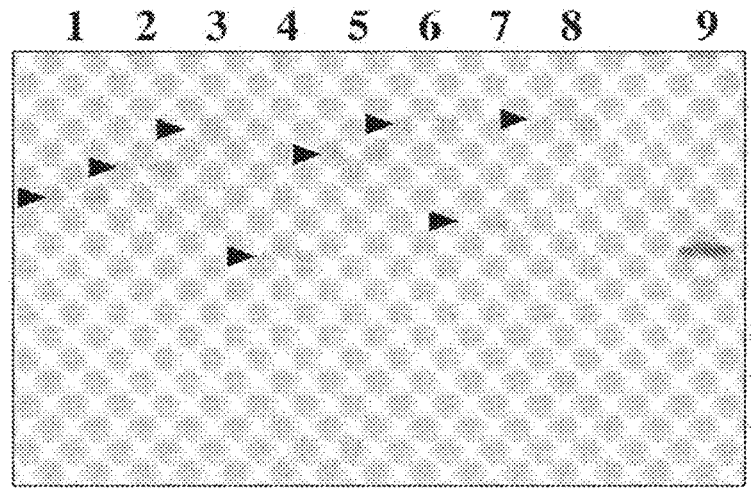
FIG. 37

FIG. 40A
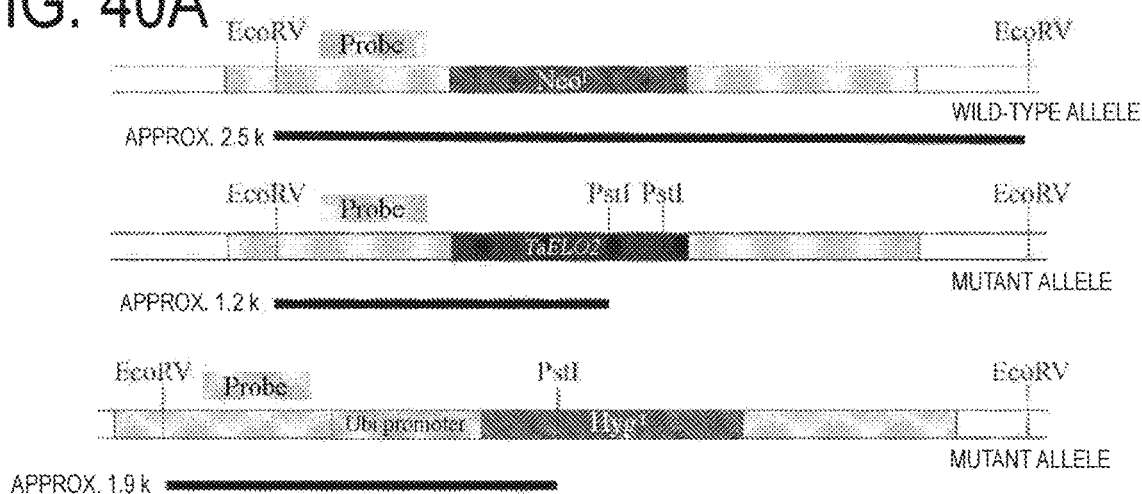
FIG. 40B
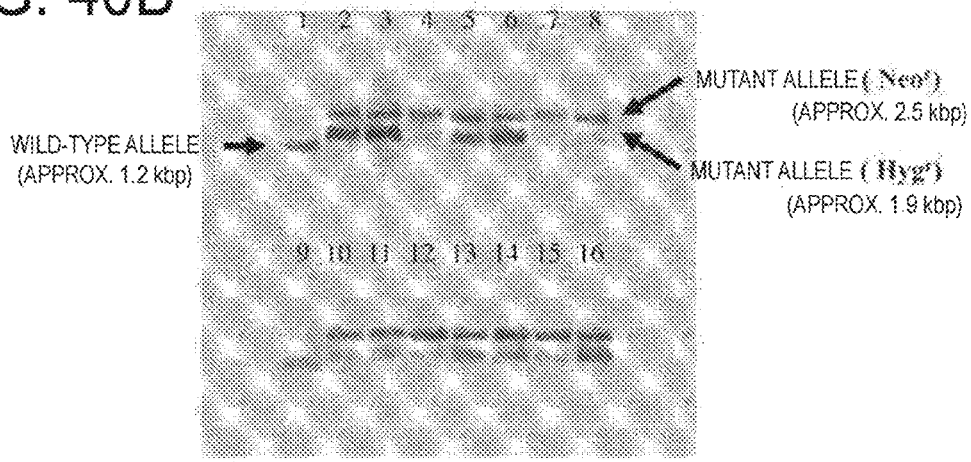
FIG. 41

| PKS(OrfA)KO | T.aureum | FA |
|---|---|---|
| 121.2% | 0.33 | 0.27 | C14:0 |
| 60.9% | 7.07 | 11.61 | C15:0 |
| 151.2% | 13.21 | 8.74 | C16:0 |
| 82.8% | 11.97 | 14.46 | C17:0 |
| 83.4% | 2.30 | 2.76 | C17:1 |
| 153.7% | 2.77 | 1.80 | C18:0 |
| 172.6% | 1.21 | 0.70 | C18:1n-9 |
| 339.0% | 3.03 | 0.89 | C18:1n-7 |
| 130.6% | 1.07 | 0.82 | C18:2n-6(LA) |
| 101.5% | 1.02 | 1.01 | C19:0 |
| 105.2% | 0.77 | 0.73 | C18:3n-6(GLA) |
| 131.6% | 0.65 | 0.49 | C19:2 |
| 125.9% | 0.23 | 0.18 | C20:3n-6(DGLA) |
| 141.2% | 3.10 | 2.19 | C20:4n-6(ARA) |
| 184.6% | 0.04 | 0.02 | C20:4n-3(ETA) |
| 126.9% | 6.82 | 5.38 | C20:5n3(EPA) |
| 169.6% | 2.00 | 1.18 | C22:4n-6(DTA) |
| 196.3% | 10.66 | 5.43 | C22:5n-6(DPA) |
| 93.6% | 1.13 | 1.20 | C22:5n-3(DPA) |
| 66.5% | 22.58 | 33.97 | C22:6n-3(DHA) |

FIG. 52

| PKS AND C20 KO | T.aureum | FA |
|---|---|---|
| 113.0% | 0.31 | 0.27 | C14:0 |
| 23.3% | 2.71 | 11.61 | C15:0 |
| 176.4% | 15.41 | 8.74 | C16:0 |
| 23.8% | 3.44 | 14.46 | C17:0 |
| 37.0% | 1.02 | 2.76 | C17:1 |
| 125.2% | 2.26 | 1.80 | C18:0 |
| 279.4% | 1.96 | 0.70 | C18:1n-9 |
| 443.0% | 3.96 | 0.89 | C18:1n-7 |
| 208.2% | 1.71 | 0.82 | C18:2n-6(LA) |
| 26.0% | 0.26 | 1.01 | C19:0 |
| 60.9% | 0.45 | 0.73 | C18:3n-6(GLA) |
| 163.7% | 0.81 | 0.49 | C19:2 |
| 996.6% | 1.81 | 0.18 | C20:3n-6(DGLA) |
| 889.0% | 19.50 | 2.19 | C20:4n-6(ARA) |
| 1550.6% | 0.31 | 0.02 | C20:4n-3(ETA) |
| 463.3% | 24.92 | 5.38 | C20:5n3(EPA) |
| 40.3% | 0.47 | 1.18 | C22:4n-6(DTA) |
| 108.6% | 5.90 | 5.43 | C22:5n-6(DPA) |
| 47.9% | 0.58 | 1.20 | C22:5n-3(DPA) |
| 20.0% | 6.78 | 33.97 | C22:6n-3(DHA) |

FIG. 64

| PKS and Δ4des KO | T. aureum | FA |
|---|---|---|
| 92.6% | 0.58 | 0.62 | C14:0 |
| 101.0% | 4.49 | 4.43 | C15:0 |
| 53.7% | 7.28 | 13.56 | C16:0 |
| 176.1% | 5.84 | 3.32 | C17:0 |
| 128.4% | 2.05 | 1.60 | C18:0 |
| 304.9% | 4.83 | 1.58 | C16:1n-9 |
| 250.1% | 4.49 | 1.80 | C16:1n-7 |
| 450.5% | 4.47 | 0.99 | C18:2n-6(LA) |
| 310.7% | 0.81 | 0.26 | C19:0 |
| 784.5% | 2.67 | 0.34 | C18:3n-6(GLA) |
| 229.0% | 0.59 | 0.26 | C19:2 |
| 359.7% | 0.90 | 0.25 | C20:3n-6(DGLA) |
| 164.2% | 6.35 | 3.87 | C20:4n-6(ARA) |
| 182.3% | 0.28 | 0.15 | C20:4n-3(ETA) |
| 78.1% | 6.22 | 7.96 | C20:5n-3(EPA) |
| 2008.9% | 11.01 | 0.55 | C22:4n-6(DTA) |
| 2.4% | 0.21 | 8.70 | C22:5n-6(DPA) |
| 2665.9% | 15.78 | 0.59 | C22:5n-3(DPA) |
| 1.2% | 0.51 | 41.71 | C22:6n-3(DHA) |

FIG. 71

LABYRINTHULID MICROORGANISM CAPABLE OF PRODUCING MICROBIAL OIL, MICROBIAL OIL, METHODS FOR PRODUCING SAID MICROORGANISM AND FOR PRODUCING SAID MICROBIAL OIL, AND USES OF SAID MICROORGANISM AND SAID MICROBIAL OIL

CROSS-REFERENCE OF RELATED APPLICATIONS

This application is a Divisional of application Ser. No. 15/740,969, filed Apr. 10, 2018, which is a 371 of International Application No. PCT/JP2016/069825, filed Jul. 4, 2016, which claims priority of Japanese Patent Application No. 2015-134715, filed Jul. 3, 2015, the entire contents of which are incorporated herein by reference.

TECHNICAL FIELD

The present invention relates to microbial oil obtained from a labyrinthulid, a labyrinthulid capable of producing microbial oil, a method for producing the microbial oil and the labyrinthulid, and a use of the microbial oil and the labyrinthulid.

More specifically, the present invention relates to polyunsaturated fatty acids (PUFAs) and the production thereof, and relates to a labyrinthulid genetically modified such that the fatty acid composition is modified, preferably a labyrinthulid that produces PUFAs only via the elongase-desaturase pathway, a method for producing PUFAs using the same, lipids (microbial oils) containing PUFAs produced using the same, and uses thereof.

BACKGROUND ART

Labyrinthulids are eukaryotic microorganisms belonging to the class Labyrinthulomycetes, which includes the order Labyrinthulales and the order Thraustochytriales Labyrinthulids are known to be universally present in oceans. Microorganisms belonging to the order Thraustochytriales are also generically called thraustochytrids.

Labyrinthulids have drawn attention as industrial oil-producing microorganisms. DHA produced by labyrinthulids has been productized as DHA-containing lipid raw materials, high DHA-containing animal feeds, and the like (Non-patent Document 1). Specific examples include breeding techniques for the genus *Thraustochytrium* and genus *Schizochytrium* (Patent Document 1), and techniques for using thraustochytrids and ω-3 HUFAs (highly unsaturated fatty acids) extracted from thraustochytrids (Patent Document 2).

It is generally known that PUFAs are biosynthesized via the elongase-desaturase pathway (also called the standard pathway), but it has also been shown that certain labyrinthulids produce PUFAs via a different pathway, namely a metabolic pathway using polyketide synthase (PKS) (Non-patent Document 2). In the present invention, this pathway will hereinafter be called the PUFA-PKS pathway or the PKS pathway. The compositions of PUFAs produced via this pathway are mostly DHA and n-6 DPA.

There are some scientists who think that labyrinthulids (particularly thraustochytrids) have only the PUFA-PKS pathway as a PUFA biosynthesis pathway, and do not have the general elongase-desaturase pathway found in other organisms (Non-patent Document 3). Actually, it has been reported that by gene-isruption of the PUFA-PKS pathway, some labyrinthulids are rendered lethal and such labyrinthulids cannot be grown unless PUFAs are added to the culture medium (Non-patent Document 3). This result means that since PUFAs are required for growth of these labyrinthulids and the gene of the PUFA-PKS pathway, which is the sole PUFA biosynthesis pathway, has been disrupted, the nature of the labyrinthulids has changed into exogenous PUFAs requirement for growth.

However, contrary to common knowledge of persons skilled in the art, some labyrinthulids having both the PUFA-PKS pathway and the elongase-desaturase pathway as PUFA biosynthesis pathways have been found through our examinations. These are specifically described in the specification of Patent Document 3 and in Non-patent Document 5.

Citing *Thraustochytrium aureum* ATCC 34304 as an example, it has been found that this strain has a Δ12 desaturase gene, which is an entry enzyme of the elongase-desaturase pathway. Furthermore, it has been found that a strain in which this gene was disrupted by homologous recombination accumulates predominantly oleic acid, which is the substrate of Δ12 desaturase, compared to the wild-type strain, and that decreases in both linoleic acid of the product and PUFAs located downstream of the biosynthesis system thereof were observed. Additionally, it has been found that because this strain is capable of producing PUFAs via the elongase-desaturase pathway, by disruption of the PUFA-PKS pathway gene it is not rendered lethal. This report was the first to show that the elongase-desaturase pathway also functions as a PUFA biosynthesis pathway in labyrinthulids, and was discussed in Non-patent Document 6 as well.

At the start, Non-patent Document 6 states that labyrinthulids that produce DHA as the main fatty acid are widely used industrially. In contrast, the creation of labyrinthulids containing desired PUFAs other than DHA as the main fatty acid was first enabled by the discovery of labyrinthulids having both the PUFA-PKS pathway and the elongase-desaturase pathway and by application of transformation techniques to these labyrinthulids (Patent Document 3, Non-patent Document 7). That is, it is possible to create strains containing certain PUFAs other than DHA as the main fatty acid by first disrupting the genes of the PUFA-PKS pathway with homologous recombination technique, and then disrupting or overexpressing the genes of the enzymes constituting the elongase-desaturase pathway appropriately. Example 12 of Patent Document 3 is cited as a specific example. In this example, the PUFA-PKS pathway genes of *Thraustochytrium aureum* ATCC 34304 were disrupted, and then the C20 elongase gene was disrupted. An ω3 desaturase gene derived from *Saprolegnia diclina* was then transformed, thereby successfully creating a strain in which arachidonic acid increased approximately 6-fold, EPA increased approximately 10-fold, and DHA decreased approximately $\frac{1}{16}$ in comparison with the wild-type strain.

CITATION LIST

Patent Documents

Patent Document 1: JP 3127161 B
Patent Document 2: JP 3669372 B
Patent Document 3: WO 2012/043826
Patent Document 4: US 2005/0,014,231 A

Non-Patent Documents

Non-patent Document 1: Zvi Cohen et al. editors, "Single Cell Oils Microbial and Algal Oils 2nd edition", (U.S.), AOCS Press, 2010, p. 88

Non-patent Document 2: Metz J G, Roessler P, Faccioti D, et al. Production of polyunsaturated fatty acids by polyketide synthesis in both prokaryotes and eukaryotes. Science 2001; 293: 290-293

Non-patent Document 3: Ratledge C. Omega-3 biotechnology: Errors and omissions, Biotechnology Advances 30 (2012) 1746-1747

Non-patent Document 4: Lippmeier J. C. et al., Lipids, 44 (7), 621-630 (2009)

Non-patent Document 5: Matsuda T, Sakaguchi K, Hamaguchi R, Kobayashi T, Abe E, Hama Y, Hayashi M, Honda D, Okita Y, Sugimoto S, Okino N, Ito M. The analysis of delta12 fatty acid desaturase function revealed that two distinct pathways are active for the synthesis of polyunsaturated fatty acids in *Thraustochytrium aureum* ATCC 34304. J. Lipid Res. 53 (6): 1210-1222 (2012)

Non-patent Document 6: ASBMB Today, June 2012, p. 30

Non-patent Document 7: Sakaguchi K, et al., Versatile Transformation System That Is Applicable to both Multiple Transgene Expression and Gene Targeting for Thraustochytrids. Appl. Environ. Microbiol. 78 (9): 3193-3202 (2012)

Non-patent Document 8: Yazawa K., Lipids, 31, Supple. 297-300 (1996)

Non-patent Document 9: Journal of the Japan Society for Bioscience, Biotechnology and Agrochem, 77, 2, 150-153 (2003)

Non-patent Document 10: "Illustrated Bio Experiments Vol. 2 Fundamentals of Gene Analysis", p. 63-68, Shujunsha, published 1995

Non-patent Document 11: Sanger, F. et al., Proc. Natl. Acad. Sci., 74, 5463 (1997)

Non-patent Document 12: Cigan and Donahue, 1987; Romanos et al., 1992

Non-patent Document 13: Ausubel F. M. et al., Current Protocols in Molecular Biology, Unit 13 (1994)

Non-patent Document 14: Guthrie C., Fink G. et al., Methods in Enzymology: Guide to Yeast Genetics and Molecular Biology, Volume 194 (1991)

Non-patent Document 15: Qiu, X. et al. J. Biol. Chem., 276, 31561-6 (2001)

Non-patent Document 16: Abe E., et al., J. Biochem., 140, 247-253 (2006)

Non-patent Document 17: "Illustrated Bio Experiments Vol. 2 Fundamentals of Gene Analysis", p. 117-128, Shujunsha, published 1995

Non-patent Document 18: DIG Manual (Japanese Edition) 8th, Roche Applied Science

SUMMARY OF THE INVENTION

Problem that the Invention is to Solve

The present invention is directed to provide a labyrinthulid genetically modified such that the fatty acid composition is modified, preferably a labyrinthulid that produces PUFAs only via the elongase-desaturase pathway the invention provides a method for producing PUFAs using the labyrinthulid thereof, lipids (microbial oils) containing PUFAs produced using the method thereof, and uses thereof.

To create a strain containing certain PUFAs other than DHA as the main fatty acids using labyrinthulids having both the PUFA-PKS pathway and the elongase-desaturase pathway, first of all, DHA production via the PUFA-PKS pathway needs to be stopped or inhibited by any means. Specifically, methods such as disrupting PUFA-PKS pathway gene with homologous recombination technique, acquisition of a spontaneous mutant by UV irradiation, drug treatment, or the like, and silencing of PUFA-PKS genes by RNAi (RNA interference), and the like may be considered.

Among these methods, gene-disruption with homologous recombination technique previously described has been technically established. However, the number of drug resistance genes that can be used as markers is generally limited, and there is the problem that when a marker is used in PUFA-PKS pathway gene disruption, the number of markers that can be used in further gene disruption or gene transfer will decrease. This means a decrease in the number of times that gene-disruption and gene-transfer can be implemented after PUFA-PKS pathway gene is disrupted, and thus it becomes an obstacle to create higher-performance strains.

Furthermore, spontaneous mutation and silencing by RNAi are methods with a track record in other organisms but it is unknown whether a desired strain in labyrinthulids can be acquired by these methods.

The present invention is directed to provide a labyrinthulid having very weak or no PUFA– producing activity via the endogenous PUFA-PKS pathway and having PUFA producing activity via the endogenous elongase-desaturase pathway, a method for producing lipids containing PUFAs produced using the labyrinthulid thereof, and lipids containing PUFAs produced using the labyrinthulid thereof.

Means for Solving the Problems

The present inventors conducted a diligent research, and discovered the existence of labyrinthulids having very weak or no PUFA producting activity via the endogenous PUFA-PKS pathway and having PUFA– producting activity via the endogenous elongase-desaturase pathway. And the present invention was accomplished pertaining to microbial oil obtained from labyrinthulids thereof, microbial oil-producing labyrinthulids, methods for producing microbial oil thereof, and uses of microbial oils.

In one aspect of the present invention, a method for producing a microbial oil includes the steps of genetically modifying a labyrinthulid by disrupting and/or silencing a gene, or by transforming another gene in addition to the disruption and/or gene silencing of the gene, and culturing the labyrinthulid, such that a fatty acid composition accumulated in the labyrinthulid comprises an increased EPA content; and collecting the microbial oil having the increased EPA content from the labyrinthulid. The labyrinthulid before the modification is selected from the group consisting of (A) and (B): (A) a labyrinthulid belonging to the genus *Parietichytrium* or genus *Schizochytrium* as disclosed below in detail, and having very weak or no activity of producing PUFAs via a PUFA-PKS pathway; and (B) a labyrinthulid belonging to the genus *Thraustochytrium* as disclosed below in detail, in which a host PUFA-PKS gene is disrupted or silenced to a very weak level. The disrupted and/or silenced gene is a fatty acid elongase gene and/or a fatty acid desaturase gene. The transformed another gene is a fatty acid elongase gene and/or a fatty acid desaturase gene. Typically, the increased EPA content is not less than 11.5% of a total fatty acid composition in labyrinthulid. The fatty acid elongase gene is a C20 elongase gene, and/or wherein the fatty acid desaturase gene is a Δ4 desaturase gene and/or an ω3 desaturase gene. The step of disrupting or transforming the gene of a labyrinthulid may utilize electroporation, a gene gun method, or gene editing, and/or wherein the step of silencing the gene utilizes an antisense method or RNA. The present invention can provide microbial oil produced by the method according to claim 1, wherein the microbial oil satisfies not less than one condition selected from the group consisting of (a) to (d):
(a) ARA is not less than 13.2% of the total fatty acid composition;
(b) The total of ARA and EPA is not less than 36.8% of the total fatty acid composition;
(c) DHA is not greater than 1.3% of the total fatty acid composition; and
(d) the total of DHA and n-6 DPA is not greater than 2.9% of the total fatty acid composition.

Further, the microbial oil may satisfy not less than one condition selected from the group consisting of (e) to (h):
(e) ARA is not less than 21.3% of the total fatty acid composition;
(f) EPA is not less than 23.8% of the total fatty acid composition;
(g) DHA is not greater than 0.5% of the total fatty acid composition; and
(h) The total of DHA and n-6 DPA is not greater than 0.7% of the total fatty acid composition.

Preferably, the microbial oil satisfies a condition that a GC area ratio of ARA after modification is not less than 4 times greater than before modification, the GC area is a peak area in a GC chart obtained by gas chromatography analysis. The microbial oil satisfies a condition that a GC area ratio of EPA after modification is not less than 8 times greater than before modification, the GC area is a peak area in a GC chart obtained by gas chromatography analysis.

In another aspect of the present invention, a labyrinthulid has been genetically modified by disrupting and/or silencing a gene, or by transforming another gene in addition to the disruption and/or gene silencing of the gene such that a fatty acid composition accumulated in the labyrinthulid comprises an increased EPA content. The labyrinthulid before the modification is selected from the group consisting of (A) and (B): (A) a labyrinthulid belonging to the genus *Parietichytrium* or genus *Schizochytrium* and having very weak or no activity of producing PUFAs via a PUFA-PKS pathway; and (B) a labyrinthulid belonging to the genus *Thraustochytrium* in which a host PUFA-PKS gene is disrupted or silenced to a very weak level. The disrupted and/or silenced gene is a fatty acid elongase gene and/or a fatty acid desaturase gene. The transformed another gene is a fatty acid elongase gene and/or a fatty acid desaturase gene. The increased EPA content is not less than 11.5% of a total fatty acid composition. The fatty acid composition may satisfy not less than one condition selected from the group consisting of (a) to (d):
(a) ARA is not less than 13.2% of the total fatty acid composition;
(b) The total of ARA and EPA is not less than 36.8% of the total fatty acid composition;
(c) DHA is not greater than 1.3% of the total fatty acid composition; and
(d) the total of DHA and n-6 DPA is not greater than 2.9% of the total fatty acid composition.

Further, the fatty acid composition satisfies not less than one condition selected from the group consisting of (e) to (h):
(e) ARA is not less than 21.3% of the total fatty acid composition;
(f) EPA is not less than 23.8% of the total fatty acid composition;
(g) DHA is not greater than 0.5% of the total fatty acid composition; and
(h) The total of DHA and n-6 DPA is not greater than 0.7% of the total fatty acid composition.

In yet another aspect, the present disclosure includes the following microbial oils (1) to (28).
(1) Microbial oil satisfying at least one condition selected from the group consisting of (a) to (g) below.
(a) ARA is not less than 5% of the total fatty acid composition.
(b) DGLA is not less than 2.5% of the total fatty acid composition.
(c) ETA is not less than 0.35% of the total fatty acid composition.
(d) EPA is not less than 4% of the total fatty acid composition.
(e) n-6 DPA is not greater than 0.20% of the total fatty acid composition.
(f) DHA is not greater than 0.50% of the total fatty acid composition.
(g) The total of DHA and n-6 DPA is not greater than 0.7% of the total fatty acid composition.
(2) The microbial oil according to (1), wherein the microbial oil satisfies at least one condition selected from the group consisting of (h) to (l) below.
(h) The value of LA/DHA by GC area is not less than 0.6 and not greater than 10.
(i) The value of GLA/DHA by GC area is not less than 0.35 and not greater than 10.
(j) The value of DGLA/DHA by GC area is not less than 0.35 and not greater than 10.
(k) The value of ARA/DHA by GC area is not less than 0.7 and not greater than 50.
(l) The value of EPA/DHA by GC area is not less than 0.35 and not greater than 50.
(3) The microbial oil according to (1) or (2), wherein the microbial oil satisfies at least one condition selected from the group consisting of (m) to (o) below.
(m) The value of LA/EPA by GC area is not less than 0.06 and not greater than 0.17.
(n) The value of GLA/EPA by GC area is not less than 0.04 and not greater than 0.12.
(o) The value of DTA/EPA by GC area is not less than 0.01 and not greater than 0.4.
(4) The microbial oil according to any one of (1) to (3), wherein the microbial oil satisfies the condition that the value of DTA/ARA by GC area is not less than 0.01 and not greater than 0.45.
(5) The microbial oil according to any one of (1) to (4), wherein the microbial oil satisfies the condition that the value of DTA/DGLA by GC area is not less than 0.01 and not greater than 1.45.
(6) The microbial oil according to any one of (1) to (5), wherein the microbial oil satisfies at least one condition selected from the group consisting of (p) to (t) below.
(p) The value of LA/n-6 DPA by GC area is not less than 0.4 and not greater than 20.
(q) The value of GLA/n-6 DPA by GC area is not less than 0.2 and not greater than 10.
(r) The value of DGLA/n-6 DPA by GC area is not less than 0.35 and not greater than 30.
(s) The value of ARA/n-6 DPA by GC area is not less than 0.7 and not greater than 60.
(t) The value of EPA/n-6 DPA by GC area is not less than 1.0 and not greater than 70.
(7) The microbial oil according to any one of (1) to (6), wherein the microbial oil satisfies at least one condition selected from the group consisting of (u) to (x) below.
(u) The value of DGLA/LA by GC area is not less than 1.4 and not greater than 10.

(v) The value of ARA/LA by GC area is not less than 5.1 and not greater than 20.
(w) The value of EPA/LA by GC area is not less than 5.5 and not greater than 30.
(x) The value of DTA/LA by GC area is not less than 0.01 and not greate than 0.4.
(8) The microbial oil according to any one of (1) to (7), wherein the microbial oil satisfies at least one condition selected from the group consisting of (y) and (z) below.
(y) The value of DGLA/GLA by GC area is not less than 4.5 and not greater than 20.
(z) The value of ARA/GLA by GC area is not less than 9 and not greater than 30.
(9) The microbial oil according to any one of (1) to (8), wherein the microbial oil satisfies the condition that the value of n-6 DPA/DTA by GC area is not greater than 1.5.
(10) The microbial oil according to any one of (1) to (9), wherein the microbial oil satisfies the condition that the value of DHA/n-3 DPA by GC area is not greater than 4.
(11) The microbial oil according to any one of (1) to (10), wherein the microbial oil satisfies the condition that the value of C20 PUFA/C22 PUFA by GC area is not less than 0.5 and not greater than 50.
(12) The microbial oil according to any one of (1) to (11), wherein the microbial oil satisfies the condition that the value of n-6 PUFA/n-3 PUFA by GC area is not less than 1.8.
(13) A microbial oil obtained from a labyrinthulid genetically modified such that the fatty acid composition is modified, the labyrinthulid being selected from the group consisting of (A) and (B) below.
(A) A labyrinthulid in which the fatty acid composition is modified by disruption and/or gene silencing.
(B) A labyrinthulid in which the fatty acid composition is modified by transforming a gene in addition to disruption and/or gene silencing.
(14) The microbial oil according to (13), wherein the disrupted and/or silenced gene is a PKS gene, a fatty acid elongase gene, and/or a fatty acid desaturase gene.
(15) The microbial oil according to (13) or (14), wherein the transformed gene is a fatty acid elongase gene and/or a fatty acid desaturase gene.
(16) The microbial oil according to (14) or (15), wherein the fatty acid elongase gene is the C20 elongase gene.
(17) The microbial oil according to any one of (13) to (16), wherein the fatty acid desaturase gene is the Δ4 desaturase gene and/or the ω3 desaturase gene.
(18) The microbial oil according to any one of (13) to (17), wherein the method for disrupting or transforming a gene of a labyrinthulid is electroporation, a gene gun method, or gene editing.
(19) The microbial oil according to any one of (13) to (18), wherein the method for gene silencing of a labyrinthulid is an antisense method or RNA interference.
(20) A microbial oil obtained from a labyrinthulid selected from the group consisting of (C) and (D) below.
(C) A labyrinthulid having very weak or no activity of producing PUFAs via the PUFA-PKS pathway.
(D) A labyrinthulid in which the host PUFA-PKS gene is disrupted or silenced to a very weak level.
(21) The microbial oil according to (20), wherein the labyrinthulid having very weak or no activity of producing PUFAs via the PUFA-PKS pathway is a labyrinthulid belonging to the genus *Parietichytrium* or genus *Schizochytrium*.
(22) The microbial oil according to (21), wherein the labyrinthulid belonging to the genus *Parietichytrium* is a labyrinthulid belonging to *Parietichytrium sarkarianum*.
(23) The microbial oil according to (21), wherein the labyrinthulid belonging to the genus *Schizochytrium* is a labyrinthulid belonging to *Schizochytrium aggregatum*.
(24) The microbial oil according to (22), wherein the microorganism belonging to *Parietichytrium sarkarianum* is *Parietichytrium* sp. SEK358 (FERM BP-11405), *Parietichytrium sarkarianum* SEK364 (FERM BP-11298), or *Parietichytrium* sp. SEK517 (FERM BP-11406).
(25) The microbial oil according to (23), wherein the microorganism belonging to *Schizochytrium aggregatum* is *Schizochytrium aggregatum* ATCC 28209.
(26) The microbial oil according to (20), wherein the labyrinthulid in which the host PUFA-PKS is disrupted or silenced to a very weak level belongs to the genus *Thraustochytrium*.
(27) The microbial oil according to (26), wherein the labyrinthulid belonging to the genus *Thraustochytrium* is *Thraustochytrium aureum*.
(28) A microbial oil that satisfies at least one condition selected from the group consisting of (E) to (H) below.
(E) A GC area ratio of ARA after modification is not less than 3 times greater than before modification.
(F) A GC area ratio of DGLA after modification is not less than 4 times greater than before modification.
(G) A GC area ratio of ETA after modification is not less than 7 times greater than before modification.
(H) A GC area ratio of EPA after modification is not less than 7 times greater than before modification.

The gist of the present invention includes the following methods for producing microbial oil (29) to (56).
(29) A method for producing microbial oil satisfying at least one condition selected from the group consisting of (a) to (g) below.
(a) ARA is not less than 5% of the total fatty acid composition.
(b) DGLA is not less than 2.5% of the total fatty acid composition.
(c) ETA is not less than 0.35% of the total fatty acid composition.
(d) EPA is not less than 4% of the total fatty acid composition.
(e) n-6 DPA is not greater than 0.20% of the total fatty acid composition.
(f) DHA is not greater than 0.50% of the total fatty acid composition.
(g) The total of DHA and n-6 DPA is not greater than 0.7% of the total fatty acid composition.
(30) The method for producing microbial oil according to (29), wherein the microbial oil satisfies at least one condition selected from the group consisting of (h) to (1) below.
(h) The value of LA/DHA by GC area is not less than 0.6 and not greater than 10.
(i) The value of GLA/DHA by GC area is not less than 0.35 and not greater than 10.
(j) The value of DGLA/DHA by GC area is not less than 0.35 and not greater than 10.

(k) The value of ARA/DHA by GC area is not less than 0.7 and not greater than 50.
(l) The value of EPA/DHA by GC area is not less than 0.35 and not greater than 50.
(31) The method for producing microbial oil according to (29) or (30), wherein the microbial oil satisfies at least one condition selected from the group consisting of (m) to (o) below.
(m) The value of LA/EPA by GC area is not less than 0.06 and not greater than 0.17.
(n) The value of GLA/EPA by GC area is not less than 0.04 and not greater than 0.12.
(o) The value of DTA/EPA by GC area is not less than 0.01 and not greater than 0.4.
(32) The method for producing microbial oil according to any one of (29) to (31), wherein the microbial oil satisfies the condition that the value of DTA/ARA by GC area is not less than 0.01 and not greater than 0.45.
(33) The method for producing microbial oil according to any one of (29) to (32), wherein the microbial oil satisfies the condition that the value of DTA/DGLA by GC area is not less than 0.01 and not greater than 1.8.
(34) The method for producing microbial oil according to any one of (29) to (33), wherein the microbial oil satisfies at least one condition selected from the group consisting of (p) to (t) below.
(p) The value of LA/n-6 DPA by GC area is not less than 0.4 and not greater than 20.
(q) The value of GLA/n-6 DPA by GC area is not less than 0.2 and not greater than 10.
(r) The value of DGLA/n-6 DPA by GC area is not less than 0.35 and not greater than 30.
(s) The value of ARA/n-6 DPA by GC area is not less than 0.7 and not greater than 60.
(t) The value of EPA/n-6 DPA by GC area is not less than 0.4 and not greater than 70.
(35) The method for producing microbial oil according to any one of (29) to (34), wherein the microbial oil satisfies at least one condition selected from the group consisting of (u) to (x) below.
(u) The value of DGLA/LA by GC area is not less than 1.4 and not greater than 10.
(v) The value of ARA/LA by GC area is not less than 5.1 and not greater than 20.
(w) The value of EPA/LA by GC area is not less than 5.5 and not greater than 30.
(x) The value of DTA/LA by GC area is not less than 0.01 and not greater than 0.4.
(36) The method for producing microbial oil according to any one of (29) to (35), wherein the microbial oil satisfies at least one condition selected from the group consisting of (y) and (z) below.
(y) The value of DGLA/GLA by GC area is not less than 4.5 and not greater than 20.
(z) The value of ARA/GLA by GC area is not less than 9 and not greater than 30.
(37) The method for producing microbial oil according to any one of (29) to (36), wherein the microbial oil has a value of n-6 DPA/DTA by GC area of not greater than 1.5.
(38) The method for producing microbial oil according to any one of (29) to (37), wherein the microbial oil has a value of DHA/n-3 DPA by GC area of not greater than 4.
(39) The method for producing microbial oil according to any one of (29) to (38), wherein the microbial oil satisfies the condition that the value of C20 PUFA/C22 PUFA by GC area is not less than 0.5 and not greater than 50.
(40) The method for producing microbial oil according to any one of (29) to (39), wherein the microbial oil satisfies the condition that the value of n-6 PUFA/n-3 PUFA by GC area is not less than 1.8.
(41) A method for producing microbial oil whereby microbial oil is caused to be produced in a labyrinthulid genetically modified such that the fatty acid composition is modified, the labyrinthulid being selected from the group consisting of (A) and (B) below.
(A) A labyrinthulid in which the fatty acid composition is modified by gene-disruption and/or gene silencing.
(B) A labyrinthulid in which the fatty acid composition is modified by transforming a gene in addition to disruption and/or gene silencing.
(42) The method for producing microbial oil according to (41), wherein the disrupted and/or silenced gene is a PKS gene, a fatty acid elongase gene, and/or a fatty acid desaturase gene.
(43) The method for producing microbial oil according to (41) or (42), wherein the transformed gene is a fatty acid elongase gene and/or a fatty acid desaturase gene.
(44) The method for producing microbial oil according to (42) or (43), wherein the fatty acid elongase gene is the C20 elongase gene.
(45) The method for producing microbial oil according to any one of claims 41 to 44, wherein the fatty acid desaturase gene is the Δ4 desaturase gene and/or the ω3 desaturase gene.
(46) The method for producing microbial oil according to any one of (41) to (45), wherein the method for disrupting or transforming a gene of a labyrinthulid is electroporation, a gene gun method, or gene editing.
(47) The method for producing microbial oil according to any one of (41) to (46), wherein the method for gene silencing of a labyrinthulid is an antisense method or RNA interference.
(48) A method for producing microbial oil, wherein microbial oil is caused to be produced in a labyrinthulid selected from the group consisting of (C) and (D) below.
(C) A labyrinthulid having very weak or no activity of producing PUFAs via the PUFA-PKS pathway.
(D) A labyrinthulid in which the host PUFA-PKS gene is disrupted or silenced to a very weak level.
(49) The method for producing microbial oil according to (48), wherein the labyrinthulid having very weak or no activity of producing PUFAs via the PUFA-PKS pathway is a labyrinthulid belonging to the genus *Parietichytrium* or genus *Schizochytrium*.
(50) The method for producing microbial oil according to (49), wherein the labyrinthulid belonging to the genus *Parietichytrium* is a labyrinthulid belonging to *Parietichytrium sarkarianum*.
(51) The method for producing microbial oil according to (50), wherein the labyrinthulid belonging to the genus *Schizochytrium* is a labyrinthulid belonging to *Schizochytrium aggregatum*.
(52) The method for producing microbial oil according to (50), wherein the microorganism belonging to *Parietichytrium sarkarianum* is *Parietichytrium* sp. SEK358 (FERM BP-11405), *Parietichytrium sarkarianum* SEK364 (FERM BP-11298), or *Parietichytrium* sp. SEK517 (FERM BP-11406).

(53) The method for producing microbial oil according to (51), wherein the microorganism belonging to *Schizochytrium aggregatum* is *Schizochytrium aggregatum* ATCC 28209.

(54) The method for producing microbial oil according to (48), wherein the labyrinthulid in which the host PUFA-PKS gene is disrupted or silenced to a very weak level belongs to the genus *Thraustochytrium*.

(55) The method for producing microbial oil according to (54), wherein the labyrinthulid belonging to the genus *Thraustochytrium* is *Thraustochytrium aureum*.

(56) A method for producing microbial oil satisfying at least one condition selected from the group consisting of (E) to (H) below.

(E) The GC area ratio of ARA after modification is not less than 3 times greater than before modification.

(F) The GC area ratio of DGLA after modification is not less than 4 times greater than before modification.

(G) The GC area ratio of ETA after modification is not less than 7 times greater than before modification.

(H) The GC area ratio of EPA after modification is not less than 7 times greater than before modification.

Furthermore, the gist of the present invention includes the following food, animal feed, medication, or industrial product (57), the following genetically modified labyrinthulid (58), and the following method for creating the genetically modified labyrinthulid (59).

(57) A food, animal feed, medication, or industrial product including the microbial oil described in any one of (1) to (28) as a lipid composition.

(58) A labyrinthulid genetically modified such that a produced fatty acid composition is modified, the labyrinthulid producing the microbial oil described in any one of (1) to (28).

(59) A method for creating the labyrinthulid genetically modified such that the produced fatty acid composition described in (58) is modified.

BRIEF DESCRIPTION OF DRAWINGS

FIG. 13 lists the fatty acid proportions of the C20 elongase gene disruption strain when the *Parietichytrium sarkarianum* SEK364 wild-type strain is taken as 100%.

FIG. 34 lists the fatty acid proportions of the C20 elongase gene disruption strain derived from the *Parietichytrium* sp. SEK571 strain when the *Parietichytrium* sp. SEK571 wild-type strain is taken as 100%.

FIG. 35 illustrates results of RACE in which an elongase gene derived from *T. aureum* ATCC 34304 is amplified in Comparative Example 1-2. (Brief description of symbols) 1: 5'-RACE using synthetic adapter-specific oligonucleotide and degenerate oligonucleotide elo-R; 2: 3'-RACE using synthetic adapter-specific oligonucleotide and degenerate oligonucleotide elo-F; 3: 5'-RACE using only elo-R (negative control); 4: 3'-RACE using only elo-F (negative control); 5: 5'-RACE using only synthetic adapter-specific oligonucleotide (negative control); 6: 3'-RACE using only synthetic adapter-specific oligonucleotide (negative control)

FIGS. 36A and 36B illustrate an evaluation of a transformant into which KONeor was transformed in Comparative Example 1-7. FIG. 36A illustrates the oligonucleotide primer pair used in evaluation of the transformant by PCR using genome DNA as a template. (Brief description of symbols) (1) Neor detection primers (SNeoF and SNeoR); (2) KO confirmation 1 (KO Pro F SmaI and KO Term R SmaI); (3) KO confirmation 2 (E2 KO ProF EcoRV and SNeoR); (4) KO confirmation 3 (SNeoF and E2 KO Term R EcoRV); (5) TaELO2 detection (E2 HindIII and E2 XbaI). FIG. 36B illustrates the agarose electrophoresis diagram in evaluation of the transformant by PCR using genome DNA as a template. (Brief description of symbols) 1, 5, 9, 13, 17: Transformant; 2, 6, 10, 14, 18: Wild-type strain; 3, 7, 11, 15, 19: Using KONeor as a template; 4, 8, 12, 16: No template. Furthermore, the used oligonucleotide primer pairs (1) to (5) are the lane numbers.

FIG. 37 illustrates the results of confirmation of TaELO2 copy number by southern blotting in Comparative Example 1-8. (Brief description of symbols) 1: Genome DNA (2.5 μg), BamHI treatment; 2: BglII treatment; 3: EcoRI treatment; 4: EcoRV treatment; 5: HindIII treatment; 6: KpnI treatment; 7: SmaI treatment; 8: XbaI treatment; 9: Positive control (PCR product amplified with 1 ng of E2 KO Pro F EcoRV and E2 KO Term R EcoRV. Including TaELO2.)

FIG. 38A is a schematic diagram of southern blotting to detect a wild-type allele or mutant allele by TKONeor transfer. FIG. 38B illustrates the results of southern blotting. (Brief description of symbols) 1: *T. aureum* wild-type strain (2.5 μg of genome DNA); 2, 3: TKONeor transfer transformant (2.5 μg of genome DNA); 4: Positive control (PCR product amplified with 50 ng of E2 KO ProF EcoRV and E2 KO Term R EcoRV. Includes TaELO2.)

FIG. 39A illustrates the oligonucleotide primer pair used. (Brief description of symbols) (1) TaELO2 ORF detection (SNeoF and SNeoR); (2) KO confirmation (E2 KO Pro F EcoRV and ubi-hygro R)

FIG. 39B illustrates the agarose electrophoresis diagram of PCR using oligonucleotide primer pair (1) of KO confirmation. The arrows indicate the transformant of which specific product amplification was confirmed and which was estimated to be TaELO2 deletion homozygote.

FIG. 39C illustrates the agarose electrophoresis diagram of PCR using oligonucleotide primer pair (2) of TaELO2 ORF detection in a transformant identified as a TaELO2 deletion homozygote. (Brief description of symbols) 1: Using KOub600Hygr as a template; 2: Wild-type strain FIGS. 40A and 40B illustrate an evaluation by southern blotting of a transformant obtained by retransfer of KOub600Hygr in Comparative Example 1-11. FIG. 40A is a schematic diagram of southern blotting to detect a wild-type allele, a mutant allele by KONeor transfer, and a mutant allele by KOub600Hygr transfer. FIG. 40B illustrates the results of southern blotting. (Brief description of symbols) 1, 9: Wild-type strain; 2 to 8 and 10 to 16: TaELO2 deletion homozygote FIG. 41 illustrates the results of southern blotting to detect TaELO2 in Comparative Example 1-11. (Brief description of symbols) 1: Wild-type strain; 2 to 5: T TaELO2 deletion homozygote

FIG. 52 lists the fatty acid proportions of the PKS pathway associated gene orfA disruption strain when the *Thraustochytrium aureum* ATCC 34304 wild-type strain is taken as 100%.

FIG. 64 lists the fatty acid proportions of the PKS pathway (orfA gene) and C20 elongase gene double disruption strain when *Thraustochytrium aureum* ATCC 34304 wild-type strain is taken as 100%.

FIG. 71 lists the fatty acid proportions of the PKS pathway (orfA gene) and Δ4 desaturase gene double disruption strain when the *Thraustochytrium aureum* ATCC 34304 wild-type strain is taken as 100%.

MODE FOR CARRYING OUT THE INVENTION

Figure 1:
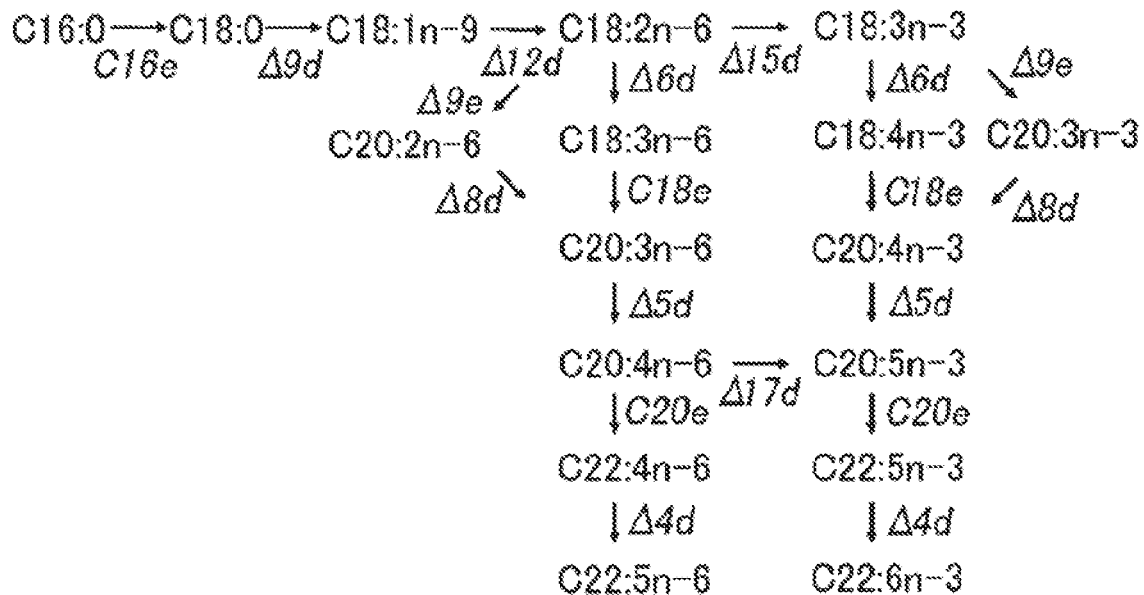
FIG. 1 illustrates the elongase-desaturase pathway and enzymes related to this biosynthesis pathway. (Brief description of symbols) C16:0: Palmitic acid; C18:0: Stearic acid; C18: ln-9: Oleic acid; C18:2n-6: Linoleic acid (LA); C18: 3n-3: α-Linolenic acid (ALA); C18:3n-6: γ-Linolenic acid (GLA); C18:4n-3: Stearidonic acid (STA); C20:2n-6: Eicosadienoic acid (EDA); C20:3n-3: Eicosatrienoic acid (ETrA); C20:3n-6: Dihomo-γ-linolenic acid (DGLA); C20: 4n-3: Eicosatetraenoic acid (ETA); C20:4n-6: Arachidonic acid (ARA); 20:5n-3: Eicosapentaenoic acid (EPA); C22: 4n-6: Docosatetraenoic acid (DTA); C22:5n-3: n-3 Docosapentaenoic acid (n-3 DPA); C22:5n-6: n-6 Docosapentaenoic acid (n-6 DPA); C22:6n-3: Docosahexaenoic acid (DHA); C16e: C16 elongase; Δ9d: Δ9 desaturase; Δ12d: Δ12 desaturase; Δ15d: Δ15 desaturase; Δ9e: Δ9 elongase; Δ6d: Δ6 desaturase; Δ8d: Δ8 desaturase; C18e: C18 elongase; Δ5d: Δ5 desaturase; C20e: C20 elongase; Δ17d: Δ17 desaturase; Δ4d: Δ4 desaturase. Δ15 desaturase and Δ17 desaturase are each sometimes called ω3 desaturase.

The opportunity for the present invention came about due to the discovery of a new pattern of biosynthesis pathway of polyunsaturated fatty acids (PUFAs) in microorganisms called labyrinthulids. Specifically, it is known that PUFAs are generally biosynthesized via the elongase-desaturase pathway, but in some organisms, PUFAs are also biosynthesized via another pathway called the PUFA-PKS pathway. In the past, two types of labyrinthulids were found to exist, namely (I) the type that produces only via the PUFA-PKS pathway and (II) the type that produces via the elongase-desaturase pathway and PUFA-PKS pathway. This time, a third type, (III) a type that produces only via the elongase-desaturase pathway, was newly discovered. In short, a new "pattern" of PUFA biosynthesis pathway was discovered.

Examples are as follows. (1) Labyrinthulids having very weak or no PUFA- producing activity via the endogenous PUFA-PKS pathway and having PUFA- producing activity via the endogenous elongase-desaturase pathway. The present invention relates to labyrinthulids of the above (III) type that produces only via the elongase-desaturase pathway. These labyrinthulids encompass labyrinthulids of type (III) produced by isolating, culturing, and amplifying a wild-type strain having a PUFA biosynthesis pathway, and labyrinthulids having "very weak or no" PUFA- producing activity via the PUFA-PKS pathway.

(2) The labyrinthulids according to (1) above that do not have the endogenous PUFA-PKS pathway. The present invention is limited to (1) above, which are labyrinthulids having no genes or enzymes themselves that constitute the PUFA-PKS pathway.

(3) The labyrinthulids according to (1) above that have very weak or no endogenous PUFA-PKS pathway activity. The present invention is limited to (1) above that have information related to genes of enzymes constituting the PUFA-PKS pathway on the genome but do not express them (and therefore have no activity), or that express them only very weakly or not at all.

(4) The labyrinthulids according to any of (1) to (3) above, wherein DHA and/or n-6 DPA production activity has been lost or the produced quantity of DHA and/or n-6 DPA has been markedly decreased by endogenous Δ4 desaturase gene disruption.

Labyrinthulids of type (III) which produce PUFAs only via the elongase-desaturase pathway differ from those of type (I) which produce only via the PUFA-PKS pathway and those of type (II) which produce via the elongase-desaturase pathway and PUFA-PKS pathway in that they have no PUFA-PKS pathway. Based on this viewpoint, the present invention defines labyrinthulids of the type that produces only via the elongase-desaturase pathway. In other words, the above endogenous Δ4 desaturase gene disruption can be considered a method for determining whether a labyrinthulid is of the type that produces only via the elongase-desaturase pathway.

(5) The labyrinthulids according to (1) to (3) above, wherein DHA and/or n-6 DPA production activity has been lost or the produced quantity of DHA and/or n-6 DPA has been markedly decreased through endogenous C20 elongase gene disruption.

Labyrinthulids of type (III) which produce only via the elongase-desaturase pathway differ from those of type (I) which produce only via the PUFA-PKS pathway and those of type (II) which produce via the elongase-desaturase pathway and PUFA-PKS pathway in that they have no PUFA-PKS pathway. Based on this viewpoint, the present invention defines labyrinthulids of the type that produces only via the elongase-desaturase pathway. In other words, the above endogenous C20 elongase gene disruption can be considered a method for determining whether a labyrinthulid is of the type that produces only via the elongase-desaturase pathway.

(6) The labyrinthulids according to (1) to (5) above that is a microorganism belonging to either the genus *Parietichytrium* or the genus *Schizochytrium*.

Labyrinthulids belonging to the genus *Parietichytrium* or the genus *Schizochytrium* were known before the filing date of the present application, but it was not known that they are labyrinthulids of type (III) which produce PUFAs only via the elongase-desaturase pathway.

(7) The labyrinthulids according to (6) above, wherein the microorganism is *Parietichytrium* sp. SEK358 (FERM BP-11405), *Parietichytrium sarkarianum* SEK364 (FERM BP-11298), *Parietichytrium* sp. SEK517 (FERM BP-11406), or *Schizochytrium aggregatum* ATCC 28209.

(8) A method for producing lipids containing PUFAs, the method including culturing the labyrinthulids described in any of (1) to (7) above in a culture medium and collecting the lipids from the culture.

(9) A method for producing lipids containing PUFAs, the method including culturing labyrinthulids, that were transformed using the labyrinthulids described in any of (1) to (7) above as hosts with the objective of modifying the fatty acid composition and/or highy accumulating fatty acids, in a culture medium and collecting the lipids from the culture.

(10) Lipids containing PUFAs, the lipids being produced by the method of (8) or (9) above.

The present invention can provide labyrinthulea that produce PUFAs via only the elongase-desaturase pathway.

The creation of labyrinthulids equivalent to type (III) which produce only via the elongase-desaturase pathway is also possible, by spontaneous mutation or genetic recombination from type (II) which produce via the elongase-desaturase pathway and PUFA-PKS pathway. Examples of these include microorganisms belonging to the genus *Thraustochytrium*. By using these microorganisms, it is possible to obtain the same polyunsaturated fatty acids as by labyrinthulids of type (III).

[Microorganisms]

Labyrinthulids having very weak or no activity of producing PUFAs via the PUFA-PKS pathway includes labyrinthulids that produce PUFAs only via the elongase-desaturase pathway. A labyrinthulid having very weak PUFA-producing activity means a labyrinthulid in which the elongase-desaturase pathway gene has been disrupted, and which cannot produce PUFAs, and cannot be cultured without supplementing the culture medium with PUFAs. It means that not greater than $1/100$ of the DHA synthesized in the organism is DHA synthesized via the PUFA-PKS pathway. The labyrinthulid that has very weak or no activity of producing PUFAs via the endogenous PUFA-PKS pathway and is capable of producing PUFAs via the endogenous elongase-desaturase pathway is not particularly limited, but particularly preferred examples are labyrinthulids belonging to the genus *Parietichytrium* or the genus *Schizochytrium*. Particularly preferred among these are *Parietichytrium* sp. SEK358 (FERM BP-11405), *Parietichytrium sarkarianum* SEK364 (FERM BP-11298), *Parietichytrium* sp. SEK517 (FERM BP-11406), or *Schizochytrium aggregatum* ATCC 28209.

*Parietichytrium* sp. SEK358 was obtained by the method described below. First, 10 mL of surface water collected in the Ishigakijima-Miyaragawa estuary region was placed in a test tube. Pine pollen was added, and the test tube was left to stand at room temperature. After 7 days, a sterilized agar culture medium (2 g of glucose, 1 g of peptone, 0.5 g of yeast extract, 0.2 g of chloramphenicol, 15 g of agar, 100 mL of distilled water, 900 mL of sea water) was swabbed with this pine pollen, and colonies that emerged after 5 days were separated and cultured. This was repeated several times, and cells were separated. This strain was internationally deposited on Aug. 11, 2011 as accession number FERM BP-11405 at the International Patent Organism Depositary, National Institute of Advanced Industrial Science and Technology (Tsukuba Central 6, 1-1-1 Higashi, Tsukuba City, Ibaraki Prefecture), and can be procured therefrom.

*Parietichytrium sarkarianum* SEK364 was obtained by culturing a sea water sample collected in the Ishigakijima-Fukidogawa estuary region and separating cells in the same manner as above. This strain was internationally deposited on Sep. 24, 2010 as accession number FERM BP-11298 at the International Patent Organism Depositary, National Institute of Advanced Industrial Science and Technology (Tsukuba Central 6, 1-1-1 Higashi, Tsukuba City, Ibaraki Prefecture), and can be procured therefrom.

*Parietichytrium* sp. SEK571 was obtained by culturing a sea water sample collected in the Iriomotejima-Shiiragawa estuary region and separating cells in the same manner as above. This strain was internationally deposited on Aug. 11, 2011 as accession number FERM BP-11406 at the International Patent Organism Depositary, National Institute of Advanced Industrial Science and Technology (Tsukuba Central 6, 1-1-1 Higashi, Tsukuba City, Ibaraki Prefecture), and can be procured therefrom.

*Schizochytrium aggregatum* ATCC 28209 has been deposited at ATCC, and can be procured therefrom. Labyrinthulids in which PUFA-PKS has been disrupted or expression has been inhibited to a very weak level include labyrinthulids that produce PUFAs via the elongase-desaturase pathway and PUFA-PKS pathway. The PUFA-PKS pathway is required to exist in labyrinthulids that produce PUFAs only via the PUFA-PKS pathway, and when disrupted, there is a requirement for PUFAs. Labyrinthulids that produce PUFAs via the elongase-desaturase pathway and PUFA-PKS pathway, even in a case where the PUFA-PKS pathway has been disrupted, differ in that there is no requirement for PUFAs.

Disruption of the Δ4-desaturase gene using the present invention can dramatically reduce the produced quantities of DHA and n-6 DPA while maintaining the produced quantity of PUFAs overall.

The properties of the microorganisms obtained by the present invention may be combined as desired.

[Microbial Oil]

The present invention relates to microbial oil containing the fatty acid profile of the present invention. The microorganism of the present invention contains not less than 15 wt. %, preferably not less than 30 wt. %, more preferably not less than 50 wt. %, and even more preferably not less than 70 wt. % of lipid components per gram of cells. The lipid components contain not less than 30 wt. %, preferably not less than 50 wt. %, and more preferably not less than 70 wt. % of fatty acid components. The fatty acid components accumulate as not less than 70 wt. %, preferably not less than 80 wt. %, and more preferably not less than 90 wt. % of triglycerides. The microbial oil of the present invention is "crude oil" or "refined oil" containing at least approximately 35 wt. % of triacylglycerol fraction. "Crude oil" is oil extracted from microbial biomass which has not undergone further treatment. "Refined oil" is oil obtained by treating crude oil by standard purification, decoloration, and/or deodorizing processes. The microbial oil further contains "final oil", which is refined oil diluted with vegetable oil. The "microorganisms" are not limited, but include classifications taxonomically associated with any "microalgae", "labyrinthulids", and the deposited microorganisms described in the present specification. The terms "labyrinthulid", "genus *Parietichytrium*", "genus *Schizochytrium*", and "genus *Thraustochytrium*" when used in association with any microbial oils of a deposited microorganism described herein are based on current taxonomic classification including phylogenetically usable information, and are not intended to be limiting if the taxonomic classification is revised after the filing date of the present application. Lipids In the present invention, lipids are lipids produced by labyrinthulids, and are mainly triglycerides, diglycerides, monoglycerides, phospholipids, free fatty acids, sterols, carotenoids, hydrocarbons, and the like.

[Lipids]

In the present invention, lipids are lipids produced by labyrinthulids, and are mainly triglycerides, diglycerides, monoglycerides, phospholipids, free fatty acids, sterols, carotenoids, hydrocarbons, and the like.

[Polyunsaturated Fatty Acids]

In the present invention, a polyunsaturated fatty acid (PUFA) is a fatty acid having not less than 18 carbon atoms and not less than three double bonds, and more preferably a fatty acid having not less than 20 carbon atoms and not less than three double bonds. Specific examples include linoleic acid (LA, 18:2n-6), α-linolenic acid (ALA, 18:3n-3), γ-linolenic acid (GLA, 18:3n-6), stearidonic acid (STA, 18:4n-3), dihomo-γ-linolenic acid (DGLA, 20:3n-6), eicosatetraenoic acid (ETA, 20:4n-3), arachidonic acid (ARA, 20:4n-6), eicosapentaenoic acid (EPA, 20:5n-3), docosatetraenoic acid (DTA, 22:4n-6), n-3 docosapentaenoic acid (n-3 DPA, 22:5n-3), n-6 docosapentaenoic acid (n-6 DPA, 22:5n-6), and docosahexaenoic acid (DHA, 22:6n-3). In the present specification, arachidonic acid is also expressed as ARA. The total fatty acid composition means the composition of fatty acids detected after a microorganism is cultured and freeze dried and the fatty acids are then methyl-esterified and analyzed by GC. Specifically, the total fatty acid composition is the composition of fatty acids having from 14 to 22 carbon chains. In the present invention, GC area means the peak area of the GC chart. A proportion relative to the total fatty acid composition means the proportion of the peak area of the targeting fatty acid relative to the total of peak areas of the entire fatty acid composition, and is expressed as a percentage. In the present invention, C20 PUFA/C22 PUFA means the value obtained by dividing the total of GC peak areas of polyunsaturated fatty acids having 20 carbon chains by the total of GC peak areas of polyunsaturated fatty acids having 22 carbon chains. In the present invention, n-6 PUFA/n-3 PUFA means the value obtained by dividing the total of peak areas of the GC chart of ω6 fatty acids having not less than 20 carbon chains by the total of peak areas of the GC chart of ω3 fatty acids having not less than 20 carbon chains.

[PUFA Biosynthesis Pathways]

Two different pathways associated with PUFA biosynthesis are known. One is a pathway that produces polyunsaturated fatty acids (PUFAs) using polyketide synthase (PKS). In the present invention, this metabolic pathway will be called the PUFA-PKS pathway or the PKS pathway. In the present invention, a PKS gene means a gene that encodes a protein that constitutes polyketide synthase. Polyketide synthase is an enzyme that catalyzes a reaction in which a long-chain substrate such as malonyl-CoA is condensed multiple times in a starter substrate such as acetyl-CoA. Polyketide synthase has generally been known as an enzyme involved in biosynthesis of secondary metabolites of plants, fungi, and the like, but it has also been reported to be involved in PUFA biosynthesis in certain organisms. For example, the marine bacillus Shewanella produces eicosapentaenoic acid (EPA) using this enzyme (Non-patent Document 8). Polyketide synthase is known to be similarly involved in PUFA biosynthesis in certain labyrinthulids as well.

The other is a pathway in which, starting from a fatty acid such as palmitic acid, desaturation by desaturase and chain elongation by elongase are repeated to produce PUFAs such as EPA and DHA. In the present invention, this is called the elongase-desaturase pathway. Examples of the enzymes that constitute this system include fatty acid synthesis associated enzymes such as C20 elongase and Δ4 desaturase.

[PUFA Biosynthesis Pathway Differentiation Method]

A method for differentiating between PUFA biosynthesis pathways of labyrinthulids will be described below. However, this is only one example, and needless to say, differentiation does not have to be performed by this method.

As stated above, two PUFA biosynthesis pathways in labyrinthulids are known. One is the PUFA-PKS pathway, by which DHA and n-6 DPA are produced. In this pathway, no PUFAs other than DHA and n-6 DPA are substantially produced such configuration differs greatly from the elongase-desaturase pathway, which is the other PUFA biosynthesis pathway.

The other pathway, namely the elongase-desaturase pathway, is illustrated in FIG. 1. Among the enzymes constituting this pathway, Δ4 desaturase is an enzyme involved in converting n-3 DPA to DHA. This enzyme is also involved in converting DTA to n-6 DPA. Thus, since these conversions do not take place when the gene of this enzyme is disrupted, n-3 DPA and DTA, which are substrates of this enzyme, accumulate, and conversely, DHA and n-6 DPA, which are products of this enzyme, decrease. In a labyrinthulid in which this Δ4 desaturase gene has been disrupted, in a case where the products DHA and/or n-6 DPA are completely undetected or markedly decreased, it is judged that the labyrinthulid has very weak or no PUFA (particularly DHA and/or n-6 DPA) production activity via the endogenous PUFA-PKS pathway.

It is also possible to select C20 elongase rather than Δ4 desaturase and disruption the gene of that enzyme instead. Specifically, C20 elongase is an enzyme involved in converting EPA to n-3 DPA. This enzyme is also involved in converting ARA to DTA. Thus, since these conversions do not take place when the gene of this enzyme is disrupted, EPA and ARA, which are substrates of this enzyme, accumulate, and conversely, n-3 DPA and DTA, which are products of this enzyme, decrease. As a result, DHA and n-6 DPA, which have n-3 DPA and DTA as substrates, also decrease. In a labyrinthulid in which this C20 elongase gene has been disrupted, when the products DHA and/or n-6 DPA are completely undetected or markedly decreased, it is judged that the labyrinthulid has very weak or no PUFA (particularly DHA and/or n-6 DPA) production activity via the endogenous PUFA-PKS pathway.

Gene disruption is performed by transforming something designed such that gene products do not produce activity using an antibiotic resistance gene or the like in all or a portion of the target gene, into a target cell by a method such as a gene gun, electroporation, or gene editing. Gene silencing is performed by transforming an antisense gene designed such that expression of the target gene is inhibited or a gene in which RNAi is expressed, into a cell by a method such as a gene gun, electroporation, or gene editing. Gene disruption and silencing are not limited to these methods provided that expression of the target gene is hindered. When disruption or silencing is performed with a PKS gene as the target, the target is not limited provided that enzyme activity can be eliminated or inhibited, but OrfA is preferably used as the target.

The present invention provides labyrinthulids having very weak or no PUFA producing activity via the endogenous PUFA-PKS pathway and having PUFA– producing activity via the endogenous elongase-desaturase pathway.

Furthermore, the present invention also includes changing the fatty acid composition produced by a labyrinthulid by manipulating the genes of enzymes constituting the elongase-desaturase pathway of the labyrinthulid. In particular, the fatty acid composition produced by a labyrinthulid can be modified by: (1) disruption and/or silencing of a fatty acid elongase gene, (2) disruption and/or silencing of a fatty acid desaturase gene, (3) transfer of a fatty acid elongase gene, (4) transfer of a fatty acid desaturase gene, and (5) a combination of the above. For example, when stearidonic acid (STA) is desired, a fatty acid elongase gene involved in conversion of stearidonic acid to eicosatetraenoic acid (ETA), specifically the C18 elongase gene, may be disrupted and/or silenced. Furthermore, for example, when eicosapentaenoic acid (EPA) is desired, a fatty acid elongase gene involved in conversion of eicosatetraenoic acid to docosapentaenoic acid (DPA), specifically the C20 elongase gene, may be disrupted and/or silenced. As another example, when eicosapentaenoic acid is desired, a fatty acid desaturase gene that converts arachidonic acid (ARA) to eicosapentaenoic acid, specifically the ω3 desaturase gene, may be transformed. For a labyrinthulid that produces via the elongase-desaturase pathway and PUFA-PKS pathway, the fatty acid composition produced by the labyrinthulid can be modified by: (1) disruption and/or silencing of a fatty acid elongase gene, (2) disruption and/or silencing of a fatty acid desaturase gene, (3) transfer of a fatty acid elongase gene, (4) transfer of a fatty acid desaturase gene, and (5) a combination of the above, using a microorganism in which the PUFA-PKS pathway has been disrupted or silenced. For example, when stearidonic acid (STA) is desired, a fatty acid elongase gene involved in conversion of stearidonic acid to eicosatetraenoic acid (ETA), specifically the C18 elongase gene, may be disrupted and/or silenced. Furthermore, for example, when eicosapentaenoic acid (EPA) is desired, a fatty acid elongase gene involved in conversion of eicosatetraenoic acid to docosapentaenoic acid (DPA), specifically the C20 elongase gene, may be disrupted and/or silenced. As another example, when eicosapentaenoic acid is desired, a fatty acid desaturase gene that converts arachidonic acid (ARA) to eicosapentaenoic acid, specifically the ω3 desaturase gene, may be transformed.

A labyrinthulid (microorganism) in which the produced fatty acid composition has been modified is obtained by transformation of the labyrinthulid. A labyrinthulid in which a fatty acid biosynthesis associated gene has been transformed and/or disrupted can be used in, for example, production of unsaturated fatty acids. In production of unsaturated fatty acids, the conditions of other steps, production equipment and instruments and the like are not particularly limited provided that the labyrinthulid that is used has very weak or no PUFA production activity via the endogenous PUFA-PKS pathway and has PUFA production activity via the endogenous elongase-desaturase pathway, or is a labyrinthulid in which the produced fatty acid composition has been modified as described above. Production of unsaturated fatty acids includes a step of culturing a labyrinthulid that has very weak or no PUFA production activity via the endogenous PUFA-PKS pathway and has PUFA production activity via the endogenous elongase-desaturase pathway, or a labyrinthulid in which the produced fatty acid composition has been modified as described above. Unsaturated fatty acids are produced using these microorganisms and their culture medium.

The above cell culturing conditions (culture medium, culture temperature, ventilation status, and the like) may be set as appropriate according to the type of cell, the targeted type and quantity of unsaturated fatty acids, and the like. Furthermore, an unsaturated fatty acid in the present invention means a substance containing an unsaturated fatty acid, without limitation on its content, purity, shape, composition, and the like. In other words, in the present invention, cells in which the fatty acid composition has been modified or their culture media are themselves considered to be unsaturated fatty acids. Additionally, a step of purifying the unsaturated fatty acids from these cells or culture media may be further included. As the method of purifying the unsaturated fatty acids, a method known as a purification method for lipids (including complex lipids) such as unsaturated fatty acids may be applied.

[Method for Highly Accumulating Unsaturated Fatty Acids in Labyrinthulids]

Accumulation of unsaturated fatty acids in a labyrinthulid is achieved by culturing a labyrinthulid having very weak or no PUFA production activity via the endogenous PUFA-PKS pathway and having PUFA production activity via the endogenous elongase-desaturase pathway, or a transformant thereof. The labyrinthulid may be cultured in, for example, a solid culture medium, liquid culture medium, or the like. The culture medium used at this time is not particularly limited provided that it is a medium commonly used for culturing labyrinthulids and appropriately combines, for example, glucose, fructose, saccharose, starch, glycerin, or the like as a carbon source, yeast extract, corn steep liquor, polypeptone, sodium glutamate, urea, ammonium acetate, ammonium sulfate, ammonium nitrate, ammonium chloride, sodium nitrate, or the like as a nitrogen source, potassium phosphate or the like as an inorganic salt, and other necessary components. However, yeast extract-glucose medium (GY medium) is particularly preferably used. After preparation of the culture medium, the pH is adjusted to within the range of 3.0 to 8.0, and then the culture medium is sterilized by autoclave or the like. Culturing may be performed by aerated and agitated culturing, shake culturing, or static culturing at 10 to 40° C., preferably 15 to 35° C., for 1 to 14 days.

To collect the produced unsaturated fatty acids, the labyrinthulids are grown in a culture medium and the microorganism cells obtained from that culture medium are treated, the lipids (polyunsaturated fatty acids or oil- and fat-containing matter containing polyunsaturated fatty acids) inside the cells are released and collected. Specifically, lipids containing PUFAs can be obtained by collecting the labyrinthulids cultured in this manner by centrifugation or the like, performing treatment such as drying and cell crushing as necessary, and performing extraction using an appropriate organic solvent or supercritical carbon dioxide, liquefied dimethylether, or the like according to conventional methods.

The microbial oil obtained in the present invention is that which satisfies any of the following conditions. The microbial oil obtained in the present invention contains ARA in a proportion of not less than 5%, not less than 7%, not less than 10%, or not less than 15% of the total fatty acid composition. Oils and fats with high ARA obtained in this manner may be used in applications such as nutritional supplements for infants and health foods and medications for adults. ARA may be not greater than 80%, not greater than 70%, not greater than 60%, or not greater than 50% of the total fatty acid composition. The microbial oil obtained in the present invention contains DGLA in a proportion of not less than 2.5%, not less than 5%, or not less than 10% of the total fatty acid composition. Microbial oil with high DGLA obtained in this manner may be used in medicinal applications such as anti-inflammatory agents. DGLA may be not greater than 80%, not greater than 70%, not greater than 60%, or not greater than 50% of the total fatty acid composition. The microbial oil obtained in the present invention contains ETA in a proportion of not less than 0.35%, not less than 0.5%, not less than 0.75%, or not less than 1% of the total fatty acid composition. Microbial oil with high ETA obtained in this manner may be used in medicinal applications such as arthritis treatment. ETA may be not greater than 50%, not greater than 40%, not greater than 30%, or not greater than 20% of the total fatty acid composition. The microbial oil obtained in the present invention contains EPA in a proportion of not less than 4%, not less than 6%, not less than 8%, not less than 10%, or not less than 12% of the total fatty acid composition. Microbial oil with high EPA obtained in this manner may be used in nutritional supplement applications and medicinal applications. EPA may be not greater than 80%, not greater than 70%, not greater than 60%, or not greater than 50% of the total fatty acid composition. The microbial oil obtained in the present invention contains n-6 DPA in a proportion of not greater than 0.20%, not greater than 0.15%, not greater than 0.1%, or not greater than 0.05% of the total fatty acid composition. The microbial oil with low n-6 DPA obtained in this manner does not tend to hinder the functions of other fatty acids. Furthermore, it is advantageous in cases where removal of n-6 DPA by refinement is desired. n-6 DPA may be not less than 0.001%, not less than 0.005%, or not less than 0.01% of the total fatty acid composition. The microbial oil obtained in the present invention contains DHA in a proportion of not greater than 0.50%, not greater than 0.3%, not greater than 0.2%, or not greater than 0.1% of the total fatty acid composition. The microbial oil with low DHA obtained in this manner does not tend to hinder the functions of other fatty acids. Furthermore, it is advantageous in cases where removal of DHA by refinement is desired. DHA may be not less than 0.005%, not less than 0.01%, or not less than 0.05% of the total fatty acid composition. The microbial oil obtained in the present invention contains a total of DHA and n-6 DPA in a proportion of not greater than 0.7%, not greater than 0.8%, not greater than 0.9%, or not greater than 1.0% of the total fatty acid composition. The microbial oil with low DHA and n-6 DPA obtained in this manner does not tend to hinder the functions of other fatty acids and is stable against oxidation. Furthermore, it is advantageous in cases where removal of DHA and n-6 DPA by refinement is desired. The total of DHA and n-6 DPA may be not less than 0.05%, not less than 0.1%, or not less than 0.5% of the total fatty acid composition. The desired concentrations of each of these fatty acids may be combined as desired, limited to a total of 100%.

In another aspect, the microbial oil obtained in the present invention is that which satisfies any of the following conditions. In the microbial oil obtained in the present invention, the value of LA/DHA by GC area is not less than 0.6, not less than 0.7, not less than 0.8, or not less than 0.9, and not greater than 10, not greater than 9, not greater than 8, not greater than 7, or not greater than 6. The microbial oil with a high LA/DHA value obtained in this manner is stable against oxidation, and the functions of LA do not tend to be hindered by DHA. In the microbial oil obtained in the present invention, the value of GLA/DHA by GC area is not less than 0.35, not less than 0.4, not less than 0.5, not less than 0.6, or not less than 0.7, and not greater than 10, not greater than 9, not greater than 8, or not greater than 7. The microbial oil with a high GLA/DHA value obtained in this manner is stable against oxidation, and the functions of GLA do not tend to be hindered by DHA.

In the microbial oil obtained in the present invention, the value of DGLA/DHA by GC area is not less than 0.35, not less than 0.4, not less than 0.5, not less than 0.6, or not less than 0.7, and not greater than 10, not greater than 9, not greater than 8, not greater than 7, or not greater than 6. Microbial oil with a high DGLA/DHA value obtained in this manner may be used in medications having an anti-inflammatory action. In the microbial oil obtained in the present invention, the value of ARA/DHA by GC area is not less than 0.7, not less than 0.8, not less than 0.9, or not less than 1.0, and not greater than 50, not greater than 45, not greater than 40, not greater than 35, or not greater than 30. Microbial oil with a high ARA/DHA value obtained in this manner may be used in modified milk for infants. The value of EPA/DHA by GC area is not less than 0.35, not less than 0.4, not less than 0.5, not less than 0.6, or not less than 0.7, and not greater than 50, not greater than 45, not greater than 40, not greater than 35, or not greater than 30. EPA used in typical medications and the like are mainly esters containing DHA, but the microbial oil with a high EPA/DHA value obtained in this manner contains EPA with a high degree of purity, and can be used in health foods, medications, and the like.

The desired ratios of each of these fatty acids may be combined as desired. In the microbial oil obtained in the present invention, the value of LA/EPA by GC area is not less than 0.06, not less than 0.07, not less than 0.08, or not less than 0.09, and not greater than 0.12, not greater than 0.1, not greater than 0.08, or not greater than 0.06. Microbial oil with a low LA/EPA value obtained in this manner may be used in infusion fluids with a low anti-inflammatory action and the like. In the microbial oil obtained in the present invention, the value of GLA/EPA by GC area is not less than 0.04 or not less than 0.45, and not greater than 0.12, not greater than 0.1, or not greater than 0.8. Microbial oil with a low GLA/EPA value obtained in this manner may be used in infusion fluids with a low anti-inflammatory action and the like. In the microbial oil obtained in the present invention, the value of DTA/EPA by GC area is not less than 0.01, not less than 0.02, not less than 0.03, not less than 0.04, or not less than 0.05, and not greater than 0.4, not greater than 0.35, or not greater than 0.3. The microbial oil with a low DTA/EPA value obtained in this manner is useful for separating high-purity EPA since DTA and EPA are close to each other in GC. The desired ratios of each of these fatty acids may be combined as desired.

In the microbial oil obtained in the present invention, the value of DTA/ARA by GC area is not less than 0.01, not less than 0.03, not less than 0.05, not less than 0.07, or not less than 0.1, and not greater than 0.45, not greater than 0.4, not greater than 0.35, or not greater than 0.3. Microbial oil with a low DTA/ARA value obtained in this manner may be used in formulated milk for infants. In the microbial oil obtained in the present invention, the value of DTA/DGLA by GC area is not less than 0.01, not less than 0.05, not less than 0.1, not less than 0.15, or not less than 0.2, and not greater than 1.45, not greater than 1.4, not greater than 1.3, not greater than 1.2, or not greater than 1.1. Microbial oil with a low DTA/DGLA value obtained in this manner may be used in medications having an anti-inflammatory action and the like. In the microbial oil obtained in the present invention, the value of LA/n-6 DPA by GC area is not less than 0.4, not less than 0.5, not less than 0.6, not less than 0.7, or not less than 0.8, and not greater than 20, not greater than 18, not greater than 16, not greater than 14, or not greater than 12. Microbial oil with a high LA/n-6 DPA value obtained in this manner may be used in edible oils. In the microbial oil obtained in the present invention, the value of GLA/n-6 DPA by GC area is not less than 0.2, not less than 0.4, not less than 0.6, or not less than 0.8, and not greater than 10, not greater than 8, not greater than 6, or not greater than 4. Microbial oil with a high GLA/n-6 DPA value obtained in this manner may be used in health foods and supplements. In the microbial oil obtained in the present invention, the value of DGLA/n-6 DPA by GC area is not less than 0.35, not less than 0.5, not less than 0.75, or not less than 1.0, and not greater than 30, not greater than 27, not greater than 25, not greater than 22, or not greater than 20. Microbial oil with a high DGLA/n-6 DPA value obtained in this manner may be used in medications having an anti-inflammatory action. In the microbial oil obtained in the present invention, the value of ARA/n-6 DPA by GC area is not less than 0.7, not less than 1.0, not less than 2.0, or not less than 3.0, and not greater than 60, not greater than 50, not greater than 40, or not greater than 30. Microbial oil with a high LA/n-6 DPA value obtained in this manner may be used in formulated milk for infants. In the microbial oil obtained in the present invention, the value of EPA/n-6 DPA by GC area is not less than 0.4, not less than 0.6, not less than 0.8, not less than 1, not less than 2, or not less than 5, and not greater than 70, not greater than 60, not greater than 50, not greater than 40, or not greater than 30. Microbial oil with a high EPA/n-6 DPA value obtained in this manner may be used in health foods, supplements, and the like. The desired ratios of each of these fatty acids may be combined as desired.

In the microbial oil obtained in the present invention, the value of DGLA/LA by GC area is not less than 1.4, not less than 2, or not less than 3, and not greater than 10, not greater than 9, not greater than 8, or not greater than 7. The microbial oil obtained in this manner may be used in foods and supplements having an anti-inflammatory action. In the microbial oil obtained in the present invention, the value of ARA/LA by GC area is not less than 5.1, not less than 7, not less than 9, or not less than 11, and not greater than 20, not greater than 17, not greater than 15, or not greater than 12. Microbial oil with a high ARA/LA value obtained in this manner may be used in animal feed and formulated milk for infants. In the microbial oil obtained in the present invention, the value of EPA/LA by GC area is not less than 5.5, not less than 7, not less than 9, not less than 11, or not less than 13, and not greater than 30, not greater than 25, not greater than 22, or not greater than 20. Microbial oil with a high EPA/LA value obtained in this manner may be used in medications and health foods. In the microbial oil obtained in the present invention, the value of DTA/LA by GC area is not less than 0.01, not less than 0.05, not less than 0.07, or not less than 0.1, and not greater than 0.4, not greater than 0.35, not greater than 0.33, not greater than 0.3, or not greater than 0.28. Microbial oil with a low DTA/LA value obtained in this manner may be used in animal feed and foods. The desired ratios of each of these fatty acids may be combined as desired.

In the microbial oil obtained in the present invention, the value of DGLA/GLA by GC area is not less than 4.5, not less than 5, not less than 6, or not less than 7, and not greater than 20, not greater than 17, not greater than 15, or not greater than 12. Microbial oil with a high DGLA/GLA value obtained in this manner may be used in medications having an anti-inflammatory action and the like. In the microbial oil obtained in the present invention, the value of ARA/GLA by GC area is not less than 9, not less than 10, not less than 12, not less than 13, or not less than 14, and not greater than 30, not greater than 28, not greater than 26, not greater than 24, or not greater than 22. Microbial oil with a high ARA/GLA value obtained in this manner may be used in formulated milk for infants. The desired ratios of each of these fatty acids may be combined as desired.

In the microbial oil obtained in the present invention, the value of n-6 DPA/DTA by GC area is not less than 0.001, not less than 0.01, or not less than 0.02, and not greater than 1.5, not greater than 1.4, not greater than 1.3, not greater than 1.2, or not greater than 1.1. The microbial oil obtained in this manner may be used in foods that prevent arteriosclerosis and the like. In the microbial oil obtained in the present invention, the value of DHA/n-3 DPA by GC area is not less than 0.001, not less than 0.01, or not less than 0.02, and not greater than 4, not greater than 4.5, not greater than 4, or not greater than 3.5. The microbial oil obtained in this manner may be used in animal feed or health foods. In the microbial oil obtained in the present invention, the value of C20 PUFA/C22 PUFA by GC area is not less than 0.5, not less than 0.7, not less than 1, or not less than 1.2, and not greater than 50, not greater than 45, not greater than 40, or not greater than 35. Microbial oil with a high C20 PUFA/C22 PUFA value obtained in this manner may be used in health foods and supplements. In the microbial oil obtained in the present invention, the value of n-6 PUFA/n-3 PUFA by GC area is not less than 1.8, not less than 2, not less than 2.5, or not less than 3, and not greater than 100, not greater than 80, not greater than 70, not greater than 60, or not greater than 50. Microbial oil with a high n-6 PUFA/n-3 PUFA value obtained in this manner may be used in edible oils and animal feed. The desired ratios of each of these fatty acids may be combined as desired.

The desired ratios of each of these fatty acids may be combined as desired. The desired concentrations of each of these fatty acids may be combined as desired, limited to a total of 100%.

The unsaturated fatty acids of the present invention also include various medications, foods, animal feeds, and industrial products, and the fields of use thereof are not particularly limited. The foods containing the unsaturated fatty acid-containing oils and fats of the present invention also include health foods such as supplements and food additives and the like. Examples of the industrial products include animal feed for organisms other than humans, films, biodegradable plastics, functional fibers, lubricating oils, and detergents.

Next, the present invention will be specifically described based on examples. Furthermore, in the present specification, the features of each invention described in embodiments related to each aspect of the invention may be combined as desired to form new embodiments, and it is to be understood that such new embodiments may be included in each of the aspects of the present invention.

Example 1

[Labyrinthulids and Culturing Method/Storage Method Thereof]
(1) Strains Used in the Present Invention
*Parietichytrium* sp. SEK358 (FERM BP-11405), *Parietichytrium sarkarianum* SEK364 (FERM BP-11298), and *Parietichytrium* sp. SEK571 (FERM BP-11406) were shared from the Department of Engineering at Konan University. *Thraustochytrium aureum* ATCC 34304 was shared from ATCC.
(2) Culture Medium Composition
i. Agar Plate Culture Medium Composition
PDA Agar Plate Culture Medium
0.78% (w/v) of potato dextrose agar medium (available from Nissui Pharmaceutical Co., Ltd.), 1.75% (w/v) of Sealife (available from Marintec Co., Ltd.), and 1.21% (w/v) of agar powder (available from Nacalai Tesque, Inc.) were mixed and then sterilized by autoclave for 20 min at 121° C. After sufficient cooling, ampicillin sodium salt (available from Nacalai Tesque, Inc.) was added so as to result in a final concentration of 100 μg/mL. This was dispensed into a Petri dish and left to stand at a level location to solidify.

ii. Liquid Culture Medium Composition

GY Liquid Culture Medium 3.18% (w/v) of glucose (available from Nacalai Tesque, Inc.), 1.06% (w/v) of dry yeast extract (available from Nacalai Tesque, Inc.), and 1.75% (w/v) of Sealife (available from Marintec Co., Ltd.) were mixed and then sterilized by autoclave for 20 min at 121° C. Ampicillin sodium salt (available from Nacalai Tesque, Inc.) was then added so as to result in a final concentration of 100 μg/mL.

PD Liquid Culture Medium 0.48% (w/v) of potato dextrose (available from Difco Laboratories Inc.) and 1.75% (w/v) of Sealife (available from Marintec Co., Ltd.) were mixed and then sterilized by autoclave for 20 min at 121° C. Ampicillin sodium salt (available from Nacalai Tesque, Inc.) was then added so as to result in a final concentration of 100 μg/mL.

(3) Culturing Method i. Agar Plate Culturing

Labyrinthulea cells were inoculated using a platinum loop or a spreader and then static cultured at 25° C., thereby causing emergence of colonies. Subculturing was performed by extracting colonies using a platinum loop and suspending them in sterilized physiological saline solution, and then spreading this suspension using a platinum loop or a spreader. Furthermore, as necessary, it was transformed to a liquid culture by inoculating cells in a liquid culture medium on a flat plate.

ii. Liquid Culturing

Labyrinthulea cells were inoculated, and suspension culturing was performed with stirring at 150 rpm at 25° C. using an Erlenmeyer flask or a test tube. Subculturing was performed by adding a culture solution in which growth was confirmed from the logarithmic growth phase to the stationary phase, in a volume ratio of 1/200 to 1/10 to a fresh GY or PD liquid culture medium.

Furthermore, as necessary, it was transformed to an agar plate culture by spreading the cell culture solution on a PDA agar plate culture medium.

(4) Preservation/Storage Method of Labyrinthulids

In addition to subculturing, cryopreservation was performed by producing glycerol stock. Specifically, glycerol (available from Nacalai Tesque, Inc.) was added to a cell suspension that used a GY liquid culture medium from the logarithmic growth phase to the stationary phase, so as to result in a final concentration of 15% (v/v), and this was stored in a deep freezer at −80° C.

Example 2

[Measurement of Fatty Acid Composition of Lipids Produced by C20 Elongase Gene Disruption and Transformation Strain of *Parietichytrium sarkarianum* SEK364]

[Example 2-1]: Subcloning of SV40 Terminator Sequence

An SV40 terminator sequence was amplified with PrimeSTAR HS DNA Polymerase (available from Takara Bio Inc.) using a pcDNA 3.1 myc-His vector (available from Invitrogen Corp.) as a template. The PCR primers used were as shown below. RHO58 was set on the SV40 terminator sequence, and includes BglII and BamHI linker sequences. RHO52 was set on the SV40 terminator sequence, and includes a BglII sequence. [RHO58: 34 mer: 5'-CAG ATC TGG ATC CGC GAA ATG ACC GAC CAA GCG A-3' (SEQ ID NO: 1), RHO52: 24 mer: 5'-ACG CAA TTA ATG TGA GAT CTA GCT-3' (SEQ ID NO: 2)]. After amplification under the following conditions, it was cloned in pGEM-T Easy Vector (available from Promega Corporation). [PCR cycles: 98° C. 2 min/98° C. 30 sec, 60° C. 30 sec, 72° C. 1 min, 30 cycles/72° C. 1 min]. After amplification with *E. coli*, the sequence was confirmed using a Dye Terminator Cycle Sequencing Kit (available from Beckman Coulter Inc.). This was named pRH27.

Figure 2:
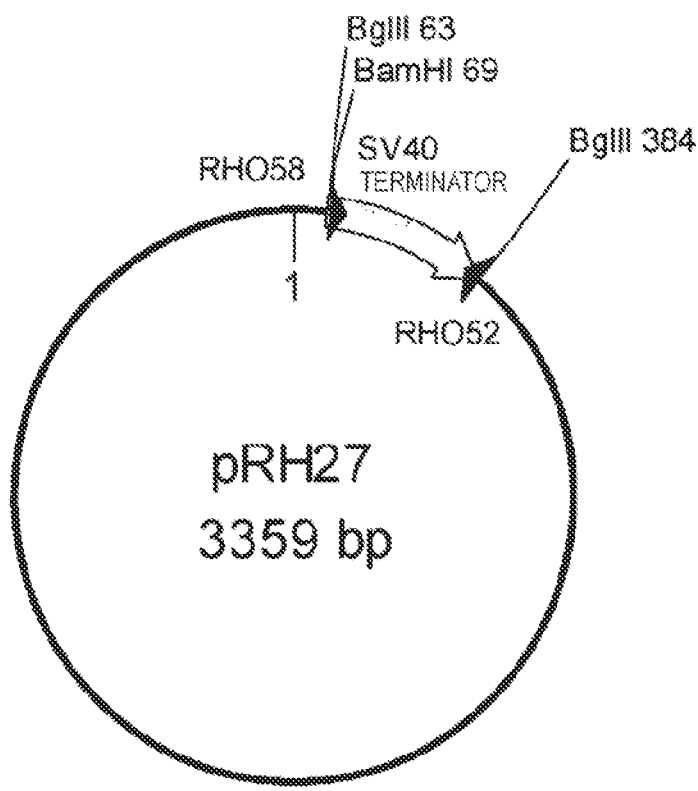
FIG. 2 illustrates a plasmid containing an SV40 terminator sequence derived from a subcloned pcDNA 3.1 Myc-His vector.

The plasmid (pRH27) containing the subcloned SV40 terminator sequence (342 bp, SEQ ID NO: 3) is illustrated in FIG. 2.

[Example 2-2]: Production of Artificially Synthesized Neomycin Resistance Gene Cassette

*Thraustochytrium aureum* ATCC 34304 strain was cultured in a GY culture medium, and cells of the latter logarithmic growth phase were centrifuged for 5 min at 4° C. at 3500×g to form pellets, and the pellets were frozen with liquid nitrogen and then crushed. After phenol extraction of the crushed cell liquid, ethanol precipitation was performed and the precipitate was dissolved in a TE solution. The nucleic acids dissolved in the TE solution were treated with RNase for 30 min at 37° C., and after further phenol extraction, ethanol precipitation was performed and the precipitate was dissolved in a TE solution. A260/280 was measured and the DNA concentration was calculated.

Using this as a template, an ubiquitin promoter sequence (619 bp, SEQ ID NO: 4) was amplified with PrimeSTAR HS DNA Polymerase with GC Buffer (available from Takara Bio Inc.). The PCR primers used were as shown below. RHO53 was set on the ubiquitin promoter sequence, and includes a BglII linker sequence. TKO1 includes the ubiquitin promoter sequence and an artificially synthesized neomycin resistance gene sequence. [RHO53: 36 mer: 5'-CCC AGA TCT GCC GCA GCG CCT GGT GCA CCC GCC GGG-3' (SEQ ID NO: 5), TKO1: 58 mer: 5'-CGT GAA GGC CGT CCT GTT CAA TCA TGT TGG CTA GTG TTG CTT AGG TCG CTT GCT GCT G-3' (SEQ ID NO: 6)]. [PCR cycles: 98° C. 2 min/98° C. 10 sec, 68° 1 min, 30 cycles/68° C. 1 min].

Using the artificially synthesized neomycin resistance gene sequence as a template, an artificially synthesized neomycin resistance gene sequence (826 bp, SEQ ID NO: 7) was amplified with PrimeSTAR HS DNA Polymerase with GC Buffer (available from Takara Bio Inc.). The PCR primers used were as shown below. TKO2 includes the ubiquitin promoter sequence and the artificially synthesized neomycin resistance gene sequence. RHO57 includes the artificially synthesized neomycin resistance gene sequence and has a BglII linker sequence. [TKO2: 54 mer: 5'-AGC GAC CTA AGC AAC ACT AGC CAA CAT GAT TGA ACA GGA CGG CCT TCA CGC TGG-3' (SEQ ID NO: 8), RHO57: 26 mer: 5'-CAG ATC TCA AAA GAA CTC GTC CAG GA-3' (SEQ ID NO: 9)] [PCR cycles: 98° C. 2 min/98° C. 10 sec, 68° 1 min, 30 cycles/68° C. 1 min].

Figure 3:
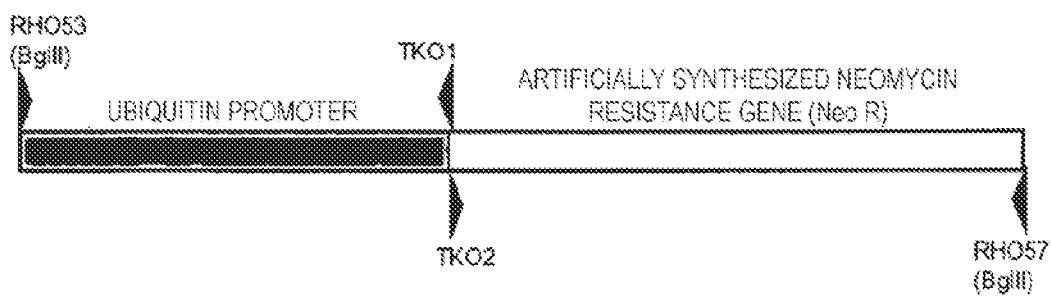
FIG. 3 is a schematic diagram of the primers used in fusion PCR and the products. The final product is a fused sequence of a ubiquitin promoter derived from *Thraustochytrium aureum* ATCC 34304 and an artificially synthesized neomycin resistance gene.

Using SEQ ID NO: 4 and SEQ ID NO: 7 as templates, fusion PCR was performed using RHO53 (SEQ ID NO: 5) and RHO57 (SEQ ID NO: 9) according to the method described in Non-patent Document 9. Amplification was performed using LA Taq Hot Start Version (available from Takara Bio Inc.) as the enzyme with PCR cycles under conditions below: 94° C. 2 min/94° C. 20 sec, 55° C. 30 sec, 68° C. 1 min, 30 cycles/68° C. 1 min (1° C./10 sec from 55° C. to 68° C.), and then the amplified product was digested with BglII. (FIG. 3).

The *Thraustochytrium aureum* ATCC 34304-derived ubiquitin promoter—artificially synthesized neomycin resistance gene sequence (1395 bp, SEQ ID NO: 10) fused as described above was digested with BglII, and the resultant was bound to the BamHI site of pRH27 described in Example 2-1. After amplification of the produced plasmid with *E. coli*, the sequence was confirmed using a Dye Terminator Cycle Sequencing Kit (available from Beckman Coulter Inc.). This was named pRH31.

Figure 4:
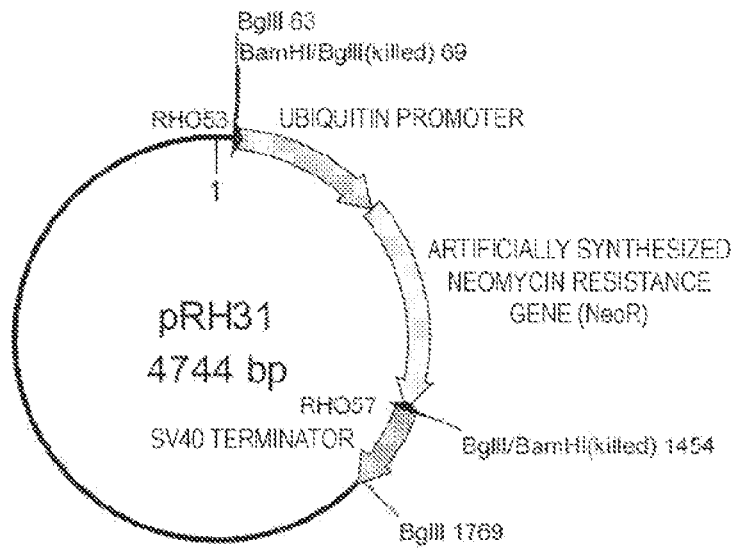
FIG. 4 illustrates the BglII cassette of the produced artificially synthesized neomycin resistance gene.

The produced artificially synthesized neomycin resistance gene cassette (pRH31) is illustrated in FIG. 4.

[Example 2-3]: Production of Hygromycin Resistance Gene Cassette

Using *Thraustochytrium aureum* ATCC 34304 genome DNA as a template, a ubiquitin promoter sequence (617 bp, SEQ ID NO: 11) was amplified with PrimeSTAR HS DNA Polymerase with GC Buffer (available from Takara Bio Inc.). The PCR primers used were as shown below. RHO53 was set on the ubiquitin promoter sequence, and includes a BglII linker sequence. KSO8 includes the ubiquitin promoter sequence and a hygromycin resistance gene sequence. [RHO53: 36 mer: 5'-CCC AGA TCT GCC GCA GCG CCT GGT GCA CCC GCC GGG-3' (described in Example 2-2, SEQ ID NO: 5), KSO8: 58 mer: 5'-TCG CGG TGA GTT CAG GCT TTT TCA TGT TGG CTA GTG TTG CTT AGG TCG CTT GCT GCT G-3' (SEQ ID NO: 12)] [PCR cycles: 98° C. 2 min/98° C. 30 sec, 68° 2 min, 30 cycles/68° C. 2 min]

Using pcDNA 3.1/Hygro (available from Invitrogen Corp.) as a template, a hygromycin resistance gene (1058 bp, SEQ ID NO: 13) was amplified with PrimeSTAR HS DNA Polymerase with GC Buffer (available from Takara Bio Inc.). The PCR primers used were as shown below. KSO7 includes the ubiquitin promoter sequence and the hygromycin resistance gene sequence. RHO56 includes the hygromycin resistance gene sequence and has a BglII linker sequence. [KSO7: 56 mer: 5'-AGC GAC CTA AGC AAC ACT AGC CAA CAT GAA AAA GCC TGA ACT CAC CGC GAC GTC TG-3' (SEQ ID NO: 14), RHO56: 36 mer: 5'-CAG ATC TCT ATT CCT TTG CCC TCG GAC GAG TGC TGG-3' (SEQ ID NO: 15)]. [PCR cycles: 98° C. 2 min/98° C. 30 sec, 68° 2 min, 30 cycles/68° C. 2 min]

Figure 5:
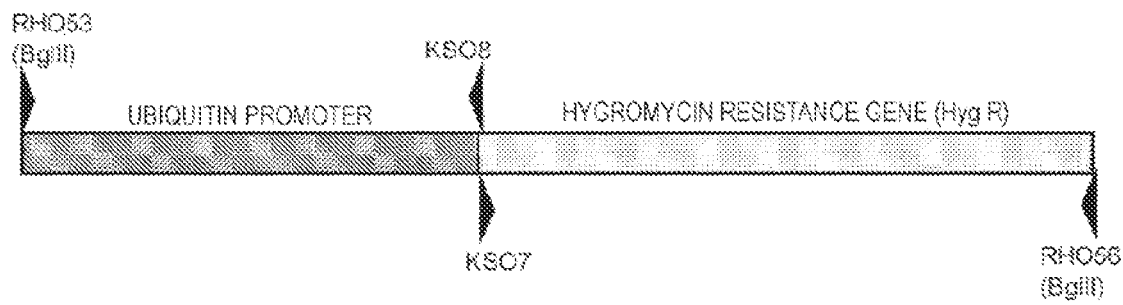
FIG. 5 is a schematic diagram of the primers used in fusion PCR and the products. The final product is a fused sequence of a ubiquitin promoter derived from *Thraustochytrium aureum* ATCC 34304 and a hygromycin resistance gene derived from pcDNA 3.1/Hygro.

Using SEQ ID NO: 11 and SEQ ID NO: 13 as templates, fusion PCR was performed using RHO53 (described in Example 2-2, SEQ ID NO: 5) and RHO56 (SEQ ID NO: 15) according to the method described in Non-patent Document 9. Amplification was performed using LA Taq Hot Start Version (available from Takara Bio Inc.) as the enzyme under the following conditions, and then the amplified product was digested with BglII. [PCR cycles: 94° C. 2 min/94° C. 20 sec, 55° C. 30 sec, 68° C. 1 min, 30 cycles/68° C. 1 min (1° C./10 sec from 55° C. to 68° C.)] (FIG. 5).

The *Thraustochytrium aureum* ATCC 34304-derived ubiquitin promoter—pcDNA 3.1/Hygro (available from Invitrogen Corp.)-derived hygromycin resistance gene (1625 bp, SEQ ID NO: 16) fused as described above was digested with BglII, and the resultant was bound to the BamHI site of pRH27 described in Example 2-1, FIG. 2. After amplification of the produced plasmid with *E. coli*, the sequence was confirmed using a Dye Terminator Cycle Sequencing Kit (available from Beckman Coulter Inc.). This was named pRH32.

Figure 6:
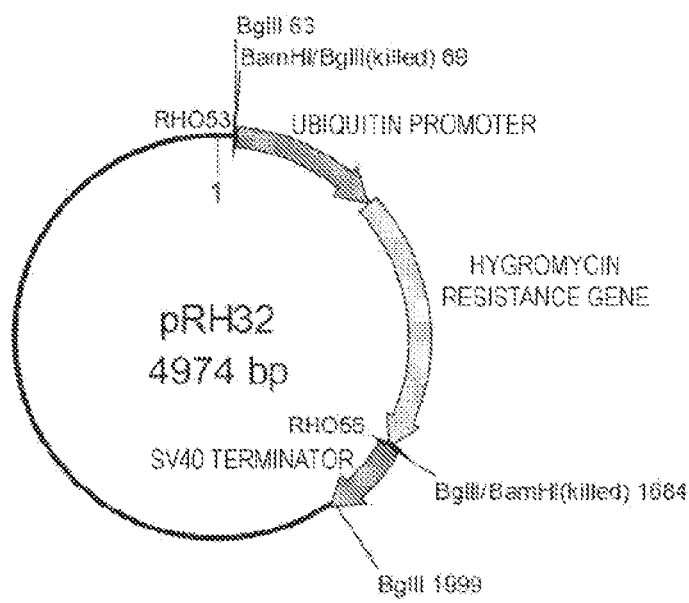
FIG. 6 illustrates the BglII cassette of the produced hygromycin resistance gene derived from pcDNA 3.1/Hygro.

The produced hygromycin resistance gene cassette (pRH32) is illustrated in FIG. 6.

[Example 2-4]: Cloning of Genus *Parietichytrium* C20 Elongase Gene

Genome DNA of *Parietichytrium sarkarianum* SEK364 was extracted by the method described in Example 2-2, and the genome was read.

With the region conserved in the C20 elongase gene as a target, a forward oligonucleotide (PsTaELO2 F1; 5'-CCT TCG GCG CTC CTC TTA TGT ATG T-3') (SEQ ID NO: 17) and a reverse oligonucleotide (PsTaELO2 R2; 5'-CAA TGC AAG AGG CGA ACT GGG AGA G-3') (SEQ ID NO: 18) were synthesized. Next, using the *Parietichytrium sarkarianum* SEK364 genome DNA prepared by the method described in Example 2-2 as a template, PCR was performed using the oligonucleotides PsTaELO2 F1 and PsTaELO2 R2 using LA Taq Hot Start Version (available from Takara Bio Inc.). [PCR cycles: 98° C. 1 min/98° C. 10 sec, 60° C. 30 sec, 72° C. 1 min, 30 cycles/72° C. 7 min/4° C. ∞]. The obtained specific amplification product underwent gel purification, and when the base sequence thereof was analyzed by direct sequencing, it exhibited significant homology to a known C20 elongase gene sequence. This shows that it was a partial sequence of the C20 elongase gene derived from *Parietichytrium sarkarianum* SEK364.

Then, the C20 elongase gene derived from *Parietichytrium sarkarianum* SEK364 was cloned by 3'- and 5'-RACE in the same manner as Comparative Example 1-2 to be described later. First, forward oligonucleotide primers (PsRACE F1; 5'-TGG GGC TCT GGA ACC GCT GCT TAC G-3') (SEQ ID NO: 19) and (PsRACE F2; 5'-CTT CCA GCT CTC CCA GTT CGC CTC T-3') (SEQ ID NO: 20), and reverse oligonucleotide primers (PsRACE R1; 5'-CGG GTT GTT GAT GTT GAG CGA GGT G-3') (SEQ ID NO: 21) and (PsRACE R2; 5'-CCC ACG CCA TCC ACG AGC ACA CCA C-3') (SEQ ID NO: 22) were designed. Next, using a cDNA library produced by SMART RACE cDNA Amplification Kit (trade name; available from Clontech Laboratories, Inc.) as a template, 3'- and 5'-RACE were performed using a synthetic adapter-specific oligonucleotide and the above oligonucleotide PsRACE F1 or PsRACE R1. [PCR cycles: 94° C. 30 sec 5 cycles/94° C. 30 sec, 70° C. 30 sec, 72° C. 3 min, 5 cycles/94° C. 30 sec, 68° C. 30 sec, 72° C. 3 min, 25 cycles/4° C. ∞]. Then, using the two obtained RACE products as templates, nested PCR was performed using a synthetic adapter-specific oligonucleotide and the above oligonucleotide PsRACE F2 or PsRACE R2. [PCR cycles: 94° C. 1 min/94° C. 30 sec, 68° C. 30 sec, 72° C. 3 min, 25 cycles/72° C. 10 min/4° C. ∞]. The obtained specific amplification product underwent gel purification, and when the base sequence thereof was analyzed after TA cloning using pGEM-Easy Vector (available from Promega Corporation), it was confirmed to be the C20 elongase gene derived from *Parietichytrium sarkarianum* SEK364.

Additionally, using the genus *Parietichytrium* genome DNA extracted by the method described in Example 2-2 as a template, a sequence containing a C20 elongase gene sequence (957 bp, SEQ ID NO: 23) was amplified with LA Taq Hot Start Version (available from Takara Bio Inc.). The PCR primers used were as shown below. RHO153 includes a start codon, and has a BamHI site as a linker sequence. RHO154 includes a stop codon, and has a BamHI site as a linker sequence. [RHO153: 32 mer: 5'-CCC GGA TCC ATG GCA GCT CGC GTG GAG AAA CA-3' (SEQ ID NO: 24), RHO154: 33 mer: 5'-CCC GGA TCC TTA CTG AGC CTT CTT GGA GGT CTC-3' (SEQ ID NO: 25)]. [PCR cycles: 98° C. 2 min/98° C. 10 sec, 68° 1 min, 30 cycles/68° C. 2 min].

The obtained DNA fragment was cloned in pGEM-T Easy Vector, and after amplification with *E. coli*, the sequence was confirmed using a Dye Terminator Cycle Sequencing Kit (available from Beckman Coulter Inc.).

Figure 7:
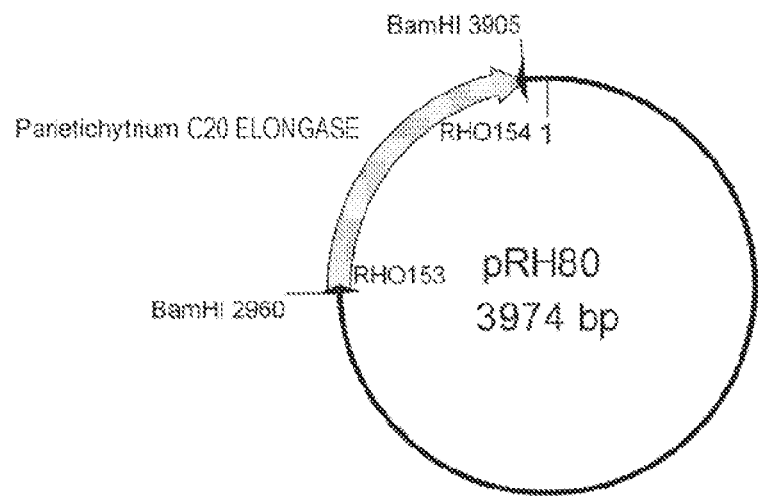
FIG. 7 illustrates a plasmid containing a C20 elongase sequence of cloned genus of *Parietichytrium*.

The genus *Parietichytrium* C20 elongase gene (936 bp, SEQ ID NO: 26) was cloned. This was named pRH80 (FIG. 7). The amino acid sequence is shown SEQ ID NO: 27.

[Example 2-5]: Production of Base Plasmid for Production of Genus *Parietichytrium* C20 Elongase Gene Targeting Vector A primer set that was set up in the reverse direction so as to insert a BglII site into the core portion of the C20 elongase gene sequence was prepared using pRH80 (FIG. 7) produced in Example 2-4 as a template, and the resultant was amplified with PrimeSTAR Max DNA Polymerase (available from Takara Bio Inc.). The PCR primers used were as shown below and have a BglII linker sequence. [RHO155: 26 mer: 5'-ACA AAG ATC TCG ACT GGA CCG ACA CC-3' (SEQ ID NO: 28), RHO156: 27 mer: 5'-AGT CGA GAT CTT TGT CAG GAG GTG GAC-3' (SEQ ID NO: 29)]. [PCR cycles: 98° C. 2 min/98° C. 10 sec, 56° C. 15 sec, 72° C. 1 min, 30 cycles/72° C. 1 min]. After amplification under the above conditions, it was digested with BglII and then self-ligated. After the ligated sample was amplified with *E. coli*, the sequence was confirmed using a Dye Terminator Cycle Sequencing Kit (available from Beckman Coulter Inc.). This was named pRH83. The C20 elongase gene sequence (935 bp) in which a BglII site was inserted is shown in SEQ ID NO: 30.

Figure 8:
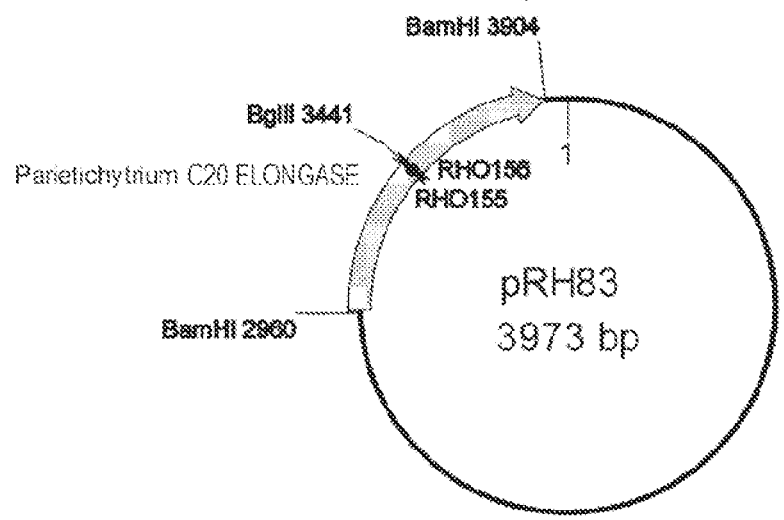
FIG. 8 illustrates a plasmid in which a BglII site has been inserted in a C20 elongase sequence of genus of *Parietichytrium* of the plasmid illustrated in FIG. 7.

FIG. 8 illustrates the produced base plasmid (pRH83) for producing a genus *Parietichytrium* C20 elongase gene targeting vector.

[Example 2-6]: Production of Targeting Vectors (Artificially Synthesized Neomycin Gene and Hygromycin Resistance Gene)

pRH31 (FIG. 4) described in Example 2-2 was digested with BglII, and a DNA fragment containing an artificially synthesized neomycin resistance gene cassette was bound to the BglII site of pRH83 (FIG. 8) described in Example 2-5. This was named pRH85.

pRH32 (FIG. 6) described in Example 2-3 was digested with BglII, and a DNA fragment containing a hygromycin resistance gene cassette was bound to the BglII site of pRH83 (FIG. 8) described in Example 2-5. This was named pRH86.

Figure 9:
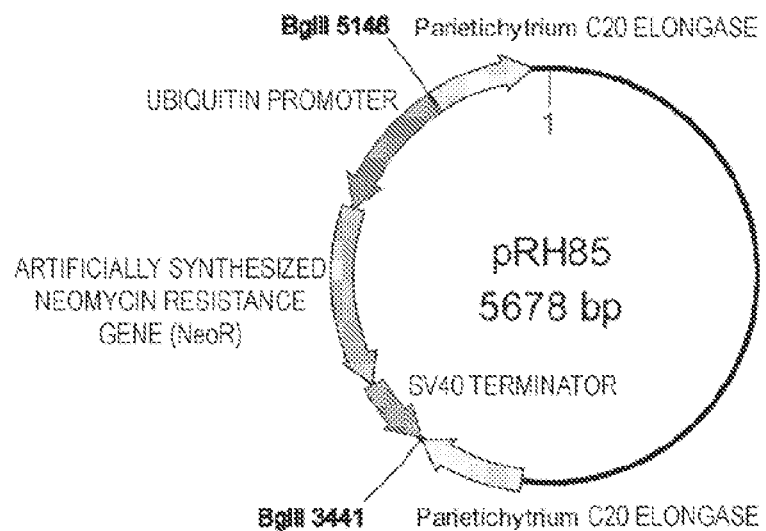
FIG. 9 illustrates the produced genus of *Parietichytrium* C20 elongase gene targeting vectors (two types). As a drug resistance marker, the vectors have a neomycin resistance gene (pRH85) or a hygromycin resistance gene (pRH86).
Figure 9:
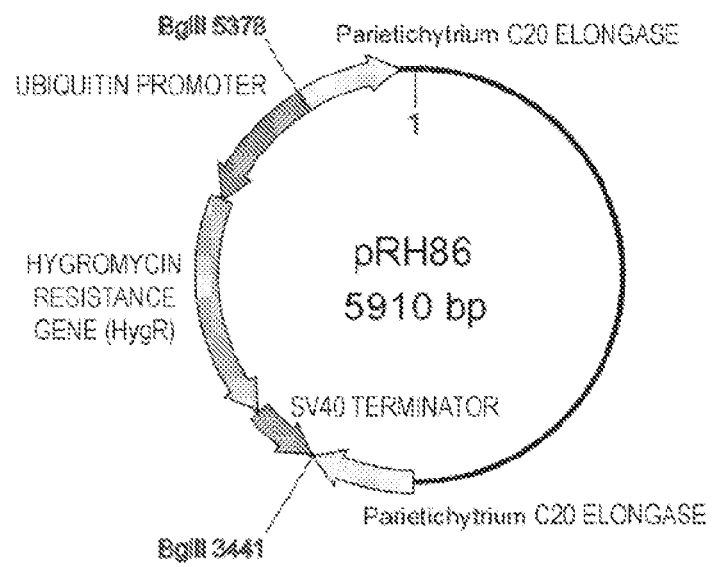

The two produced targeting vectors (pRH85 and 86) are illustrated in FIG. 9.

[Example 2-7]: C20 Elongase Gene Targeting Vector Transfer

Using the two targeting vectors produced in Example 2-6 as templates, the genes were amplified with PrimeSTAR Max DNA Polymerase (available from Takara Bio Inc.) using RHO153 (described in Example 2-4, SEQ ID NO: 24) and RHO154 (described in Example 2-4, SEQ ID NO: 25) as primers. [PCR cycles: 98° C. 2 min/98° C. 30 sec, 68° 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH85 (FIG. 9) described in Example 2-6 was used as a template was 2661 bp, and resulted in a sequence composed of genus *Parietichytrium* C20 elongase gene front half—SV40 terminator sequence—artificially synthesized neomycin resistance gene sequence—ubiquitin promoter sequence—genus *Parietichytrium* C20 elongase gene back half (SEQ ID NO: 31). The transfer fragment obtained when pRH86 (FIG. 9) described in Example 2-6 was used as a template was 2892 bp, and resulted in a sequence composed of genus *Parietichytrium* C20 elongase gene front half—SV40 terminator sequence—hygromycin resistance gene sequence—ubiquitin promoter sequence—genus *Parietichytrium* C20 elongase gene back half (SEQ ID NO: 32).

The *Parietichytrium sarkarianum* SEK364 strain was cultured for 4 days in a GY culture medium, and cells in the logarithmic growth phase were used for gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium (containing 2 mg/mL of G418 or containing 2 mg/mL of hygromycin). As a result, from 10 to 20 cells of drug resistant strain per shot were obtained.

Figure 10:
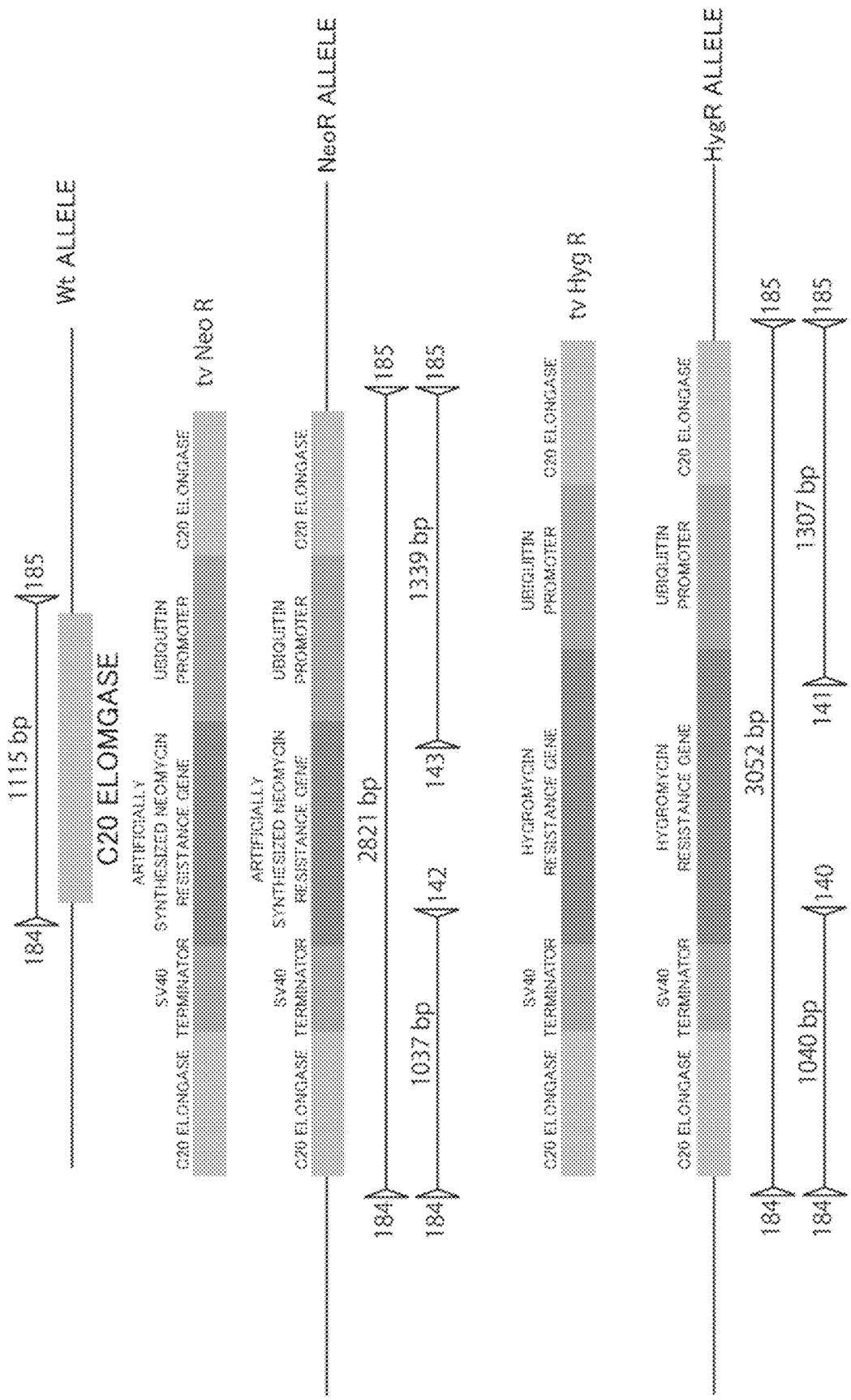
FIG. 10 is a schematic diagram illustrating the positions of the PCR primers used in identification of a C20 elongase gene disruption strain of *Parietichytrium sarkarianum* SEK364, and the expected product.

[Example 2-8]: Identification of C20 Elongase Gene Targeting Homologous Recombinant Genome DNA of the *Parietichytrium sarkarianum* SEK364 strain, a C20 elongase gene hetero homologous recombinant, and a C20 elongase gene homo homologous recombinant (gene disruption strain) were extracted by the method described in Example 2-2, and then A260/280 was measured and the DNA concentration was calculated. Using the genome DNA as templates, PCR for genome structure confirmation was performed using LA Taq Hot Start Version (available from Takara Bio Inc.). The positions of the primers used, the combinations used in amplification, and the expected sizes of the amplification products are illustrated in FIG. 10. RHO184 was set upstream of C20 elongase; RHO185 was set downstream; RHO142 and RHO143 were set on the artificially synthesized neomycin resistance gene; and RHO140 and RHO141 were set on the hygromycin resistance gene. [RHO140: 20 mer: 5'-GGT TGA CGG CAA TTT CGA TG-3' (SEQ ID NO: 33), RHO141: 22 mer: 5'-CCT CCT ACA TCG AAG CTG AAA G-3' (SEQ ID NO: 34), RHO142: 21 mer: 5'-CTT CTC GGG CTT TAT CGA CTG-3' (SEQ ID NO: 35), RHO143: 22 mer: 5'-TAA GGT CGG TCT TGA CAA ACA G-3' (SEQ ID NO: 36), RHO184: 24 mer: 5'-AGT AGT CCC CGA TTT GGT AGT TGA-3' (SEQ ID NO: 37), RHO185: 22 mer: 5'-GGC AGA GAG CAA AAA CAC GAG C-3' (SEQ ID NO: 38)]. [PCR cycles: 98° C. 2 min/98° C. 10 sec, 68° 4 min, 30 cycles/68° C. 7 min].

Figure 11:
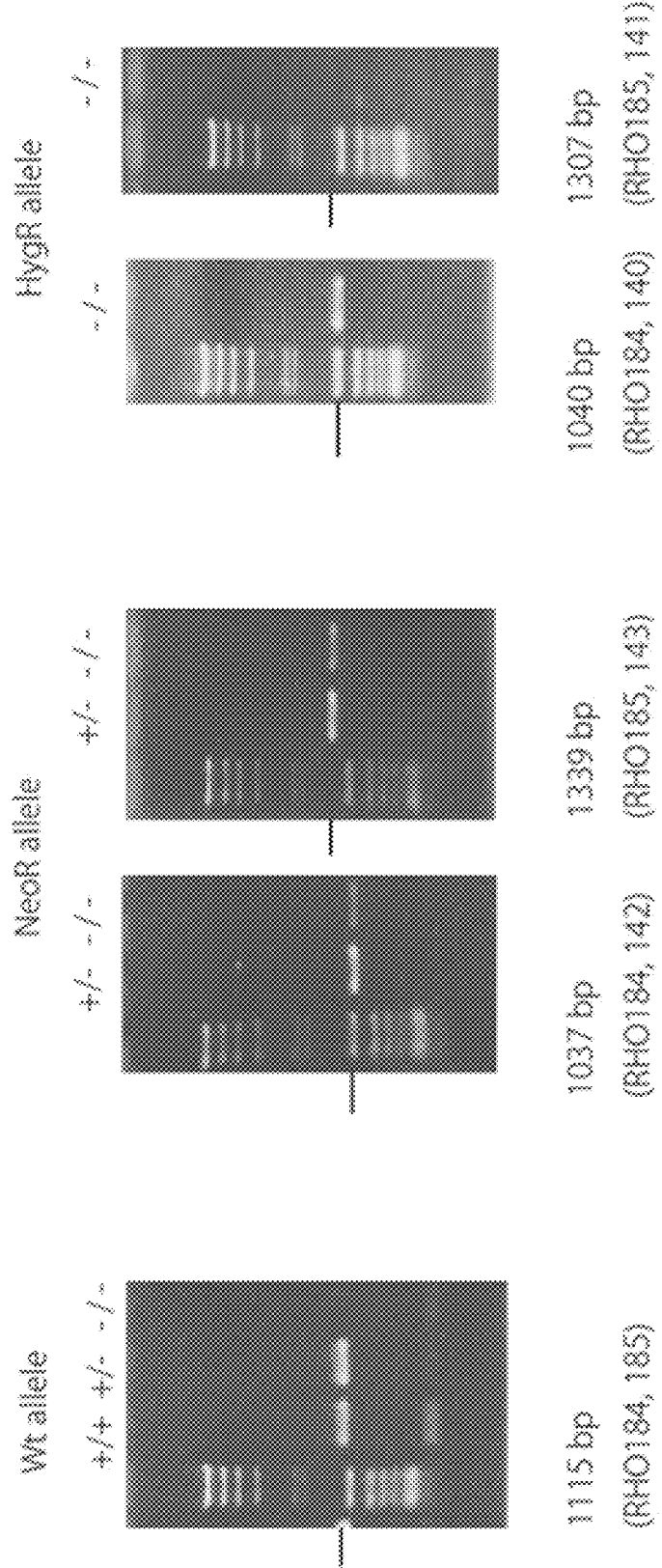
FIG. 11 illustrates an evaluation of C20 elongase gene disruption by PCR using *Parietichytrium sarkarianum* SEK364 genome DNA as a template. (Description of symbols)+/+: *Parietichytrium sarkarianum* SEK364 wild-type strain; +/−: C20 elongase gene first allele homologous recombinant derived from *Parietichytrium sarkarianum* SEK364; −/−: C20 elongase disruption strain derived from *Parietichytrium sarkarianum* SEK364

A C20 elongase gene disruption strain in which there is no amplification in the wild-type allele (Wt allele) and there is amplification in the artificially synthesized neomycin resistance gene allele (NeoR allele) and the hygromycin resistance gene allele (HygR allele) was obtained (FIG. 11).

Example 2-9: Change in Fatty Acid Composition by C20 Elongase Gene Disruption

The *Parietichytrium sarkarianum* SEK364 wild-type strain and the gene disruption strain thereof (C20 elongase gene disruption strain, C20-/-) were cultured in a GY culture medium. The cells of the latter phase of the logarithmic growth phase were centrifuged for 10 min at 4° C. at 3000 rpm to form pellets, and the obtained pellets were suspended in 0.9% NaCl and washed. Then, the resultant was centrifuged for 10 min at 4° C. at 3000 rpm, and the pellets were suspended in sterilized water and washed. The resultant was further centrifuged for 10 min at 3000 rpm, the supernatant was removed and the precipitate was freeze-dried.

To the freeze-dried cells, 2 mL of methanolic KOH (7.5% KOH in 95% methanol) was added, and after vortexing, the cells were crushed by ultrasound (80° C., 30 min). Then, 500 μL of sterilized water was added and vortexing was performed, and then 2 mL of n-hexane was added and vortexing was performed. The resultant was then centrifuged for 10 min at 3000 rpm, and the top layer was discarded. Another 2 mL of n-hexane was added and vortexing was performed. The resultant was centrifuged for 10 min at 3000 rpm, and the top layer was discarded. One mL of 6 N HCl was added to the remaining bottom layer and vortexing was performed, and then 2 mL of n-hexane was added and vortexing was performed. The resultant was then centrifuged for 10 min at 3000 rpm, and the top layer was collected. Another 2 mL of n-hexane was added and vortexing was performed. The resultant was centrifuged for 10 min at 3000 rpm, and the top layer was collected. The collected top layer was concentrated and dried with nitrogen gas. Two mL of 3 N methanolic HCl was added to the concentrated and dried sample, and the resultant was incubated overnight at 80° C.

The sample was cooled to room temperature, and 1 mL of 0.9% NaCl was added. Then, 2 mL of n-hexane was added and vortexing was performed. The resultant was centrifuged for 10 min at 3000 rpm, and the top layer was collected. Another 2 mL of n-hexane was added and vortexing was performed. The resultant was centrifuged for 10 min at 3000 rpm, and the top layer was collected. A small amount of anhydrous sodium sulfate was added to the collected top layer and then vortexing was performed. The resultant was centrifuged for 10 min at 3000 rpm, and the top layer was collected. The collected top layer was concentrated and dried with nitrogen gas. The concentrated and dried sample was dissolved in 0.5 mL of n-hexane, and 1 μL of the resultant was subjected to GC analysis. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 12:
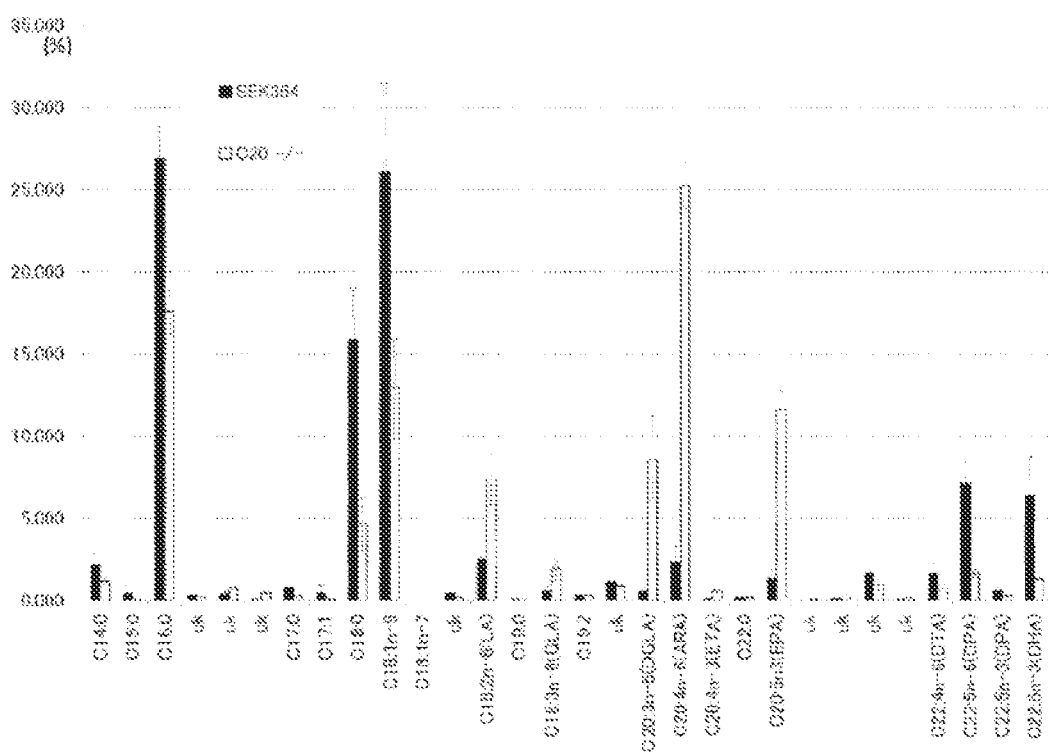
FIG. 12 illustrates a comparison of fatty acid compositions of the *Parietichytrium sarkarianum* SEK364 wild-type strain and the C20 elongase gene disruption strain. The black bars and white bars represent the fatty acid composition of the wild-type strain and the gene disruption strain, respectively. The values are mean±standard deviation.

As a result, when the C20 elongase gene was disrupted in *Parietichytrium sarkarianum* SEK364, fatty acids having not less than 22 carbon chains decreased while fatty acids having 20 carbon chains increased (FIG. 12). FIG. 13 shows the proportion when the wild-type strain is taken as 100%. FIG. 13 shows that, of the total fatty acid composition, ARA is 25.22%, DGLA is 8.62%, ETA is 0.56%, EPA is 11.58%, n-6 DPA is 1.64%, and DHA is 1.28%. FIG. 13 shows that, by GC area, LA/DHA is 5.8, GLA/DHA is 1.5, DGLA/DHA is 6.7, ARA/DHA is 19.7, EPA/DHA is 9.0, LA/EPA is 0.64, GLA/EPA is 0.16, DTA/EPA is 0.06, DTA/ARA is 0.03, DTA/DGLA is 0.08, LA/n-6 DPA is 4.5, GLA/n-6 DPA is 1.2, DGLA/n-6 DPA is 5.3, ARA/n-6 DPA is 15.4, EPA/n-6 DPA is 7.1, DGLA/LA is 1.2, ARA/LA is 3.4, EPA/LA is 1.6, DTA/LA is 0.09, DGLA/GLA is 4.5, ARA/GLA is 13.2, n-6 DPA/DTA is 2.4, DHA/n-3 DPA is 4.9, C20 PUFA/C22 PUFA is 11.94, and n-6 PUFA/n-3 PUFA is 2.67.

In these results, arachidonic acid increased approximately 10-fold, EPA approximately 8-fold, and DGLA approximately 16-fold, while DPA decreased to approximately ¼ and DHA to approximately ⅕.

By selecting the labyrinthulid *Parietichytrium sarkarianum* SEK364 having no PUFA-PKS pathway in this manner, a strain that accumulates PUFAs other than DHA and n-6 DPA can be produced without PUFA-PKS pathway gene disruption. This strain may also be used as a strain that produces EPA and/or ARA, and further disruption or transforming elongase or desaturase genes can create strains that produce desired PUFAs.

Example 3

[Measurement of Fatty Acid Composition of Lipids Produced by Δ4 Desaturase Gene Disruption and Transformation Strain of *Parietichytrium sarkarianum* SEK364]

[Example 3-1]: Cloning of Genus *Parietichytrium* Δ4 Desaturase Gene

Genome DNA of *Parietichytrium* sp. SEK571 was extracted by the method described in Example 2-2. Using the extracted genome DNA as a template, a sequence containing the Δ4 desaturase gene sequence (5003 bp, SEQ ID NO: 39) was amplified with LA Taq Hot Start Version (available from Takara Bio Inc.). The PCR primers used were as shown below. [RHO241: 23 mer: 5'-GTT TGA GGA GCG AGG CAT TTC TT-3' (SEQ ID NO: 40), RHO242: 23 mer: 5'-AGT GCT CGT ACA ATG ACT GGC GT-3' (SEQ ID NO: 41)].

The obtained DNA fragment was cloned in pGEM-T Easy Vector, and after amplification with *E. coli*, the sequence was confirmed using a Dye Terminator Cycle Sequencing Kit (available from Beckman Coulter Inc.). This was named pRH112 (SEQ ID NO: 42).

Figure 14:
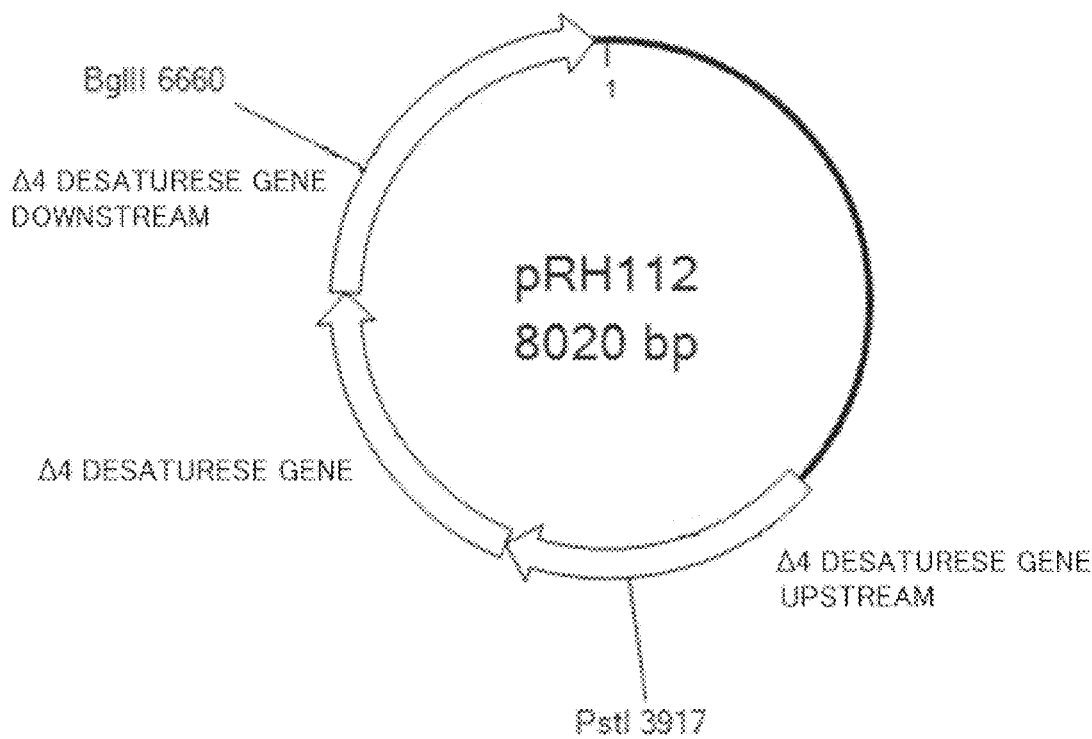
FIG. 14 illustrates a plasmid containing a cloned *Parietichytrium* sp. SEK571 Δ4 desaturase gene sequence and the peripheral sequence.

The plasmid (pRH112) containing the genus of *Parietichytrium* Δ4 desaturase gene sequence (1542 bp, SEQ ID NO: 43) is illustrated in FIG. 14.

[Example 3-2]: Production of Plasmid Serving as Base for Production of Δ4 Desaturase Gene Targeting Vector Using pRH112 (FIG. 14) produced in Example 3-1 as a template, a primer set designed so as to delete the Δ4 desaturase gene and 600 bp downstream of the Δ4 desaturase gene and to produce a BglII site in the deleted portion was prepared. [RHO243: 26 mer: 5'-GGC AAG ATC TAA CTT TCT GAG GCT CT-3' (SEQ ID NO: 44), RHO244: 26 mer: 5'-AAG TTA GAT CTT GCC TAT TCC ACG AT-3' (SEQ ID NO: 45)]. PrimeSTAR Max DNA Polymerase (available from Takara Bio Inc.) was used in amplification. After the amplified sample was digested with BglII, the resultant was self-ligated. After the ligated sample was amplified with *E. coli*, the sequence was confirmed using a Dye Terminator Cycle Sequencing Kit (available from Beckman Coulter Inc.). This was named pRH117.

Figure 15:
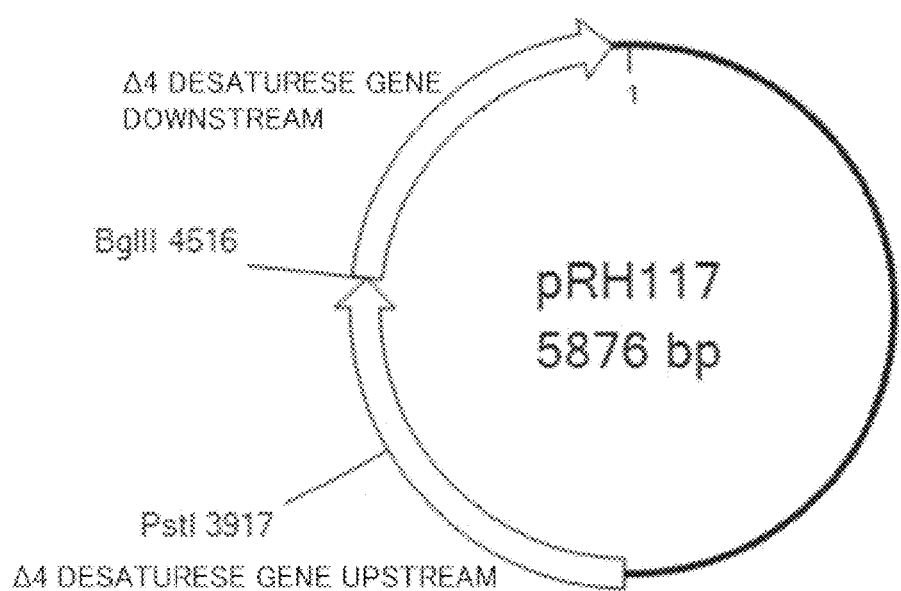
FIG. 15 illustrates a plasmid in which the *Parietichytrium* sp. SEK571 Δ4 desaturase gene sequence and a 600 bp downstream of the Δ4 desaturase gene sequence have been deleted from the plasmid illustrated in FIG. 14 and a BglII site has been inserted.

The produced plasmid (pRH117) serving as a base for production of a Δ4 desaturase gene targeting vector is illustrated in FIG. 15.

Figure 16:
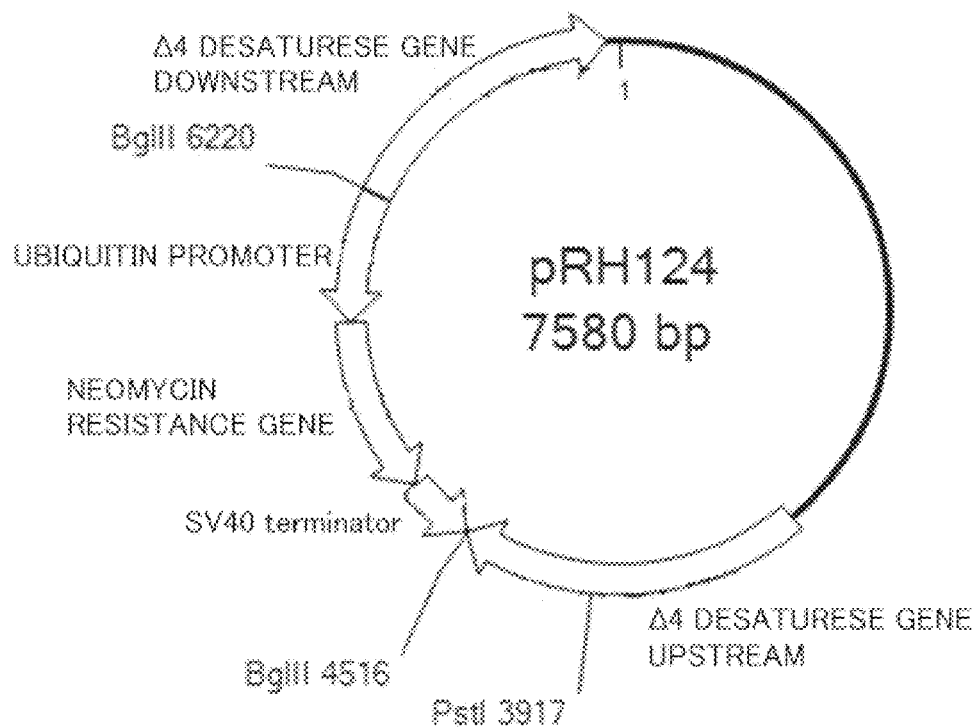
FIG. 16 illustrates a plasmid in which a DNA fragment containing an artificially synthesized neomycin resistance gene cassette has been bound at the BglII site of the plasmid illustrated in FIG. 15.

[Example 3-3]: Production of Δ4 Desaturase Gene Targeting Vector pRH31 (FIG. 4) described in Example 2-2 was digested with BglII, and a DNA fragment containing an artificially synthesized neomycin resistance gene cassette was bound to the BglII site of pRH117 (FIG. 15) described in Example 3-2. This was named pRH124 (FIG. 16). Using this pRH124 as a template, a primer set that was set up so as to delete PstI was prepared. [RHO261: 26 mer: 5'-GTG CAG ACG CAG AAG AAG ACT GAC AA-3' (SEQ ID NO: 46), RHO262: 25 mer: 5'-CTT CTG CGT CTG CAC GAG GAA TCG A-3' (SEQ ID NO: 47)]. PrimeSTAR Max DNA Polymerase (available from Takara Bio Inc.) was used in amplification. After transforming the PCR product into *E. coli* and amplifying, the sequence was confirmed using a Dye Terminator Cycle Sequencing Kit (available from Beckman Coulter Inc.). This was named pRH126 (SEQ ID NO: 48).

Figure 17:
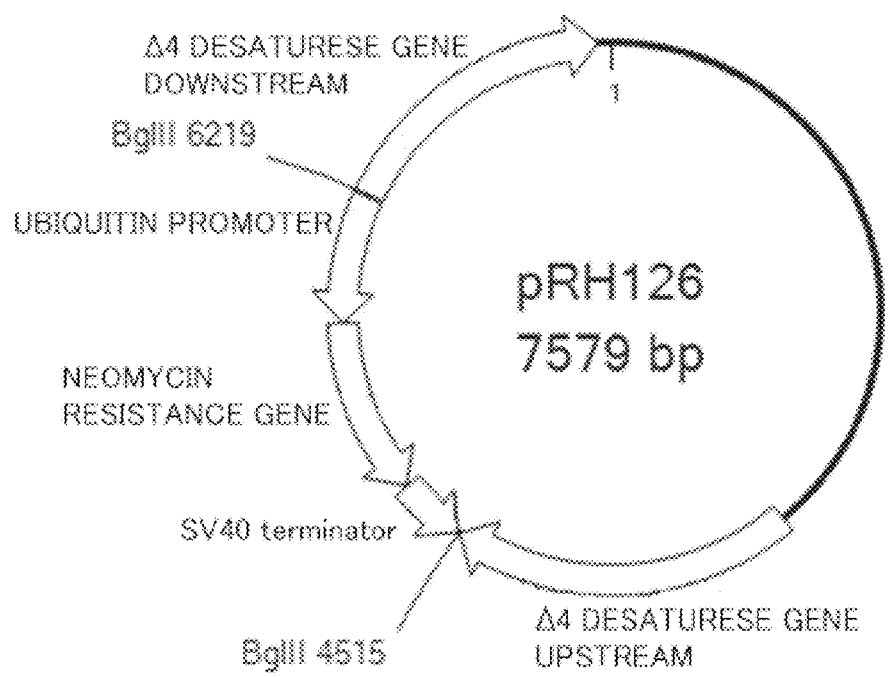
FIG. 17 illustrates the produced genus of *Parietichytrium* Δ4 desaturase gene targeting vector. As a drug resistance marker, the vector has a neomycin resistance gene.

The produced Δ4 desaturase gene targeting vector (pRH126) is illustrated in FIG. 17.

[Example 3-4]: Transfer of Δ4 Desaturase Gene Targeting Vector to *Parietichytrium sarkarianum* SEK364

Using the targeting vector pRH126 (FIG. 17) produced in Example 3-3 as a template, the gene was amplified with PrimeSTAR Max DNA Polymerase (available from Takara Bio Inc.) using RHO241 (described in Example 3-1, SEQ ID NO: 40) and RHO242 (described in Example 3-1, SEQ ID NO: 41) as primers. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH126 (FIG. 17) described in Example 3-3 was used as a template was 4562 bp.

The *Parietichytrium sarkarianum* SEK364 strain was cultured for 1 to 2 days in a GY culture medium, and cells in the logarithmic growth phase were used for gene transfer. To cells corresponding to OD600=1 to 2, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium containing 1 mg/mL of G418. As a result, from 0 to 2 cells of drug resistant strain per shot were obtained.

Figure 18:
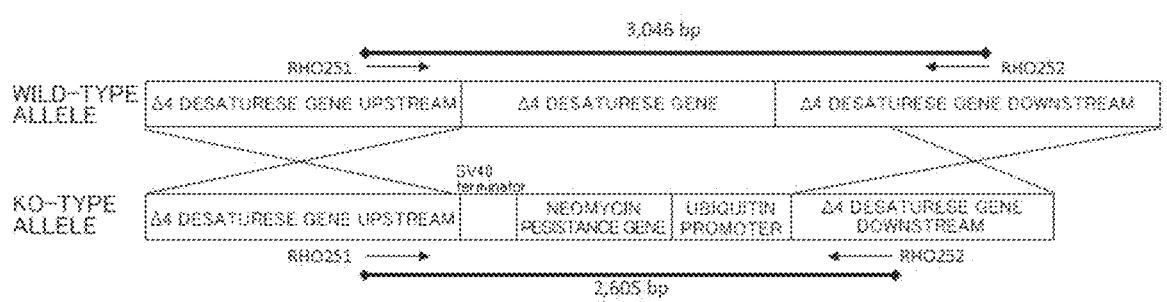
FIG. 18 is a schematic diagram illustrating the positions of the PCR primers used in identification of a Δ4 desaturase gene disruption strain of a genus of *Parietichytrium* labyrinthulid, and the expected product (primers are set within the homologous recombination region).

[Example 3-5]: Identification of Δ4 Desaturase Gene Targeting Homologous Recombinant Genome DNA of the *Parietichytrium sarkarianum* SEK364 strain and the Δ4 desaturase gene disruption strain were extracted by the method described in Example 2-2, and then A260/280 was measured and the DNA concentration was calculated. Using the genome DNA as templates, PCR for genome structure confirmation was performed using PrimeSTAR GXL DNA Polymerase (available from Takara Bio Inc.). The positions of the primers used, the combinations used in amplification, and the expected sizes of the amplification products are illustrated in FIG. 18 (within homologous region). In the primer set designed within the homologous recombination region, 3046 bp was amplified in the *Parietichytrium sarkarianum* SEK364 strain, and 2605 bp was amplified in the Δ4 desaturase gene disruption strain. [RHO251: 20 mer: 5'-GTG GTC GAA GTG GAG TAT CT-3' (SEQ ID NO: 49), RHO252: 20 mer: 5'-ACT CGC CAT ACA ACT TTA CA-3' (SEQ ID NO: 50)].

Figure 19:
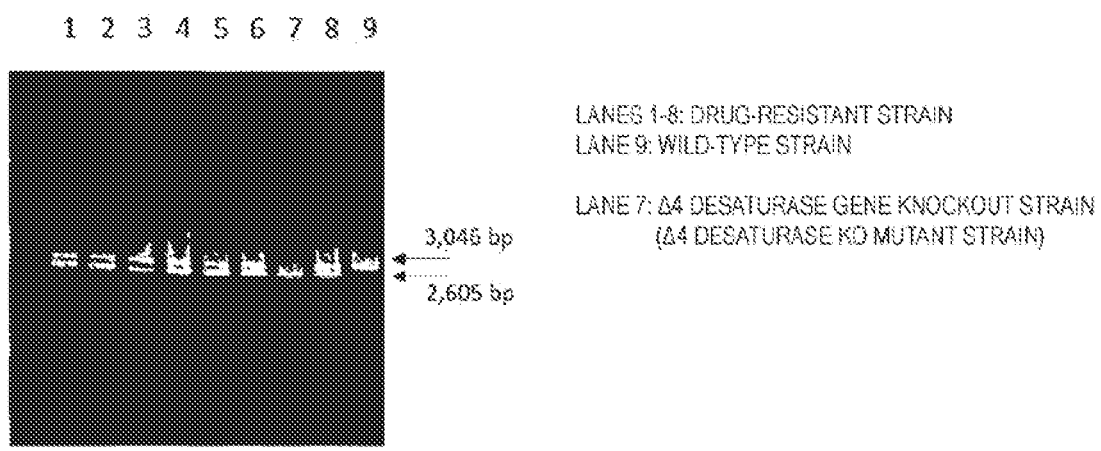
FIG. 19 illustrates evaluation results of Δ4 desaturase gene disruption by PCR using *Parietichytrium sarkarianum* SEK364 genome DNA as a template.

As a result, a Δ4 desaturase gene disruption strain in which there is no amplification derived from the wild-type allele (Wt allele) and there is amplification derived from the Δ4 desaturase gene KO allele (NeoR allele) was obtained (FIG. 19 lane 7: Δ4 desaturase KO mutant strain).

Example 3-6: Change in Fatty Acid Composition by Δ4 Desaturase Gene Disruption

The *Parietichytrium sarkarianum* SEK364 wild-type strain and the Δ4 desaturase gene disruption strain thereof were cultured according to the method described in Example 2-9, and after freeze drying, the fatty acids were methyl-esterified and analyzed using GC. In culturing, the GY liquid culture medium described in Example 1 supplemented with 0.1% of a vitamin solution (vitamin $B_1$ 200 mg, vitamin $B_2$ 1 mg, and vitamin $B_{12}$ 1 mg are dissolved in 100 mL of distilled water) and 0.2% of a trace element solution (EDTA disodium salt 30.0 g, $FeCl_3 \cdot 6H_2O$ 1.45 g, $H_3BO_3$ 34.2 g, $MnCl_2 \cdot 4H_2O$ 4.3 g, $ZnCl_2$ 1.335 g, $CoCl_2 \cdot 6H_2O$ 0.13 g, $NiSO_4 \cdot 6H_2O$ 0.26 g, $CuSO_4 \cdot 5H_2O$ 0.01 g, and $NaMoO_4 \cdot 2H_2O$ 0.025 g are dissolved in 1 L of distilled water) was used. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→ (2° C./min)→220° C. (10 min); carrier gas: He (1.3 mL/min).

Figure 20:
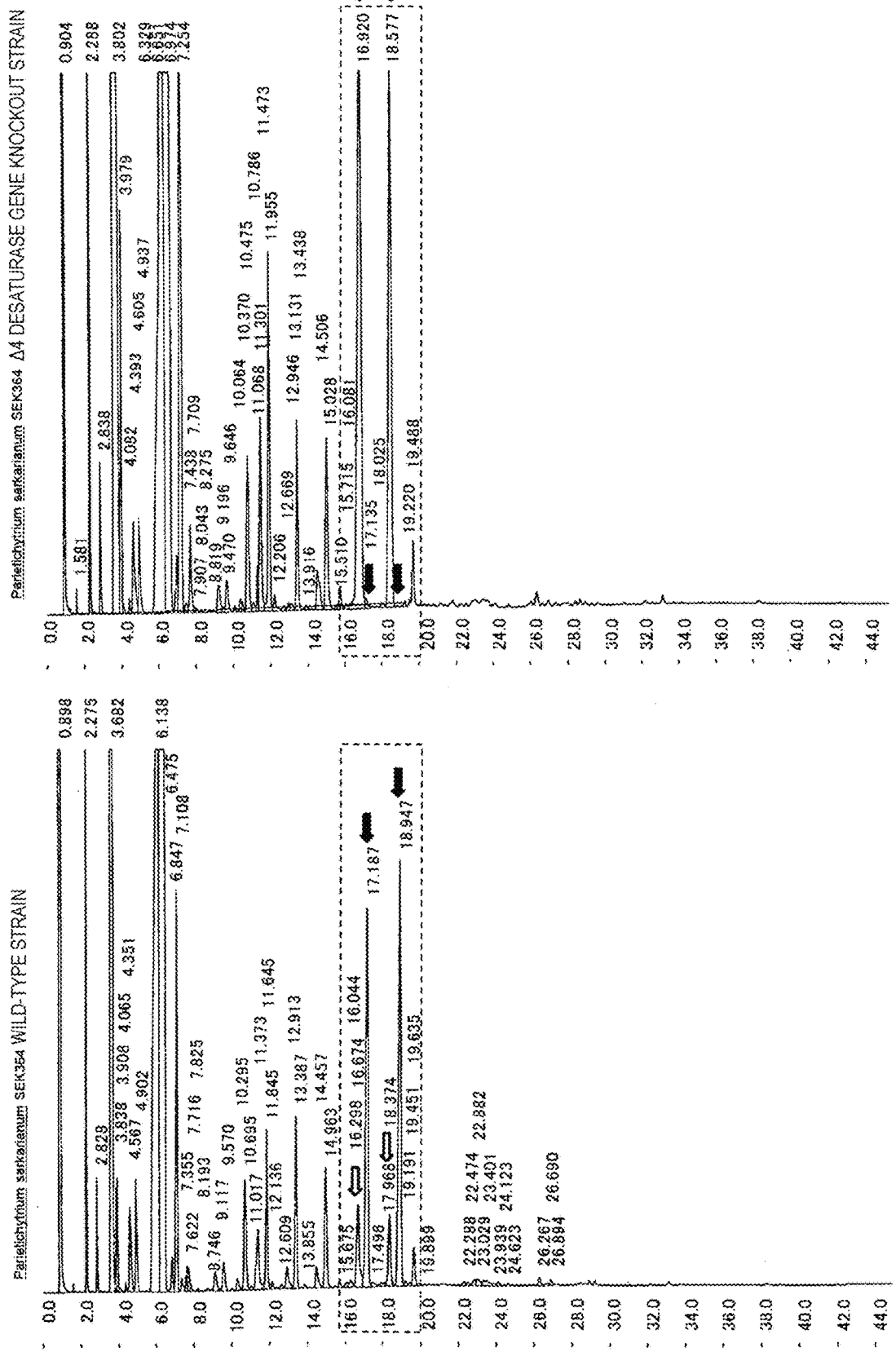
FIG. 20 is a gas chromatograph analysis chart of the fatty acid compositions of the *Parietichytrium sarkarianum* SEK364 wild-type strain and the Δ4 desaturase gene disruption strain thereof.
Figure 21:
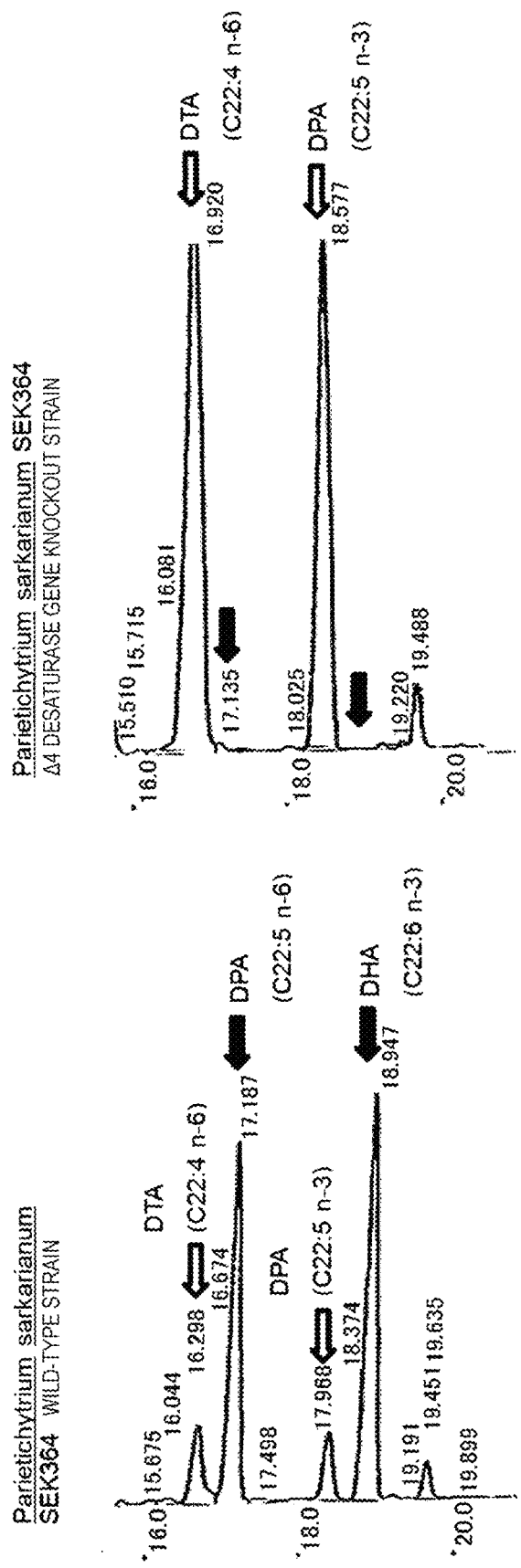
FIG. 21 is a partial enlarged diagram of FIG. 20.
Figures 22, 23:
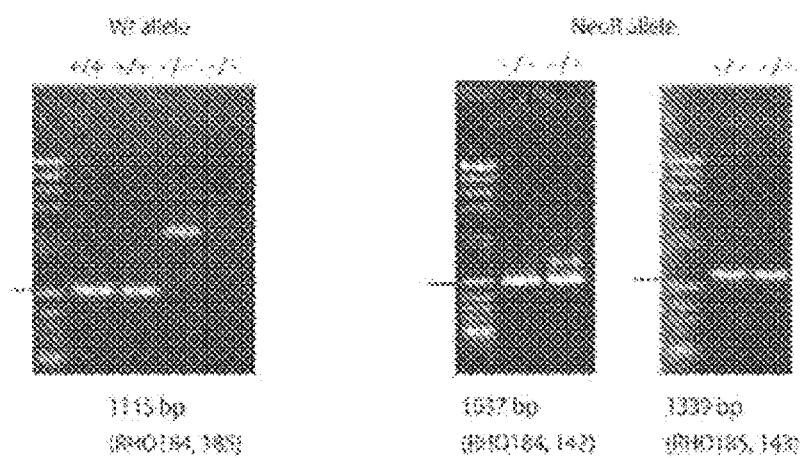
FIG. 22 shows a comparison of the fatty acid compositions of the *Parietichytrium sarkarianum* SEK364 wild-type strain and the Δ4 desaturase gene disruption strain thereof. This table is a quantification of the chart of FIG. 20. In the table, the less-than sign (<) indicates less than or equal to the number following it.
FIG. 23 illustrates an evaluation of C20 elongase gene disruption by PCR using *Parietichytrium* sp. SEK358 strain genome DNA as a template. (Description of symbols)+/+: *Parietichytrium* sp. SEK358 wild-type strain; −/−: C20 elongase gene disruption strain derived from *Parietichytrium* sp. SEK358 strain

The analysis results chart is shown in FIG. 20, and a partial enlarged diagram thereof is shown in FIG. 21. FIG. 22 shows a quantification of the chart of FIG. 20. This table shows a comparison of the fatty acid compositions of the *Parietichytrium sarkarianum* SEK364 wild-type strain and the Δ4 desaturase gene disruption strain thereof. This table is the quantification of the chart of FIG. 20. The table shows that, of the total fatty acid composition, ARA is 1.59%, DGLA is 0.98%, ETA is 0.05%, EPA is 0.79%, n-6 DPA is 0.00%, and DHA is 0.00%. The table shows that, by GC area, LA/EPA is 5.09, GLA/EPA is 0.48, DTA/EPA is 7.44, DTA/ARA is 3.73, DTA/DGLA is 6.06, DGLA/LA is 0.24, ARA/LA is 0.39, EPA/LA is 0.20, DTA/LA is 1.46, DGLA/GLA is 2.57, ARA/GLA is 4.19, and n-6 DPA/DTA is 0.00.

These results show that when the Δ4 desaturase gene is disrupted in the *Parietichytrium sarkarianum* SEK364 strain, DHA and DPA n-6 cannot be substantially biosynthesized, and conversely, DPA n-3 and DTA, which are substrates thereof, increase.

By selecting the labyrinthulid *Parietichytrium sarkarianum* SEK364 having no PUFA-PKS pathway in this manner, a strain that accumulates PUFAs other than DHA and DPA n-6 can be produced without PUFA-PKS pathway gene disruption. This strain may also be used as a strain that produces n-3 DPA and/or DTA, and further disruption or transforming elongase or desaturase genes can create strains that produce desired PUFAs.

Example 4

[Measurement of Fatty Acid Composition of Lipids Produced by C20 Elongase Gene Disruption and Transformation Strain of *Parietichytrium* sp. SEK358]

[Example 4-1]: Transfer of C20 Elongase Gene Targeting Vector to *Parietichytrium* sp. SEK358 Strain Using the targeting vector produced with pRH85 (FIG. 9) described in Example 2-6 as a template, the gene was amplified with PrimeSTAR Max DNA Polymerase (available from Takara Bio Inc.) using RHO153 (described in Example 2-4, SEQ ID NO: 24) and RHO154 (described in Example 2-4, SEQ ID NO: 25) as primers. [PCR cycles: 98° C. 2 min/98° C. 30 sec, 68° 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH85 (FIG. 9) described in Example 2-6 was used as a template was 2661 bp, and resulted in a sequence composed of genus *Parietichytrium* C20 elongase gene front half—SV40 terminator sequence—artificially synthesized neomycin resistance gene sequence—ubiquitin promoter sequence—genus *Parietichytrium* C20 elongase gene back half (described in Example 2-7, SEQ ID NO: 31).

The *Parietichytrium* sp. SEK358 strain was cultured for 3 days in a GY culture medium, and cells in the logarithmic growth phase were used for gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 900 psi). After a recovery time of 24 hr, the transgenic cells were spread on a PDA agar plate culture medium containing 0.5 mg/mL of G418. As a result, from 10 to 30 cells of drug resistant strain per shot were obtained.

[Example 4-2]: Identification of C20 Elongase Gene Targeting Homologous Recombinant Genome DNA of the *Parietichytrium* sp. SEK358 strain and the C20 elongase gene disruption strain were extracted by the method described in Example 2-2, and then A260/280 was measured and the DNA concentration was calculated. Using the genome DNA as templates, PCR for genome structure confirmation was performed using Mighty Amp DNA Polymerase (available from Takara Bio Inc.). The positions of the primers used, the combinations used in amplification, and the expected sizes of the amplification products are illustrated in FIG. 10 described in Example 2-8.

RHO184 (described in Example 2-8, SEQ ID NO: 37) was set upstream of C20 elongase; RHO185 (described in Example 2-8, SEQ ID NO: 38) was set downstream; RHO142 (described in Example 2-8, SEQ ID NO: 35) and RHO143 (described in Example 2-8, SEQ ID NO: 36) were set on the artificially synthesized neomycin resistance gene. [PCR cycles: 98° C. 2 min/98° C. 10 sec, 68° 2 min, 30 cycles/68° C. 7 min].

A C20 elongase gene disruption strain in which there is no amplification in the wild-type allele (Wt allele) and there is amplification in the artificially synthesized neomycin resistance gene allele (NeoR allele) was obtained (FIG. 23).

[Example 4-3]: Change in Fatty Acid Composition by C20 Elongase Gene Disruption

Figure 24:
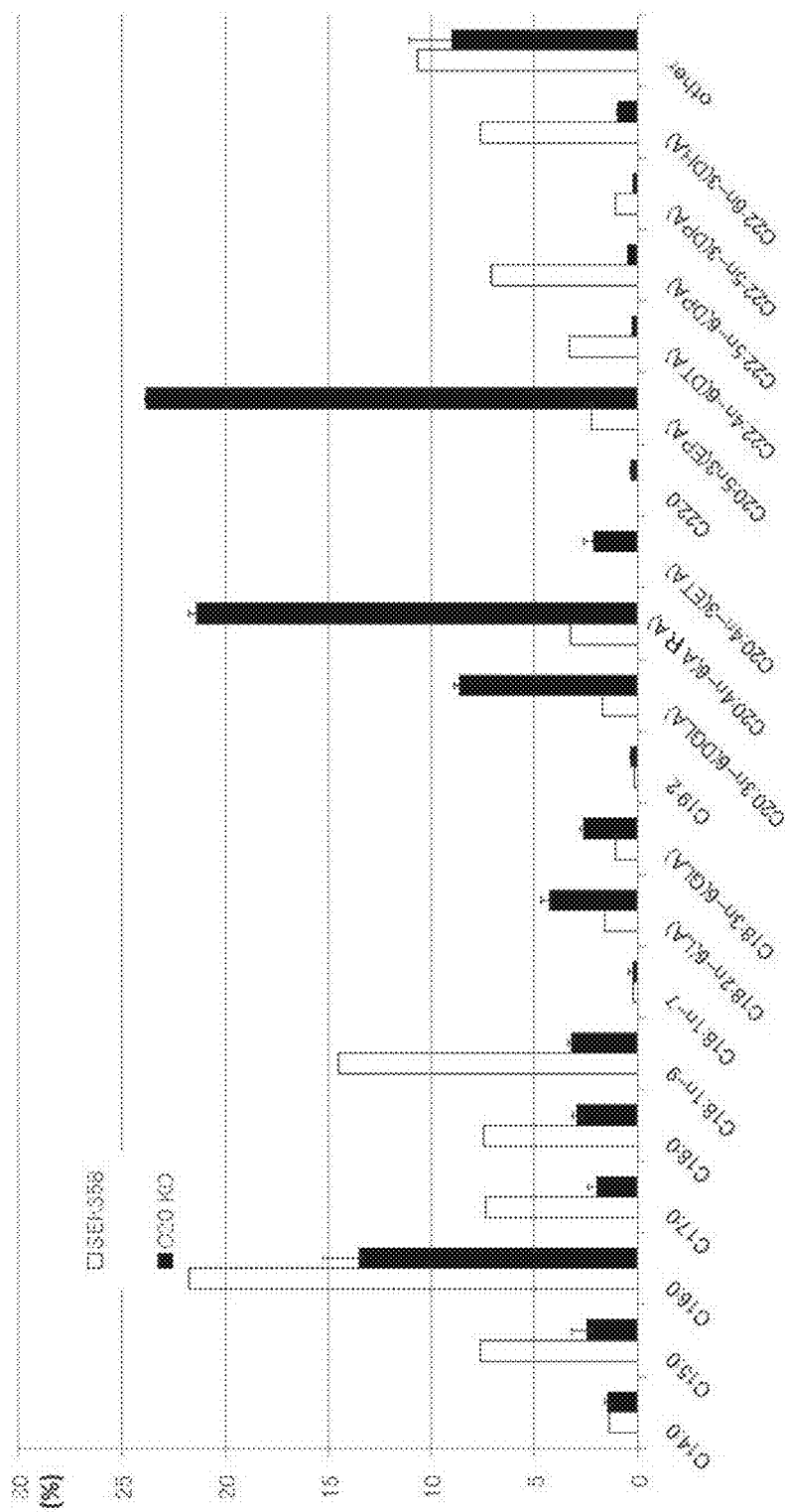
FIG. 24 illustrates a comparison of fatty acid compositions of the *Parietichytrium* sp. SEK358 wild-type strain and the C20 elongase gene disruption strain derived from *Parietichytrium* sp. SEK358 strain. The white bars and black bars represent the fatty acid composition of the wild-type strain and the gene disruption strain, respectively.

The *Parietichytrium* sp. SEK358 wild-type strain and the gene disruption strain thereof (C20 elongase gene disruption strain, C20 KO) were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min). The changes in the fatty acid composition are shown in FIG. 24. Furthermore, FIG. 25 shows the proportion when the wild-type strain is taken as 100%.

Figures 25, 26:
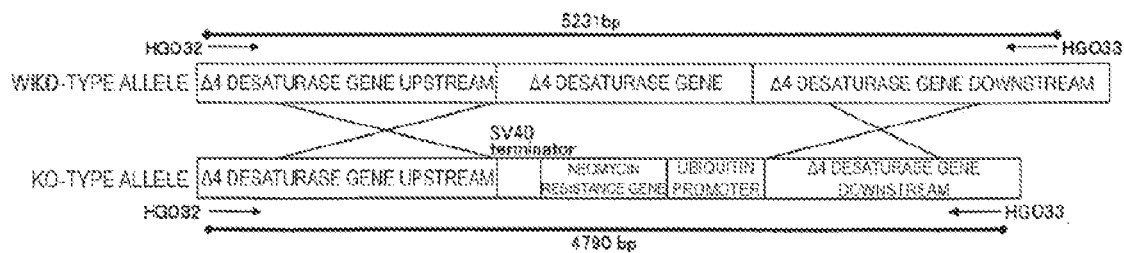
FIG. 25 lists the fatty acid proportions of the C20 elongase gene disruption strain derived from the *Parietichytrium* sp. SEK358 strain when the *Parietichytrium* sp. SEK358 wild-type strain is taken as 100%. In the *Parietichytrium* sp. SEK358 wild-type strain, cases where the relevant fatty acid is below the detection limit are indicated by a diagonal line.
FIG. 26 is a schematic diagram illustrating the positions of the PCR primers used in identification of a Δ4 desaturase gene disruption strain of a genus of *Parietichytrium* labyrinthulid, and the expected product (primers are set outside the homologous recombination region).

FIG. 25 shows that, of the total fatty acid composition, ARA is 21.35%, DGLA is 8.64%, ETA is 2.14%, EPA is 23.83%, n-6 DPA is 0.46%, and DHA is 0.94%. FIG. 25 shows that, by GC area, LA/DHA is 4.6, GLA/DHA is 2.8, DGLA/DHA is 9.19, ARA/DHA is 22.7, EPA/DHA is 25.4, LA/EPA is 0.18, GLA/EPA is 0.11, DTA/EPA is 0.01, DTA/ARA is 0.01, DTA/DGLA is 0.03, LA/n-6 DPA is 9.3, GLA/n-6 DPA is 5.7, DGLA/n-6 DPA is 18.8, R/n-6 DPA is 46.4, EPA/n-6 DPA is 51.8, DGLA/LA is 2.0, ARA/LA is 5.0, EPA/LA is 5.6, DTA/LA is 0.06, DGLA/GLA is 3.3, ARA/GLA is 8.2, n-6 DPA/DTA is 1.8, DHA/n-3 DPA is 4.1, C20 PUFA/C22 PUFA is 29.61, and n-6 PUFA/n-3 PUFA is 1.1.

As a result, when the C20 elongase gene was disrupted in the *Parietichytrium* sp. SEK358 strain, fatty acids having not less than 22 carbon chains decreased while fatty acids having 20 carbon chains increased. Specifically, arachidonic acid increased approximately 7-fold and EPA increased approximately 11-fold, while DPA decreased to approximately ⅟15 and DHA decreased to approximately ⅛.

By selecting the labyrinthulid *Parietichytrium* sp. SEK358 having no PUFA-PKS pathway in this manner, a strain that accumulates PUFAs other than DHA and DPA n-6 can be produced without PUFA-PKS pathway gene disruption. This strain may also be used as a strain that produces EPA and/or ARA, and further disruption or transforming elongase or desaturase genes can create strains that produce desired PUFAs.

Example 5

[Measurement of Fatty Acid Composition of Lipids Produced by Δ4 Desaturase Gene Disruption and Transformation Strain of *Parietichytrium* sp. SEK358]

[Example 5-1]: Transfer of Δ4 Desaturase Gene Targeting Vector to *Parietichytrium* sp. SEK358 Strain Using the targeting vector produced with pRH126 (FIG. 17) described in Example 3-3 as a template, the gene was amplified with PrimeSTAR Max DNA Polymerase (available from Takara Bio Inc.) using RHO241 (described in Example 3-1, SEQ ID NO: 40) and RHO242 (described in Example 3-1, SEQ ID NO: 41) as primers. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH126 (FIG. 17) described in Example 3-3 was used as a template was 4562 bp.

The *Parietichytrium* sp. SEK358 strain was cultured for 1 to 2 days in a GY culture medium, and cells in the logarithmic growth phase were used in gene transfer. To cells corresponding to OD600=1 to 2, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium containing 1 mg/mL of G418. As a result, from 0 to 2 cells of drug resistant strain per shot were obtained.

[Example 5-2]: Identification of Δ4 Desaturase Gene Targeting Homologous Recombinant Genome DNA from the *Parietichytrium* sp. SEK358 strain and the Δ4 desaturase gene disruption strain were extracted by the method described in Example 2-2, and then A260/280 was measured and the DNA concentration was calculated. Using the genome DNA as templates, PCR for genome structure confirmation was performed using Prime-STAR GXL DNA Polymerase (available from Takara Bio Inc.). The positions of the primers used, the combinations used in amplification, and the expected sizes of the amplification products are illustrated in FIG. 18 (within homologous region) and FIG. 26 (outside homologous region). In the primer set designed within the homologous recombination region, 3046 bp was amplified in the *Parietichytrium* sp. SEK358 strain, and 2605 bp was amplified in the Δ4 desaturase gene disruption strain. [RHO251: 20 mer: 5'-GTG GTC GAA GTG GAG TAT CT-3' (SEQ ID NO: 49), RHO252: 20 mer: 5'-ACT CGC CAT ACA ACT TTA CA-3' (SEQ ID NO: 50)]. In the primer set designed outside the homologous recombination region, 5231 bp was amplified in the *Parietichytrium* sp. SEK358 strain, and 4790 bp was amplified in the Δ4 desaturase gene disruption strain. [HGO32: 25 mer: 5'-CGG AGC TCG GAG AAC AAC ATA GAA G-3' (SEQ ID NO: 51), HGO33: 23 mer: 5'-GTG CAA CCA GGT GGC AAG ATT GT-3' (SEQ ID NO: 52)].

Figure 27:
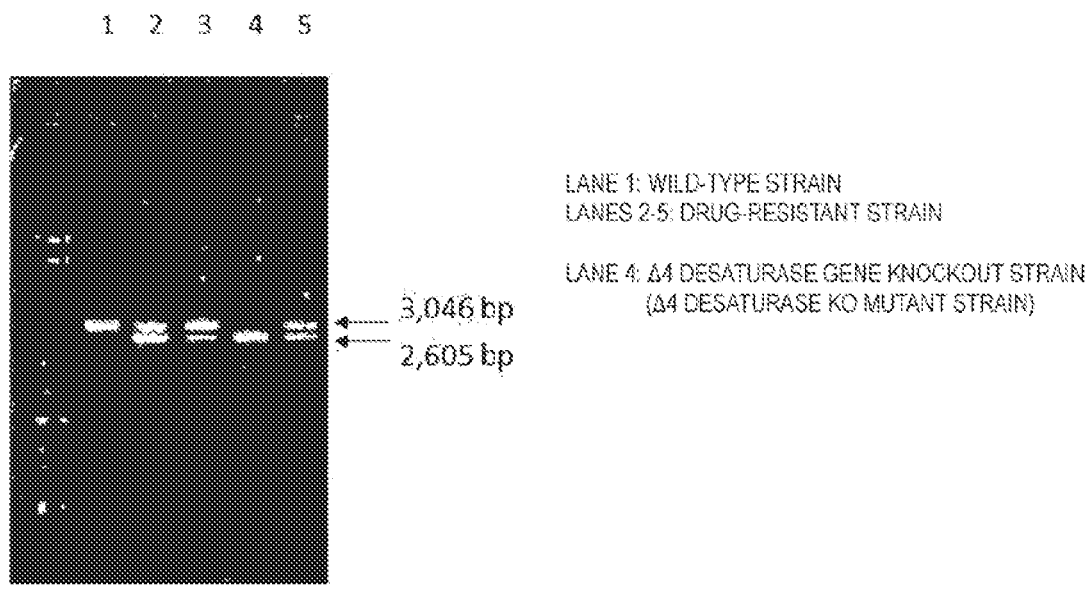
FIG. 27 illustrates evaluation results of Δ4 desaturase gene disruption by PCR using *Parietichytrium* sp. SEK358 genome DNA as a template in the case where the primers are set within the homologous recombination region.
Figure 28:
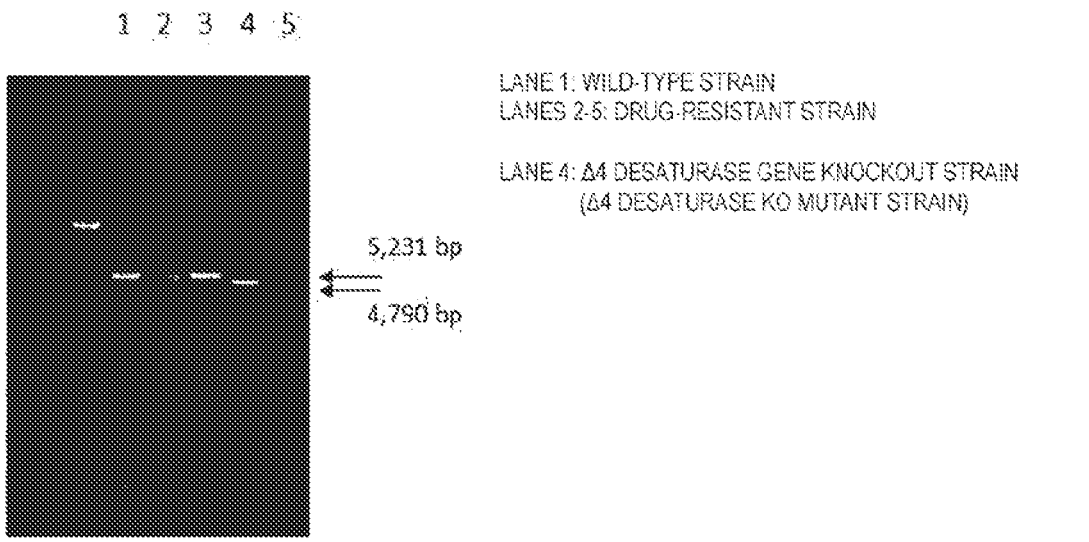
FIG. 28 illustrates evaluation results of Δ4 desaturase gene disruption by PCR using *Parietichytrium* sp. SEK358 genome DNA as a template in the case where the primers are set outside the homologous recombination region.

As a result, a Δ4 desaturase gene disruption strain in which there is no amplification derived from the wild-type allele (Wt allele) and there is amplification derived from the Δ4 desaturase gene KO allele (NeoR allele) was obtained (FIG. 27 lane 4, FIG. 28 lane 4: Δ4 desaturase KO mutant strain).

[Example 5-3]: Change in Fatty Acid Composition by Δ4 Desaturase Gene Disruption The *Parietichytrium* sp. SEK358 wild-type strain and the Δ4 desaturase gene disruption strain thereof (SEK358 delta4 des. KO mutant strain) were cultured according to the method described in Example 2-9, and after freeze drying, the fatty acids were methyl-esterified and analyzed using GC. In culturing, the GY liquid culture medium described in Example 1 supplemented with 0.1% of a vitamin solution (vitamin $B_1$ 200 mg, vitamin $B_2$ 1 mg, and vitamin $B_{12}$ 1 mg are dissolved in 100 mL of distilled water) and 0.2% of a trace element solution (EDTA disodium salt 30.0 g, $FeCl_3 \cdot 6H_2O$ 1.45 g, $H_3BO_3$ 34.2 g, $MnCl_2 \cdot 4H_2O$ 4.3 g, $ZnCl_2$ 1.335 g, $CoCl_2 \cdot 6H_2O$ 0.13 g, $NiSO_4 \cdot 6H_2O$ 0.26 g, $CuSO_4 \cdot 5H_2O$ 0.01 g, and $NaMoO_4 \cdot 2H_2O$ 0.025 g are dissolved in 1 L of distilled water) was used. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(2° C./min)→220° C. (10 min); carrier gas: He (1.3 mL/min).

Figure 29:
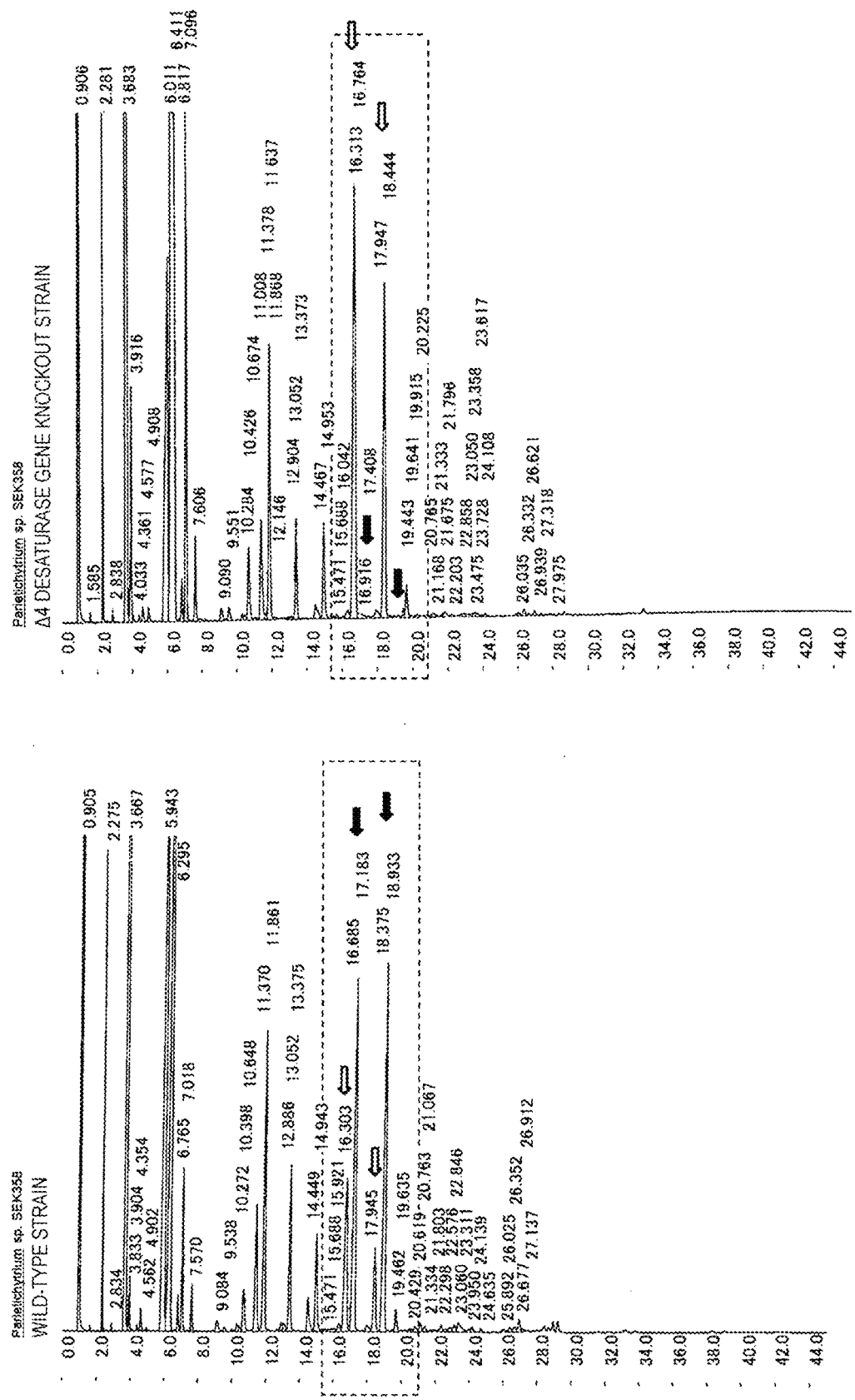
FIG. 29 is a gas chromatograph analysis chart of the fatty acid compositions of the *Parietichytrium* sp. SEK358 wild-type strain and the Δ4 desaturase gene disruption strain thereof.
Figure 30:
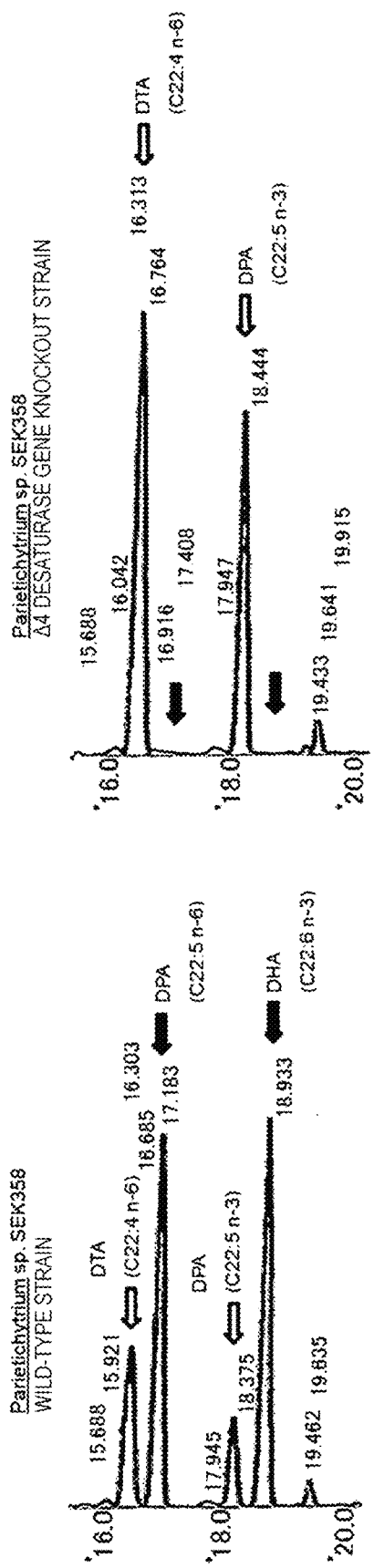
FIG. 30 is a partial enlarged diagram of FIG. 29.
Figures 31, 32:
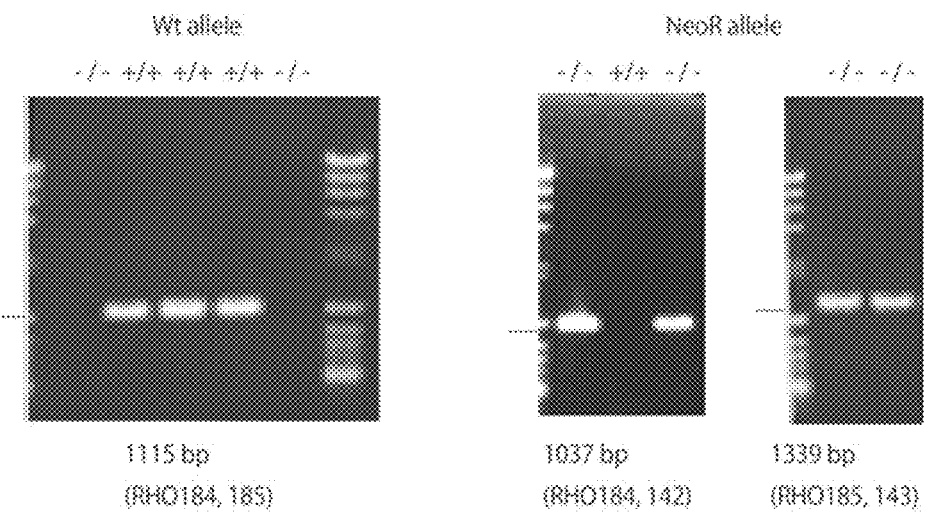
FIG. 31 shows a comparison of the fatty acid compositions of the *Parietichytrium* sp. SEK358 wild-type strain and the Δ4 desaturase gene disruption strain thereof. This table is a quantification of the chart of FIG. 29. In the table, the less-than sign (<) indicates less than or equal to the number following it.
FIG. 32 illustrates an evaluation of C20 elongase gene disruption by PCR using *Parietichytrium* sp. SEK571 genome DNA as a template. (Description of symbols)+/+: *Parietichytrium* sp. SEK571 wild-type strain; −/−: C20 elongase gene disruption strain derived from *Parietichytrium* sp. SEK571 strain

The analysis results chart is shown in FIG. 29, and a partial enlarged diagram of the chart is shown in FIG. 30. The table in FIG. 31 shows a quantification of the chart of FIG. 29. This table shows a comparison of the fatty acid compositions of the *Parietichytrium* sp. SEK358 wild-type strain and the Δ4 desaturase gene disruption strain thereof. The table shows that, of the total fatty acid composition, ARA is 3.03%, DGLA is 1.35%, ETA is 0.03%, EPA is 1.10%, n-6 DPA is 0.00%, and DHA is 0.00%. FIG. 31 shows that, by GC area, LA/EPA is 4.2, GLA/EPA is 0.71, DTA/EPA is 7.19, DTA/ARA is 2.60, DTA/DGLA is 5.85, DGLA/LA is 0.29, ARA/LA is 0.66, EPA/LA is 0.24, DTA/LA is 1.71, DGLA/GLA is 1.72, ARA/GLA is 3.87, C20 PUFA/C22 PUFA is 0.42, and n-6 PUFA/n-3 PUFA is 2.0.

The results showed that when the Δ4 desaturase gene was disrupted in the *Parietichytrium* sp. SEK358 strain, DHA and DPA n-6 cannot be substantially biosynthesized, and conversely, n-3 DPA and DTA, which are substrates thereof, increase.

By selecting the labyrinthulid *Parietichytrium* sp. SEK358 having no PUFA-PKS pathway in this manner, a strain that accumulates PUFAs other than DHA and n-6 DPA can be produced without PUFA-PKS pathway gene disruption. This strain may also be used as a strain that produces n-3 DPA and/or DTA, and further disruption or transforming elongase or desaturase genes can create strains that produce desired PUFAs.

Example 6

[Measurement of Fatty Acid Composition of Lipids Produced by C20 Elongase Gene Disruption and Transformation Strain of *Parietichytrium* sp. SEK571]

[Example 6-1]: Transfer of C20 Elongase Gene Targeting Vector to *Parietichytrium* sp. SEK571 Strain Using the targeting vector produced with pRH85 (FIG. 9) described in Example 2-6 as a template, the gene was amplified with PrimeSTAR Max DNA Polymerase (available from Takara Bio Inc.) using RHO153 (described in Example 2-4, SEQ ID NO: 24) and RHO154 (described in Example 2-4, SEQ ID NO: 25) as primers. [PCR cycles: 98° C. 2 min/98° C. 30 sec, 68° C. 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH85 (FIG. 9) described in Example 2-6 was used as a template was 2661 bp, and resulted in a sequence including genus *Parietichytrium* C20 elongase gene front half—SV40 terminator sequence—artificially synthesized neomycin resistance gene sequence—ubiquitin promoter sequence—genus *Parietichytrium* C20 elongase gene back half (described in Example 2-7, SEQ ID NO: 31).

The *Parietichytrium* sp. SEK571 strain was cultured for 3 days in a GY culture medium, and cells in the logarithmic growth phase were used in gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1550 psi). After a recovery time of 24 hr, the transgenic cells were spread on a PDA agar plate culture medium containing 0.5 mg/mL of G418. As a result, from 5 to 15 cells of drug resistant strain per shot were obtained.

[Example 6-2]: Identification of C20 Elongase Gene Targeting Homologous Recombinant Genome DNA of the *Parietichytrium* sp. SEK571 strain and the C20 elongase gene disruption strain were extracted by the method described in Example 2-2, and then A260/280 was measured and the DNA concentration was calculated.

Using the genome DNA as templates, PCR for genome structure confirmation was performed using Mighty Amp DNA Polymerase (available from Takara Bio Inc.). The positions of the primers used, the combinations used in amplification, and the expected sizes of the amplification products are illustrated in FIG. 10 described in Example 2-8.

RHO184 (described in Example 2-8, SEQ ID NO: 37) was set upstream of C20 elongase; RHO185 (described in Example 2-8, SEQ ID NO: 38) was set downstream; RHO142 (described in Example 2-8, SEQ ID NO: 35) and RHO143 (described in Example 2-8, SEQ ID NO: 36) were set on the artificially synthesized neomycin resistance gene. [PCR cycles: 98° C. 2 min/98° C. 10 sec, 68° 2 min, 30 cycles/68° C. 7 min].

A C20 elongase gene disruption strain in which there is no amplification in the wild-type allele (Wt allele) and there is amplification in the artificially synthesized neomycin resistance gene allele (NeoR allele) was obtained (FIG. 32).

[Example 6-3]: Change in Fatty Acid Composition by C20 Elongase Gene Disruption

The *Parietichytrium* sp. SEK571 strain and the gene disruption strain thereof (C20 elongase gene disruption strain, C20 KO) were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 33:
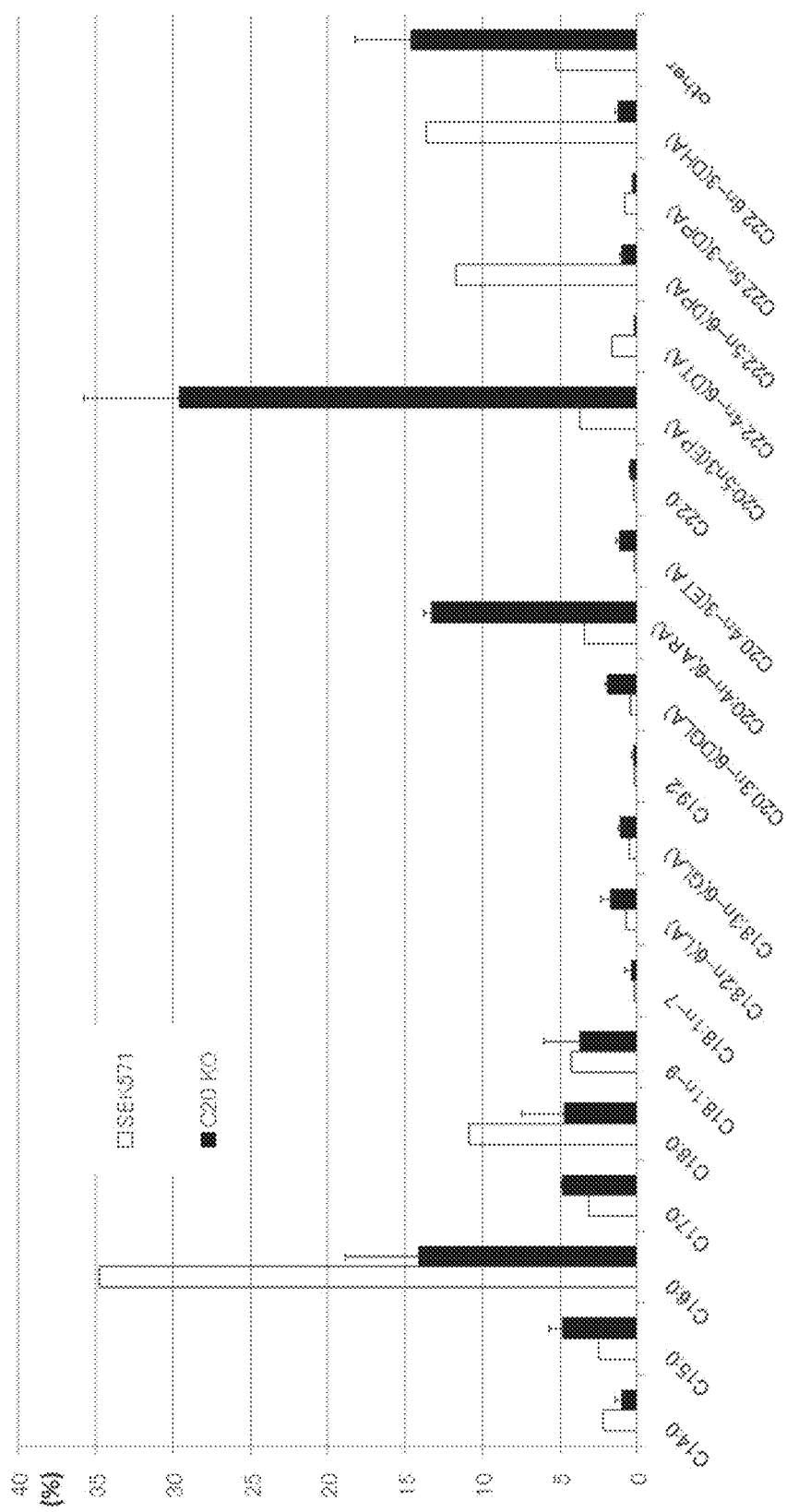
FIG. 33 illustrates a comparison of fatty acid compositions of the *Parietichytrium* sp. SEK571 wild-type strain and the C20 elongase gene disruption strain derived from *Parietichytrium* sp. SEK571 strain. The white bars and black bars represent the fatty acid composition of the wild-type strain and the gene disruption strain, respectively.

The changes in the fatty acid composition are shown in FIG. 33. Furthermore, FIG. 34 shows the proportion when the wild-type strain is taken as 100%.

FIG. 34 shows that, of the total fatty acid composition, ARA is 13.24%, DGLA is 1.93%, ETA is 1.14%, EPA is 29.58%, n-6 DPA is 0.96%, and DHA is 1.17%. FIG. 34 shows that, by GC area, LA/DHA is 1.5, GLA/DHA is 0.9, DGLA/DHA is 1.65, ARA/DHA is 11.3, EPA/DHA is 25.3, LA/EPA is 0.06, GLA/EPA is 0.04, DTA/EPA is 0.01, DTA/ARA is 0.01, DTA/DGLA is 0.08, LA/n-6 DPA is 1.8, GLA/n-6 DPA is 1.1, DGLA/n-6 DPA is 2.0, ARA/n-6 DPA is 13.8, EPA/n-6 DPA is 30.8, DGLA/LA is 1.1, ARA/LA is 7.8, EPA/LA is 17.4, DTA/LA is 0.09, DGLA/GLA is 1.8, ARA/GLA is 12.4, n-6 DPA/DTA is 6.4, DHA/n-3 DPA is 4.7, C20 PUFA/C22 PUFA is 18.1, and n-6 PUFA/n-3 PUFA is 0.51.

As a result, when the C20 elongase gene was disrupted in the *Parietichytrium* sp. SEK571 strain, fatty acids having not less than 22 carbon chains decreased while fatty acids having 20 carbon chains increased. Specifically, arachidonic acid increased approximately 4-fold and EPA increased approximately 8-fold, while DPA decreased to approximately 1/12 and DHA decreased to approximately 1/12.

The results show that *Parietichytrium* sp. SEK571 has very weak or no PUFA production activity via the PUFA-PKS pathway, and by selecting the labyrinthulid *Parietichytrium* sp. SEK571, a strain that accumulates PUFAs other than DHA and n-6 DPA can be produced without PUFA-PKS pathway gene disruption. This strain may also be used as a strain that produces EPA and/or ARA, and further disruption or transforming elongase or desaturase genes can create strains that produce desired PUFAs.

Comparative Example 1

[Measurement of Fatty Acid Composition of Lipids Produced by C20 Elongase Gene Disruption and Transformation Strain of *Thraustochytrium aureum* ATCC 34304]

[Comparative Example 1-1]: Extraction of Total RNA Derived from *T. aureum* ATCC 34304, and mRNA Purification A *T. aureum* ATCC 34304 culture solution on the third day of culturing using a GY liquid culture medium was centrifuged for 15 min at 3500×g, and the cells were collected. The obtained cells were washed by suspending in a sterilized physiological saline solution and then centrifuging again, and were then rapidly frozen with liquid nitrogen, and then ground into powder form in a mortar. Total RNA was extracted from the obtained crushed cell solution using Sepasol-RNA I Super (available from Nacalai Tesque, Inc.). Then, mRNA was purified from the total RNA according to manufacturer's instructions using Oligotex-dT30<Super> mRNA Purification Kit (trade name; available from Takara Bio Inc.). The obtained total RNA and mRNA were dissolved in an appropriate amount of TE, and then subjected to electrophoresis using formalin-modified gel (1% agarose/MOPS buffer). The result showed that total RNA extraction was successful, that mRNA was purified from the total RNA, and that the RNA was not decomposed by RNase. Furthermore, to proactively avoid RNA decomposition, rubber gloves, a mask, and the like were donned through the experimental operation, and the instruments used were completely RNase-free or the RNase used was inactivated by treatment with diethylpyrocarbonate (available from Nacalai Tesque, Inc.). Furthermore, when decomposing RNA, a solution obtained by adding the recombinant RNase inhibitor RNaseOUT (trade name; available from Invitrogen Corp.) to sterilized MilliQ water treated with diethylpyrocarbonate was used.

[Comparative Example 1-2]: Isolation of *T. Aureum* ATCC 34304-Derived Elongase Gene by RACE Using a histidine box (His box) in which the elongase gene was conserved to a high degree as a target, forward (elo-F; 5'-TTY YTN CAY GTN TAY CAY CAY-3') (SEQ ID NO: 53) and reverse (elo-R; 5'-GCR TGR TGR TAN ACR TGN ARR AA-3') (SEQ ID NO: 54) degenerate oligonucleotides were synthesized. The oligonucleotides were synthesized using a DNA synthesizer (available from Applied Biosystems Corp.). Next, 3'- and 5'-RACE cDNA libraries in which synthetic adapters were appended to the 3' and 5' terminals were produced according to manufacturer's instructions using SMART RACE cDNA Amplification Kit (trade name; available from Clontech Laboratories, Inc.). Using these as templates, 3'- and 5'-RACE were performed using the synthetic adapter-specific oligonucleotides and the above degenerate oligonucleotides elo-F and elo-R. [PCR cycles: 94° C. 1 min/94° C. 30 sec, 60° C. 30 sec, 72° C. 3 min, 30 cycles/72° C. 10 min/4° C. ∞]. As a result, bands of specifically amplified 3'- and 5'-RACE products were confirmed (FIG. 35). Next, the entire amounts of the RACE products were subjected to electrophoresis using 1% agarose gel, the separated DNA fragments were cut with a clean cutter or the like, and DNA fragments were extracted according to the method described in Non-patent Document 10. Then, TA cloning of the DNA fragments was performed using pGEM-T Easy Vector (available from Promega Corporation), and the base sequences thereof were determined according to the method of Sanger et al. (Non-patent Document 11). Specifically, using BigDye (trade name) Terminator v3.1 Cycle Sequencing Kit and 3130 Genetic Analyzer (available from Applied Biosystems Corp.), the base sequence was determined by the dye terminator method according to manufacturer's instructions.

As a result, two respective sequences of 190 bp and 210 bp named elo1 (SEQ ID NO: 55) and elo2 (SEQ ID NO: 56) were successfully identified in the 3'-RACE product, and one 200 bp sequence named elo3 (SEQ ID NO: 57) was successfully identified in the 5'-RACE product. The fact that these elo1, elo2, and elo3 sequences exhibited significant homology to various elongase gene sequences shows that these sequences are partial sequences of elongase genes derived from *T. aureum* ATCC 34304. Additionally, respective oligonucleotide primers were again designed for elo1, elo2, and elo3, and acquisition of cDNA sequences was attempted by RACE. The produced oligonucleotide primers are shown below. elo1 forward oligonucleotide primer (elo1-F1; 5'-TAT GAT CGC CAA GTA CGC CCC-3') (SEQ ID NO: 58) and reverse oligonucleotide primer (elo1-R1; 5'-GAA CTG CGT CAT CTG CAG CGA-3') (SEQ ID NO: 59), elo2 forward oligonucleotide primer (elo2-F1; 5'-TCT CGC CCT CGA CCA CCA AC-3') (SEQ ID NO: 60) and reverse oligonucleotide primer (elo2-R1: 5'-CGG TGA CCG AGT TGA GGT AGC C-3') (SEQ ID NO: 61), elo3 forward oligonucleotide primer (elo3-F1; 5'-CAA CCC TTT CGG CCT CAA CAA G-3') (SEQ ID NO: 62) and reverse oligonucleotide primer (elo3-R1; 5'-TTC TTG AGG ATC ATC ATG AAC GTG TC-3') (SEQ ID NO: 63).

Using the produced forward and reverse oligonucleotide primers, RACE and base sequence analysis of the amplified products were performed by the same methods as described above. As a result, for elo1, specifically amplified 3'- and 5'-RACE products were obtained, and since the duplicate portions thereof matched completely, they were proved to be an 1139 bp elo1 cDNA sequence (SEQ ID NO: 64). Similarly, for elo3, specifically amplified 3'- and 5'-RACE products were obtained, and since the duplicate portions thereof matched completely, they were proved to be a 1261 bp elo3 cDNA sequence (SEQ ID NO: 65).

As a result of sequence analysis, it was found that elo1 is composed of an 825 bp translation sequence (SEQ ID NO: 67) that encodes 275 amino acid residues (SEQ ID NO: 66), and as a result of a BLAST search, it was found not only that elo1 exhibited significant homology to various elongase genes, but also that elo1 completely matches a known presumed Δ5 elongase gene sequence derived from *T. aureum* (NCBI accession no. CS486301). On the other hand, elo3 was estimated to constituted of a 951 bp translation region (SEQ ID NO: 69) that encodes 317 amino acid residues (SEQ ID NO: 68), and as a result of a BLAST search, elo3 was found to exhibit significant homology to various elongase genes, and thus was confirmed to be a presumed elongase gene derived from *T. aureum* ATCC 34304. Furthermore, a His box in which the elongase gene was conserved to a high degree was found within the presumed amino acid sequences of the two genes. From the above results, the elo1 and elo3 gene were considered to be presumed elongase genes derived from *T. aureum* ATCC 34304 and were designated as TaELO1 and TaELO2, respectively.

[Comparative Example 1-3]: Expression of TaELO1 and TaELO2 with Brewer's Yeast *Saccharomyces cerevisiae* as Host, and Analysis of Fatty Acid Composition of Transgenic Strains Respective expression vectors were constructed in order to cause expression of TaELO1 and TaELO2 using brewer's yeast *S. cerevisiae* as a host. An outline thereof is given below. A pair of oligonucleotide primers (E1 HindIII; 5'-ATA AGC TTA AAA TGT CTA GCA ACA TGA GCG CGT GGG GC-3') (SEQ ID NO: 70) and (E1 XbaI; 5'-TGT CTA GAA CGC GCG GAC GGT CGC GAA A-3') (SEQ ID NO: 71) were produced based on the sequence of the TaELO1 translation region. E1 HindIII is a forward oligonucleotide primer and has a restriction enzyme HindIII site (AAGCTT) at the 5' terminal. Furthermore, the sequence near the start codon of TaELO1 has been modified in reference to the yeast consensus sequence ((A/Y) A (A/U) A AUG UCU; underlined portion is start codon) (Non-patent Document 12). E1 XbaI is a reverse oligonucleotide primer, and has an XbaI site (TCTAGA) at the 5' terminal.

Similarly, a pair of oligonucleotide primers (E2 HindIII; 5'-TAA GCT TAA AAT GTC TAC GCA CCT CGA AGA GCG CTC C-3') (SEQ ID NO: 72) and (E2 XbaI; 5'-CAT CTA GAC TCG GAC TTG GTG GGG GCG CTT G-3') (SEQ ID NO: 73) were produced based on the sequence of the TaELO2 translation region. E2 HindIII is a forward oligonucleotide primer and has a restriction enzyme HindIII site at the 5' terminal. Furthermore, the sequence near the start codon of TaELO2 has been modified in reference to the yeast consensus sequence. E2 XbaI is a reverse oligonucleotide primer, and has an XbaI site at the 5' terminal.

With the 5'-RACE cDNA library described in Comparative Example 1-2 as a template, PCR was performed using the above two oligonucleotide primer pairs. A 949 bp TaELO1 translation region (SEQ ID NO: 74) and a 967 bp TaELO2 translation region (SEQ ID NO: 75), in which the vicinity of the start codon was modified to the consensus sequence and having the restriction enzyme HindII at the 5' terminal and the restriction enzyme XbaI site at the 3' terminal, were amplified. Furthermore, to avoid elongation mistakes, PrimeSTAR DNA Polymerase (trade name; available from Takara Bio Inc.) having high correction activity was used. [PCR cycles: 98° C. 2 min/98° C. 5 sec, 60° C. 5 sec, 72° C. 1.5 min, 30 cycles/72° C. 7 min/4° C. ∞].

Next, the amplified PCR products were separated with 1% agarose gel, and then DNA fragments were cut and extracted from the agarose gel. Additionally, after treatment with restriction enzymes HindIII and XbaI, the DNG fragments were again purified using agarose gel, and a cyclized vector was constructed by ligation using DNA Ligation Kit "Mighty Mix" (available from Takara Bio Inc.) to a brewer's yeast expression vector pYES2/CT (available from Invitrogen Corp.) which was made into a straight chain by treatment with restriction enzymes HindIII and XbaI. Furthermore, by analyzing the base sequence, it was confirmed that mutations due to PCR elongation mistakes had not been introduced into the sequences of the TaELO1 and TaELO2 translation regions transformed into pYES2/CT. From the above result, a TaELO1 expression vector pYEELO1 and a TaELO2 expression vector pYEELO2 were successfully constructed.

Transformants in which the two constructed expression vectors and pYES2/CT had been transformed into brewer's yeast *S. cerevisiae* by the lithium acetate method were selected according to the methods described in Non-patent Document 13 and Non-patent Document 14. Next, the obtained transformants (pYEELO1 transgenic strain, pYEELO2 transgenic strain, and mock transgenic strain) were cultured according to the method of Qiu et al. (Non-patent Document 15), and cell-derived fatty acid extraction and methyl-esterification were performed. However, culturing was carried out after adding 0.02 mM each of the following acids in respective final concentrations: α-linolenic acid (ALA, C18:3Δ9, 12, 15) and linoleic acid (LA, C18:2Δ9, 12) as Δ9 elongase substrates; stearidonic acid (STA, C18:4Δ6, 9, 12, 15) and γ-linolenic acid (GLA, C18:3Δ6, 9, 12) as Δ6 elongase substrates; eicosapentaenoic acid (EPA, C20:5Δ5, 8, 11, 14, 17) and arachidonic acid (AA, C20:4Δ5, 8, 11, 14) as Δ5 elongase substrates. Then, gas chromatography (GC) analysis of the methyl-esterified fatty acids was performed according to the method of Abe et al. (Non-patent Document 16). In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

As a result, the pYEELO1 transgenic strain exhibited Δ6 elongase activity, by which stearidonic acid (STA) is converted to eicosatetraenoic acid (ETA, 20:4Δ8, 11, 14, 17) and γ-linolenic acid (GLA) is converted to dihomo-γ-linolenic acid (DGLA, C20:3Δ8, 11, 14), which was not seen in the host (mock transgenic strain). On the other hand, the pYEELO1 transgenic strain exhibited Δ9 elongase activity, by which α-linolenic acid (ALA) is converted to eicosatrienoic acid (ETrA, C20:3Δ11, 14, 17) and linoleic acid (LA) is converted to eicosadienoic acid (EDA, C20:3Δ11, 14), as well as Δ5 elongase (=C20 elongase) activity, by which eicosapentaenoic acid (EPA) is converted to ω3 docosapentaenoic acid (ω3 DPA, C22:5Δ7, 10, 13, 16, 19) and arachidonic acid (ARA) is converted to docosatetraenoic acid (DTA, C22: 4Δ7, 10, 13, 16) (Table 1).

Furthermore, the pYEELO2 transgenic strain exhibited Δ5 elongase (=C20 elongase) activity by which EPA is converted to ω3 DPA (C22: 5Δ7, 10, 13, 16, 19) and ARA is converted to DTA, which was not seen in the host. On the other hand, the pYEELO2 transgenic strain exhibited slight Δ6 elongase activity, by which STA is converted to ETA and GLA is converted to DGLA (Table 1). The above result shows that TaELO1 is Δ6/Δ9/Δ5 elongase, and TaELO2 is Δ5/Δ6 elongase.

TABLE 1

|  | mock | TaELO1 | TaELO2 |  | mock | TaELO1 | TaELO2 |
| --- | --- | --- | --- | --- | --- | --- | --- |
| LA supplemented (0.2 mM) | | | | ALA supplemented (0.2 mM) | | | |
| LA | 30.5 | 23.5 | 36.3 | ALA | 49.1 | 25.8 | 47.1 |
| EDA | 0.2 | 8.9 | 0.2 | ETrA | 0.2 | 17.9 | 0.3 |
| Conversion efficiency (%) | | 27.4 | | Conversion efficiency (%) | | 41 | |
| GLA supplemented (0.2 mM) | | | | STA supplemented (0.2 mM) | | | |
| GLA | 44.0 | 7.6 | 43.6 | STA | 46.2 | 8.3 | 40.5 |
| DGLA | 0.2 | 29.0 | 0.8 | ETA | 0.3 | 28.1 | 1.7 |
| Conversion efficiency (%) | | 79.3 | 1.9 | Conversion efficiency (%) | | 77.2 | 4.0 |
| ARA supplemented (0.2 mM) | | | | EPA supplemented (0.2 mM) | | | |
| ARA | 30.9 | 23.2 | 8.9 | EPA | 42.0 | 31.2 | 13.1 |
| ADA | — | 5.8 | 13.6 | DPA | 0.1 | 10.6 | 24.5 |
| Conversion efficiency (%) | | 20.1 | 60.3 | Conversion efficiency (%) | | 25.3 | 65.1 |

Conversion efficiency (%) = 100 × product (area)/substrate (area) + product (area) (n = 1)

[Comparative Example 1-4]: Acquisition of TaELO2 ORF Upstream and Downstream Regions by PCR Genome Walking In the targeting vector for TaELO2 disruption, the regions upstream and downstream of TaELO2 ORF serving as homologous recombination sites were acquired by PCR genome walking. An overview is given below.

Cells of the *T. aureum* ATCC 34304 strain on the third day of culturing in a GY liquid culture medium were rapidly frozen with liquid nitrogen, and then ground into powder form in a mortar. After genome DNA was extracted according to the method described in Non-patent Document 17, and was dissolved in an appropriate quantity of TE. The quantity and purity of the genome DNA were tested by O.D. 260 and O.D. 280 measurement. Next, a genome DNA library was constructed, wherein a cassette sequence having restriction enzyme sites was appended to genome DNA cut with various restriction enzymes according to the manufacturer's protocol using TaKaRa LA PCR (trade name) in vitro Cloning Kit (available from Takara Bio Inc.). Then, using the produced genome DNA library as a template, nested PCR was performed according to the manufacturer's protocol using forward oligonucleotide primers E2 XbaI (described in Comparative Example 1-3, SEQ ID NO: 73) produced based on the sequence of TaELO2 and elo3-F1 (described in Comparative Example 1-2, SEQ ID NO: 62), or the reverse oligonucleotide primers E2 HindIII (described in Comparative Example 1-3, SEQ ID NO: 72) and elo3-R1 (described in Comparative Example 1-2, SEQ ID NO: 63), together with oligonucleotide primers complementary to the sequences of cassettes included in the kit. As a result, an 1122 bp TaELO2 ORF upstream sequence (SEQ ID NO: 76) and a 1204 bp TaELO2 ORF downstream sequence (SEQ ID NO: 77) were successfully acquired.

[Comparative Example 1-5]: Construction of TaELO2 Targeting Vector with Neor as Selection Marker A DNA fragment in which TaELO2 ORF upstream sequence/artificially synthesized Neor/TaELO2 ORF downstream sequence were ligated and produced by fusion PCR. The oligonucleotide primers used were as shown below.

```
KO Pro F SmaI
                                     (SEQ ID NO: 78)
(31mer: 5'-CTC CCG GGT GGA CCT AGC GCG TGT GTC
ACC T-3')

(SEQ ID NO: 79)
Pro R (25mer: 5'-GGT CGC GTT TAC AAA GCA GCG CAG
C-3')

(SEQ ID NO: 80)
SNeo F (52mer: 5'-GCT GCG CTG CTT TGT AAA CGC GAC
CAT GAT TGA ACA GGA CGG CCT TCA CGC T-3')

(SEQ ID NO: 81)
SNeo R (52mer: 5'-TCG GGA GCC AGC CGG AAA CAG GTT
CAA AAG AAC TCG TCC AGG AGG CGG TAG A-3')

(SEQ ID NO: 82)
Term F (23mer: 5'-ACC TGT TTC CGG CTG GCT CCC
GA-3')
```

-continued

KO Term R SmaI (27mer: 5'-ATC CCG GGG CCG AGA ACG
GGG TCG CCC-3') (SEQ ID NO: 83)

Of these oligonucleotide primers, KO Pro F SmaI/Pro R were used in amplification of the TaELO2 ORF upstream sequence using the *T. aureum* ATCC 34304 genome DNA described in Comparative Example 1-4 as a template, SNeo F/SNeo R were used in amplification of artificially synthesized Neor using artificially synthesized Neor as a template, and Term F/KO Term R SmaI were used in amplification of the TaELO2 ORF downstream sequence using the *T. aureum* ATCC 34304 genome DNA described in Comparative Example 1-4 as a template. As PCR conditions, denaturation was performed at 98° C. for 10 sec, and annealing and the elongation reaction were performed while adjusting as appropriate according to Tm of the primers and the lengths of the amplification products.

As a result, a 2696 bp (SEQ ID NO: 84) TaELO2 ORF upstream sequence/artificially synthesized Neor/TaELO2 ORF downstream sequence was successfully ligated. The result of TA cloning of this sequence using pGEM-T Easy Vector (available from Promega Corporation) was used as a disruption vector, and was named pTKONeor.

[Comparative Example 1-6]: Transfer of TKONeor into *T. Aureum* ATCC 34304

Using, as a template, pTKONeor, which is the TaELO2 targeting vector with the artificially synthesized Neor as a selection marker produced in Comparative Example 1-5, TaELO2 ORF upstream sequence/artificially synthesized Neor/TaELO2 ORF downstream sequence was amplified using a pair of oligonucleotide primers KO Pro F SmaI (Comparative Example 1-5, SEQ ID NO: 78)/KO Term R SmaI (Comparative Example 1-5, SEQ ID NO: 83) and using PrimeSTAR (trade name) HS DNA Polymerase (available from Takara Bio Inc.). [PCR cycles: 98° C. 2 min/98° C. 10 sec, 68° C. 3 min, 30 cycles/68° C. 10 min/4° C. ∞]. After electrophoresis using 1% agarose gel, the DNA fragments were extracted, and after ethanol precipitation, the extracted DNA were dissolved in an appropriate quantity of TE. The quantity and purity of the DNA fragments were tested by O.D. 260 and O.D. 280 measurement. The obtained DNA fragment is called TKONeor hereinafter.

Next, the introduction of DNA was performed by the gene gun method. Specifically, the *T. aureum* ATCC 34304 strain was cultured at 25° C. at 150 rpm using a GY liquid culture medium, and cells of the middle to latter logarithmic growth phase were centrifuged for 10 min at 4° C. at 3500×g, and the supernatant was removed. Then, the obtained cells were resuspended in a GY liquid culture medium so as to result in 100 times the concentration of the original culture solution. 20 μL of this cell suspension was thinly spread uniformly and dried in a diameter of approximately 3 cm on PDA agar plate culture medium 5 cm in diameter containing 1 mg/mL of G418 (available from Nacalai Tesque, Inc.). Using a PDS-1000/He System (available from Bio-Rad Laboratories, Inc.), implantation was performed on under the conditions of target distance: 6 cm, vacuum: 26 inches Hg, microcarrier size: 0.6 μm, rupture disk (implantation pressure): 1100 psi. After that, 100 μL of PD liquid culture medium was added drop-wise to the PDA agar plate culture medium, and the cells were spread out again and static culturing was performed. As a result, transformants conferred with G418 resistance were obtained with efficiency of $4.7 \times 10^1$ cfu/μg DNA.

[Comparative Example 1-7]: PCR Using Genome DNA of Transformant in which TKONeor was Transformed as a Template Seven colonies of transformants were extracted with a toothpick, and were then inoculated in a GY liquid culture medium containing 0.5 mg/mL of G418 (available from Nacalai Tesque, Inc.). After subculturing multiple times, genome DNA was extracted from the cells by the method described in Comparative Example 1-4, and after ethanol precipitation, the extracted genome DNA was dissolved in an appropriate amount of TE. The quantity and purity of the extracted genome DNA were tested by O.D. 260 and O.D. 280 measurement. Then, with the obtained genome DNA of the obtained transformant and the wild-type as templates, PCR was performed using various oligonucleotide primer pairs. The used oligonucleotide primer pairs were as follows:

(1) Neor detection—Sneo F (described in Comparative Example 1-5, SEQ ID NO: 80) and SNeo R (described in Comparative Example 1-5, SEQ ID NO: 81);
(2) KO confirmation 1—KO Pro F SmaI (described in Comparative Example 1-5, SEQ ID NO: 78) and KO Term R SmaI (described in Comparative Example 1-5, SEQ ID NO: 83);
(3) KO confirmation 2—E2 KO ProF EcoRV (30 mer: 5'-GGA TAT CCC CCG CGA GGC GAT GGC TGC TCC-3') (SEQ ID NO: 85) and SNeo R (described in Comparative Example 1-5, SEQ ID NO: 81);
(4) KO confirmation 3—Sneo F (described in Comparative Example 1-5, SEQ ID NO: 80) and E2 KO Term R EcoRV (30 mer: 5'-TGA TAT CGG GCC GCG CCC TGG GCC GTA GAT-3') (SEQ ID NO: 86);
(5) TaELO2 amplification—E2 HindIII (described in Comparative Example 1-3, SEQ ID NO: 72) and E2 XbaI (described in Comparative Example 1-3, SEQ ID NO: 73) (FIG. 36A).

As a result, it was confirmed that six of the seven analyzed clones were transformants by random integration, but in one clone, TaELO2 ORF was substituted for Neor by homologous recombination (FIG. 36B, lanes 9, 13). At the same time, however, it was found that TaELO2 ORF was amplified (FIG. 36B, lane 17). This suggests the possibility that *T. aureum* ATCC 34304 is at least diploid or TaELO2 is a multicopy gene.

[Comparative Example 1-8]: Confirmation of TaELO2 Copy Number by Southern Blotting The following experiment was conducted in accordance with the method described in "DIG Manual [Japanese Edition] 8th, Roche Applied Science" (Non-patent Document 18). Specifically, wild-type genome DNA was cut with various restriction enzymes and then subjected to electrophoresis using 2.5 μg of 0.7% SeaKem (trade name) GTG (trade name) agarose (available from Takara Bio Inc.) per lane. This was transformed to a nylon membrane (Hybond (trade name)-N+, available from GE Healthcare Inc.), and hybridized at 48° C. for 16 hr with a DIG labeled probe produced using PCR DIG Probe Synthesis Kit (available from Roche Applied Science, Inc.). The pair of oligonucleotide primers used in producing the DIG labeled probe were TaELO2 det F (25 mer: 5'-GTA CGT GCT CGG TGT GAT GCT GCT C-3') (SEQ ID NO: 87) and TaELO2 det R (24 mer: 5'-GCG GCG TCC GAA CAG GTA GAG CAT-3') (SEQ ID NO: 88). [PCR cycles: 98° C. 2 min/98° C. 30 sec, 65° C. 30 sec, 72° C. 1 min, 30 cycles/72° C. 7 min/4° C. ∞]. The hybridized probes were detected using the color development method (NBT/BCIP solution).

The results demonstrated that TaELO2 is a single copy gene from the fact that single bands were detected in all lanes treated with the various restriction enzymes (FIG. 37). This suggests that *T. aureum* ATCC 34304 is at least diploid.

Figure 38A:
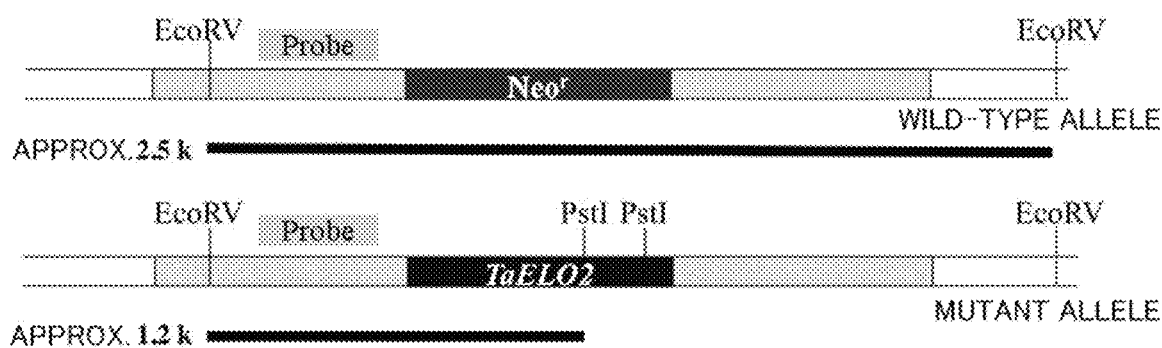
FIGS. 38A and 38B illustrate an evaluation by southern blotting of a transformant into which TKONeor was transformed in Comparative Example 1-9.
Figure 38B:
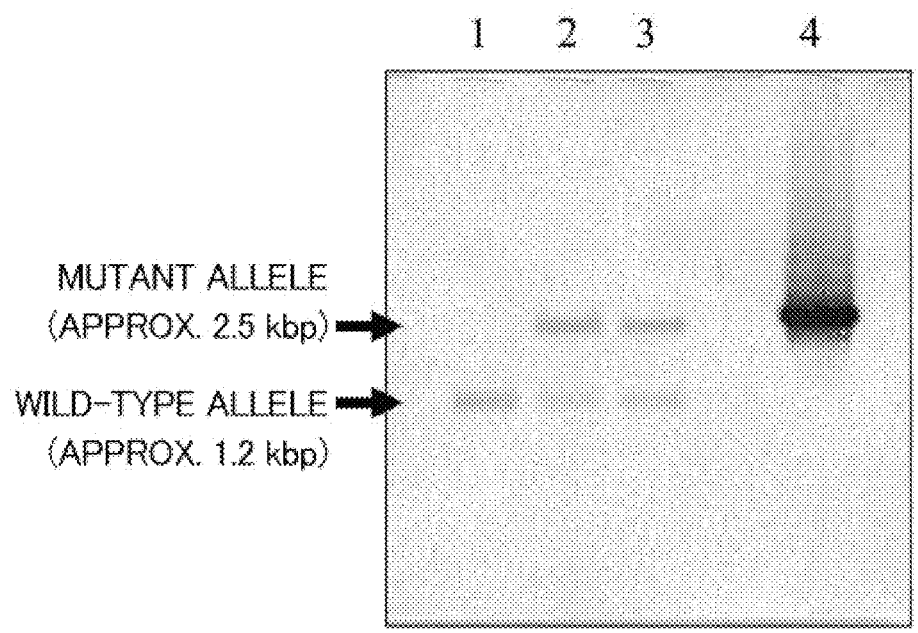

[Comparative Example 1-9]: Evaluation by Southern Blotting of Transformant in which TKONeor was Transformed Southern blotting was performed by the method described in Comparative Example 1-8. Specifically, southern blotting was performed using the color development method (NBT/BCIP solution) relative to genome DNA of the transformant and a wild-type strain digested with EcoRV and PstI, using a DIG labeled probe amplified using the pair of oligonucleotide primers uprobe F (35 mer: 5'-ATC CGC GTA TAT ATC CGT AAA CAA CGG AAC ATT CT-3') (SEQ ID NO: 89) and uprobe R (26 mer: 5'-CTT CGG GTG GAT CAG CGA GCG ACA GC-3') (SEQ ID NO: 90). [PCR cycles: 98° C. 2 min/98° C. 30 sec, 65° C. 30 sec, 72° C. 1 min, 30 cycles/72° C. 7 min/4° C. ∞]. In this case, in the wild-type allele, a DNA fragment of approximately 1.2 kbp was detected, but in the mutant allele in which TaELO2 ORF was substituted for Neor by homologous recombination, a DNA fragment of approximately 2.5 kbp was detected (FIG. 38A).

The result of analysis shows that *T. aureum* ATCC 34304 is at least diploid, since the wild-type allele band was also detected at the same time as the mutant allele.

[Comparative Example 1-10]: Construction of TaELO2 Targeting Vector with Hygr as Selection Marker To disruption the remaining wild-type allele, a TaELO2 targeting vector with Hygr as a selection marker was constructed.

First, a ubiquitin promoter sequence derived from *T. aureum* ATCC 34304 and Hygr were ligated by fusion PCR. The oligonucleotide primers used were as shown below.

```
ubi-600p F
                                         (SEQ ID NO: 91)
(27mer: 5'-GCC GCA GCG CCT GGT GCA CCC GCC GGG-3')

ubi-hygro R
                                         (SEQ ID NO: 92)
(59mer: 5'-TCG CGGG TGA GTT CAG GCT TTT TCA TGT

TGG CTA GTG TTG CTT AGG TCG CTT GCT GCT G-3')

ubi-hygro F
                                         (SEQ ID NO: 93)
(57mer: 5'-AGC GAC CTA AGC AAC ACT AGGC CAA CAT

GAA AAA GCC TGA ACT CAC CGC GAC GTC TG-3')

hygro R
                                         (SEQ ID NO: 94)
(29mer: 5'-CTA TTC CTT TGC CCT CGG ACG AGT GCT

GG-3')
```

Of these oligonucleotide primers, ubi-600p F/ubi-hygro R were used in amplification of the *T. aureum* ATCC 34304-derived ubiquitin promoter sequence using the *T. aureum* ATCC 34304 genome DNA described in Comparative Example 1-4 as a template. Ubi-hygro F/hygro R were used in amplification of artificially synthesized Hygr using pcDNA 3.1 Zeo (available from Invitrogen Corp.) as a template. As PCR conditions, denaturation was performed at 98° C. for 10 sec, and annealing and the elongation reaction were performed while adjusting as appropriate according to Tm of the primers and the lengths of the amplification products.

As a result, 1636 bp (SEQ ID NO: 95) of *T. aureum* ATCC 34304-derived ubiquitin promoter sequence/Hygr was successfully ligated. The result of TA cloning of this sequence using pGEM-T Easy Vector (available from Promega Corporation) was named pTub600Hygr.

Then, using pTub600Hygr as a template, PCR was performed using a pair of oligonucleotide primers ubi-600p F NheI (33 mer: 5'-GTG CTA GCC GCA GCG CCT GGT GCA CCC GCC GGG-3') (SEQ ID NO: 96) and hygro R XbaI (37 mer: 5'-GTT CTA GAC TAT TCC TTT GCC CTC GGA CGA GTG CTG G-3') (SEQ ID NO: 97) and using PrimeSTAR HS DNA Polymerase (available from Takara Bio Inc.). [PCR cycles: 98° C. 2 min/98° C. 10 sec, 68° C. 3 min, 30 cycles/68° C. 10 min/4° C. ∞]. As a result, a *T. aureum* ATCC 34304-derived ubiquitin promoter sequence/Hygr DNA fragment with NheI appended at the 5' terminal and an XbaI site appended at the 3' terminal was prepared. Furthermore, using pTKONeor described in Comparative Example 1-5 as a template, PCR was performed using a pair of oligonucleotide primers KO vec F XbaI (37 mer: 5'-GTT CTA GAC CTG TTT CCG GCT GGC TCC CGA GCC ATG C-3') (SEQ ID NO: 98) and KO vec R NheI (40 mer: 5'-GTG CTA GCG GTC GCG TTT ACA AAG CAG CGC AGC AAC AGA A-3') (SEQ ID NO: 99) and using PrimeSTAR HS DNA Polymerase (available from Takara Bio Inc.). [PCR cycles: 98° C. 2 min/98° C. 10 sec, 68° C. 3 min, 30 cycles/68° C. 10 min/4° C. ∞]. As a result, a linear vector in which Neor of pTKONeor described in Comparative Example 1-5 was removed and having NheI appended at the 3' terminal and an XbaI site appended at the 5' terminal was prepared. After the two DNA fragments were digested with NheI and XbaI, the DNA fragments were purified using agarose gel, and cyclic vectors were constructed using Ligation Convenience Kit (available from Nippon Gene Co., Ltd.).

The constructed TaELO2 targeting vector having Hygr as a selection marker includes pGEM-T Easy Vector (available from Promega Corporation) as a basic framework, and as an insertion sequence, had a 3537 bp (SEQ ID NO: 100) TaELO2 ORF upstream sequence/*T. aureum* ATCC 34304-derived ubiquitin promoter sequence/Hygr/TaELO2 ORF downstream sequence. This was named pTKOub600Hygr.

[Comparative Example 1-11]: Evaluation of Transformant by PCR Using KOub600Hygr Retransfer and Genome DNA as Templates, Southern Blotting, and RT-PCR Using, as a template, pTKOub600Hygr (described in Comparative Example 1-10), which is the constructed TaELO2 targeting vector with Hygr as a selection marker, TaELO2 ORF upstream sequence/*T. aureum* ATCC 34304-derived ubiquitin promoter sequence/Hygr/TaELO2 ORF downstream sequence was amplified using a pair of oligonucleotide primers KO Pro F SmaI (Comparative Example 1-5, SEQ ID NO: 78)/KO Term R SmaI (Comparative Example 1-5, SEQ ID NO: 83) and using PrimeSTAR HS DNA Polymerase (available from Takara Bio Inc.). [PCR cycles: 98° C. 2 min/98° C. 10 sec, 68° C. 3.5 min, 30 cycles/68° C. 10 min/4° C. ∞]. The obtained DNA fragment was named KOub600Hygr. This was transformed into the transformant obtained in Comparative Example 1-7 by the same technique, and after static culturing for 24 hr on PDA agar plate culture medium containing 1 mg/mL of G418 (available from Nacalai Tesque, Inc.), the cells were collected. The static culturing was continued on PDA agar plate culture medium containing 1 mg/mL of G418 (available from Nacalai Tesque, Inc.) and 2 mg/mL of hygromycin B (available from Wako Pure Chemical Industries, Ltd.) to obtain numerous transformants (transfer efficiency: 1.02× $10^3$ cfu/μg DNA).

Figure 39A:
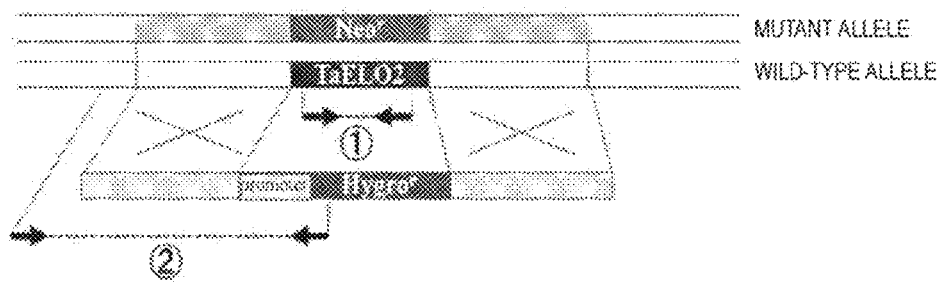
FIGS. 39A to 39C illustrate an evaluation by PCR using as a template genome DNA of a transformant obtained by retransfer of KOub600Hygr in Comparative Example 1-11.

Among them, 50 clones were extracted, and after subculturing multiple times in a GY liquid culture medium containing 1 mg/mL of G418 (available from Nacalai Tesque, Inc.) and 2 mg/mL of hygromycin B (available from Wako Pure Chemical Industries, Ltd.), genome DNA was extracted by the same technique as described in Comparative Example 1-4, and after ethanol precipitation, the extracted genome DNA was dissolved in an appropriate quantity of TE. The quantity and purity of the extracted genome DNA were tested by OD260 and OD280 measurement. Then, with the obtained transformant and wild-type genome DNA as templates, PCR was performed using various oligonucleotide primer pairs. [PCR cycles: 98° C. 2 min/98° C. 10 sec, 68° C. 1 min, 30 cycles/68° C. 10 min/4° C. ∞]. The used oligonucleotide primer pairs were as follows:
 (1) TaELO2 ORF detection—Sneo F (described in Comparative Example 1-5, SEQ ID NO: 80) and SNeo R (described in Comparative Example 1-5, SEQ ID NO: 81);
 (2) KO confirmation—E2 KO Pro F EcoRV (described in Comparative Example 1-7, SEQ ID NO: 85) and ubi-hygro R (described in Comparative Example 1-10, SEQ ID NO: 92) (FIG. 39A).

Figure 39B:
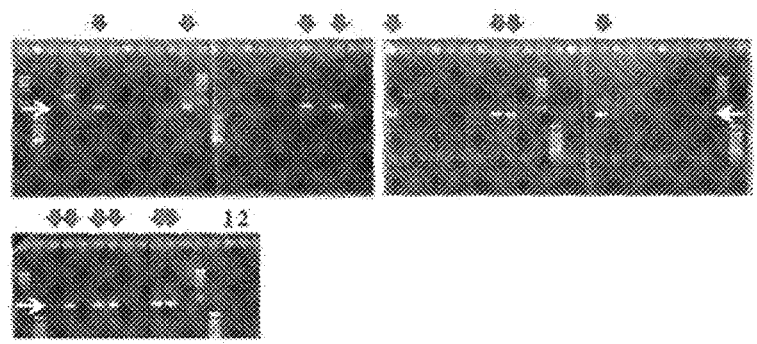
Figure 39C:
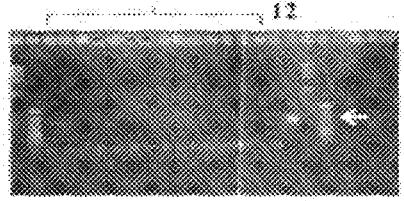

The results showed that of the 50 analyzed clones, 14 clones were transformants which caused homologous recombination in the form of substituting TaELO2 ORF (FIG. 39B, arrows). For these clones, it was confirmed that TaELO2 ORF was not amplified (FIG. 39C).

Then, southern blotting was performed using the technique described in Comparative Example 1-9. Specifically, southern blotting was performed by the color development method (NBT/BCIP solution) relative to genome DNA of the transformant and a wild-type strain digested with EcoRV and PstI, using a DIG labeled probe prepared using the pair of oligonucleotide primers uprobe F (SEQ ID NO: 89) and uprobe R (SEQ ID NO: 90). In this case, in the wild-type allele, a DNA fragment of approximately 1.2 kbp was detected; in the mutant allele in which TaELO2 ORF was substituted for Neor by homologous recombination, a DNA fragment of approximately 2.5 kbp was detected; in the mutant allele in which TaELO2 ORF was substituted for Hygr, a DNA fragment of approximately 1.9 kbp was detected (FIG. 40A).

As a result of analysis, a band of the wild-type allele of approximately 2.5 kbp was disappeared, and instead, a band of the mutant allele of approximately 1.9 kbp in which TaELO2 ORF was substituted for Hygr was detected (FIG. 40B).

Similarly, a DIG labeled probe that detects TaELO2 was prepared by PCR using the pair of oligonucleotide primers TaELO2 probe F (30 mer: 5'-ATG GCG ACG CGC ACC TCG AAG AGC GCT CCG-3') (SEQ ID NO: 101) and TaELO2 probe R (30 mer: 5'-AGG ATC ATC ATG AAC GTG TCG CTC CAG TCG-3') (SEQ ID NO: 102). [PCR cycles: 98° C. 2 min/98° C. 30 sec, 65° C. 30 sec, 72° C. 1 min, 30 cycles/72° C. 7 min/4° C. ∞]. Southern blotting was performed by the color development method (NBT/BCIP solution) relative to genome DNA of transformants (clones 1, 8, 9, 10) and a wild-type strain digested with EcoRV. In this case, TaELO2 was detected as a DNA fragment of approximately 2.5 kbp (FIG. 38A).

The result of analysis showed that TaELO2 was detected in the wild-type strain (FIG. 41, lane 1), whereas in the transformant, TaELO2 was not detected at all (FIG. 41, lanes 2 to 5).

Furthermore, to verify TaELO2 disruption at an mRNA level, TaELO2 mRNA was detected by RT-PCR. From the cells of the transformant (clones 1, 8, 9, 10) and the wild-type strain on the third day of culturing using a GY liquid culture medium, total RNA was extracted using Sepasol-RNA I Super (available from Nacalai Tesque, Inc.) in the same manner as Comparative Example 1-1. Then, 50 μg of total RNA cleaned up using RNeasy Mini Kit (available from QIAGEN N.V.) according to the manufacturer's protocol was treated for 1 hr at 37° C. using 50 U of Recombinant DNase I (available from Takara Bio Inc.), and contaminated genome DNA was decomposed and removed. Then, using the obtained total RNA as a template, a single-strand cDNA library was prepared according to manufacturer's instructions using oligo (dT) primer (available from Novagen Corp.) and PrimeScript Reverse Transcriptase (available from Takara Bio Inc.). Additionally, using the obtained single-strand cDNA library as a template, TaELO2 ORF was amplified using a pair of oligonucleotide primers E2 HindIII (described in Comparative Example 1-3, SEQ ID NO: 72) and E2 XbaI (described in Comparative Example 1-3, SEQ ID NO: 73) and using LA Taq Hot Start Version (available from Takara Bio Inc.). [PCR cycles: 98° C. 2 min/98° C. 10 sec, 68° C. 1 min, 30 cycles/68° C. 10 min/4° C. ∞].

Figure 42:
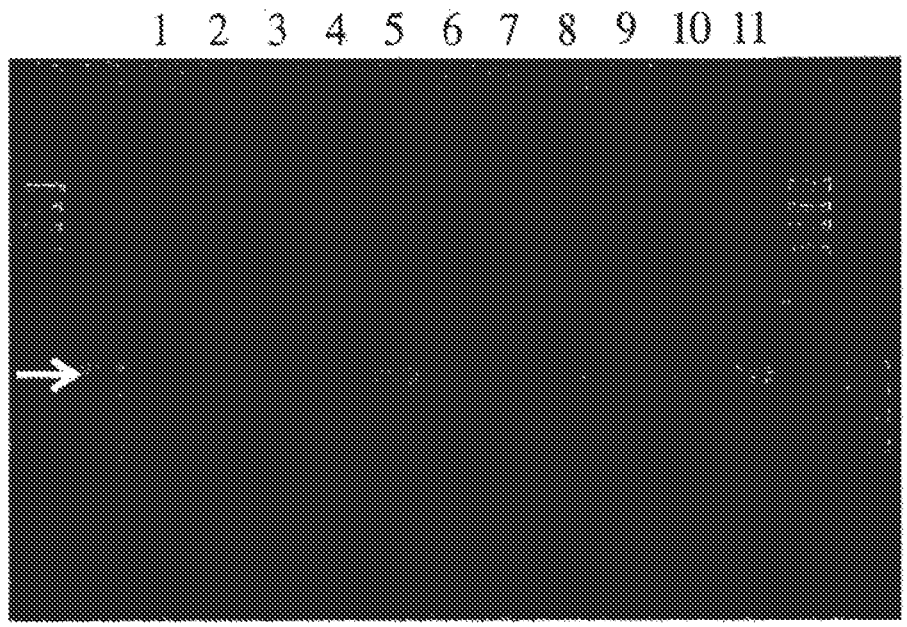
FIG. 42 illustrates the results of agarose electrophoresis of RT-PCR to detect TaELO2 mRNA in Comparative Example 1-11. (Brief description of symbols) 1 to 4: TaELO2 deletion homozygote; 5: Wild-type strain; 6 to 9: TaELO2 deletion homozygote, using total RNA as a template (negative control); 10: Wild-type strain, using total RNA as a template (negative control); 11: Using wild-type genome DNA as a template (positive control)

The result showed that TaELO2 mRNA was detected in the wild-type strain (FIG. 42, lane 5), whereas TaELO2 mRNA was not detected at all in the transformant (clones 1, 8, 9, 10) (FIG. 42, lanes 1 to 4).

The above results showed that a TaELO2 deletion homozygote in which TaELO2 had been completely disrupted was successfully obtained. The above results demonstrate that *T. aureum* ATCC 34304 is diploid.

[Comparative Example 1-12]: Comparison of Fatty Acid Compositions of Wild-Type Strain and TaELO2 Deletion Homozygote The fatty acid compositions of the TaELO2 deletion homozygote obtained in Comparative Example 1-11 and the wild-type strain were compared by GC analysis of the methyl-esterified fatty acids. Specifically, the cells of the wild-type strain and the TaELO2 deletion homozygote after 5 days of culturing in a GY liquid culture medium were collected. The fungus body-derived fatty acids were extracted and methyl-esterified by the method described in Comparative Example 1-3, and GC analysis was performed. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 43:
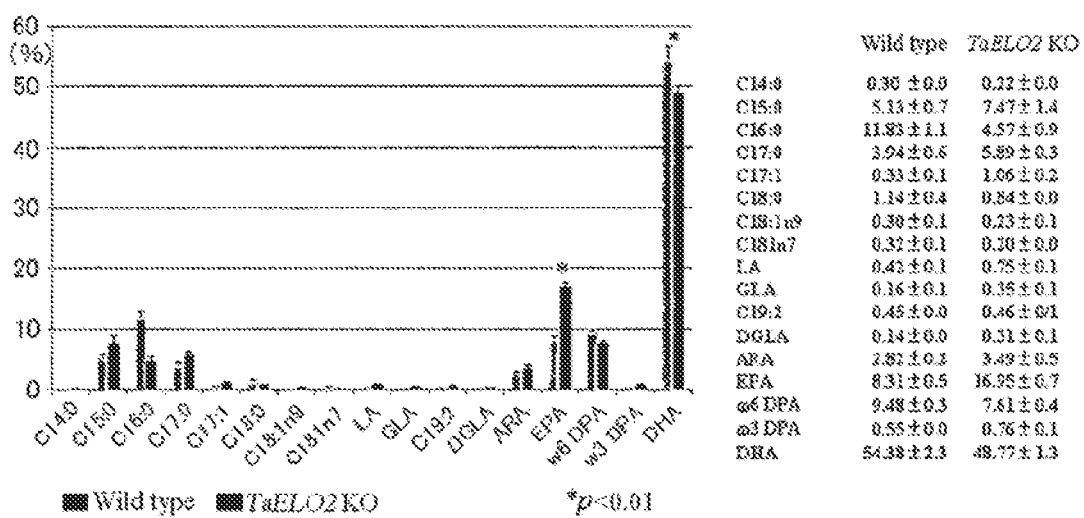
FIG. 43 illustrates the results of a fatty acid composition comparison of the wild-type strain and TaELO2 deletion homozygote in Comparative Example 1-12.

As a result, the quantity of EPA serving as a substrate of TaELO2 increased up to approximately 2-fold in the TaELO2 deletion homozygote (TaELO2 KO) compared to the wild-type strain (Wild type), and a decrease in the amount of the downstream metabolite DHA was observed (FIG. 43).

As described above, it was confirmed that due to C20 elongase gene disruption in *T. aureum* ATCC 34304, similar to genus *Parietichytrium* labyrinthulids, the quantity of the C20 elongase substrate EPA increased compared to the wild-type strain, and conversely, the downstream metabolite DHA and the like decreased. However, unlike the genus *Parietichytrium* labyrinthulids, the proportion of DHA did not really decrease in *T. aureum* ATCC 34304 even when the C20 elongase gene was disrupted. Specifically, the proportion of DHA in the wild-type strain was 54.38%, whereas the proportion of DHA was 48.77%, which is only slightly less in the C20 elongase gene KO strain. A similar trend was seen for n-6 DPA as well.

As described in Comparative Example 1-2, in *T. aureum* ATCC 34304, TaELO1 is present in addition to TaELO2, which was disrupted this time. In Comparative Example 1-3, it was shown that both have Δ5 elongase activity (=C20 elongase activity). However, it was also clear that the Δ5 elongase activity of TaELO1 is considerably lower than the Δ5 elongase activity of TaELO2, and the reason that DHA and n-6 DPA did not really decrease in the TaELO2 deletion homozygote (TaELO2 KO) is difficult to explain by the Δ5 elongase activity (=C20 elongase activity) of TaELO1. This suggests the possibility that in *Thraustochytrium aureum* ATCC 34304, DHA and n-6 DPA are produced via another biosynthesis pathway in addition to the elongase-desaturase pathway.

When such a labyrinthulid is selected, unlike Examples 2, 4, and 6, it is not possible to create a strain which accumulates PUFAs other than DHA and n-6 DPA even by disruption the C20 elongase gene. Therefore, creating such a strain requires disruption of a gene associated with a DHA and n-6 DPA biosynthesis pathway other than the elongase-desaturase pathway.

Comparative Example 2

[Measurement of Fatty Acid Composition of Lipids Produced by PUFA-PKS Gene Disruption and Transformation Strain of *Thraustochytrium aureum* ATCC 34304]

[Comparative Example 2-1]: PUFA-PKS Pathway Associated Gene: OrfA Upstream Sequence Cloning After genome DNA was extracted from *Thraustochytrium aureum* ATCC 34304 by the method described in Example 2-2, A260/280 was measured and the DNA concentration was calculated. Using this extracted genome DNA, a genome cassette library was produced using LA PCR (trade name) in vitro Cloning Kit (available from Takara Bio Inc.). A PCR lower primer [RHO20: 23 mer: 5'-CGA TGA AAG GTC ACA GAA GAG TC-3' (SEQ ID NO: 103)] was set on the PUFA-PKS pathway associated gene: OrfA described in Patent Document 4, and DNA was amplified by combining with the cassette primers contained in the above kit. [1st PCR cycles: 98° C. 2 min/98° C. 30 sec, 56° C. 30 sec, 72° C. 4 min, 30 cycles/72° C. 5 min]. Then, the 1st PCR amplification product was diluted 100-fold, and the DNA was amplified by combining the PCR lower primer [RHO20] and the nested primers contained in the above kit. [2nd PCR cycles: 98° C. 2 min/98° C. 30 sec, 56° C. 30 sec, 72° C. 4 min, 30 cycles/72° C. 5 min]. The obtained DNA fragment was cloned in pGEM-T Easy Vector, and after amplification with *E. coli*, the sequence was confirmed using a Dye Terminator Cycle Sequencing Kit (available from Beckman Coulter Inc.).

A DNA fragment of 3377 bp (SEQ ID NO: 105) containing 3181 bp (SEQ ID NO: 104) upstream of OrfA was cloned. It became clear that the OrfA upstream DNA sequence information was a total of 3181 bp.

[Comparative Example 2-2]: PUFA-PKS Pathway Associated Gene: OrfA Downstream Sequence Cloning The genome cassette library produced in Comparative Example 2-1 was used as a template. A PCR upper primer [RHO21: 21 mer: 5'-CAG GGC GAG CGA GTG TGG TTC-3' (SEQ ID NO: 106)] was set on the PUFA-PKS pathway associated gene: OrfA described in Patent Document 4, and DNA was amplified by the method described in Comparative Example 2-1. The obtained DNA fragment was cloned in pGEM-T Easy Vector, and after amplification with *E. coli*, the sequence was confirmed using a Dye Terminator Cycle Sequencing Kit (available from Beckman Coulter Inc.). A DNA fragment of 1204 bp (SEQ ID NO: 108) containing 1160 bp (SEQ ID NO: 107) downstream of OrfA was cloned.

A PCR upper primer [RHO28: 20 mer: 5'-TGA TGC CGA TGC TAC AAA AG-3' (SEQ ID NO: 109)] was again produced on SEQ ID NO: 94, and DNA was amplified by the method described in Comparative Example 1-2. The obtained DNA fragment was cloned in pGEM-T Easy Vector, and after amplification with *E. coli*, the sequence was confirmed using a Dye Terminator Cycle Sequencing Kit (available from Beckman Coulter Inc.).

Furthermore, a 1488 bp DNA fragment (SEQ ID NO: 110) containing the downstream sequence was cloned. It became clear that the OrfA downstream DNA sequence information is a total of 2551 bp (SEQ ID NO: 111).

[Comparative Example 2-3]: Production of PUFA-PKS Pathway Associated Gene: OrfA Targeting Vector Using *Thraustochytrium aureum* ATCC 34304 genome DNA as a template, an 18S rDNA sequence (1835 bp, SEQ ID NO: 112) was amplified with PrimeSTAR HS DNA Polymerase (available from Takara Bio Inc.). The PCR primers used were as shown below. TMO30 was set on the 18S rDNA sequence. TMO31 includes the 18S rDNA sequence and the EF1α promoter sequence. [TMO30: 30 mer: 5'-CGA ATA TTC CTG GTT GAT CCT GCC AGT AGT-3' (SEQ ID NO: 113), TMO31: 46 mer: 5'-GTA ACG GCT TTT TTT GAA TTG CAG GTT CAC TAC GCT TGT TAG AAA C-3' (SEQ ID NO: 114)]. [PCR cycles: 98° C. 10 sec/98° C. 10 sec, 58° C. 30 sec, 72° C. 2 min, 30 cycles/72° C. 2 min].

Furthermore, using *Thraustochytrium aureum* ATCC 34304 genome DNA as a template, an EF1α promoter sequence (661 bp, SEQ ID NO: 115) was amplified with PrimeSTAR HS DNA Polymerase (available from Takara Bio Inc.). The PCR primers used were as shown below. TMO32 includes the 18S rDNA sequence and the EF1α promoter sequence. TMO33 includes the EF1α promoter sequence and an artificially synthesized neomycin resistance gene sequence. [TMO32: 46 mer: 5'-GGT TTC CGT AGT GAA CCT GCA ATT CAA AAA AAG CCG TTA CTC ACA T-3' (SEQ ID NO: 116), TMO33: 46 mer: 5'-GCG TGA AGG CCG TCC TGT TCA ATC ATC TAG CCT TCC TTT GCC GCT G-3' (SEQ ID NO: 117)]. [PCR cycles: 98° C. 10 sec/98° C. 10 sec, 58° C. 30 sec, 72° C. 1 min, 30 cycles/72° C. 1 min].

Using the artificially synthesized neomycin resistance gene sequence as a template, an artificially synthesized neomycin resistance gene sequence (835 bp, SEQ ID NO: 118) was amplified with PrimeSTAR HS DNA Polymerase (available from Takara Bio Inc.). The PCR primers used were as shown below. TMO34 includes the EF1α promoter sequence and the artificially synthesized neomycin resistance gene sequence. TMO35 includes the artificially synthesized neomycin resistance gene sequence and the EF1α terminator sequence. [TMO34: 45 mer: 5'-CAT CGG CAA AGG AAG GCT AGA TGA TTG AAC AGG ACG GCC TTC ACG-3' (SEQ ID NO: 119), TMO35: 46 mer: 5'-GCG CAT AGC CGG CGC GGA TCT CAA AAG AAC TCG TCC AGG AGG CGG T-3' (SEQ ID NO: 120)]. [PCR cycles: 98° C. 10 sec/98° C. 10 sec, 58° C. 30 sec, 72° C. 1 min, 30 cycles/72° C. 1 min].

Using *Thraustochytrium aureum* ATCC 34304 genome DNA as a template, an EF1α terminator sequence (1249 bp, SEQ ID NO: 121) was amplified with PrimeSTAR HS DNA Polymerase (available from Takara Bio Inc.). The PCR primers used were as shown below. TMO36 includes the artificially synthesized neomycin resistance gene sequence and the EF1α terminator sequence. TMO37 was set within the EF1α terminator. [TMO36: 46 mer: 5'-TCC TGG ACG AGT TCT TTT GAG ATC CGC GCC GGC TAT GCG CCC GTG C-3' (SEQ ID NO: 122), TMO37: 30 mer: 5'-CAC TGC AGC GAA AGA CGG GCC GTA AGG ACG-3' (SEQ ID NO: 123)]. [PCR cycles: 98° C. 10 sec/98° C. 10 sec, 58° C. 30 sec, 72° C. 2 min, 30 cycles/72° C. 2 min].

Using SEQ ID NOS: 112, 115, 118, and 121 as templates, fusion PCR was performed according to the method described in Non-patent Document 9. LA Taq Hot Start Version (available from Takara Bio Inc.) was used for the enzymes. In the first amplification, the set of TMO30 (SEQ ID NO: 113) and TMO33 (SEQ ID NO: 117) and the set of TMO34 (SEQ ID NO: 119) and TMO37 (SEQ ID NO: 123) were used. In the second amplification, the set of TMO30 (SEQ ID NO: 113) and TMO37 (SEQ ID NO: 123) was used. As conditions of the PCR reaction, denaturation was performed at 98° C. for 10 sec, and annealing and the elongation reaction were performed while adjusting as appropriate according to Tm of the primers and the lengths of the amplification fragments (FIG. 42).

The DNA fragment ligated in this manner (FIG. 44, SEQ ID NO: 124, 4Δ53 bp) was cut at the EcoRI site in *T. aureum* 18S rDNA and at the NcoI site in the *T. aureum* EF1α terminator, and was bound to the vector derived from pGEM-T Easy Vector. This was named pRH5 (FIG. 45).

Using *Thraustochytrium aureum* ATCC 34304 genome DNA as a template, the PCR primers were set in the upstream sequence clarified in Comparative Example 2-1 (SEQ ID NO: 104) and the PUFA-PKS pathway associated gene: OrfA described in Patent Document 4, and DNA was amplified with PrimeSTAR HS DNA Polymerase with GC Buffer (available from Takara Bio Inc.). A 1218 bp DNA fragment (SEQ ID NO: 125) was obtained by this amplification. This was used as the 5' homologous region of the targeting vector. The PCR primers used are as shown below. As a linker sequence, an EcoRI site or a HindIII site was appended to each. [RHO33: 32 mer: 5'-CCC GAA TTC GGA CGA TGA CTG ACT GAC TGA TT-3' (SEQ ID NO: 126), RHO34: 28 mer: 5'-CCC AAG CTT GTC TGC CTC GGC TCT TGG T-3' (SEQ ID NO: 127)]. [PCR cycles: 98° C. 2 min/98° C. 30 sec, 57° C. 30 sec, 72° C. 1 min, 30 cycles/72° C. 3 min].

Using *Thraustochytrium aureum* ATCC 34304 genome DNA as a template, the PCR primers were set in the downstream sequence clarified in Comparative Example 2-2 (SEQ ID NO: 111), and DNA was amplified with PrimeSTAR HS DNA Polymerase with GC Buffer (available from Takara Bio Inc.). A 1000 bp DNA fragment (SEQ ID NO: 128) was obtained by this amplification. This was used as the 3' homologous region of the targeting vector. The PCR primers used were as shown below. An NcoI site as a linker sequence was appended to each. [RHO29: 28 mer: 5'-CCC CCA TGG TGT TGC TGT GGG ATT GGT C-3' (SEQ ID NO: 129), RHO30: 30 mer: 5'-CCC CCA TGG CTC GGT TAC ATC TCT GAG GAA-3' (SEQ ID NO: 130)]. [PCR cycles: 98° C. 2 min/98° C. 30 sec, 57° C. 30 sec, 72° C. 1 min, 30 cycles/72° C. 3 min].

The amplified upstream sequence was ligated to the EcoRI site and the HindIII site in pRH5 illustrated in FIG. 43. The amplified downstream sequence was ligated to the NcoI site. This vector was named pRH21.

Figure 44:
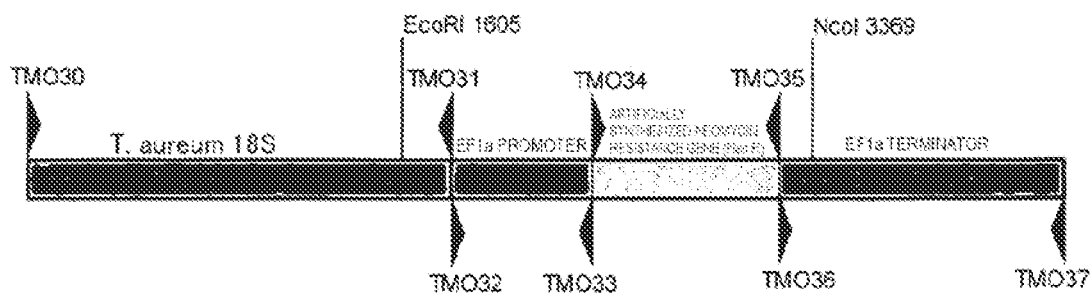
FIG. 44 is a schematic diagram of the primers used in fusion PCR and the products. The final product is a fused sequence of 18S rDNA derived from *Thraustochytrium aureum* ATCC 34304, an EF1α promoter derived from *Thraustochytrium aureum* ATCC 34304, an artificially synthesized neomycin resistance gene, and an EF1α terminator derived from *Thraustochytrium aureum* ATCC 34304.
Figure 45:
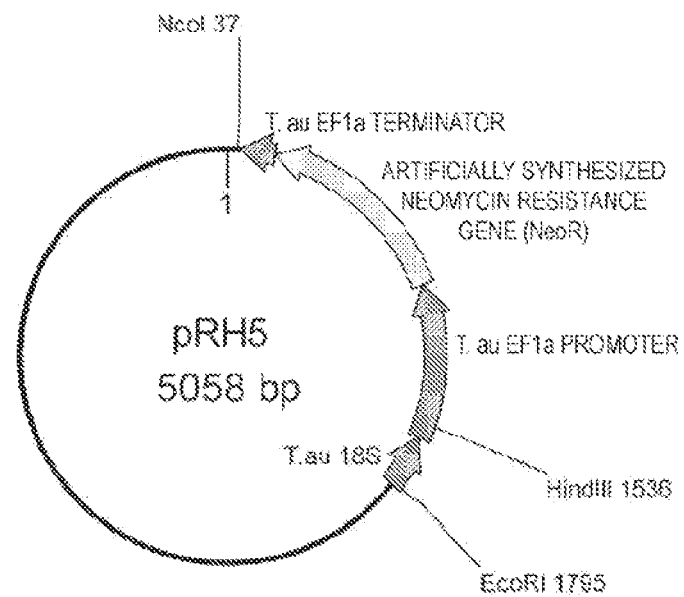
FIG. 45 illustrates a plasmid in which a portion of the ligated DNA fragment in FIG. 42 was cloned. The plasmid contains a partial sequence of the 3' side from the EcoRI site of 18S rDNA derived from *Thraustochytrium aureum* ATCC 34304, an EF1α promoter derived from *Thraustochytrium aureum* ATCC 34304, an artificially synthesized neomycin resistance gene, and a partial sequence of the 5' side from the NcoI site of the EF1α terminator derived from *Thraustochytrium aureum* ATCC 34304.

The targeting vector (pRH21) obtained using the produced artificially synthesized neomycin resistance gene is illustrated in FIG. 44.

[Comparative Example 2-4]: Production of PUFA-PKS Pathway Associated Gene: OrfA Targeting Vector (Hygromycin Resistance Gene)

Using pRH32 (FIG. 6) described in Example 2-3 as a template, a ubiquitin promoter—hygromycin resistance gene fragment (1632 bp, SEQ ID NO: 131) was amplified with PrimeSTAR HS DNA Polymerase with GC Buffer (available from Takara Bio Inc.). The PCR primers used were as shown below. RHO59 was set on the ubiquitin promoter, and a HindIII site was appended as a linker sequence. RHO60 contains a stop codon of the hygromycin resistance gene sequence, and has the linker sequences SphI and SalI. [RHO59: 36 mer: 5'-CCC AAG CTT GCC GCA GCG CCT GGT GCA CCC GCC GGG-3' (SEQ ID NO: 132), RHO60: 43 mer: 5'-CCC GCA TGC GTC GAC TAT TCC TTT GCC CTC GGA CGA GTG CTG G-3' (SEQ ID NO: 133)]. [PCR cycles: 98° C. 2 min/98° C. 30 sec, 68° ° C. 2 min, 30 cycles/68° C. 2 min].

Figure 46:
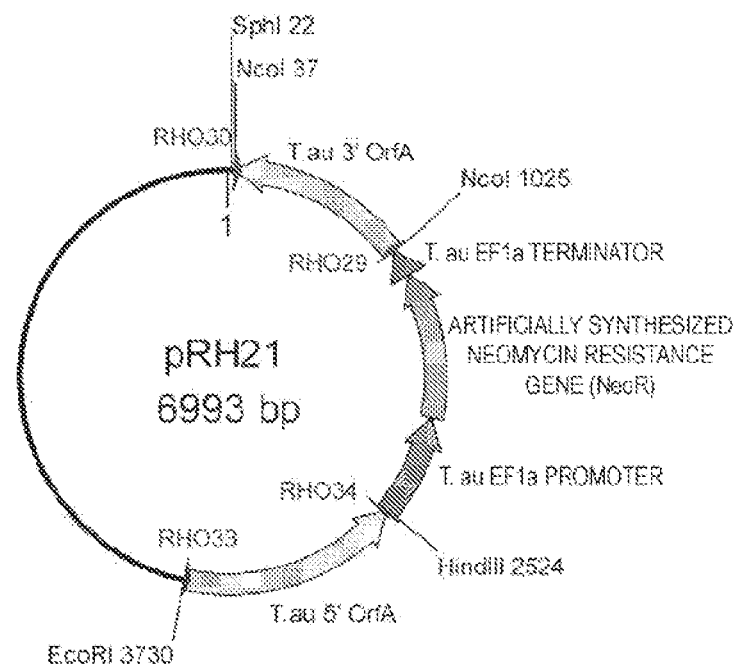
FIG. 46 illustrates the produced targeting vector of *Thraustochytrium aureum* ATCC 34304 PKS pathway associated gene orfA. As a drug resistance marker, the vector has a neomycin resistance gene.
Figure 47:
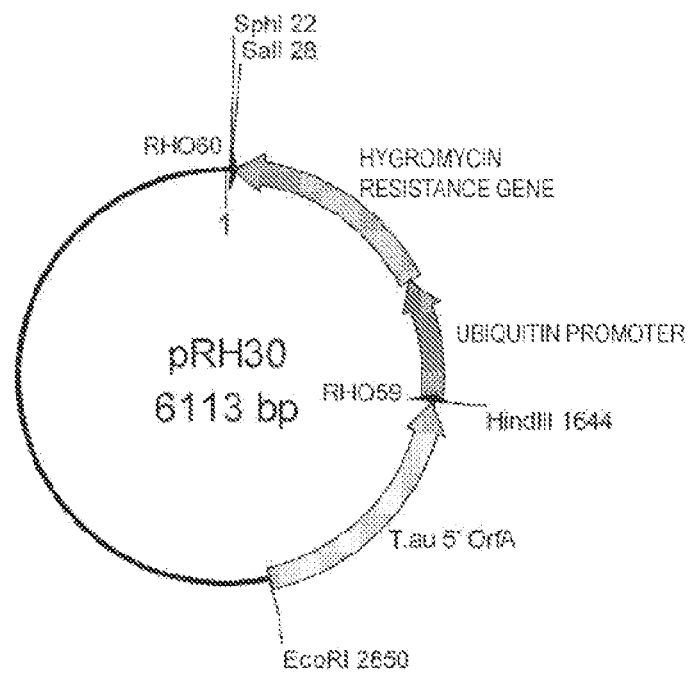
FIG. 47 illustrates a plasmid containing an upstream sequence of the *Thraustochytrium aureum* ATCC 34304 PKS pathway associated gene orfA, a ubiquitin promoter derived from *Thraustochytrium aureum* ATCC 34304, and a hygromycin resistance gene.

The amplified fragment was ligated to the HindIII and SphI sites of pRH21 (FIG. 46) described in Comparative Example 2-3 (FIG. 47, pRH30).

Using *Thraustochytrium aureum* ATCC 34304 genome DNA as a template, the DNA was amplified with PrimeSTAR HS DNA Polymerase with GC Buffer (available from Takara Bio Inc.) using the produced PCR primers in the downstream sequence (SEQ ID NO: 111) clarified in Comparative Example 2-2. A 1000 bp DNA fragment (SEQ ID NO: 134) was obtained by this amplification. This was used as the 3' homologous region of the targeting vector. The PCR primers used were as shown below. A SalI site as a linker sequence was also appended. [RHO61: 29 mer: 5'-CCC GTC GAC GTG TTG CTG TGG GAT TGG TC-3' (SEQ ID NO: 135), RHO62: 29 mer: 5'-CCC GTC GAC TCG GTT ACA TCT CTG AGG AA-3' (SEQ ID NO: 136)]. [PCR cycles: 98° C. 2 min/98° C. 30 sec, 57° C. 30 sec, 72° C. 1 min, 30 cycles/72° C. 3 min].

Figure 48:
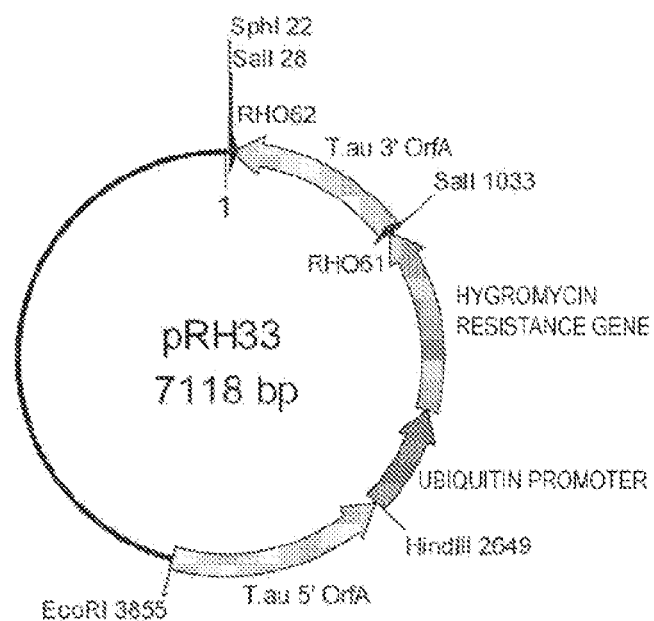
FIG. 48 illustrates the produced targeting vector of *Thraustochytrium aureum* ATCC 34304 PKS pathway associated gene orfA. As a drug resistance marker, the vector has a hygromycin resistance gene.

The amplified downstream sequence was ligated to the SalI site of pRH30 (FIG. 45). This was named pRH33. The targeting vector (pRH33) obtained using the produced hygromycin resistance gene is illustrated in FIG. 48.

[Comparative Example 2-5]: PUFA-PKS Pathway Associated Gene: OrfA Targeting Vector Transfer Using the targeting vectors produced in Comparative Examples 2-3 and 2-4 as templates, the genes were amplified with PrimeSTAR Max DNA Polymerase (available from Takara Bio Inc.) using RHO30 (described in Comparative Example 2-3, SEQ ID NO: 130) and RHO33 (described in Comparative Example 2-3, SEQ ID NO: 126) as primers. [PCR cycles: 98° C. 2 min/98° C. 30 sec, 60° C. 30 sec, 72° C. 1 min, 30 cycles/72° C. 3 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH21 (FIG. 46) described in Comparative Example 2-3 was used as a template was 3705 bp, and resulted in a sequence including *Thraustochytrium aureum* OrfA gene upstream—EF1α promoter sequence—artificially synthesized neomycin resistance gene sequence—*Thraustochytrium aureum* OrfA gene downstream (SEQ ID NO: 137). The transfer fragment obtained when pRH33 (FIG. 46) described in Comparative Example 2-4 was used as a template was 3826 bp, and resulted in a sequence including *Thraustochytrium aureum* OrfA gene upstream—ubiquitin promoter sequence—hygromycin resistance gene sequence—*Thraustochytrium aureum* OrfA gene downstream (SEQ ID NO: 138).

The *Thraustochytrium aureum* ATCC 34304 strain was cultured for 4 days in a GY culture medium, and cells in the logarithmic growth phase were used in gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1100 psi). After a recovery time of 4 to 6 hr, the transgenic cells were spread on a PDA agar plate culture medium (containing 2 mg/mL of G418 or containing 2 mg/mL of hygromycin). As a result, from 100 to 200 cells of drug resistant strain per shot were obtained.

[Comparative Example 2-6]: Identification of PUFA-PKS Pathway Associated Gene: OrfA Gene Targeting Homologous Recombinant After genome DNA was extracted from *Thraustochytrium aureum* ATCC 34304 and a hetero homologous recombinant and homo homologous recombinant (PKS pathway associated gene disruption strain) by the method described in Example 2-2, A260/280 was measured and the DNA concentration was calculated.

Figure 49:
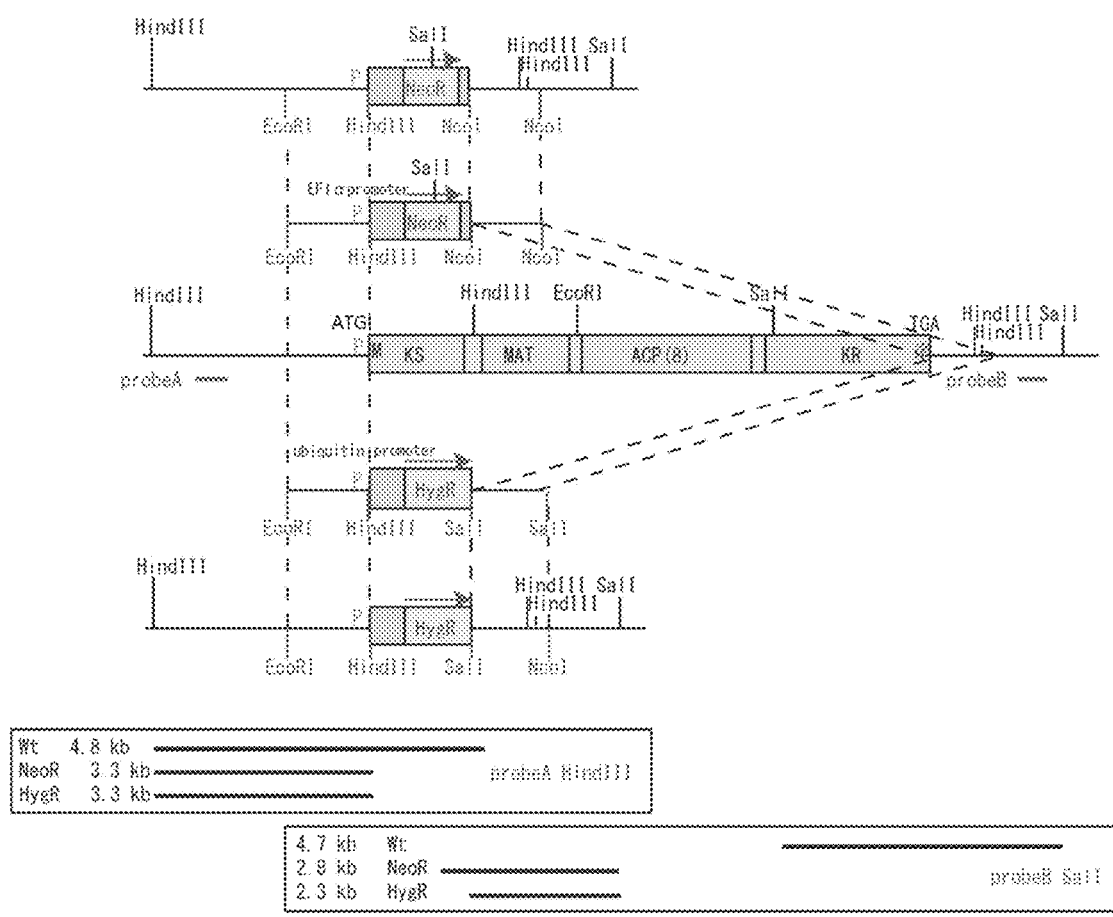
FIG. 49 is a schematic diagram illustrating the positions of the southern hybridization analysis probes used in identification of the PKS pathway associated gene orfA disruption strain of *Thraustochytrium aureum* ATCC 34304, and the expected size of the gene fragment.

After the genome DNA was cut with a restriction enzyme, the obtained genome DNA underwent electrophoresis in approximately 2 to 3 μg per well of 0.7% SeaKem GTG agarose gel (available from Takara Bio Inc.). This was transformed to a nylon membrane, and hybridized at 54° C. for 16 hr with a probe produced using DIG System (available from Roche Applied Science, Inc.). The primers used in probe production were as follows. 5' side [RHO37: 22 mer: 5'-GAA GCG TCC CGT AGA TGT GGT C-3' (SEQ ID NO: 139), RHO38: 21 mer: 5'-GCC CGA GAG GTC AAA GTA CGC-3' (SEQ ID NO: 140)]; 3' side [RHO39: 20 mer: 5'-GCG AGC CCA GGT CCA CTT GC-3' (SEQ ID NO: 141), RHO40: 22 mer: 5'-CAG CCC GAT GAA AAA CTT GGT C-3' (SEQ ID NO: 142)]. [PCR cycles: 98° C. 2 min/98° C. 30 sec, 60° C. 30 sec, 72° C. 2 min, 30 cycles/72° C. 3 min]. The positions of the restriction enzymes and the probes used are illustrated in FIG. 49. The hybridized probes were detected using the color development method (NBT/BCIP solution).

Figure 50:
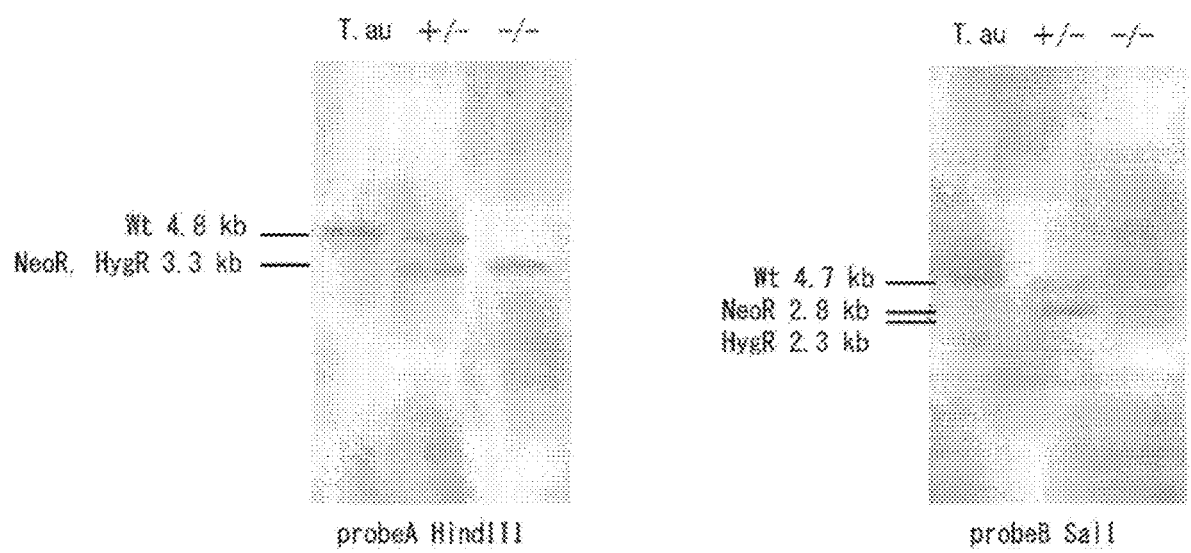
FIG. 50 illustrates an evaluation of PKS pathway associated gene orfA disruption by southern hybridization using *Thraustochytrium aureum* ATCC 34304 genome DNA. (Brief description of symbols) T. au: *Thraustochytrium aureum* ATCC 34304 wild-type strain; +/−: PKS pathway associated gene orfA first allele homologous recombinant derived from *Thraustochytrium aureum* ATCC 34304; −/−: PKS pathway associated gene orfA disruption strain derived from *Thraustochytrium aureum* ATCC 34304

In analysis of both the 5' side and the 3' side, bands were observed at the expected sizes when the drug resistance genes caused homologous recombination (FIG. 50).

Comparative Example 2-7

*Thraustochytrium aureum* ATCC 34304 and the gene disruption strain were cultured according to the method described in Example 2-9, and after freeze drying, the fatty acids were methyl-esterified and analyzed using GC.

Figure 51:
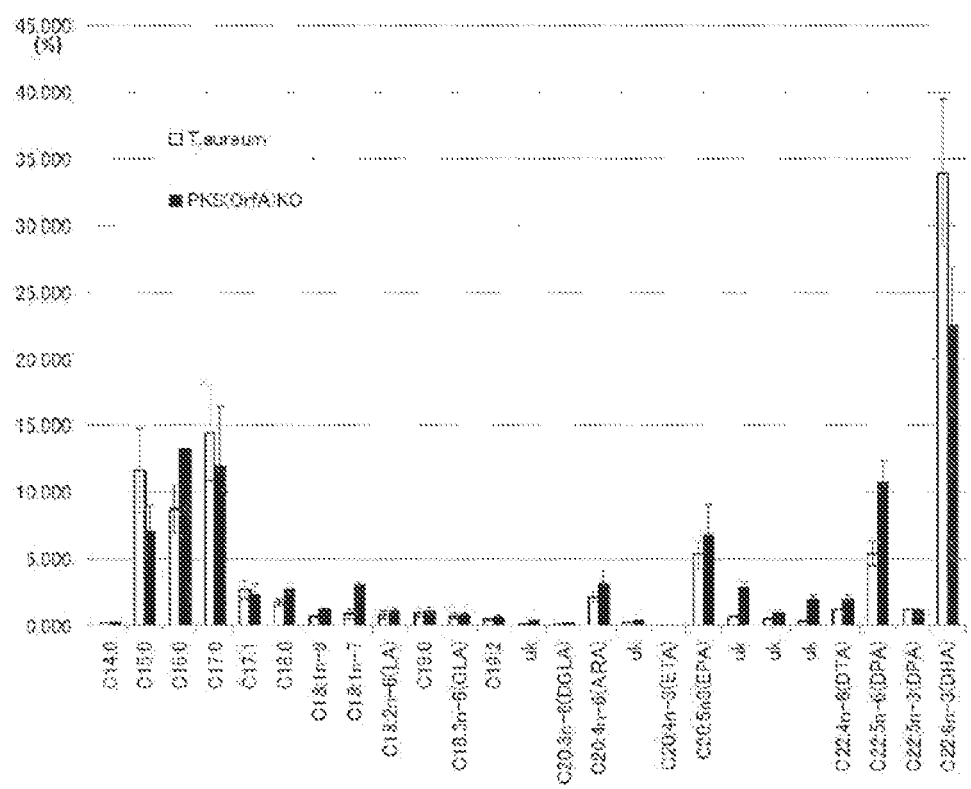
FIG. 51 illustrates a comparison of fatty acid compositions of the *Thraustochytrium aureum* ATCC 34304 wild-type strain and the PKS pathway associated gene orfA disruption strain. The white bars and black bars represent the fatty acid composition of the wild-type strain and the gene disruption strain, respectively. The values are mean±standard deviation.

The changes in the fatty acid composition are shown in FIG. 51. FIG. 52 shows the proportion when the wild-type strain is taken as 100%. FIG. 52 shows that, of the total fatty acid composition, ARA is 3.10%, DGLA is 0.23%, ETA is 0.04%, EPA is 6.82%, n-6 DPA is 10.66%, and DHA is 22.58%. FIG. 52 shows that, by GC area, LA/DHA is 0.05, GLA/DHA is 0.03, DGLA/DHA is 0.01, ARA/DHA is 0.1, EPA/DHA is 0.3, LA/EPA is 0.16, GLA/EPA is 0.11, DTA/EPA is 0.29, DTA/ARA is 0.65, DTA/DGLA is 8.7, LA/n-6 DPA is 0.1, GLA/n-6 DPA is 0.07, DGLA/n-6 DPA is 0.02, ARA/n-6 DPA is 0.3, EPA/n-6 DPA is 0.6, DGLA/LA is 0.2, ARA/LA is 2.9, EPA/LA is 6.4, DTA/LA is 1.9, DGLA/GLA is 0.3, ARA/GLA is 4.0, n-6 DPA/DTA is 5.3, DHA/n-3 DPA is 20.0, C20 PUFA/C22 PUFA is 0.3, and n-6 PUFA/n-3 PUFA is 0.52.

As a result, when the PUFA-PKS pathway associated gene: OrfA was disrupted in *Thraustochytrium aureum*, DPA (C22:5n-6) exhibited an increasing trend and DHA (C22:6n-3) exhibited a decreasing trend.

It is known that in the genus *Schizochytrium* and genus *Aurantiochytrium*, exogenous PUFAs become necessary when a PUFA-PKS pathway gene is disrupted, and breeding is not possible unless exogenous PUFAs are supplied (Non-patent Document 4). Unlike these organisms, however, *Thraustochytrium aureum* ATCC 34304 can be cultured without supplementing the culture medium with exogenous PUFAs when a PUFA-PKS pathway associated gene is disrupted. Furthermore, disruption of a PUFA-PKS pathway associated gene, decreased DHA only to approximately ⅔ and slightly increased DPA (C22:5n-6) compared to the wild-type strain.

The above results suggest the possibility that DHA and n-6 DPA are produced via another biosynthesis pathway in addition to the PUFA-PKS pathway in *Thraustochytrium aureum* ATCC 34304. The reason that *Thraustochytrium aureum* ATCC 34304 can be cultured without supplementing the culture medium with exogenous PUFAs is surmised to be that endogenous PUFAs are supplied via a biosynthesis pathway other than the PUFA-PKS pathway.

Comparative Example 3

[Measurement of Fatty Acid Composition of Lipids Produced by PUFA-PKS Gene and C20 Elongase Gene Disruption and Transformation Strain of *Thraustochytrium aureum* ATCC 34304]

[Comparative Example 3-1]: Cloning of Upstream Sequence of *Thraustochytrium aureum* C20 Elongase Gene The genome cassette library produced in Comparative Example 2-1 was used as a template. A PCR lower primer

[RHO71: 22 mer: 5'-GGG AGC GCA GGG AAA ACG GTC T-3' (SEQ ID NO: 143)] was produced on the C20 elongase gene upstream sequence (SEQ ID NO: 76) described in Comparative Example 1-4, and the gene was amplified by combining with the cassette primers contained in the kit described in Comparative Example 2-1. [1st PCR cycles: 98° C. 2 min/98° C. 30 sec, 56° C. 30 sec, 72° C. 4 min, 30 cycles/72° C. 5 min]. Then, the 1st PCR amplification product was diluted 100-fold, and the gene was amplified by combining a PCR lower primer [RHO72: 20 mer: 5'-CCA GCC CAC GTC GTC GGA GC-3' (SEQ ID NO: 144)] and the nested primers contained in the kit described in Comparative Example 2-1. [2nd PCR cycles: 98° C. 2 min/98° C. 30 sec, 56° C. 30 sec, 72° C. 4 min, 30 cycles/72° C. 5 min]. The obtained DNA fragment was cloned in pGEM-T Easy Vector, and after amplification with E. coli, the sequence was confirmed using a Dye Terminator Cycle Sequencing Kit (available from Beckman Coulter Inc.).

A 2297 bp DNA fragment (SEQ ID NO: 145) containing the 3277 bp to 981 bp region upstream of the C20 elongase gene was cloned.

[Comparative Example 3-2]: Cloning of Downstream Sequence of C20 Elongase Gene

The genome cassette library produced in Comparative Example 2-1 was used as a template. A PCR upper primer [RHO87: 23 mer: 5'-GCC GCT CAT GCC CAC GCT CAA AC-3' (SEQ ID NO: 146)] was produced on the C20 elongase gene downstream sequence (SEQ ID NO: 77) described in Comparative Example 1-4, and the gene was amplified by combining with the cassette primers contained in the kit described in Comparative Example 2-1. [1st PCR cycles: 98° C. 2 min/98° C. 30 sec, 56° C. 30 sec, 72° C. 4 min, 30 cycles/72° C. 5 min]. Then, the 1st PCR amplification product was diluted 100-fold, and the gene was amplified by combining a PCR lower primer [RHO73: 23 mer: 5'-CTT TCG GCT GCC AGG AAT CTA CG-3' (SEQ ID NO: 147)] and the nested primers contained in the kit described in Comparative Example 2-1. [2nd PCR cycles: 98° C. 2 min/98° C. 30 sec, 56° C. 30 sec, 72° C. 4 min, 30 cycles/72° C. 5 min]. The obtained DNA fragment was cloned in pGEM-T Easy Vector, and after amplification with E. coli, the sequence was confirmed using a Dye Terminator Cycle Sequencing Kit (available from Beckman Coulter Inc.).

A 2189 bp DNA fragment (SEQ ID NO: 148) containing the 1106 bp to 3294 bp region downstream of the C20 elongase gene was cloned.

[Comparative Example 3-3]: Production of Blasticidin Resistance Gene Cassette

Using genome DNA from Thraustochytrium aureum ATCC 34304 as a template, an ubiquitin promoter sequence (618 bp, SEQ ID NO: 149) was amplified with PrimeSTAR HS DNA Polymerase with GC Buffer (available from Takara Bio Inc.). The PCR primers used were as shown below. RHO53 was set on the ubiquitin promoter sequence, and includes a BglII linker sequence (Example 2-2, SEQ ID NO: 5). RHO48 includes the ubiquitin promoter sequence and a blasticidin resistance gene sequence. [RHO48: 58 mer: 5'-CTT CTT GAG ACA AAG GCT TGG CCA TGT TGG CTA GTG TTG CTT AGG TCG CTT GCT GCT G-3') (SEQ ID NO: 150)]. [PCR cycles: 98° C. 2 min/98° C. 10 sec, 68° C. 1 min, 30 cycles/68° C. 1 min].

Using pTracer-CMV/Bsd/lacZ (available from Invitrogen Corp.) as a template, a blasticidin resistance gene (432 bp, SEQ ID NO: 151) was amplified with PrimeSTAR HS DNA Polymerase with GC Buffer. The PCR primers used were as shown below. RHO47 includes the ubiquitin promoter sequence and the blasticidin resistance gene sequence. RHO49 includes the blasticidin resistance gene sequence and has a BglII linker sequence. [RHO47: 54 mer: 5'-AGC GAC CTA AGC AAC ACT AGC CAA CAT GGC CAA GCC TTT GTC TCA AGA AGA ATC-3' (SEQ ID NO: 152), RHO49: 38 mer: 5'-CCC AGA TCT TAG CCC TCC CAC ACA TAA CCA GAG GGC AG-3' (SEQ ID NO: 153)]. [PCR cycles: 98° C. 2 min/98° C. 10 sec, 68° C. 1 min, 30 cycles/68° C. 1 min].

Figure 53:
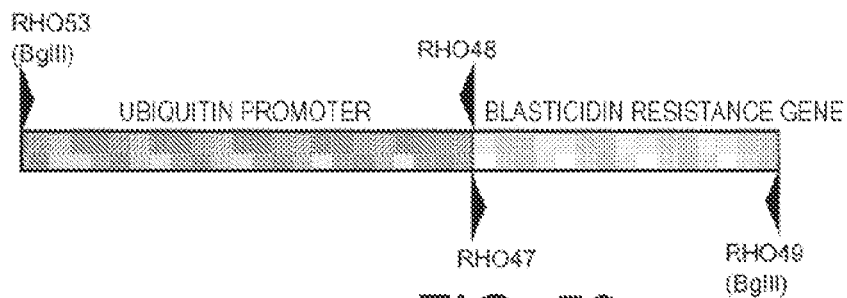
FIG. 53 is a schematic diagram of the primers used in fusion PCR and the products. The final product is a fused sequence of a ubiquitin promoter derived from *Thraustochytrium aureum* ATCC 34304 and a blasticidin resistance gene derived from pTracer-CMV/Bsd/lacZ.

Using SEQ ID NOS: 149 and 151 as templates, fusion PCR was performed using RHO53 (described in Example 2-2, SEQ ID NO: 5) and RHO49 (SEQ ID NO: 153) according to the method described in Non-patent Document 9. Amplification was performed using LA Taq Hot Start Version (available from Takara Bio Inc.) as the enzyme under the following conditions, and then the amplified product was digested with BglII. [PCR cycles: 94° C. 2 min/94° C. 20 sec, 55° C. 30 sec, 68° C. 1 min, 30 cycles/68° C. 1 min (1° C./10 sec from 55° C. to 68° C.)]. (FIG. 53).

The Thraustochytrium aureum ATCC 34304-derived ubiquitin promoter—pTracer-CMV/Bsd/lacZ-derived blasticidin resistance gene sequence (1000 bp, SEQ ID NO: 154) fused as described above was digested with BglII, and the resultant was bound to the BamHI site of pRH27 (FIG. 2) described in Example 2-1. After amplification of the produced plasmid with E. coli, the sequence was confirmed using a Dye Terminator Cycle Sequencing Kit (available from Beckman Coulter Inc.). This was named pRH38.

Figure 54:
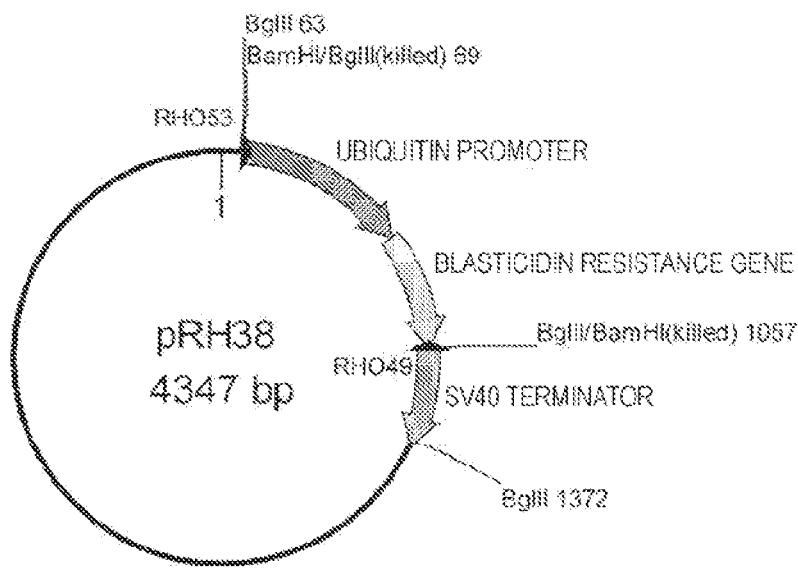
FIG. 54 illustrates the produced BglII cassette of the blasticidin resistance gene derived from pTracer-CMV/Bsd/lac.

The produced blasticidin resistance gene cassette (pRH38) is illustrated in FIG. 54.

[Comparative Example 3-4]: Production of GFP Fusion Zeocin Resistance Gene Cassette Using genome DNA from Thraustochytrium aureum ATCC 34304 as a template, a ubiquitin promoter sequence (812 bp, SEQ ID NO: 155) was amplified with PrimeSTAR HS DNA Polymerase with GC Buffer (available from Takara Bio Inc.). The PCR primers used were as shown below. TMO38 was set on the ubiquitin promoter sequence. TMO39 includes the ubiquitin promoter sequence and an enhanced GFP gene sequence. [TMO38: 29 mer: 5'-TCG GTA CCC GTT AGA ACG CGT AAT ACG AC-3' (SEQ ID NO: 156), TMO39: 41 mer: 5'-TCC TCG CCC TTG CTC ACC ATG TTG GCT AGT GTT GCT TAG GT-3' (SEQ ID NO: 157)]. [PCR cycles: 98° C. 10 sec/98° C. 10 sec, 58° C. 30 sec, 72° C. 1 min, 30 cycles/72° C. 1 min].

Using an enhanced GFP gene sequence (available from Clontech Laboratories, Inc.) as a template, the enhanced GFP gene sequence (748 bp, SEQ ID NO: 158) was amplified with PrimeSTAR HS DNA Polymerase (available from Takara Bio Inc.). The PCR primers used were as shown below. TMO40 includes the ubiquitin promoter sequence and the enhanced GFP gene sequence. RHO91 includes the enhanced GFP sequence and a zeocin resistance gene sequence. [TMO40: 41 mer: 5'-ACC TAA GCA ACA CTA GCC AAC ATG GTG AGC AAG GGC GAG GA-3' (SEQ ID NO: 159), RHO91: 58 mer: 5'-GAA CGG CAC TGG TCA ACT TGG CGT CCA TGC CGA GAG TGA TCC CGG CGG CGG TCA CGA A-3' (SEQ ID NO: 160)]. [PCR cycles: 98° C. 10 sec/98° C. 10 sec, 58° C. 30 sec, 72° C. 2 min, 30 cycles/72° C. 2 min].

Figure 55:
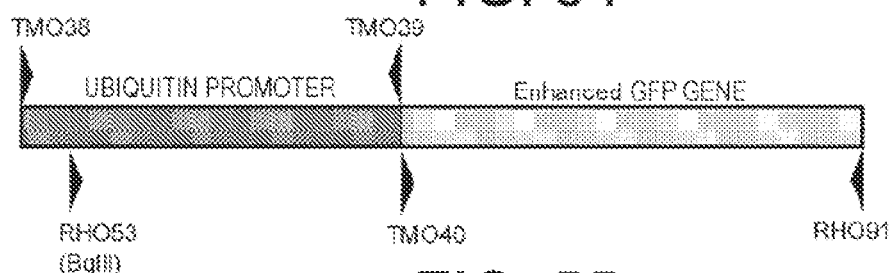
FIG. 55 is a schematic diagram of the primers used in fusion PCR and the products. The final product is a fused sequence of a ubiquitin promoter derived from *Thraustochytrium aureum* ATCC 34304 and an enhanced GFP gene (available from Clontech Laboratories, Inc.).

Using SEQ ID NOS: 156 and 158 as templates, fusion PCR was performed by LA Taq Hot Start Version (available from Takara Bio Inc.) according to the method described in Non-patent Document 9. TMO38 (SEQ ID NO: 156) and RHO91 (SEQ ID NO: 160) were used as primers, and the conditions were as follows: PCR cycles: 94° C. 2 min/94° C. 20 sec, 55° C. 30 sec, 68° C. 2 min, 30 cycles/68° C. 2 min (1° C./10 sec from 55° C. to 68° C.) (FIG. 55, 1519 bp, SEQ ID NO: 161).

Using SEQ ID NO: 161 as a template, the ubiquitin promoter sequence—enhanced GFP gene sequence (1319 bp, SEQ ID NO: 162) was amplified with PrimeSTAR HS DNA Polymerase (available from Takara Bio Inc.). The primers used were as follows. RHO53 (Example 2-2, SEQ ID NO: 5) contains the ubiquitin promoter sequence and has a BglII site. RHO91 (SEQ ID NO: 160) includes the enhanced GFP sequence and a zeocin resistance gene sequence. [PCR cycles: 98° C. 2 min/98° C. 10 sec, 68° C. 2 min, 30 cycles/68° C. 2 min].

Using pcDNA 3.1 Zeo(+) as a template, a zeocin resistance gene sequence (408 bp, SEQ ID NO: 163) was amplified with PrimeSTAR HS DNA Polymerase (available from Takara Bio Inc.). RHO92 includes the enhanced GFP sequence and a zeocin resistance gene sequence. RHO64 contains the zeocin resistance gene sequence and has a BglII site. [RHO92: 54 mer: 5'-CGC CGC CGG GAT CAC TCT CGG CAT GGA CGC CAA GTT GAC CAG TGC CGT TCC GGT-3' (SEQ ID NO: 164), RHO64: 38 mer: 5'-CCC AGA TCT CAG TCC TGC TCC TCG GCC ACG AAG TGC AC-3' (SEQ ID NO: 165)]. [PCR cycles: 98° C. 2 min/98° C. 10 sec, 68° ° C. 1 min, 30 cycles/68° C. 1 min].

Figure 56:
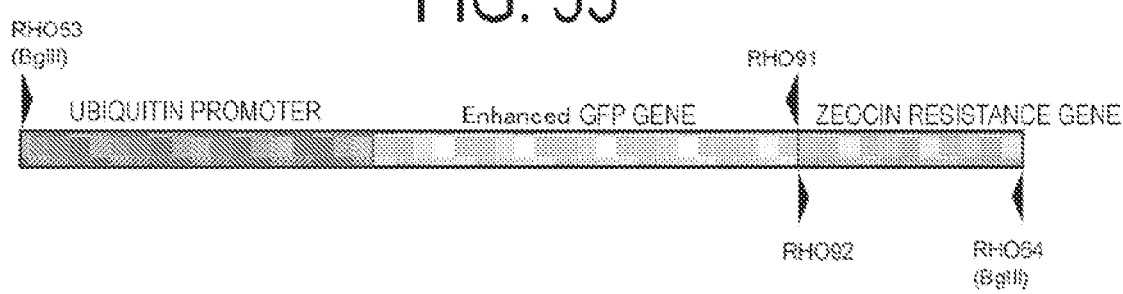
FIG. 56 is a schematic diagram of the primers used in fusion PCR and the products. The final product is a fused sequence of a ubiquitin promoter derived from *Thraustochytrium aureum* ATCC 34304, an enhanced GFP gene (available from Clontech Laboratories, Inc.), and a zeocin resistance gene derived from pcDNA 3.1 Zeo(+).

Using SEQ ID NOS: 162 and 163 as templates, fusion PCR was performed by LA Taq Hot Start Version (available from Takara Bio Inc.) according to the method described in Non-patent Document 9. RHO53 (Example 2-2, SEQ ID NO: 5) and RHO64 (SEQ ID NO: 165) were used as primers, and the conditions were as follows: PCR cycles: 94° C. 2 min/94° C. 20 sec, 68° C. 2 min, 30 cycles/68° C. 2 min (1° C./10 sec from 55° C. to 68° C.) (FIG. 56).

The *Thraustochytrium aureum* ATCC 34304-derived ubiquitin promoter—enhanced GFP gene—pcDNA 3.1 Zeo (+)-derived zeocin resistance gene (FIG. 56, 1677 bp, SEQ ID NO: 166) fused as described above was digested with BglII, and the resultant was bound to the BamHI site of pRH27 (FIG. 2) described in Example 2-1. After amplification of the produced plasmid with *E. coli*, the sequence was confirmed using a Dye Terminator Cycle Sequencing Kit (available from Beckman Coulter Inc.). This was named pRH51.

Figure 57:
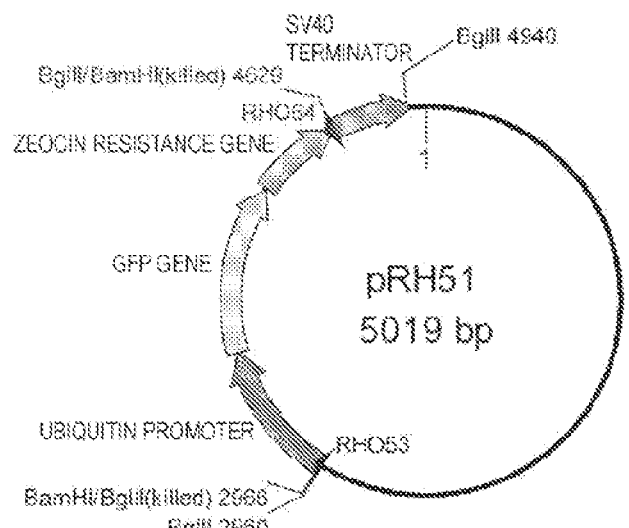
FIG. 57 illustrates the produced BglII cassette of the enhanced GFP-zeocin resistance fusion gene.

The produced GFP fusion zeocin resistance gene cassette (pRH51) is illustrated in FIG. 57.

[Comparative Example 3-5]: Production of Plasmid Serving as Base for Production of C20 Elongase Gene Targeting Vector Using *Thraustochytrium aureum* ATCC 34304 genome DNA as a template, a C20 elongase gene and its surrounding sequence were amplified with PCR by PrimeSTAR HS DNA Polymerase (available from Takara Bio Inc.) (2884 bp, SEQ ID NO: 167). The PCR primers used were as follows. Both primers contained an EcoI linker sequence. KSO9 was set in the C20 elongase gene upstream (SEQ ID NO: 76), and KSO10 was set in the C20 elongase gene downstream (SEQ ID NO: 77). [KSO9: 50 mer: 5'-CCC GAA TTC ACT AGT GAT TCT CCC GGG TGG ACC TAG CGC GTG TGT CAC CT-3' (SEQ ID NO: 168), KSO10: 40 mer: 5'-CCC GAA TTC GAT TAT CCC GGG GCC GAG AAC GGG GTC GCC C-3' (SEQ ID NO: 169)]. [PCR cycles: 98° C. 2 min/98° C. 10 sec, 68° C. 3.5 min, 30 cycles/68° C. 10 min]. PrimeSTAR HS DNA Polymerase (available from Takara Bio Inc.) was used for the enzymes, and after amplification, the amplified products were digested with EcoRI, and then cloned at the vector EcoRI site of pBlueScript (SK) (available from Stratagene Corp.). After amplification with *E. coli*, the sequence was confirmed using a Dye Terminator Cycle Sequencing Kit (available from Beckman Coulter Inc.) (FIG. 58).

Figure 58:
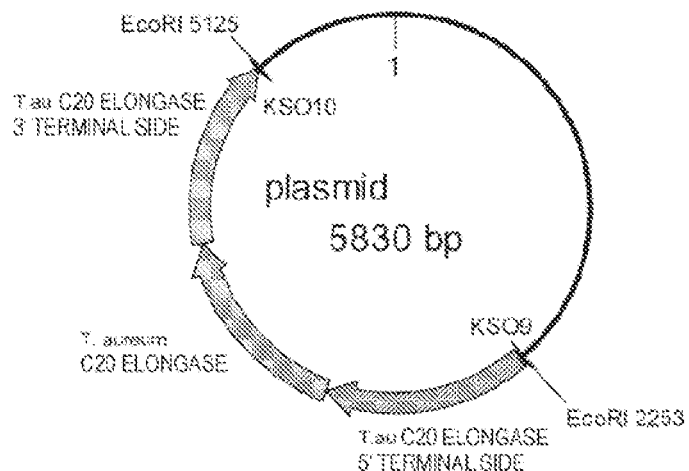
FIG. 58 illustrates a plasmid containing a cloned *Thraustochytrium aureum* ATCC 34304 C20 elongase sequence and the peripheral sequence.

A primer set that was set up in the reverse direction with the objective of deleting a portion of the C20 elongase gene sequence and inserting a BglII site (1939 bp, SEQ ID NO: 170) was prepared using the plasmid illustrated in FIG. 58 as a template, and the set was amplified with PrimeSTAR Max DNA Polymerase (available from Takara Bio Inc.). The PCR primers used were as shown below, both of which have a BglII linker sequence. [RHO69: 38 mer: 5'-CCC AGA TCT ACC TGT TTC CGG CTG GCT CCC GAG CCA TG-3' (SEQ ID NO: 171), RHO70: 38 mer: 5'-CCC AGA TCT GGT CGC GTT TAC AAA GCA GCG CAG CAA CA-3' (SEQ ID NO: 172)]. [PCR cycles: 98° C. 2 min/98° C. 10 sec, 68° C. 1.5 min, 30 cycles/68° C. 1.5 min]. After amplification under the above conditions, the amplified product was digested with BglII and then self-ligated. After the ligated sample was amplified with *E. coli*, the sequence was confirmed using a Dye Terminator Cycle Sequencing Kit (available from Beckman Coulter Inc.). This was named pRH40.

Figure 59:
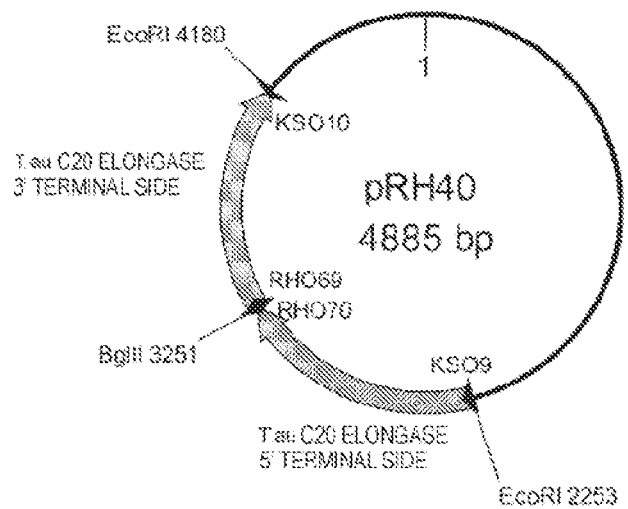
FIG. 59 illustrates a plasmid in which the *Thraustochytrium aureum* ATCC 34304 C20 elongase sequence has been completely deleted from the plasmid illustrated in FIG. 56 and a BglII site has been inserted.

The produced plasmid (pRH40) serving as a base for production of a C20 elongase gene targeting vector is illustrated in FIG. 59.

[Comparative Example 3-6]: Production of Targeting Vectors (Blasticidin Resistance Gene and GFP Fusion Zeocin Resistance Gene)

pRH38 (FIG. 52) described in Comparative Example 3-3 was digested with BglII, and a DNA fragment containing a blasticidin resistance gene cassette was bound to the BglII site of pRH40 (FIG. 59) described in Comparative Example 3-5. This was named pRH43.

pRH51 (FIG. 55) described in Comparative Example 3-4 was digested with BglII, and a DNA fragment containing a GFP fusion zeocin resistance gene cassette was bound to the BglII site of pRH40 (FIG. 57) described in Comparative Example 3-5. This was named pRH54.

Figure 60:
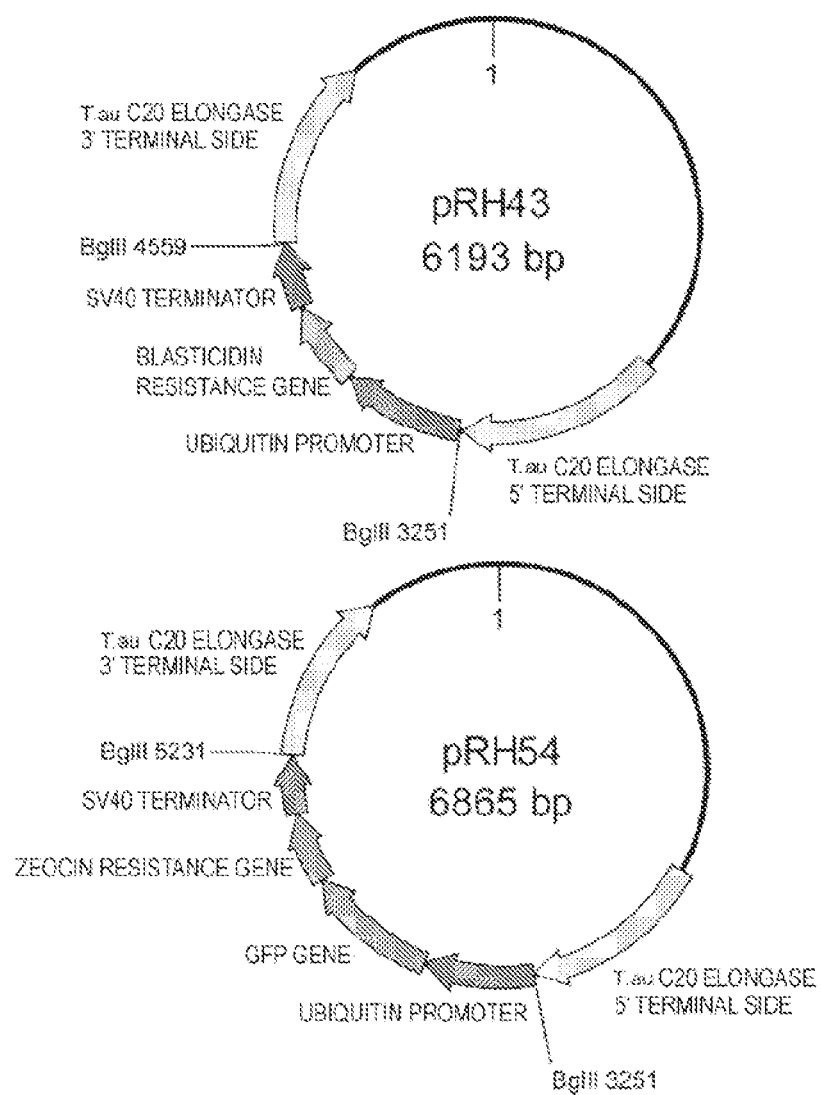
FIG. 60 illustrates the produced *Thraustochytrium aureum* ATCC 34304 C20 elongase gene targeting vectors (two types). As a drug resistance marker, the vectors have a blasticidin resistance gene (pRH43) or an enhanced GFP-zeocin resistance fusion gene (pRH54).

The two produced targeting vectors (pRH43 and 54) are illustrated in FIG. 60.

[Comparative Example 3-7]: Transfer of C20 Elongase Gene Targeting Vectors into *Thraustochytrium aureum* OrfA Disruption Strain Using the two targeting vectors produced in Comparative Example 3-6 as templates, the genes were amplified with PrimeSTAR Max DNA Polymerase (available from Takara Bio Inc.) using KSO11 and KSO12 as primers. KSO11 was set upstream of the *Thraustochytrium aureum* C20 elongase gene, and KSO12 was set downstream of the *Thraustochytrium aureum* C20 elongase gene. [KSO11: 31 mer: 5'-CTC CCG GGT GGA CCT AGC GCG TGT GTC ACC T-3' (SEQ ID NO: 173), KSO12: 27 mer: 5'-ATC CCG GGG CCG AGA ACG CCC TCG CCC-3' (SEQ ID NO: 174)]. [PCR cycles: 98° C. 2 min/98° C. 30 sec, 68° C. 2 min, 30 cycles/68° C. 2 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pRH43 (FIG. 60) described in Comparative Example 3-6 was used as a template was 3215 bp, and resulted in a sequence including *Thraustochytrium aureum* C20 elongase gene upstream—ubiquitin promoter—blasticidin resistance gene sequence—SV40 terminator sequence—*Thraustochytrium aureum* C20 elongase gene downstream (SEQ ID NO: 175). The transfer fragment obtained when pRH54 (FIG. 60) described in Comparative Example 3-6 was used as a template was 3887 bp, and resulted in a sequence including *Thraustochytrium aureum* C20 elongase gene upstream—ubiquitin promoter—enhanced GFP gene sequence—zeocin resistance gene sequence—SV40 terminator sequence—*Thraustochytrium aureum* C20 elongase gene downstream (SEQ ID NO: 176).

The PUFA-PKS pathway associated gene: OrfA gene disruption strain described in Comparative Example 2 was cultured for 4 days in a GY culture medium, and cells in the logarithmic growth phase were used in gene transfer. To cells corresponding to OD600=1 to 1.5, 0.625 µg of DNA fragment was transformed by the gene gun method (microcarrier: 0.6 micron gold particles, target distance: 6 cm, chamber vacuum: 26 mmHg, rupture disk: 1100 psi). After a recovery time of 4 to 6 hr, the transgenic cells were spread on a PDA agar plate culture medium (containing 2 mg/mL of G418 or containing 2 mg/mL of hygromycin). As a result, from 100 to 200 cells of drug resistant strain per shot were obtained.

[Comparative Example 3-8]: Identification of C20 Elongase Gene Targeting Homologous Recombinant After genome DNA was extracted from the C20 elongase gene disruption strain in the *Thraustochytrium aureum* OrfA disruption strain and *Thraustochytrium aureum* by the method described in Example 2-2, A260/A280 was measured and the DNA concentration was calculated.

Figure 61:
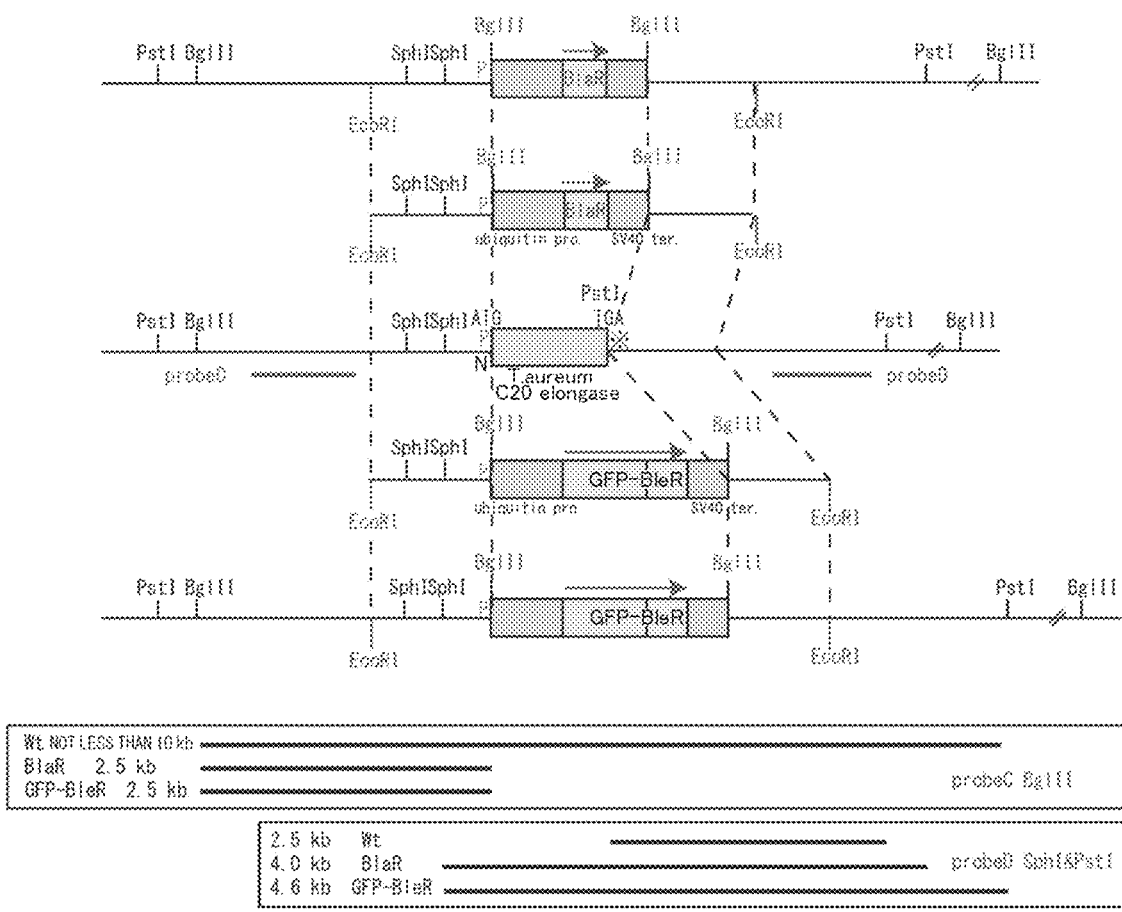
FIG. 61 is a schematic diagram illustrating the position of the southern hybridization analysis probe used in identification of the C20 elongase gene disruption strain of the *Thraustochytrium aureum* ATCC 34304 PKS pathway (orfA gene) disruption strain, and the expected size of the gene fragment.

After the genome DNA was cut with a restriction enzyme, and underwent electrophoresis in approximately 2 to 3 µg per well of 0.7% SeaKem GTG agarose gel (available from Takara Bio Inc.). This was transformed to a nylon membrane, and hybridized for at 51° C. 16 hr with a probe produced using DIG System (available from Roche Applied Science, Inc.). The primers used in probe production were as follows. 5' side [RHO94: 21 mer: 5'-ACG TCC GCT TCA AAC ACC TCG-3' (SEQ ID NO: 177), RHO95: 24 mer: 5'-TCG GAA CAA CTG GAA CAA CTA AAG-3' (SEQ ID NO: 178)]; 3' side [RHO96: 22 mer: 5'-ATG TCG CTC TCC TTC TTC TCA G-3' (SEQ ID NO: 179), RHO97: 21 mer: 5'-TCG GCT CCT GGA AAG TGC TCT-3' (SEQ ID NO: 180)]. [PCR cycles: 98° C. 2 min/98° C. 30 sec, 58° C. 30 sec, 72° C. 1 min, 30 cycles/72° C. 3 min]. The positions of the restriction enzymes and the probes used are illustrated in FIG. 61. The hybridized probes were detected using the color development method (NBT/BCIP solution).

Figure 62:
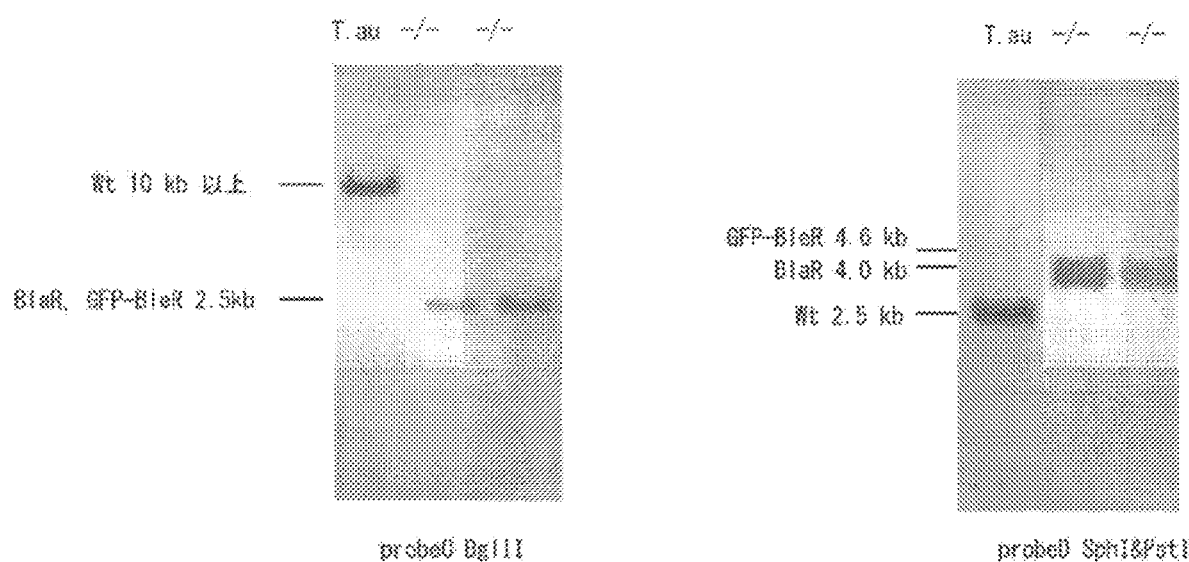
FIG. 62 illustrates an evaluation of C20 elongase gene disruption by southern hybridization using *Thraustochytrium aureum* ATCC 34304 genome DNA. (Brief description of symbols) T. au: *Thraustochytrium aureum* ATCC 34304 wild-type strain; −/−: PKS pathway (orfA gene) and C20 elongase gene double disruption strain derived from *Thraustochytrium aureum* ATCC 34304

In analysis of both the 5' side and the 3' side, bands were observed at the expected sizes when the drug resistance genes caused homologous recombination (FIG. 62). The experiment reveals that the *Thraustochytrium aureum* ATCC 34304 strain does not require nutrients even when the PKS pathway associated gene: OrfA and the C20 elongase gene are deleted.

[Comparative Example 3-9]: Change in Fatty Acid Composition by C20 Elongase Gene Disruption in *Thraustochytrium aureum* OrfA Disruption Strain

*Thraustochytrium aureum* ATCC 34304 and the gene disruption strain were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 63:
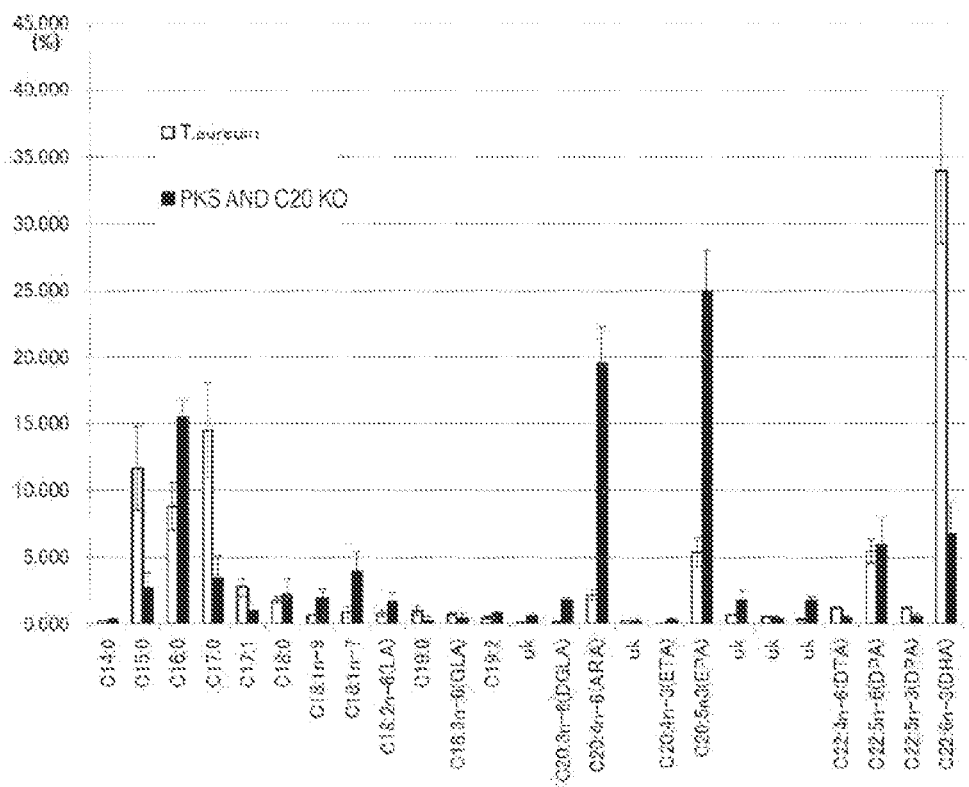
FIG. 63 illustrates a comparison of fatty acid compositions of the *Thraustochytrium aureum* ATCC 34304 wild-type strain and the PKS pathway (orfA gene) and C20 elongase gene double disruption strain. The white bars and black bars represent the fatty acid composition of the wild-type strain and the gene disruption strain, respectively. The values are mean±standard deviation.

The changes in the fatty acid composition are shown in FIG. 63. Furthermore, FIG. 64 shows the proportion when the wild-type strain is taken as 100%. FIG. 64 shows that, of the total fatty acid composition, ARA is 19.50%, DGLA is 1.81%, ETA is 0.31%, EPA is 24.92%, n-6 DPA is 5.90%, and DHA is 6.78%. FIG. 64 shows that, by GC area, LA/DHA is 0.25, GLA/DHA is 0.07, DGLA/DHA is 0.27, ARA/DHA is 2.88, EPA/DHA is 3.68, LA/EPA is 0.07, GLA/EPA is 0.02, DTA/EPA is 0.02, DTA/ARA is 0.02, DTA/DGLA is 0.26, LA/n-6 DPA is 0.29, GLA/n-6 DPA is 0.08, DGLA/n-6 DPA is 0.31, ARA/n-6 DPA is 3.31, EPA/n-6 DPA is 4.22, DGLA/LA is 1.06, ARA/LA is 11.40, EPA/LA is 14.57, DTA/LA is 0.27, DGLA/GLA is 4.02, ARA/GLA is 43.33, n-6 DPA/DTA is 12.55, DHA/n-3 DPA is 11.69, C20 PUFA/C22 PUFA is 3.39, and n-6 PUFA/n-3 PUFA is 0.85.

As a result, when the C20 elongase gene was disrupted in the *Thraustochytrium aureum* OrfA disruption strain, C20:4n-6 (ARA) increased approximately 8-fold, C20:5n-3 (EPA) increased approximately 4-fold, and C22:6n-3 (DHA) decreased to approximately ⅕.

Thus, it was demonstrated that in order to create a strain in which the produced quantity of DHA and DPA n-6 are markedly reduced from *Thraustochytrium aureum* ATCC 34304, which has both an endogenous elongase-desaturase pathway and an endogenous PUFA-PKS pathway, both a gene of an enzyme constituting the elongase-desaturase pathway (for example, the C20 elongase gene) and a PUFA-PKS pathway associated gene need to be disrupted.

Comparative Example 4

[Measurement of Fatty Acid Composition of Lipids Produced by PUFA-PKS Gene and Δ4 Desaturase Gene Disruption and Transformation Strain of *Thraustochytrium aureum* ATCC 34304]

Figure 65:
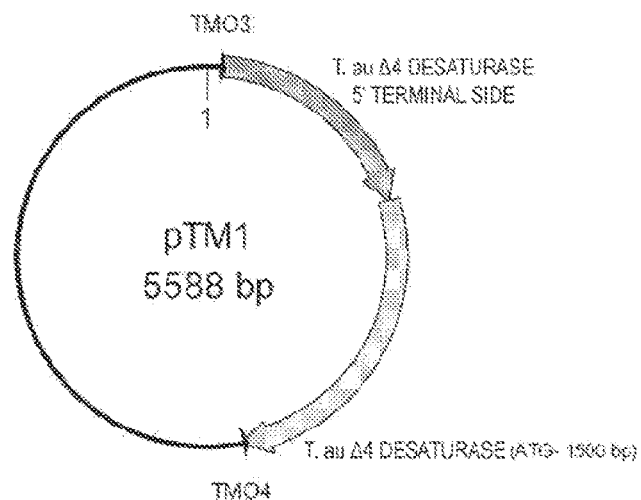
FIG. 65 illustrates a plasmid containing from 1071 bp upstream of the Δ4 desaturase gene to 1500 bp within the Δ4 desaturase gene of a cloned *Thraustochytrium aureum* ATCC 34304 strain.

[Comparative Example 4-1]: Cloning Sequence of 1071 bp Upstream of Δ4 Desaturase Gene to 1500 bp within Δ4 Desaturase Gene of *Thraustochytrium aureum* ATCC 34304 Strain Genome DNA of the *Thraustochytrium aureum* ATCC 34304 strain extracted by the method described in Example 2-2 was read, and a gene sequence having high homology to known Δ4 desaturase was searched for. Two PCR primers were designed based on the search results. TMO3 is a sequence located at 1071 to 1049 bp upstream of the Δ4 desaturase gene of the *Thraustochytrium aureum* ATCC 34304 strain, and TMO4 is a sequence within the protein coding region located at 1477 to 1500 bp counting from the start codon. [TMO3: 23 mer: 5'-GGC GGA GCG AAG TGT GAA AGT TA-3' (SEQ ID NO: 181), TMO4: 24 mer:

5'-GCG ACA GCA TCT TGA AAT AGG CAG-3' (SEQ ID NO: 182)]. Using genome DNA of the *Thraustochytrium aureum* ATCC 34304 strain as a primer, the sequence of 1071 bp upstream of the Δ4 desaturase gene to 1500 bp within the Δ4 desaturase gene (2571 bp, SEQ ID NO: 183) of *Thraustochytrium aureum* ATCC 34304 strain was amplified using these two primers. The amplification conditions were as follows. [PCR cycles: 98° C. 2 min/98° C. 20 sec, 60° C. 30 sec, 72° C. 3 min, 30 cycles/72° C. 8 min]. The obtained DNA fragment was cloned in pGEM-T Easy Vector, and after amplification with *E. coli*, the sequence was confirmed using a Dye Terminator Cycle Sequencing Kit (available from Beckman Coulter Inc.). This was named pTM1 (FIG. 65).

[Comparative Example 4-2]: Production of Plasmid Serving as Base for Production of Δ4 Desaturase Gene Targeting Vector Using pTM1 (FIG. 65) produced in Comparative Example 4-1 as a template, a primer set set in the reverse direction so as to delete a 556 bp sequence (616 bp, SEQ ID NO: 184) containing 60 bp upstream of the Δ4 desaturase gene and the start codon within the Δ4 desaturase gene and to produce a BglII site in the deleted portion was prepared. TMO7 and TMO8 both contain a BglII sequence. PrimeSTAR Max DNA Polymerase (available from Takara Bio Inc.) was used in amplification. [TMO7: 25 mer: 5'-CAG GAG ATC TCC AAG TCG CGA TTC A-3' (SEQ ID NO: 185), TMO8: 26 mer: 5'-CTT GGA GAT CTC CTG CCC GTC CCG AA-3' (SEQ ID NO: 186)]. [PCR cycles: 98° C. 3 min/98° C. 10 sec, 55° C. 15 sec, 72° C. 30 sec, 30 cycles/72° C. 30 sec]. After amplification under the above conditions, the amplified product was purified by electrophoresis using agarose gel. After transforming the obtained DNA fragment into *E. coli* and amplifying, the sequence was confirmed using a Dye Terminator Cycle Sequencing Kit (available from Beckman Coulter Inc.). This was named pTM2.

Figure 66:
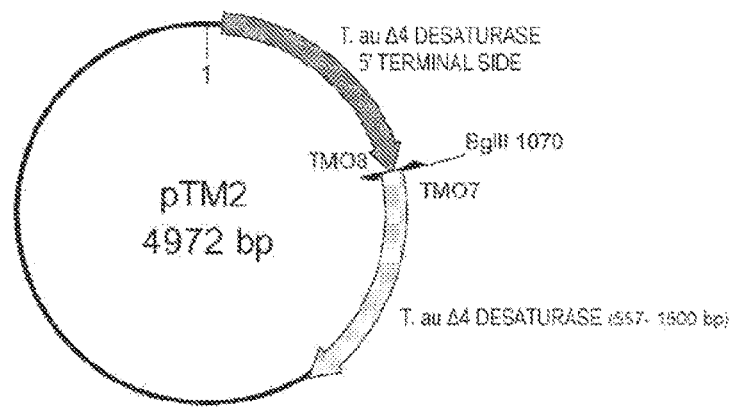
FIG. 66 illustrates a plasmid in which a sequence of 60 bp upstream of the Δ4 desaturase gene of the plasmid illustrated in FIG. 63 and a sequence of 556 bp containing the start codon within the Δ4 desaturase gene (616 bp, SEQ ID NO: 205) have been deleted and a BglII site has been inserted in the deleted portion.

The produced plasmid (pTM2) serving as a base for production of a Δ4 desaturase gene targeting vector is illustrated in FIG. 66.

[Comparative Example 4-3]: Production of Targeting Vectors (Blasticidin Resistance Gene and GFP Fusion Zeocin Resistance Gene)

pRH38 (FIG. 54) described in Comparative Example 3-3 was digested with BglII, and a DNA fragment containing a blasticidin resistance gene cassette was bound to the BglII site of pTM2 (FIG. 66) described in Comparative Example 4-2. This was named pTM6.

pRH51 (FIG. 57) described in Comparative Example 3-4 was digested with BglII, and a DNA fragment containing a GFP fusion zeocin resistance gene cassette was bound to the BglII site of pTM2 (FIG. 66) described in Comparative Example 4-2. This was named pTM8.

Figure 67:
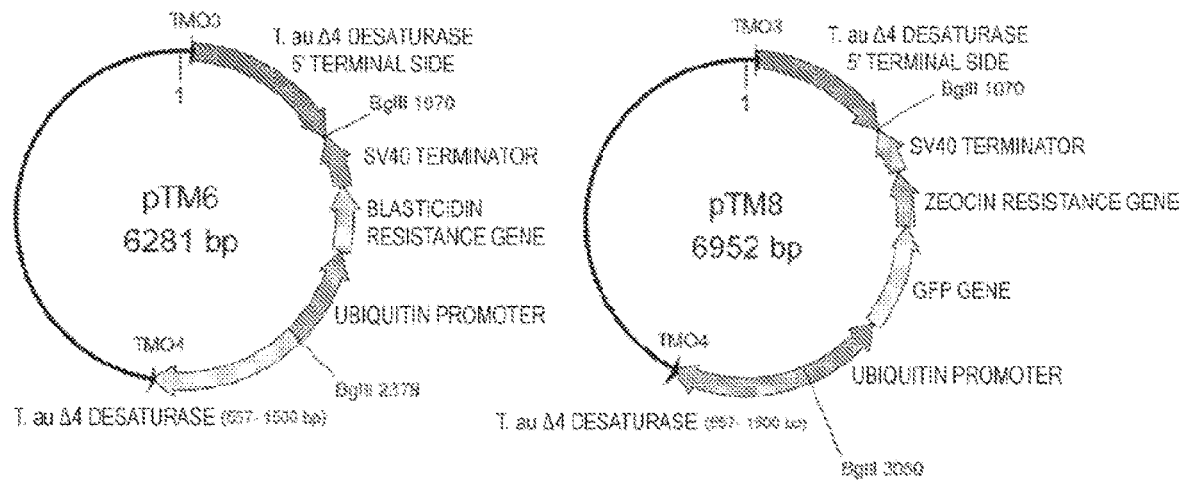
FIG. 67 illustrates the produced *Thraustochytrium aureum* ATCC 34304 strain Δ4 desaturase gene targeting vectors (two types). As a drug resistance marker, the vectors have a blasticidin resistance gene (pTM6) or an enhanced GFP-zeocin resistance fusion gene (pTM8).

The two produced targeting vectors (pTM6 and 8) are illustrated in FIG. 67.

[Comparative Example 4-4]: Transfer of Δ4 Desaturase Gene Targeting Vectors into *Thraustochytrium aureum* OrfA Disruption Strain Using the two targeting vectors produced in Comparative Example 4-3 as templates, the genes were amplified with PrimeSTAR Max DNA Polymerase (available from Takara Bio Inc.) using TMO3 (described in Comparative Example 4-1, SEQ ID NO: 181) and TMO4 (described in Comparative Example 4-1, SEQ ID NO: 182) as primers. [PCR cycles: 98° C. 3 min/98° C. 10 sec, 55° C. 5 sec, 72° C. 4 min, 30 cycles/72° C. 3 min]. After phenol chloroform extraction and chloroform extraction, the DNA underwent ethanol precipitation, and the precipitate was dissolved in 0.1×TE. A260/280 was measured and the DNA concentration was calculated. The transfer fragment obtained when pTM6 (FIG. 67) described in Comparative Example 4-3 was used as a template was 3264 bp, and resulted in a sequence within *Thraustochytrium aureum* Δ4 desaturase gene upstream—SV40 terminator sequence—blasticidin resistance gene sequence—ubiquitin promoter—*Thraustochytrium aureum* Δ4 desaturase gene (SEQ ID NO: 187). The transfer fragment obtained when pTM8 (FIG. 67) described in Comparative Example 4-3 was used as a template was 3935 bp, and resulted in a sequence within *Thraustochytrium aureum* Δ4 desaturase gene upstream—SV40 terminator sequence—zeocin resistance gene sequence—enhanced GFP gene sequence—ubiquitin promoter—*Thraustochytrium aureum* Δ4 desaturase gene (SEQ ID NO: 188).

The PUFA-PKS pathway associated gene: OrfA gene disruption strain described in Comparative Example 2 was cultured for 4 days in a GY culture medium, and cells in the logarithmic growth phase were used in gene transfer. To cells corresponding to OD600=1 to 1.5, 0.625 μg of DNA fragment was transformed by the gene gun method (microcarrier: 0.6 micron gold particles, target distance: 6 cm, chamber vacuum: 26 mmHg, rupture disk: 1100 psi). After a recovery time of 4 to 6 hr, the transgenic cells were spread on a PDA agar plate culture medium (containing 20 mg/mL of zeocin or containing 0.2 mg/mL of blasticidin). As a result, from 100 to 200 cells of drug resistant strain per shot were obtained.

Figure 68:
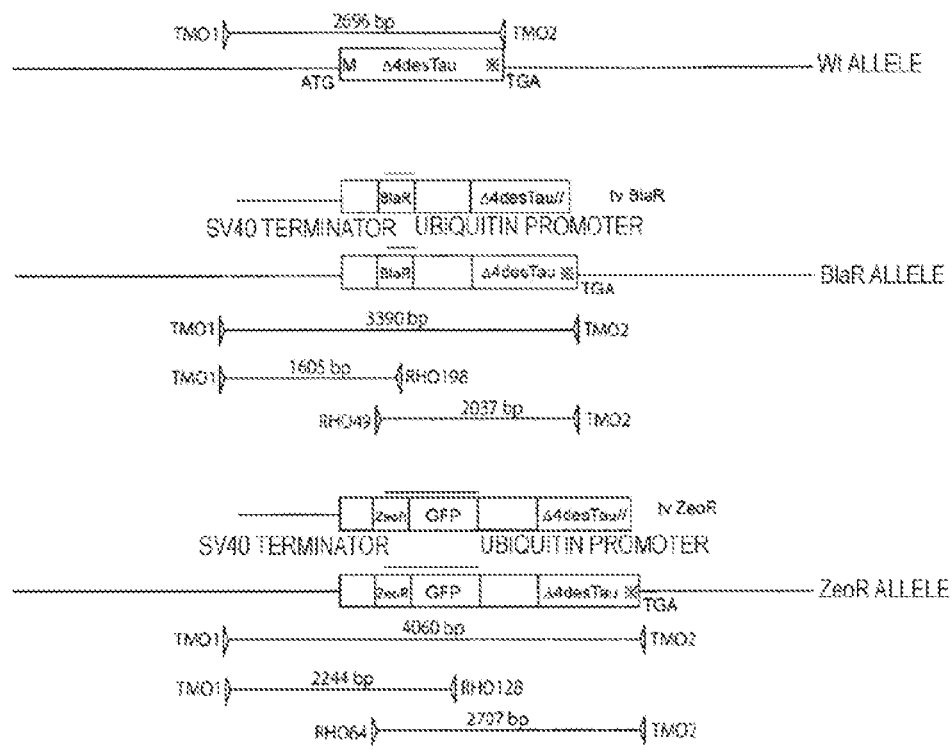
FIG. 68 is a schematic diagram illustrating the positions of the PCR primers used in identification of the Δ4 desaturase gene disruption strain of the *Thraustochytrium aureum* ATCC 34304 PKS pathway (orfA gene) disruption strain, and the expected products.
Figure 69:
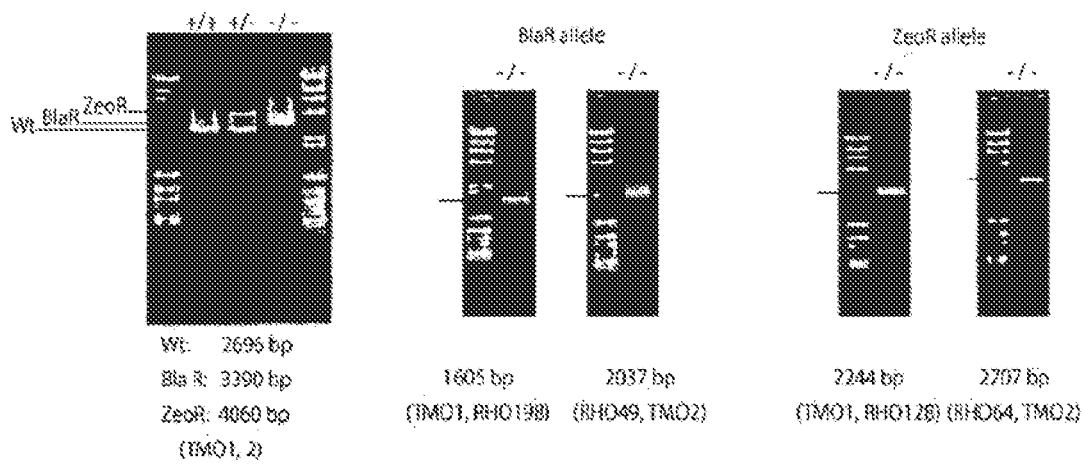
FIG. 69 illustrates an evaluation of Δ4 desaturase gene disruption by PCR using *Thraustochytrium aureum* ATCC 34304 strain genome DNA as a template. (Brief description of symbols)+/+: PKS pathway (orfA gene) disruption strain derived from *Thraustochytrium aureum* ATCC 34304; +/−: Δ4 desaturase first allele homologous recombinant derived from PKS pathway (orfA gene) disruption strain derived from *Thraustochytrium aureum* ATCC 34304; −/−: PKS pathway (orfA gene) and Δ4 desaturase gene double disruption strain derived from *Thraustochytrium aureum* ATCC 34304

[Comparative Example 4-5]: Identification of Δ4 Desaturase Gene Targeting Homologous Recombinant After genome DNA was extracted from the Δ4 desaturase gene disruption strain in the *Thraustochytrium aureum* OrfA disruption strain and *Thraustochytrium aureum* by the method described in Example 2-2, A260/A280 was measured and the DNA concentration was calculated. Using the genome DNA as templates, PCR for genome structure confirmation was performed using Mighty Amp DNA Polymerase (available from Takara Bio Inc.). The positions of the primers used, the combinations used in amplification, and the expected sizes of the amplification products are illustrated in FIG. 68. TMO1 was set upstream of the Δ4 desaturase gene, TMO2 was set downstream of the Δ4 desaturase gene, RHO198 (SEQ ID NO: 191) and RHO49 (described in Comparative Example 3-3, SEQ ID NO: 153) were set on the blasticidin resistance gene, RHO128 was set on the enhanced GFP gene, and RHO64 (described in Comparative Example 3-4, SEQ ID NO: 165) was set on the zeocin resistance gene. [TMO1: 23 mer: 5'-AAA AGA ACA AGC CCT CTC CTG GA-3' (SEQ ID NO: 189), TMO2: 23 mer: 5'-GAG GTT TGT ATG TTC GGC GGT TT-3' (SEQ ID NO: 190), RHO198: 26 mer: 5'-TGG GGG ACC TTG TGC AGA ACT CGT GG-3' (SEQ ID NO: 191), RHO128: 22 mer: 5'-GAC CTA CGG CGT GCA GTG CTT C-3' (SEQ ID NO: 192)]. [PCR cycles: 98° C. 2 min/98° C. 10 sec, 68° C. 4 min 30 sec, 30 cycles/68° C. 4 min]. A Δ4 desaturase gene disruption strain was obtained, wherein there was no amplification in the wild-type allele (Wt allele), and there was amplification in the blasticidin resistance gene allele (BlaR allele) and the zeocin resistance gene allele (ZeoR allele) (FIG. 69). The experiment reveals that the *Thraustochytrium aureum* ATCC 34304 strain does not require nutrients even when the PKS pathway associated gene: OrfA and the Δ4 desaturase gene are deleted.

[Comparative Example 4-6]: Change in Fatty Acid Composition by Δ4 Desaturase Gene Disruption in *Thraustochytrium aureum* OrfA Disruption Strain

*Thraustochytrium aureum* ATCC 34304 and the gene disruption strain were cultured according to the method described in Example 2-9, and after freeze drying, the fatty acids were methyl-esterified and analyzed using GC. In GC analysis, measurement was performed using a gas chromatograph GC-2014 (available from Shimadzu Corporation) under the following conditions. Column: HR-SS-10 (30 m×0.25 mm; available from Shinwa Chemical Industries Ltd.); column temperature: 150° C.→(5° C./min)→220° C. (10 min); carrier gas: He (1.3 mL/min).

Figure 70:
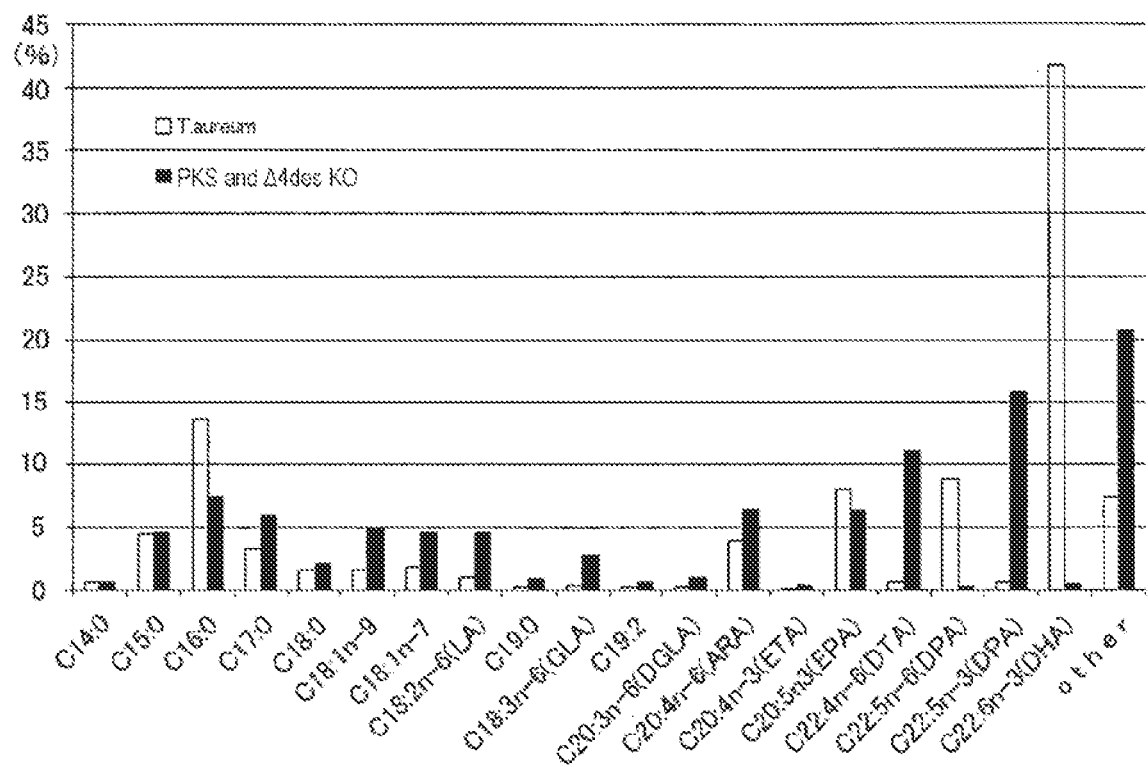
FIG. 70 illustrates a comparison of fatty acid compositions of the *Thraustochytrium aureum* ATCC 34304 wild-type strain and the PKS pathway (orfA gene) and Δ4 desaturase gene double disruption strain. The white bars and black bars represent the fatty acid composition of the wild-type strain and the gene disruption strain, respectively.

The changes in the fatty acid composition are shown in FIG. 70. Furthermore, FIG. 71 shows the proportion when the wild-type strain is taken as 100%. FIG. 71 shows that, of the total fatty acid composition, ARA is 6.35%, DGLA is 0.90%, ETA is 0.28%, EPA is 6.22%, n-6 DPA is 0.21%, and DHA is 0.51%. FIG. 71 shows that, by GC area, LA/DHA is 8.76, GLA/DHA is 1.59, DGLA/DHA is 1.76, ARA/DHA is 12.45, EPA/DHA is 12.20, LA/EPA is 0.72, GLA/EPA is 0.13, DTA/EPA is 1.77, DTA/ARA is 1.73, DTA/DGLA is 12.23, LA/n-6 DPA is 21.29, GLA/n-6 DPA is 3.86, DGLA/n-6 DPA is 4.29, ARA/n-6 DPA is 30.24, EPA/n-6 DPA is 29.62, DGLA/LA is 0.20, ARA/LA is 1.42, EPA/LA is 1.39, DTA/LA is 2.46, DGLA/GLA is 1.11, ARA/GLA is 7.84, n-6 DPA/DTA is 0.02, DHA/n-3 DPA is 0.03, C20 PUFA/C22 PUFA is 0.50, and n-6 PUFA/n-3 PUFA is 0.81.

As a result, when the Δ4 desaturase gene is disrupted in the *Thraustochytrium aureum* OrfA disruption strain, C22:5n-6 (DPA) and C22:6n-3 (DHA) are not substantially biosynthesized, and the Δ4 desaturase substrates C22:4n-6 (DTA) and C22:5n-3 (DPA) are accumulated.

Thus, it was demonstrated that in order to create a strain that cannot substantially biosynthesize DHA and n-6 DPA from *Thraustochytrium aureum* ATCC 34304, which has both an endogenous elongase-desaturase pathway and an endogenous PUFA-PKS pathway, both a gene of an enzyme constituting the elongase-desaturase pathway (for example, the Δ4 desaturase gene) and a PUFA-PKS pathway associated gene needs to be disrupted.

By using the microbial oil obtained in this manner, it is possible to obtain microbial oil having a fatty acid composition in which the composition ratios of PUFAs other than DHA and n-6 DPA are increased. It is possible to produce any PUFAs by modifying the genes of a microorganism that produces a large amount of DHA. Furthermore, by producing microbial oil that contains particularly little DHA and n-6 DPA, it is possible to produce microbial oil that requires little refinement. Additionally, by transforming elongase and desaturase into a microorganism in this manner, it is possible to obtain a microorganism that produces microbial oil.

INDUSTRIAL APPLICABILITY

A new "pattern" of biosynthesis pathway of polyunsaturated fatty acids (PUFAs) was discovered in microorganisms called labyrinthulids. Because it is possible to provide labyrinthulea that produce PUFAs via only the elongase-desaturase pathway, it is anticipated that PUFAs will be mass produced using only the elongase-desaturase pathway.

The invention claimed is:

1. A method for producing a microbial oil, comprising:
genetically modifying a labyrinthulid by disrupting and/or silencing a fatty acid desaturase gene;
culturing the labyrinthulid; and
collecting the microbial oil from the labyrinthulid,
wherein the labyrinthulid before the modification belongs to the genus *Parietichytrium* or the genus *Schizochytrium* having an activity of synthesizing DHA via a PUFA-PKS pathway in an amount of not more than 1/100 of a total amount of DHA synthesized in the labyrinthulid or no activity of producing PUFAs via the PUFA-PKS pathway, and having an activity of producing PUFAs via an endogenous elongase-desaturase pathway, wherein the fatty acid desaturase gene is a Δ4 desaturase gene, wherein the microbial oil satisfies (a) and (b):

(a) DHA is not greater than 0.50% of the total fatty acid composition; and (b) a total of DHA and n-6 DPA is not greater than 0.7% of the total fatty acid composition.

2. The method for producing microbial oil according to claim 1, wherein the step of disrupting the gene of the labyrinthulid utilizes electroporation, a gene gun method, or gene editing, and/or wherein the step of gene silencing of a labyrinthulid utilizes an antisense method or RNA interference.

3. The method for producing microbial oil according to claim 1, wherein the labyrinthulid belonging to the genus *Parietichytrium* is *Parietichytrium sarkarianum*, and/or wherein the labyrinthulid belonging to the genus *Schizochytrium* is *Schizochytrium aggregatum*.

4. The method for producing microbial oil according to claim 1, wherein the labyrinthulid belonging to the genus *Parietichytrium* is *Parietichytrium* sp. SEK358 (FERM BP-11405), *Parietichytrium sarkarianum* SEK364 (FERM BP-11298), or *Parietichytrium* sp. SEK571 (FERM BP11406), and/or wherein the labyrinthulid belonging to the genus *Schizochytrium* is *Schizochytrium aggregatum* ATCC 28209.

* * * * *

SEQUENCE LISTING

```
<160> NUMBER OF SEQ ID NOS: 192

<210> SEQ ID NO 1
<211> LENGTH: 34
<212> TYPE: DNA
<213> ORGANISM: Artificial Sequence
<220> FEATURE:
<223> OTHER INFORMATION: primer

<400> SEQUENCE: 1
cagatctgga tccgcgaaat gaccgaccaa gcga                              34

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
acgcaattaa tgtgagatct agct                                        24

<210> SEQ ID NO 3
<211> LENGTH: 342
<212> TYPE: DNA
<213> ORGANISM: Artificial Sequence
<220> FEATURE:
<223> OTHER INFORMATION: SV40 terminator
```

<400> SEQUENCE: 3

```
cagatctgga tccgcgaaat gaccgaccaa gcgacgccca acctgccatc acgagatttc    60
gattccaccg ccgccttcta tgaaaggttg ggcttcggaa tcgttttccg ggacgccggc   120
tggatgatcc tccagcgcgg ggatctcatg ctggagttct tcgcccaccc caacttgttt   180
attgcagctt ataatggtta caaataaagc aatagcatca caaatttcac aaataaagca   240
ttttttcac tgcattctag ttgtggtttg tccaaactca tcaatgtatc ttatcatgtc   300
tgtataccgt cgacctctag ctagatctca cattaattgc gt                      342
```

<210> SEQ ID NO 4
<211> LENGTH: 619
<212> TYPE: DNA
<213> ORGANISM: Artificial Sequence
<220> FEATURE:
<223> OTHER INFORMATION: ubiquitin promoter

<400> SEQUENCE: 4

```
cccagatctg ccgcagcgcc tggtgcaccc gccgggcgtt gttggtgtgc tcttcttgcc    60
tccgagagag agagcggagc ggatgcatag gaaatcgggc cacgcgggag ggccatgcgt   120
tcgcccaca cgccactttc cacgcccgct ctctctccgg ccggcaggca gcgcataact   180
ctccgacgct ggcaggctgg tagcaactgg cagggacaac tcgcgcgcgg gtcccggtcg   240
ttcgatgtgc caacccgaga gaatccagcc agcagggcgg ttggcctcat cgcccacctg   300
ctatggtgca gcgaaccaac tcccgaagcg gccggttctg cgattccctc ttctgaattc   360
tgaattctga actgattccg gaggagaacc ctctggaagc gcgggttgcc tctccagttc   420
tgccgaacta gacagggagt gagcagaga gtgaccctga cgcgggagcg agctggttgc   480
tggaaaagtc gcgaacgctg gctgtgtca cgcgtccact cgggcagac cccaaacgac   540
aagcagaaca gcaacacca gcagcagcaa gcgacctaag caacactagc caacatgatt   600
gaacaggacg gccttcacg                                                619
```

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5

```
cccagatctg ccgcagcgcc tggtgcaccc gccggg                              36
```

<210> SEQ ID NO 6
<211> LENGTH: 58
<212> TYPE: DNA
<213> ORGANISM: Artificial Sequence
<220> FEATURE:
<223> OTHER INFORMATION: primer

<400> SEQUENCE: 6

```
cgtgaaggcc gtcctgttca atcatgttgg ctagtgttgc ttaggtcgct tgctgctg      58
```

<210> SEQ ID NO 7
<211> LENGTH: 826
<212> TYPE: DNA
<213> ORGANISM: Artificial Sequence
<220> FEATURE:
<223> OTHER INFORMATION: Neomycin resistance gene (Neor)

<400> SEQUENCE: 7
```

```
agcgacctaa gcaacactag ccaacatgat tgaacaggac ggccttcacg ctggctcgcc        60
cgctgcttgg gtggaacggc tgttcggcta cgactgggct cagcagacga tcggctgctc       120
ggacgcggcc gtgttccgcc ttagcgcgca gggccggccg gtcctgtttg tcaagaccga       180
ccttagcggc gccctcaacg agctccagga cgaagctgcc cgcctcagct ggcttgccac       240
gacgggggtt ccgtgcgccg ctgtgctcga cgtcgtcacc gaagccggcc gcgactggct       300
gctcctcggg gaagtgcccg gccaggacct cctcagcagc cacctcgcgc cgctgagaa       360 ggtgtccatc atggccgacg ccatgcgccg cctgcacacc ctcgaccccg ccacctgccc       420
cttcgaccac caggcgaagc acaggatcga acgcgcccgc acgcggatgg aggctggcct       480
cgtcgaccaa gacgacctcg acgaggagca ccagggcctc gcgccggcgg aactgttcgc       540
caggcttaag gctaggatgc cggacggcga ggacctcgtg gtcacgcacg cgacgcctg       600 cctccccaac atcatggtcg agaacggccg cttctcgggc tttatcgact gcgggcgcct       660
gggcgtggcg gaccgctacc aagacatcgc gctcgccacg cgggacatcg ccgaggagct       720 tgcggcgag tgggccgacc gctttctcgt gctctacggc atcgccgccc cggacagcca       780
gaggattgcg ttctaccgcc tcctggacga gttctttga gatctg                      826

<210> SEQ ID NO 8
<211> LENGTH: 54
<212> TYPE: DNA
<213> ORGANISM: Artificial Sequence
<220> FEATURE:
<223> OTHER INFORMATION: primer

<400> SEQUENCE: 8
agcgacctaa gcaacactag ccaacatgat tgaacaggac ggccttcacg ctgg             54

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
cagatctcaa aagaactcgt ccagga                                            26

<210> SEQ ID NO 10
<211> LENGTH: 1395
<212> TYPE: DNA
<213> ORGANISM: Artificial Sequence
<220> FEATURE:
<223> OTHER INFORMATION: fusion DNA (T. aureum ATCC 34304 ubiquitin
      promoter/Neor)

<400> SEQUENCE: 10
cccagatctg ccgcagcgcc tggtgcaccc gccgggcgtt gttggtgtgc tcttcttgcc        60
tccgagagag agagcggagc ggatgcatag gaaatcgggc cacgcgggag ggccatgcgt       120
tcgccccaca cgccactttc cacgcccgct ctctctccgg ccggcaggca gcgcataact       180
ctccgacgct ggcaggctgg tagcaactgg caggacaac tcgcgcgcgg gtcccggtcg       240
ttcgatgtgc caacccgaga gaatccagcc agcagggcgg ttggcctcat cgcccacctg       300
ctatggtgca gcgaaccaac tcccgaagcg gccggttctg cgattccctc ttctgaattc       360
tgaattctga actgattccg gaggagaacc ctctggaagc gcgggttgcc tctccagttc       420
tgccgaacta gacaggggag tgagcagaga gtgaccctga cgcgggagcg agctggttgc       480
```

```
tggaaaagtc gcgaacgctg ggctgtgtca cgcgtccact tcgggcagac cccaaacgac      540
aagcagaaca agcaacacca gcagcagcaa gcgacctaag caacactagc caacatgatt      600
gaacaggacg gccttcacgc tggctcgccc gctgcttggg tggaacggct gttcggctac      660
gactgggctc agcagacgat cggctgctcg gacgcggccg tgttccgcct tagcgcgcag      720
ggccggccgg tcctgtttgt caagaccgac cttagcggcg ccctcaacga gctccaggac      780
gaagctgccc gcctcagctg gcttgccacg acggggttc cgtgcgccgc tgtgctcgac       840
gtcgtcaccg aagccggccg cgactggctg ctcctcgggg aagtgcccgg ccaggacctc      900
ctcagcagcc acctcgcgcc cgctgagaag gtgtccatca tggccgacgc catgcgccgc      960
ctgcacaccc tcgaccccgc cacctgcccc ttcgaccacc aggcgaagca caggatcgaa     1020
cgcgcccgca cgcggatgga ggctggcctc gtcgaccaag acgacctcga cgaggagcac     1080
cagggcctcg cgccggcgga actgttcgcc aggcttaagg ctaggatgcc ggacggcgag     1140
gacctcgtgg tcacgcacgg cgacgcctgc ctccccaaca tcatggtcga aacggccgc      1200 ttctcgggct ttatcgactg cgggcgcctg ggcgtggcgg accgctacca agacatcgcg     1260
ctcgccacgc gggacatcgc cgaggagctt ggcggcgagt gggccgaccg ctttctcgtg     1320
ctctacggca tcgccgcccc ggacagccag aggattgcgt tctaccgcct cctggacgag     1380
ttcttttgag atctg                                                      1395

<210> SEQ ID NO 11
<211> LENGTH: 617
<212> TYPE: DNA
<213> ORGANISM: Artificial Sequence
<220> FEATURE:
<223> OTHER INFORMATION: ubiquitin promoter

<400> SEQUENCE: 11
cccagatctg ccgcagcgcc tggtgcaccc gccgggcgtt gttgtgtgct cttcttgcct       60
ccgagagaga gagcggagcg gatgcatagg aaatcgggcc acgcgggagg gccatgcgtt      120
cgccccacac gccactttcc acgcccgctc tctctccggc cggcaggcag cgcataactc      180
tccgacgctg gcaggctggt agcaactggc agggacaact cgcgcgcggg tcccggtcgt      240
tcgatgtgcc aacccgagag aatccagcca gcagggcggt tggcctcatc gcccacctgc      300
tatggtgcag cgaaccaact cccgaagcgg ccggttctgc gattccctct tctgaattct      360
gaattctgaa ctgattccgg aggagaaccc tctggaagcg cgggttgcct ctccagttct      420
gccgaactag acagggagt gagcagagag tgacccctgac gcggagcgag ctggttgctg      480
gaaaagtcgc gaacgctggg ctgtgtcacg cgtccacttc gggcagaccc caaacgacaa      540
gcagaacaag caacaccagc agcagcaagc gacctaagca acactagcca acatgaaaaa      600
gcctgaactc accgcga                                                    617

<210> SEQ ID NO 12
<211> LENGTH: 58
<212> TYPE: DNA
<213> ORGANISM: Artificial Sequence
<220> FEATURE:
<223> OTHER INFORMATION: primer

<400> SEQUENCE: 12
tcgcggtgag ttcaggcttt ttcatgttgg ctagtgttgc ttaggtcgct tgctgctg         58

<210> SEQ ID NO 13
```

<211> LENGTH: 1058
<212> TYPE: DNA
<213> ORGANISM: Artificial Sequence
<220> FEATURE:
<223> OTHER INFORMATION: Hygromycin resistance gene (Hygr)

<400> SEQUENCE: 13

| | |
|---|---|
| agcgacctaa gcaacactag ccaacatgaa aaagcctgaa ctcaccgcga cgtctgtcga | 60 |
| gaagtttctg atcgaaaagt tcgacagcgt ctccgacctg atgcagctct cggagggcga | 120 |
| agaatctcgt gctttcagct tcgatgtagg agggcgtgga tatgtcctgc gggtaaatag | 180 |
| ctgcgccgat ggtttctaca agatcgtta tgtttatcgg cactttgcat cggccgcgct | 240 |
| cccgattccg gaagtgcttg acattgggga attcagcgag agcctgacct attgcatctc | 300 |
| ccgccgtgca cagggtgtca cgttgcaaga cctgcctgaa accgaactgc ccgctgttct | 360 |
| gcagccggtc gcggaggcca tggatgcgat cgctgcggcc gatcttagcc agacgagcgg | 420 |
| gttcggccca ttcggaccgc aaggaatcgg tcaatacact acatggcgtg atttcatatg | 480 |
| cgcgattgct gatccccatg tgtatcactg gcaaactgtg atggacgaca ccgtcagtgc | 540 |
| gtccgtcgcg caggctctcg atgagctgat gctttgggcc gaggactgcc ccgaagtccg | 600 |
| gcacctcgtg cacgcggatt tcggctccaa caatgtcctg acggacaatg gccgcataac | 660 |
| agcggtcatt gactggagcg aggcgatgtt cggggattcc caatacgagg tcgccaacat | 720 |
| cttcttctgg aggccgtggt tggcttgtat ggagcagcag acgcgctact cgagcggag | 780 |
| gcatccggag cttgcaggat cgccgcggct ccgggcgtat atgctccgca ttggtcttga | 840 |
| ccaactctat cagagcttgg ttgacggcaa tttcgatgat gcagcttggg cgcagggtcg | 900 |
| atgcgacgca atcgtccgat ccggagccgg gactgtcggg cgtacacaaa tcgcccgcag | 960 |
| aagcgcggcc gtctggaccg atggctgtgt agaagtactc gccgatagtg gaaaccgacg | 1020 |
| ccccagcact cgtccgaggg caaaggaata gagatctg | 1058 |

<210> SEQ ID NO 14
<211> LENGTH: 56
<212> TYPE: DNA
<213> ORGANISM: Artificial Sequence
<220> FEATURE:
<223> OTHER INFORMATION: primer

<400> SEQUENCE: 14

| | |
|---|---|
| agcgacctaa gcaacactag ccaacatgaa aaagcctgaa ctcaccgcga cgtctg | 56 |

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15

| | |
|---|---|
| cagatctcta ttcctttgcc ctcggacgag tgctgg | 36 |

<210> SEQ ID NO 16
<211> LENGTH: 1625
<212> TYPE: DNA
<213> ORGANISM: Artificial Sequence
<220> FEATURE:
<223> OTHER INFORMATION: fusion DNA (Thraustochytrium aureum ATCC 34304 ubiquitin promoter[pc]DNA 3.1/ Hygr)

<400> SEQUENCE: 16

```
cccagatctg ccgcagcgcc tggtgcaccc gccgggcgtt gttgtgtgct cttcttgcct    60
ccgagagaga gagcggagcg gatgcatagg aaatcgggcc acgcgggagg gccatgcgtt   120
cgccccacac gccactttcc acgcccgctc tctctccggc cggcaggcag cgcataactc   180
tccgacgctg gcaggctggt agcaactggc agggacaact cgcgcgcggg tcccggtcgt   240
tcgatgtgcc aacccgagag aatccagcca gcagggcggt tggcctcatc gcccacctgc   300
tatggtgcag cgaaccaact cccgaagcgg ccggttctgc gattccctct tctgaattct   360
gaattctgaa ctgattccgg aggagaaccc tctggaagcg cgggttgcct ctccagttct   420
gccgaactag acaggggagt gagcagagag tgaccctgac gcggagcgag ctggttgctg   480
gaaaagtcgc gaacgctggg ctgtgtcacg cgtccacttc gggcagaccc caaacgacaa   540
gcagaacaag caacaccagc agcagcaagc gacctaagca acactagcca acatgaaaaa   600
gcctgaactc accgcgacgt ctgtcgagaa gtttctgatc gaaaagttcg acagcgtctc   660
cgacctgatg cagctctcgg agggcgaaga atctcgtgct ttcagcttcg atgtaggagg   720
gcgtggatat gtcctgcggg taaatagctg cgccgatggt ttctacaaag atcgttatgt   780
ttatcggcac tttgcatcgg ccgcgctccc gattccggaa gtgcttgaca ttggggaatt   840
cagcgagagc ctgacctatt gcatctcccg ccgtgcacag ggtgtcacgt tgcaagacct   900
gcctgaaacc gaactgcccg ctgttctgca gccggtcgcg gaggccatgg atgcgatcgc   960
tgcggccgat cttagccaga cgagcgggtt cggcccattc ggaccgcaag gaatcggtca  1020
atacactaca tggcgtgatt tcatatgcgc gattgctgat ccccatgtgt atcactggca  1080
aactgtgatg gacgacaccg tcagtgcgtc cgtcgcgcag gctctcgatg agctgatgct  1140
ttgggccgag gactgccccg aagtccggca cctcgtgcac gcggatttcg gctccaacaa  1200
tgtcctgacg gacaatggcc gcataacagc ggtcattgac tggagcgagg cgatgttcgg  1260
ggattcccaa tacgaggtcg ccaacatctt cttctggagg ccgtggttgg cttgtatgga  1320
gcagcagacg cgctacttcg agcggaggca tccggagctt gcaggatcgc gcggctccg   1380
ggcgtatatg ctccgcattg gtcttgacca actctatcag agcttggttg acggcaattt  1440
cgatgatgca gcttgggcgc agggtcgatg cgacgcaatc gtccgatccg gagccgggac  1500
tgtcgggcgt acacaaatcg cccgcagaag cgcggccgtc tggaccgatg gctgtgtaga  1560
agtactcgcc gatagtggaa accgacgccc cagcactcgt ccgagggcaa aggaatagag  1620
atctg                                                              1625

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
ccttcggcgc tcctcttatg tatgt                                          25

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
caatgcaaga ggcgaactgg gagag                                          25
```

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
tggggctctg gaaccgctgc ttacg                                     25

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
cttccagctc tcccagttcg cctct                                     25

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
cgggttgttg atgttgagcg aggtg                                     25

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
cccacgccat ccacgagcac accac                                     25

<210> SEQ ID NO 23
<211> LENGTH: 957
<212> TYPE: DNA
<213> ORGANISM: Artificial Sequence
<220> FEATURE:
<223> OTHER INFORMATION: cDNA (Parietichytrium genomic DNA contains C20
      elongase coding region)

<400> SEQUENCE: 23
cccggatcca tggcagctcg cgtggagaaa cagcaggcac ctgcgaaggc cgccaagaag     60
gtggggtcgc gtgtggaccg cagtgatggg ttctttcgca ctttcaacct ctgtgcgctg    120
tacggaagcg cgttcgcgta cgcttacaac aatgggccag tggacaacga cggcaagggc    180
ttgtactttt caaagtctcc attctacgca ttcctcgtct cggacgccat gaccttcggc    240
gctcctctta tgtatgtaat tgctgtcatg gcactcagcc gatacatggc agacaagcag    300
cccctcactg gcttcattaa aagctacatt cagccagttt acaacattgt gcaaatcgtg    360
gtgtgctcgt ggatggcgtg gggccttttg ccacaggtgg acatcttcaa cctcaaccca    420
ttcggtctca acaagcagcg tgatgccaac atcgagttct tgtcatggt ccacctcctg    480 acaaagttcc tcgactggac cgacaccttc atcatgattt tcaagaagaa ctatgcacag    540
gtctcttttc tccaggtgtt ccaccatgcc accatcggaa tggtgtggtc cttcctcctc    600

```
cagcgcggct ggggctctgg aaccgctgct tacggagcgt tcatcaactc ggtcacccat    660
gtcatcatgt acactcatta ctttgtcacc tcgctcaaca tcaacaaccc gttcaagagg    720
tacatcaccg gcttccagct ctcccagttc gcctcttgca ttgtacatgc tctcctcgtc    780
cttgccttcg aggaggtgta ccccctcgag tacgcttacc ttcagatcag ctaccacatc    840
atcatgctct acctcttcgg caggagaatg aactggagcc ctctctggtg cactggcgag    900
gtcgacgggc ttgacgtcaa cgtcgagacc tccaagaagg ctcagtaagg atccggg      957
```

```
<210> SEQ ID NO 24
<211> LENGTH: 32
<212> TYPE: DNA
<213> ORGANISM: Artificial Sequence
<220> FEATURE:
<223> OTHER INFORMATION: primer

<400> SEQUENCE: 24
cccggatcca tggcagctcg cgtggagaaa ca                                  32
```

```
<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
cccggatcct tactgagcct tcttggaggt ctc                                 33
```

```
<210> SEQ ID NO 26
<211> LENGTH: 936
<212> TYPE: DNA
<213> ORGANISM: Artificial Sequence
<220> FEATURE:
<223> OTHER INFORMATION: genomic DNA (Parietichytrium C20 elongase gene)

<400> SEQUENCE: 26
atggcagctc gcgtggagaa acagcaggca cctgcgaagg ccgccaagaa ggtggggtcg     60
cgtgtggacc gcagtgatgg gttctttcgc actttcaacc tctgtgcgct gtacggaagc    120
gcgttcgcgt acgcttacaa caatgggcca gtggacaacg acggcaaggg cttgtacttt    180
tcaaagtctc cattctacgc attcctcgtc tcggacgcca tgaccttcgg cgctcctctt    240
atgtatgtaa ttgctgtcat ggcactcagc cgatacatgg cagacaagca gcccctcact    300
ggcttcatta aaagctacat tcagccagtt tacaacattg tgcaaatcgt ggtgtgctcg    360
tggatggcgt ggggcctttt gccacaggtg gacatcttca acctcaaccc attcggtctc    420
aacaagcagc gtgatgccaa catcgagttc tttgtcatgg tccacctcct gacaaagttc    480
ctcgactgga ccgacacctt catcatgatt ttcaagaaga actatgcaca ggtctctttt    540
ctccaggtgt tccaccatgc caccatcgga atggtgtggt ccttcctcct ccagcgcggc    600
tggggctctg gaaccgctgc ttacggagcg ttcatcaact cggtcaccca tgtcatcatg    660
tacactcatt actttgtcac ctcgctcaac atcaacaacc cgttcaagag gtacatcacc    720
ggcttccagc tctcccagtt cgcctcttgc attgtacatg ctctcctcgt ccttgccttc    780
gaggaggtgt accccctcga gtacgcttac cttcagatca gctaccacat catcatgctc    840
tacctcttcg gcaggagaat gaactggagc cctctctggt gcactggcga ggtcgacggg    900
cttgacgtca acgtcgagac tccaagaag gctcag                               936
```

```
<210> SEQ ID NO 27
<211> LENGTH: 312
<212> TYPE: PRT
<213> ORGANISM: Parietichytrium

<400> SEQUENCE: 27
```

| | | | | | | | | | | | | | | |
|---|---|---|---|---|---|---|---|---|---|---|---|---|---|---|
| Met | Ala | Ala | Arg | Val | Glu | Lys | Gln | Gln | Ala | Pro | Ala | Lys | Ala | Lys |
| 1 | | | | 5 | | | | | 10 | | | | | 15 |
| Lys | Val | Gly | Ser | Arg | Val | Asp | Arg | Ser | Asp | Gly | Phe | Phe | Arg | Thr | Phe |
| | | | 20 | | | | | 25 | | | | | 30 | |
| Asn | Leu | Cys | Ala | Leu | Tyr | Gly | Ser | Ala | Phe | Ala | Tyr | Ala | Tyr | Asn | Asn |
| | | | 35 | | | | | 40 | | | | | 45 | | |
| Gly | Pro | Val | Asp | Asn | Asp | Gly | Lys | Gly | Leu | Tyr | Phe | Ser | Lys | Ser | Pro |
| | | 50 | | | | | 55 | | | | | 60 | | | |
| Phe | Tyr | Ala | Phe | Leu | Val | Ser | Asp | Ala | Met | Thr | Phe | Gly | Ala | Pro | Leu |
| 65 | | | | 70 | | | | | 75 | | | | | 80 | |
| Met | Tyr | Val | Ile | Ala | Val | Met | Ala | Leu | Ser | Arg | Tyr | Met | Ala | Asp | Lys |
| | | | | 85 | | | | | 90 | | | | | 95 | |
| Gln | Pro | Leu | Thr | Gly | Phe | Ile | Lys | Ser | Tyr | Ile | Gln | Pro | Val | Tyr | Asn |
| | | | 100 | | | | | 105 | | | | | 110 | | |
| Ile | Val | Gln | Ile | Val | Cys | Ser | Trp | Met | Ala | Trp | Gly | Leu | Leu | Pro |
| | | | 115 | | | | | 120 | | | | | 125 | |
| Gln | Val | Asp | Ile | Phe | Asn | Leu | Asn | Pro | Phe | Gly | Leu | Asn | Lys | Gln | Arg |
| | | 130 | | | | | 135 | | | | | 140 | | | |
| Asp | Ala | Asn | Ile | Glu | Phe | Phe | Val | Met | Val | His | Leu | Leu | Thr | Lys | Phe |
| 145 | | | | | 150 | | | | | 155 | | | | | 160 |
| Leu | Asp | Trp | Thr | Asp | Thr | Phe | Ile | Met | Ile | Phe | Lys | Lys | Asn | Tyr | Ala |
| | | | | 165 | | | | | 170 | | | | | 175 | |
| Gln | Val | Ser | Phe | Leu | Gln | Val | Phe | His | His | Ala | Thr | Ile | Gly | Met | Val |
| | | | 180 | | | | | 185 | | | | | 190 | | |
| Trp | Ser | Phe | Leu | Leu | Gln | Arg | Gly | Trp | Gly | Ser | Gly | Thr | Ala | Ala | Tyr |
| | | | 195 | | | | | 200 | | | | | 205 | | |
| Gly | Ala | Phe | Ile | Asn | Ser | Val | Thr | His | Val | Ile | Met | Tyr | Thr | His | Tyr |
| | | 210 | | | | | 215 | | | | | 220 | | | |
| Phe | Val | Thr | Ser | Leu | Asn | Ile | Asn | Asn | Pro | Phe | Lys | Arg | Tyr | Ile | Thr |
| 225 | | | | | 230 | | | | | 235 | | | | | 240 |
| Gly | Phe | Gln | Leu | Ser | Gln | Phe | Ala | Ser | Cys | Ile | Val | His | Ala | Leu | Leu |
| | | | | 245 | | | | | 250 | | | | | 255 | |
| Val | Leu | Ala | Phe | Glu | Glu | Val | Tyr | Pro | Leu | Glu | Tyr | Ala | Tyr | Leu | Gln |
| | | | 260 | | | | | 265 | | | | | 270 | | |
| Ile | Ser | Tyr | His | Ile | Ile | Met | Leu | Tyr | Leu | Phe | Gly | Arg | Arg | Met | Asn |
| | | | 275 | | | | | 280 | | | | | 285 | | |
| Trp | Ser | Pro | Leu | Trp | Cys | Thr | Gly | Glu | Val | Asp | Gly | Leu | Asp | Val | Asn |
| | | 290 | | | | | 295 | | | | | 300 | | | |
| Val | Glu | Thr | Ser | Lys | Lys | Ala | Gln |
| 305 | | | | 310 | | | |

```
<210> SEQ ID NO 28
<211> LENGTH: 26
<212> TYPE: DNA
<213> ORGANISM: Artificial Sequence
<220> FEATURE:
<223> OTHER INFORMATION: primer

<400> SEQUENCE: 28
acaaagatct cgactggacc gacacc                                              26
```

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29

```
agtcgagatc tttgtcagga ggtggac                                        27
```

<210> SEQ ID NO 30
<211> LENGTH: 935
<212> TYPE: DNA
<213> ORGANISM: Artificial Sequence
<220> FEATURE:
<223> OTHER INFORMATION: BglIIinserted C20 elongase

<400> SEQUENCE: 30

```
atggcagctc gcgtggagaa acagcaggca cctgcgaagg ccgccaagaa ggtggggtcg     60
cgtgtggacc gcagtgatgg gttctttcgc actttcaacc tctgtgcgct gtacggaagc    120
gcgttcgcgt acgcttacaa caatgggcca gtggacaacg acggcaaggg cttgtacttt    180
tcaaagtctc cattctacgc attcctcgtc tcggacgcca tgaccttcgg cgctcctctt    240
atgtatgtaa ttgctgtcat ggcactcagc cgatacatgg cagacaagca gcccctcact    300
ggcttcatta aaagctacat tcagccagtt tacaacattg tgcaaatcgt ggtgtgctcg    360
tggatggcgt ggggcctttt gccacaggtg gacatcttca acctcaaccc attcggtctc    420
aacaagcagc gtgatgccaa catcgagttc tttgtcatgg tccacctcct gacaaagatc    480
tcgactggac cgacaccttc atcatgattt caagaagaa ctatgcacag gtctcttttc     540
tccaggtgtt ccaccatgcc accatcggaa tggtgtggtc cttcctcctc cagcgcggct    600
ggggctctgg aaccgctgct tacgagcgt tcatcaactc ggtcacccat gtcatcatgt     660
acactcatta ctttgtcacc tcgctcaaca tcaacaaccc gttcaagagg tacatcaccg    720
gcttccagct ctcccagttc gcctcttgca ttgtacatgc tctcctcgtc cttgccttcg    780
aggaggtgta cccctcgag tacgcttacc ttcagatcag ctaccacatc atcatgctct     840
acctcttcgg caggagaatg aactggagcc ctctctggtg cactggcgag gtcgacgggc    900
ttgacgtcaa cgtcgagacc tccaagaagg ctcag                               935
```

<210> SEQ ID NO 31
<211> LENGTH: 2661
<212> TYPE: DNA
<213> ORGANISM: Artificial Sequence
<220> FEATURE:
<223> OTHER INFORMATION: fusion DNA (Parietichytrium C20 elongase 5'
       region/SV40 terminator/Neor/ubiquitin promoter/Parietichytrium C20
       elongase 3' region)

<400> SEQUENCE: 31

```
cccggatcca tggcagctcg cgtggagaaa cagcaggcac ctgcgaaggc cgccaagaag     60
gtggggtcgc gtgtggaccg cagtgatggg ttctttcgca ctttcaacct ctgtgcgctg    120
tacggaagcg cgttcgcgta cgcttacaac aatgggccag tggacaacga cggcaagggc    180
ttgtactttt caaagtctcc attctacgca ttcctcgtct cggacgccat gaccttcggc    240
gctcctctta tgtatgtaat tgctgtcatg gcactcagcc gatacatggc agacaagcag    300
cccctcactg gcttcattaa aagctacatt cagccagttt acaacattgt gcaaatcgtg    360
```

```
gtgtgctcgt ggatggcgtg gggccttttg ccacaggtgg acatcttcaa cctcaaccca      420
ttcggtctca acaagcagcg tgatgccaac atcgagttct tgtcatggt ccacctcctg       480 acaaagatct agctagaggt cgacggtata cagacatgat aagatacatt gatgagtttg      540
gacaaaccac aactagaatg cagtgaaaaa aatgctttat ttgtgaaatt tgtgatgcta      600
ttgctttatt tgtaaccatt ataagctgca ataaacaagt tggggtgggc gaagaactcc      660
agcatgagat ccccgcgctg gaggatcatc cagccggcgt cccggaaaac gattccgaag      720
cccaaccttt catagaaggc ggcggtggaa tcgaaatctc gtgatggcag gttgggcgtc      780
gcttggtcgg tcatttcgcg gatctcaaaa gaactcgtcc aggaggcggt agaacgcaat      840
cctctggctg tccggggcgg cgatgccgta gagcacgaga aagcggtcgg cccactcgcc      900
gccaagctcc tcggcgatgt cccgcgtggc gagcgcgatg tcttggtagc ggtccgccac      960
gcccaggcgc ccgcagtcga taaagcccga gaagcggccg ttctcgacca tgatgttggg     1020
gaggcaggcg tcgccgtgcg tgaccacgag gtcctcgccg tccggcatcc tagccttaag     1080
cctggcgaac agttccgccg gcgcgaggcc ctggtgctcc tcgtcgaggt cgtcttggtc     1140
gacgaggcca gcctccatcc gcgtgcgggc gcgttcgatc ctgtgcttcg cctggtggtc     1200
gaaggggcag gtggcggggt cgagggtgtg caggcggcgc atggcgtcgg ccatgatgga     1260
caccttctca gcgggcgcga ggtggctgct gaggaggtcc tggccgggca cttccccgag     1320
gagcagccag tcgcggccgg cttcggtgac gacgtcgagc acagcggcgc acggaaccgc     1380
cgtcgtggca agccagctga ggcgggcagc ttcgtcctgg agctcgttga gggcgccgct     1440
aaggtcggtc ttgacaaaca ggaccggccg gccctgcgcg ctaaggcgga cacggccgc     1500 gtccgagcag ccgatcgtct gctgagccca gtcgtagccg aacagccgtt ccacccaagc     1560
agcgggcgag ccagcgtgaa ggccgtcctg ttcaatcatg ttggctagtg ttgcttaggt     1620
cgcttgctgc tgctggtgtt gcttgttctg cttgtcgttt ggggtctgcc cgaagtggac     1680
gcgtgacaca gcccagcgtt cgcgactttt ccagcaacca gctcgctccg cgtcagggtc     1740
actctctgct cactcccctg tctagttcgg cagaactgga gaggcaaccc gcgcttccag     1800
agggttctcc tccggaatca gttcagaatt cagaattcag aagagggaat cgcagaaccg     1860
gccgcttcgg gagttggttc gctgcaccat agcaggtggg cgatgaggcc aaccgccctg     1920
ctggctggat tctctcgggt tggcacatcg aacgaccggg acccgcgcgc gagttgtccc     1980
tgccagttgc taccagcctg ccagcgtcgg agagttatgc gctgcctgcc ggccggagag     2040
agagcgggcg tggaaagtgg cgtgtgggc gaacgcatgg ccctcccgcg tggcccgatt      2100
tcctatgcat ccgctccgct ctctctctcg gaggcaagaa gagcacacca acaacgcccg     2160
gcgggtgcac caggcgctgc ggcagatcca gatctcgact ggaccgacac cttcatcatg     2220
attttcaaga agaactatgc acaggtctct tttctccagg tgttccacca tgccaccatc     2280
ggaatggtgt ggtccttcct cctccagcgc ggctggggct ctggaaccgc tgcttacgga     2340
gcgttcatca actcggtcac ccatgtcatc atgtacactc attactttgt cacctcgctc     2400
aacatcaaca cccgttcaa gaggtacatc accggcttcc agctctccca gttcgcctct      2460
tgcattgtac atgctctcct cgtccttgcc ttcgaggagg tgtaccccct cgagtacgct     2520
taccttcaga tcagctacca catcatcatg ctctacctct cggcaggag aatgaactgg      2580 agccctctct ggtgcactgg cgaggtcgac gggcttgacg tcaacgtcga gacctccaag     2640
aaggctcagt aaggatccgg g                                               2661
```

<210> SEQ ID NO 32
<211> LENGTH: 2892
<212> TYPE: DNA
<213> ORGANISM: Artificial Sequence
<220> FEATURE:
<223> OTHER INFORMATION: fusion DNA (Parietichytrium C20 elongase 5'
      region/SV40 terminator/Hygr/ubiquitin promoter/Parietichytrium C20
      elongase 3' region)

<400> SEQUENCE: 32

| | | | | | |
|---|---|---|---|---|---|
| cccggatcca | tggcagctcg | cgtggagaaa | cagcaggcac | ctgcgaaggc | cgccaagaag | 60 |
| gtggggtcgc | gtgtggaccg | cagtgatggg | ttctttcgca | ctttcaacct | ctgtgcgctg | 120 |
| tacgaaagcg | cgttcgcgta | cgcttacaac | aatgggccag | tggacaacga | cggcaagggc | 180 |
| ttgtactttt | caaagtctcc | attctacgca | ttcctcgtct | cggacgccat | gaccttcggc | 240 |
| gctcctctta | tgtatgtaat | tgctgtcatg | gcactcagcc | gatacatggc | agacaagcag | 300 |
| cccctcactg | gcttcattaa | aagctacatt | cagccagttt | acaacattgt | gcaaatcgtg | 360 |
| gtgtgctcgt | ggatggcgtg | gggccttttg | ccacaggtgg | acatcttcaa | cctcaaccca | 420 |
| tcggtctca | acaagcagcg | tgatgccaac | atcgagttct | tgtcatggt | ccacctcctg | 480 |
| acaaagatct | agctagaggt | cgacggtata | cagacatgat | aagatacatt | gatgagtttg | 540 |
| gacaaaccac | aactagaatg | cagtgaaaaa | atgctttat | ttgtgaaatt | tgtgatgcta | 600 |
| ttgctttatt | tgtaaccatt | ataagctgca | ataaacaagt | tggggtgggc | aagaactcc | 660 |
| agcatgagat | ccccgcgctg | gaggatcatc | cagccggcgt | cccggaaaac | gattccgaag | 720 |
| cccaaccttt | catagaaggc | ggcggtggaa | tcgaaatctc | gtgatggcag | gttgggcgtc | 780 |
| gcttggtcgg | tcatttcgcg | gatctctatt | cctttgccct | cggacgagtg | ctggggcgtc | 840 |
| ggtttccact | atcggcgagt | acttctacac | agccatcggt | ccagacgcc | gcgcttctgc | 900 |
| gggcgatttg | tgtacgcccg | acagtcccgg | ctccggatcg | gacgattgcg | tcgcatcgac | 960 |
| cctgcgccca | agctgcatca | tcgaaattgc | cgtcaaccaa | gctctgatag | agttggtcaa | 1020 |
| gaccaatgcg | gagcatatac | gcccggagcc | gcggcgatcc | tgcaagctcc | ggatgcctcc | 1080 |
| gctcgaagta | gcgcgtctgc | tgctccatac | aagccaacca | cggcctccag | aagaagatgt | 1140 |
| tggcgacctc | gtattgggaa | tccccgaaca | tcgcctcgct | ccagtcaatg | accgctgtta | 1200 |
| tgcggccatt | gtccgtcagg | acattgttgg | agccgaaatc | cgcgtgcacg | aggtgccgga | 1260 |
| cttcggggca | gtcctcggcc | caaagcatca | gctcatcgag | agcctgcgcg | acggacgcac | 1320 |
| tgacggtgtc | gtccatcaca | gtttgccagt | gatacacatg | gggatcagca | atcgcgcata | 1380 |
| tgaaatcacg | ccatgtagtg | tattgaccga | ttccttgcgg | tccgaatggg | ccgaacccgc | 1440 |
| tcgtctggct | aagatcggcc | gcagcgatcg | catccatggc | ctccgcgacc | ggctgcagaa | 1500 |
| cagcgggcag | ttcggtttca | ggcaggtctt | gcaacgtgac | accctgtgca | cggcgggaga | 1560 |
| tgcaataggt | caggctctcg | ctgaattccc | caatgtcaag | cacttccgga | atcgggagcg | 1620 |
| cggccgatgc | aaagtgccga | taaacataac | gatctttgta | gaaaccatcg | gcgcagctat | 1680 |
| ttacccgcag | gacatatcca | cgccctccta | catcgaagct | gaaagcacga | gattcttcgc | 1740 |
| cctccgagag | ctgcatcagg | tcggagacgc | tgtcgaactt | ttcgatcaga | aacttctcga | 1800 |
| cagacgtcgc | ggtgagttca | ggcttttca | tgttggctag | tgttgcttag | gtcgcttgct | 1860 |
| gctgctggtg | ttgcttgttc | tgcttgtcgt | ttggggtctg | cccgaagtgg | acgcgtgaca | 1920 |
| cagcccagcg | ttcgcgactt | ttccagcaac | cagctcgctc | cgcgtcaggg | tcactctctg | 1980 |
| ctcactcccc | tgtctagttc | ggcagaactg | gagaggcaac | ccgcgcttcc | agagggttct | 2040 |

-continued

| | |
|---|---|
| cctccggaat cagttcagaa ttcagaattc agaagaggga atcgcagaac cggccgcttc | 2100 |
| gggagttggt tcgctgcacc atagcaggtg ggcgatgagg ccaaccgccc tgctggctgg | 2160 |
| attctctcgg gttggcacat cgaacgaccg ggacccgcgc gcgagttgtc cctgccagtt | 2220 |
| gctaccagcc tgccagcgtc ggagagttat gcgctgcctg ccggccggag agagagcggg | 2280 |
| cgtggaaagt ggcgtgtggg gcgaacgcat ggccctcccg cgtggcccga tttcctatgc | 2340 |
| atccgctccg ctctctctct cggaggcaag aagagcacac aacaacgccc ggcgggtgca | 2400 |
| ccaggcgctg cggcagatcc agatctcgac tggaccgaca ccttcatcat gattttcaag | 2460 |
| aagaactatg cacaggtctc tttctccag gtgttccacc atgccaccat cggaatggtg | 2520 |
| tggtccttcc tcctccagcg cggctggggc tctggaaccg ctgcttacgg agcgttcatc | 2580 |
| aactcggtca cccatgtcat catgtacact cattactttg tcacctcgct caacatcaac | 2640 |
| aacccgttca gaggtacat caccggcttc agctctccc agttcgcctc ttgcattgta | 2700 |
| catgctctcc tcgtccttgc cttcgaggag gtgtaccccc tcgagtacgc ttaccttcag | 2760 |
| atcagctacc acatcatcat gctctacctc ttcggcagga gaatgaactg gagccctctc | 2820 |
| tggtgcactg gcgaggtcga cgggcttgac gtcaacgtcg agacctccaa gaaggctcag | 2880 |
| taaggatccg gg | 2892 |

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ggttgacggc aatttcgatg          20

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
cctcctacat cgaagctgaa ag          22

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
cttctcgggc tttatcgact g          21

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
taaggtcggt cttgacaaac ag          22

```
<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
agtagtcccc gatttggtag ttga                                         24

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ggcagagagc aaaaacacga gc                                           22

<210> SEQ ID NO 39
<211> LENGTH: 5003
<212> TYPE: DNA
<213> ORGANISM: Artificial Sequence
<220> FEATURE:
<223> OTHER INFORMATION: cDNA contains delta4-desaturase

<400> SEQUENCE: 39
gtttgaggag cgaggcattt cttcatttct tcgtggagaa gaaagggcac acctgcagac     60
taaacagcca agtaagaaaa gttatttatc atcatcacaa tatcctttct ggcctgtctc    120
caagagaaag aaacttttaa acttttttaaa ttttaacttt tgcttgtgct cgtatgctta   180
caaaagcttg caacgaaaca cagcggaagc aagttcagaa cacgccaatg acatctttgc    240
tctccaaaat tgaaaattgt tttgtcaaat tttaaaaact gattctgtaa gaaaccttaa    300 ttttttgcaaa caatcaaaaa atcgccgttg actgagtgtg attgaactca ctccaacgaa   360
agcgttagtc cctcttccta tactttacca taataatatc cctcttagat tccatcccga    420
cctgttccta ctacgagctt ataaaccccct acgccccaag ccaggtaaga gagactagta   480
aattcttgac aatctgactg actatcctaa accttctcga ctactatgca aaggactagt    540
cgctgtagtc ccagttgtgt gtactatagc agtaaagcgt tggtgtactt aacagtaaaa    600
cagtaaaacc aaagccccccc taaattcccc aaacagaatg agttgtctca gtccgaaact   660
ttctttgcaa tgaaatacga ttggtttgga aagttgacag tgagtgaaaa gcctttcgat    720
tgattgattt gcttcggtca ttcattcact cattcattca ctcattcaaa ttgaaatgag    780
catgaaagtg gtcgaagtgg agtatctagg cgatctacat gaacgacttc aaggagcaag    840
agtgcgagag gtaaaagta tgttaaagcg ttaaaagctg caaaagctgt aaaagtgaaa     900
gcccatctgg aaaccataga aacgttctca attcctcgat tcctcgattc ctcgtgcaga    960
ctgcagaaga agactgacaa agcatcggca ctggcactga catgcgggta cgagtaggta   1020
cggacagcga gtgcccacac agccccaagc ccacacattc attacattca ttcattgaac   1080
acattgaacg cattgaacaa tcaatcactc cacattgtca ctgtcaactg atgtcaactg   1140
gtaaacttgt aacttgtatt gtattgacct cgcttggtgc atagagtgcg tagagtgcgt   1200
agagtgcgta gccgtcgccc cggagagacg ctgttgactg acaactgtgt taaggtgtcg   1260
attacaacaa acaaacaaat aaacaaacaa ccaaacaaac acctcccaac acacgagctt   1320
tgacgtcctc accacccggt ttgccctcgc agtcgcggtc agttcagtgc cacgagtgcc   1380
```

-continued

| | | | | | |
|---|---|---|---|---|---|
| acggggcgta | aggaagttta | ggaaggcgtg | tttcgaatcc | ctttacagcg | cggcgctcgc | 1440 |
| gaactgaaga | cgcggagata | cgcagtagtg | agtgggtgga | gcaagaaaag | tagagggccc | 1500 |
| ccgtacgtcc | cggaggagag | accgattgtg | gattggactg | ctggatcgtg | gaataggcaa | 1560 |
| gatgacggcc | ggatttgaag | aagtgatcac | catgaagcag | gtgaaggacc | ggaatacgcc | 1620 |
| ggacgatgcg | tggtgcgtgg | tgcatggcaa | ggtgtacgac | atcaccaagt | tcaagaacgc | 1680 |
| tcacccggt | ggagatataa | tcatgttggc | ggctggcaag | gacgccacca | tcctgttcga | 1740 |
| gacttaccac | atccgcggtg | tgcccgatgc | cgtgttgcgc | aagtatcaga | tcggcaaact | 1800 |
| tccggacgga | aagaacaaag | agggcggcaa | cggcctcgac | agcgcctcgt | actactcctg | 1860 |
| ggacagcgag | ttttaccgcg | tccttcgcga | gcgcgtcttg | aagcgcctga | acgagctcaa | 1920 |
| gctgtccaga | cgcggaggct | tcgagatttg | ggccaaggct | atctttctct | tgaccggctt | 1980 |
| ctggtcttgc | ctctacctca | tgtgcacact | caacccaaat | gggcttgcga | ttcctgccgc | 2040 |
| catgatgttg | ggaatctttg | ctgccttcgt | aggaacctgc | attcagcacg | acgggaatca | 2100 |
| cggtgcgttc | gcccaatctt | cgtggcttaa | caaggccgct | ggttggactt | tggacatgat | 2160 |
| tggttccagc | gccatgacct | gggagatgca | gcacgtgctt | ggacatcatc | cgtacaccaa | 2220 |
| cttgattgaa | atggagaatg | gcaatcaaaa | ggtctccggc | aagcctgttg | acaccaagac | 2280 |
| tgtcgaccag | gagagcgacc | ctgatgtctt | tagcacctac | cctatgcttc | gccttcaccc | 2340 |
| ttggcacagc | aaaaagtggt | accacaaata | ccagcacatc | tatgcaccat | tcatctttgg | 2400 |
| gttcatgacc | atcaacaagg | tcattgcaca | ggacgtcggc | gttatcacac | gcaagcgtct | 2460 |
| cttccagatt | gacgccaact | gccgctacgc | ttctccgact | tacgtcgctc | gcttctggat | 2520 |
| catgaaggtt | cttaccgttc | tctacatggt | tggcctgcca | atgtacatgc | aaggtccatg | 2580 |
| ggagggtctc | aagttgttct | ttattgcgca | ctttacttgc | ggcgagctgc | tggccacaat | 2640 |
| gttcatcgta | aaccacatca | tcgagggtgt | cagctacgca | agcaaagatg | ccatcaaggg | 2700 |
| cgagatggcc | ccaccgaaaa | cggtccgcgg | tgtcacccca | atgcacgaga | cgcaaaaggt | 2760 |
| tctcgaccag | cgcgagaaag | acatggacga | aacttctaag | aagagccgca | tccctctcaa | 2820 |
| cgactgggcc | gctgtacagt | gccagacctc | cgtgaactgg | gctatcggtt | cttggttctg | 2880 |
| gaaccacttt | tccgggggcc | tcaatcatca | gattgagcat | catctgttcc | ccggcttgac | 2940 |
| tcacaccacc | tatgttcact | ttcacgatgt | ggtcaaagat | acttgcgctg | agtacggggt | 3000 |
| tccataccag | cacgaggaga | gtctatacac | tgcctacttt | aagatgttga | atcatctcaa | 3060 |
| gaccctaggc | aacgagccaa | tgcctgcctg | ggacaagaac | taacagtaaa | caaacatcac | 3120 |
| gcgtcctcaa | agcctgacta | tcgcgggctg | cgctttcact | ttgcctgccg | ttttggagga | 3180 |
| tatctgcttt | tgcgatcaaa | actaggaatg | gagtgtacag | ccagccactc | gttcttcagt | 3240 |
| acgaatcaac | gaagactttg | tctcctttcc | taaaaagag | gatgttttc | ttacctagct | 3300 |
| aacaaggcgg | tgtctggcca | ttgtacccttt | ggattcgcta | catacacaca | tacatacacg | 3360 |
| cctttcgttg | cgctgctcga | aatttgtagt | gacgtgagat | gaaagataaa | aaaaatagaa | 3420 |
| ttcaggtctc | gttcaaaagt | tcgtaattct | cttctccaat | tccattcgtc | tccggagaaa | 3480 |
| gtctaggtcg | gcattctgta | ttgaagcaat | gtgcagcagc | gaaacagaaa | aaacgagcag | 3540 |
| tcaaaagact | agctactagt | cttcgagtgg | atcgccccca | gccaatctca | aatacatctt | 3600 |
| tgcgaaaaca | gacactttttg | tttcctgaga | gcttttgatg | aaggtttccg | tcaaagtatc | 3660 |
| tgacgaggcg | ttgcacgggt | tctcgaaacc | cggcaaagca | ggtagatcta | actttctgag | 3720 |
| gctctccata | aaaccctgca | cacgatcttt | ggcttttggc | tcattcgtca | aacgaaacaa | 3780 |

```
aatgccaggc ttgtcgttgg ttccaactac ggttgtaaag ttgtatggcg agtgcactcg    3840 ttttcgtcg aaccagtctg gatgcttctg catcatggct ttcttgaagg caacagtttc    3900
cgtgaaagta gactccaggg ctgtataaga acctggagca agggtggtct tcatgccttg    3960
ctccatcatg tggatgacac tgtgactcac aaaattgcat ccaatctcag acatgtacat    4020
attgaggttg tagttttccg ggtccgtcac gttggagatg gagattccgc tcgccgaagc    4080
atcgcagcag taccaatgac ttgagcgatc cgccacccag tgtaggtata gtccaaatcg    4140
tacaatctct tcggggacag gatccccgtt gataagtgaa taaggtgcgc tcgagttgag    4200
atattcccca agctggcttg ccagtactac atccgtcatc ttgtagtttt cgttatggtc    4260
tgggtcctcg caggtcccgt tgcaagcgca agccggatca cagttgtagt taacgtattg    4320
ctcacctaac atcatatcgc ctccggcgag agggattgga ccgctcacca atttggagat    4380
gtgtttagaa gtgacggttc cgcttttagg gcaggtctcg ccagtgaatg gagatccatc    4440
agggccaatg ctagtatagc ctccaacaca aagcagatcc gtctctccaa aagcccatcg    4500
tcgagcagaa gcgagcgcac cctcgtaaaa gttgtcgtcc atatttgggg ccaggcccgg    4560
gcaatgcgca cggtaaaact catacgactt tttgaagcga tacctctgac agtcaccctc    4620
cttgccaccc gtgtgctcct tggcgctctc ggttaaaatg gagccattga agtgtccgat    4680
gtacgggatt cctaagtgcc gctgtgttcc tcccagcttg gtgtttgtac ggagaaaacc    4740
tctcataggt ggagtccacc actccaatcc catgtccgcg ccacagctgt caattgcgcg    4800
gtactgtacg aaatcaatcg cctgagaata cgcggccatg aagtaagcgt actctgcttt    4860
gaggccctgt gccacagcaa tataatagat cgcgtaaaag tgaatgaagc ctctgcaggc    4920
ggaggtatcg ttgaacccgg ttgtcatctg tgggagcaga cttgccagga tgcactttgg    4980
acgccagtca ttgtacgagc act                                           5003

<210> SEQ ID NO 40
<211> LENGTH: 23
<212> TYPE: DNA
<213> ORGANISM: Artificial
<220> FEATURE:
<223> OTHER INFORMATION: primer

<400> SEQUENCE: 40
gtttgaggag cgaggcattt ctt                                             23

<210> SEQ ID NO 41
<211> LENGTH: 23
<212> TYPE: DNA
<213> ORGANISM: Artificial
<220> FEATURE:
<223> OTHER INFORMATION: primer

<400> SEQUENCE: 41
agtgctcgta caatgactgg cgt                                             23

<210> SEQ ID NO 42
<211> LENGTH: 8020
<212> TYPE: DNA
<213> ORGANISM: Artificial
<220> FEATURE:
<223> OTHER INFORMATION: plasmid

<400> SEQUENCE: 42
tatagtgagt cgtattacaa ttcactggcc gtcgttttac aacgtcgtga ctgggaaaac    60
```

-continued

```
cctggcgtta cccaacttaa tcgccttgca gcacatcccc ctttcgccag ctggcgtaat    120
agcgaagagg cccgcaccga tcgcccttcc caacagttgc gcagcctgaa tggcgaatgg    180
acgcgccctg tagcggcgca ttaagcgcgg cgggtgtggt ggttacgcgc agcgtgaccg    240
ctacacttgc cagcgcccta cgcccgctc ctttcgcttt cttcccttcc tttctcgcca    300
cgttcgccgg ctttccccgt caagctctaa atcgggggct ccctttaggg ttccgattta    360
gtgctttacg gcacctcgac cccaaaaaac ttgattaggg tgatggttca cgtagtgggc    420
catcgccctg atagacggtt tttcgccctt tgacgttgga gtccacgttc tttaatagtg    480
gactcttgtt ccaaactgga acaacactca accctatctc ggtctattct tttgatttat    540
aagggatttt gccgatttcg gcctattggt taaaaaatga gctgatttaa caaaaattta    600
acgcgaattt taacaaaata ttaacgctta caatttcctg atgcggtatt ttctccttac    660
gcatctgtgc ggtatttcac accgcatcag gtggcacttt tcggggaaat gtgcgcggaa    720
cccctatttg tttatttttc taaatacatt caaatatgta tccgctcatg agacaataac    780
cctgataaat gcttcaataa tattgaaaaa ggaagagtat gagtattcaa catttccgtg    840
tcgcccttat tccctttttt gcggcatttt gccttcctgt ttttgctcac ccagaaacgc    900
tggtgaaagt aaaagatgct gaagatcagt tgggtgcacg agtgggttac atcgaactgg    960
atctcaacag cggtaagatc cttgagagtt ttcgccccga agaacgtttt ccaatgatga   1020
gcacttttaa agttctgcta tgtggcgcgg tattatcccg tattgacgcc gggcaagagc   1080
aactcggtcg ccgcatacac tattctcaga atgacttggt tgagtactca ccagtcacag   1140
aaaagcatct tacggatggc atgacagtaa agagaattatg cagtgctgcc ataaccatga   1200
gtgataacac tgcggccaac ttacttctga caacgatcgg aggaccgaag gagctaaccg   1260
cttttttgca acatggggg gatcatgtaa ctcgccttga tcgttgggaa ccggagctga   1320
atgaagccat accaaacgac gagcgtgaca ccacgatgcc tgtagcaatg caacaacgt   1380 tgcgcaaact attaactggc gaactactta ctctagcttc ccggcaacaa ttaatagact   1440
ggatggaggc ggataaagtt gcaggaccac ttctgcgctc ggcccttccg gctggctggt   1500
ttattgctga taaatctgga gccggtgagc gtgggtctcg cggtatcatt gcagcactgg   1560
ggccagatgg taagccctcc cgtatcgtag ttatctacac gacggggagt caggcaacta   1620
tggatgaacg aaatagacag atcgctgaga taggtgcctc actgattaag cattggtaac   1680
tgtcagacca gtttactca tatatacttt agattgattt aaaacttcat ttttaattta   1740
aaaggatcta ggtgaagatc ctttttgata atctcatgac caaaatccct taacgtgagt   1800
tttcgttcca ctgagcgtca gaccccgtag aaaagatcaa aggatcttct tgagatcctt   1860 ttttttctgcg cgtaatctgc tgcttgcaaa caaaaaaacc accgctacca gcggtggttt   1920
gtttgccgga tcaagagcta ccaactcttt ttccgaaggt aactggcttc agcagagcgc   1980
agataccaaa tactgttctt ctagtgtagc cgtagttagg ccaccacttc aagaactctg   2040
tagcaccgcc tacatacctc gctctgctaa tcctgttacc agtggctgct gccagtggcg   2100
ataagtcgtg tcttaccggg ttggactcaa gacgatagtt accggataag gcgcagcggt   2160
cgggctgaac ggggggttcg tgcacacagc ccagcttgga gcgaacgacc tacaccgaac   2220
tgagatacct acagcgtgag ctatgagaaa gcgccacgct tcccgaaggg agaaaggcgg   2280
acaggtatcc ggtaagcggc agggtcggaa caggagagcg cacgagggag cttccagggg   2340
gaaacgcctg gtatctttat agtcctgtcg ggtttcgcca cctctgactt gagcgtcgat   2400
ttttgtgatg ctcgtcaggg gggcggagcc tatggaaaaa cgccagcaac gcggcctttt   2460
```

```
tacggttcct ggccttttgc tggccttttg ctcacatgtt ctttcctgcg ttatcccctg   2520
attctgtgga taaccgtatt accgcctttg agtgagctga taccgctcgc cgcagccgaa   2580
cgaccgagcg cagcgagtca gtgagcgagg aagcggaaga gcgcccaata cgcaaaccgc   2640
ctctccccgc gcgttggccg attcattaat gcagctggca cgacaggttt cccgactgga   2700
aagcgggcag tgagcgcaac gcaattaatg tgagttagct cactcattag gcacccccagg   2760 ctttacactt tatgcttccg gctcgtatgt tgtgtggaat tgtgagcgga taacaatttc   2820
acacaggaaa cagctatgac catgattacg ccaagctatt taggtgacac tatagaatac   2880
tcaagctatg catccaacgc gttgggagct ctcccatatg gtcgacctgc aggcggccgc   2940
gaattcacta gtgattgttt gaggagcgag gcatttcttc atttcttcgt ggagaagaaa   3000
gggcacacct gcagactaaa cagccaagta agaaaagtta tttatcatca tcacaatatc   3060
ctttctggcc tgtctccaag agaaagaaac ttttaaactt tttaaatttt aacttttgct   3120
tgtgctcgta tgcttacaaa agcttgcaac gaaacacagc ggaagcaagt tcagaacacg   3180
ccaatgacat ctttgctctc caaaattgaa aattgttttg tcaaatttta aaaactgatt   3240
ctgtaagaaa ccttaatttt tgcaaacaat caaaaaatcg ccgttgactg agtgtgattg   3300
aactcactcc aacgaaagcg ttagtccctc ttcctatact ttaccataat aatatccctc   3360
ttagattcca tcccgacctg ttcctactac gagcttataa accccctacgc cccaagccag   3420 gtaagagaga ctagtaaatt cttgacaatc tgactgacta tcctaaacct tctcgactac   3480
tatgcaaagg actagtcgct gtagtcccag ttgtgtgtac tatagcagta aagcgttggt   3540
gtacttaaca gtaaaacagt aaaaccaaag cccccctaaa ttccccaaac agaatgagtt   3600
gtctcagtcc gaaactttct ttgcaatgaa atacgattgg tttggaaagt tgacagtgag   3660
tgaaaagcct ttcgattgat tgatttgctt cggtcattca ttcactcatt cattcactca   3720
ttcaaattga aatgagcatg aaagtggtcg aagtggagta tctaggcgat ctacatgaac   3780
gacttcaagg agcaagagtg cgagaggtaa aaagtatgtt aaagcgttaa aagctgcaaa   3840
agctgtaaaa gtgaaagccc atctggaaac catagaaacg ttctcaattc ctcgattcct   3900
cgattcctcg tgcagactgc agaagaagac tgacaaagca tcggcactgg cactgacatg   3960
cgggtacgag taggtacgga cagcgagtgc ccacacagcc ccaagcccac acattcatta   4020
cattcattca ttgaacacat tgaacgcatt gaacaatcaa tcactccaca ttgtcactgt   4080
caactgatgt caactggtaa acttgtaact tgtattgtat tgacctcgct tggtgcatag   4140
agtgcgtaga gtgcgtagag tgcgtagccg tcgccccgga gagacgctgt tgactgacaa   4200
ctgtgttaag gtgtcgatta caacaaacaa acaaataaac aaacaaccaa acaaacacct   4260
cccaacacac gagctttgac gtcctcacca cccggtttgc cctcgcagtc gcggtcagtt   4320
cagtgccacg agtgccacgg ggcgtaagga agtttaggaa ggcgtgtttc gaatcccttt   4380
acagcgcggc gctcgcgaac tgaagacgcg gagatacgca gtagtgagtg ggtggagcaa   4440
gaaaagtaga gggccccccgt acgtcccgga ggagagaccg attgtggatt ggactgctgg   4500
atcgtggaat aggcaagatg acggccggat ttgaagaagt gatcaccatg aagcaggtga   4560
aggaccggaa tacgccggac gatgcgtggt gcgtggtgca tggcaaggtg tacgacatca   4620
ccaagttcaa gaacgctcac cccggtggag atataatcat gttggcggct ggcaaggacg   4680
ccaccatcct gttcgagact taccacatcc gcggtgtgcc cgatgccgtg ttgcgcaagt   4740
atcagatcgg caaacttccg gacggaaaga acaaagaggg cggcaacggc ctcgacagcg   4800
```

```
cctcgtacta ctcctgggac agcgagtttt accgcgtcct tcgcgagcgc gtcttgaagc    4860
gcctgaacga gctcaagctg tccagacgcg gaggcttcga gatttgggcc aaggctatct    4920
ttctcttgac cggcttctgg tcttgcctct acctcatgtg cacactcaac ccaaatgggc    4980
ttgcgattcc tgccgccatg atgttgggaa tctttgctgc cttcgtagga acctgcattc    5040
agcacgacgg gaatcacggt gcgttcgccc aatcttcgtg gcttaacaag gccgctggtt    5100
ggactttgga catgattggt tccagcgcca tgacctggga gatgcagcac gtgcttggac    5160
atcatccgta caccaacttg attgaaatgg agaatggcaa tcaaaaggtc tccggcaagc    5220
ctgttgacac caagactgtc gaccaggaga gcgaccctga tgtctttagc acctacccta    5280
tgcttcgcct tcacccttgg cacagcaaaa agtggtacca caaataccag cacatctatg    5340
caccattcat ctttgggttc atgaccatca acaaggtcat tgcacaggac gtcggcgtta    5400
tcacacgcaa gcgtctcttc cagattgacg ccaactgccg ctacgcttct ccgacttacg    5460
tcgctcgctt ctggatcatg aaggttctta ccgttctcta catggttggc ctgccaatgt    5520
acatgcaagg tccatgggag ggtctcaagt tgttctttat tgcgcacttt acttgcggcg    5580
agctgctggc cacaatgttc atcgtaaacc acatcatcga gggtgtcagc tacgcaagca    5640
aagatgccat caagggcgag atggctccac cgaaaacggt ccgcggtgtc accccaatgc    5700
acgagacgca aaaggttctc gaccagcgcg agaaagacat ggacgaaact tctaagaaga    5760
gccgcatccc tctcaacgac tgggccgctg tacagtgcca gacctccgtg aactgggcta    5820
tcggttcttg gttctggaac cacttttccg ggggcctcaa tcatcagatt gagcatcatc    5880
tgttccccgg cttgactcac accacctatg ttcactttca cgatgtggtc aaagatactt    5940
gcgctgagta cggggttcca taccagcacg aggagagtct atacactgcc tactttaaga    6000
tgttgaatca tctcaagacc ctaggcaacg agccaatgcc tgcctgggac aagaactaac    6060
agtaaacaaa catcacgcgt cctcaaagcc tgactatcgc gggctgcgct ttcactttgc    6120
ctgccgtttt ggaggatatc tgcttttgcg atcaaaacta ggaatggagt gtacagccag    6180
ccactcgttc ttcagtacga atcaacgaag actttgtctc ctttcctaaa aagaggatg    6240
tttttcttac ctagctaaca aggcggtgtc tggccattgt acctttggat tcgctacata    6300
cacacataca tacacgcctt tcgttgcgct gctcgaaatt tgtagtgacg tgagatgaaa    6360
gataaaaaaa atagaattca ggtctcgttc aaaagttcgt aattctcttc tccaattcca    6420
ttcgtctccg gagaaagtct aggtcggcat tctgtattga agcaatgtgc agcagcgaaa    6480
cagaaaaaac gagcagtcaa aagactagct actagtcttc gagtggatcg cccccagcca    6540
atctcaaata catctttgcg aaaacagaca cttttgtttc ctgagagctt ttgatgaagg    6600
tttccgtcaa agtatctgac gaggcgttgc acgggttctc gaaacccggc aaagcaggta    6660
gatctaactt tctgaggctc tccataaaac cctgcacacg atctttggct tttggctcat    6720
tcgtcaaacg aaacaaaatg ccaggcttgt cgttggttcc aactacggtt gtaaagttgt    6780
atggcgagtg cactcgtttt tcgtcgaacc agtctggatg cttctgcatc atggctttct    6840
tgaaggcaac agtttccgtg aaagtagact ccagggctgt ataagaacct ggagcaaggg    6900
tggtcttcat gccttgctcc atcatgtgga tgacactgtg actcacaaaa ttgcatccaa    6960
tctcagacat gtacatattg aggttgtagt tttccgggtc cgtcacgttg gagatggaga    7020
ttccgctcgc cgaagcatcg cagcagtacc aatgacttga gcgatccgcc acccagtgta    7080
ggtatagtcc aaatcgtaca atctcttcgg ggacaggatc cccgttgata agtgaataag    7140
gtgcgctcga gttgagatat tccccaagct ggcttgccag tactacatcc gtcatcttgt    7200
```

```
agttttcgtt atggtctggg tcctcgcagg tcccgttgca agcgcaagcc ggatcacagt   7260
tgtagttaac gtattgctca cctaacatca tatcgcctcc ggcagagggg attggaccgc   7320
tcaccaattt ggagatgtgt ttagaagtga cggttccgct tttagggcag gtctcgccag   7380
tgaatggaga tccatcaggg ccaatgctag tatagcctcc aacacaaagc agatccgtct   7440
ctccaaaagc ccatcgtcga gcagaagcga gcgcaccctc gtaaaagttg tcgtccatat   7500
ttggggccag gcccgggcaa tgcgcacggt aaaactcata cgactttttg aagcgatacc   7560
tctgacagtc accctccttg ccacccgtgt gctccttggc gctctcggtt aaaatggagc   7620
cattgaagtg tccgatgtac gggattccta agtgccgctg tgttcctccc agcttggtgt   7680
ttgtacggag aaaacctctc ataggtggag tccaccactc caatcccatg tccgcgccac   7740
agctgtcaat tgcgcggtac tgtacgaaat caatcgcctg agaatacgcg gccatgaagt   7800
aagcgtactc tgctttgagg ccctgtgcca cagcaatata atagatcgcg taaaagtgaa   7860
tgaagcctct gcaggcggag gtatcgttga acccggttgt catctgtggg agcagacttg   7920
ccaggatgca ctttggacgc cagtcattgt acgagcacta atcgaattcc cgcggccgcc   7980
atggcggccg ggagcatgcg acgtcgggcc caattcgccc                         8020
```

<210> SEQ ID NO 43
<211> LENGTH: 1542
<212> TYPE: DNA
<213> ORGANISM: Parietichytrium sp. SEK571

<400> SEQUENCE: 43

```
atgacggccg gatttgaaga agtgatcacc atgaagcagg tgaaggaccg gaatacgccg     60
gacgatgcgt ggtgcgtggt gcatggcaag gtgtacgaca tcaccaagtt caagaacgct    120
caccccggtg gagatataat catgttggcg gctggcaagg acgccaccat cctgttcgag    180
acttaccaca tccgcggtgt gcccgatgcc gtgttgcgca agtatcagat cggcaaactt    240
ccggacggaa agaacaaaga gggcggcaac ggcctcgaca gcgcctcgta ctactcctgg    300
gacagcgagt tttaccgcgt ccttcgcgag gcgtcttga agcgcctgaa cgagctcaag    360
ctgtccagac gcggaggctt cgagatttgg gccaaggcta tctttctctt gaccggcttc    420
tggtcttgcc tctacctcat gtgcacactc aacccaaatg gcttgcgat tcctgccgcc    480 atgatgttgg gaatctttgc tgccttcgta ggaacctgca ttcagcacga cgggaatcac    540
ggtgcgttcg cccaatcttc gtggcttaac aaggccgctg gttggacttt ggacatgatt    600
ggttccagcg ccatgacctg ggagatgcag cacgtgcttg acatcatcc gtacaccaac    660 ttgattgaaa tggagaatgg caatcaaaag gtctccggca agcctgttga caccaagact    720
gtcgaccagg agagcgaccc tgatgtcttt agcacctacc ctatgcttcg ccttcaccct    780
tggcacagca aaagtggta ccacaaatac cagcacatct atgcaccatt catctttggg    840
ttcatgacca tcaacaaggt cattgcacag gacgtcggcg ttatcacacg caagcgtctc    900
ttccagattg acgccaactg ccgctacgct tctccgactt acgtcgctcg cttctggatc    960
atgaaggttc ttaccgttct ctacatggtt ggcctgccaa tgtacatgca aggtccatgg   1020
gagggtctca agttgttctt tattgcgcac tttacttgcg gcgagctgct ggccacaatg   1080
ttcatcgtaa accacatcat cgagggtgtc agctacgcaa gcaaagatgc catcaagggc   1140
gagatggctc caccgaaaac ggtccgcggt gtcaccccaa tgcacgagac gcaaaaggtt   1200
ctcgaccagc gcgagaaaga catggacgaa acttctaaga gagccgcat ccctctcaac   1260
```

```
gactgggccg ctgtacagtg ccagacctcc gtgaactggg ctatcggttc ttggttctgg    1320
aaccactttt ccgggggcct caatcatcag attgagcatc atctgttccc cggcttgact    1380
cacaccacct atgttcactt tcacgatgtg gtcaaagata cttgcgctga gtacggggtt    1440
ccataccagc acgaggagag tctatacact gcctacttta agatgttgaa tcatctcaag    1500
accctaggca acgagccaat gcctgcctgg gacaagaact aa                       1542
```

<210> SEQ ID NO 44
<211> LENGTH: 26
<212> TYPE: DNA
<213> ORGANISM: Artificial
<220> FEATURE:
<223> OTHER INFORMATION: primer

<400> SEQUENCE: 44

```
ggcaagatct aactttctga ggctct                                           26
```

<210> SEQ ID NO 45
<211> LENGTH: 26
<212> TYPE: DNA
<213> ORGANISM: Artificial
<220> FEATURE:
<223> OTHER INFORMATION: primer

<400> SEQUENCE: 45

```
aagttagatc ttgcctattc cacgat                                           26
```

<210> SEQ ID NO 46
<211> LENGTH: 26
<212> TYPE: DNA
<213> ORGANISM: Artificial
<220> FEATURE:
<223> OTHER INFORMATION: primer

<400> SEQUENCE: 46

```
gtgcagacgc agaagaagac tgacaa                                           26
```

<210> SEQ ID NO 47
<211> LENGTH: 25
<212> TYPE: DNA
<213> ORGANISM: Artificial
<220> FEATURE:
<223> OTHER INFORMATION: primer

<400> SEQUENCE: 47

```
cttctgcgtc tgcacgagga atcga                                            25
```

<210> SEQ ID NO 48
<211> LENGTH: 7579
<212> TYPE: DNA
<213> ORGANISM: Artificial
<220> FEATURE:
<223> OTHER INFORMATION: plasmid

<400> SEQUENCE: 48

```
tatagtgagt cgtattacaa ttcactggcc gtcgttttac aacgtcgtga ctgggaaaac     60
cctggcgtta cccaacttaa tcgccttgca gcacatcccc ctttcgccag ctggcgtaat    120
agcgaagagg cccgcaccga tcgcccttcc caacagttgc gcagcctgaa tggcgaatgg    180
acgcgccctg tagcggcgca ttaagcgcgg cgggtgtggt ggttacgcgc agcgtgaccg    240
ctacacttgc cagcgcccta gcgcccgctc ctttcgcttt cttcccttcc tttctcgcca    300
cgttcgccgg ctttccccgt caagctctaa atcgggggct ccctttaggg ttccgattta    360
```

```
gtgctttacg gcacctcgac cccaaaaaac ttgattaggg tgatggttca cgtagtgggc      420
catcgccctg atagacggtt tttcgccctt tgacgttgga gtccacgttc tttaatagtg      480
gactcttgtt ccaaactgga acaacactca accctatctc ggtctattct tttgatttat      540
aagggatttt gccgatttcg gcctattggt taaaaaatga gctgatttaa caaaaattta      600
acgcgaattt taacaaaata ttaacgctta caatttcctg atgcggtatt ttctccttac      660
gcatctgtgc ggtatttcac accgcatcag gtggcacttt tcggggaaat gtgcgcggaa      720
cccctatttg tttattttc taaatacatt caaatatgta tccgctcatg agacaataac       780
cctgataaat gcttcaataa tattgaaaaa ggaagagtat gagtattcaa catttccgtg      840
tcgcccttat tcccttttt gcggcatttt gccttcctgt ttttgctcac cagaaacgc        900 tggtgaaagt aaaagatgct gaagatcagt tgggtgcacg agtgggttac atcgaactgg      960
atctcaacag cggtaagatc cttgagagtt ttcgccccga gaacgttttt ccaatgatga     1020
gcacttttaa agttctgcta tgtggcgcgg tattatcccg tattgacgcc gggcaagagc     1080
aactcggtcg ccgcatacac tattctcaga atgacttggt tgagtactca ccagtcacag     1140
aaaagcatct tacggatggc atgacagtaa gagaattatg cagtgctgcc ataaccatga     1200
gtgataacac tgcggccaac ttacttctga caacgatcgg aggaccgaag gagctaaccg     1260
cttttttgca caacatgggg gatcatgtaa ctcgccttga tcgttgggaa ccggagctga     1320
atgaagccat accaaacgac gagcgtgaca ccacgatgcc tgtagcaatg gcaacaacgt     1380
tgcgcaaact attaactggc gaactactta ctctagcttc ccggcaacaa ttaatagact     1440
ggatggaggc ggataaagtt gcaggaccac ttctgcgctc ggcccttccg gctggctggt     1500
ttattgctga taaatctgga gccggtgagc gtgggtctcg cggtatcatt gcagcactgg     1560
ggccagatgg taagccctcc cgtatcgtag ttatctacac gacggggagt caggcaacta     1620
tggatgaacg aaatagacag atcgctgaga taggtgcctc actgattaag cattggtaac     1680
tgtcagacca agtttactca tatatacttt agattgattt aaaacttcat ttttaattta     1740
aaaggatcta ggtgaagatc cttttttgata atctcatgac caaaatccct taacgtgagt     1800
tttcgttcca ctgagcgtca gaccccgtag aaaagatcaa aggatcttct tgagatcctt     1860 ttttttctgcg cgtaatctgc tgcttgcaaa caaaaaaacc accgctacca gcggtggttt     1920
gtttgccgga tcaagagcta ccaactcttt ttccgaaggt aactggcttc agcagagcgc     1980
agataccaaa tactgttctt ctagtgtagc cgtagttagg ccaccacttc aagaactctg     2040
tagcaccgcc tacatacctc gctctgctaa tcctgttacc agtggctgct gccagtggcg     2100
ataagtcgtg tcttaccggg ttggactcaa gacgatagtt accggataag gcgcagcggt     2160
cgggctgaac ggggggttcg tgcacacagc ccagcttgga gcgaacgacc tacaccgaac     2220
tgagatacct acagcgtgag ctatgagaaa gcgccacgct tcccgaaggg agaaaggcgg     2280
acaggtatcc ggtaagcggc agggtcggaa caggagagcg cacgagggag cttccagggg     2340
gaaacgcctg gtatctttat agtcctgtcg ggtttcgcca cctctgactt gagcgtcgat     2400
ttttgtgatg ctcgtcaggg gggcggagcc tatggaaaaa cgccagcaac gcggcctttt     2460
tacggttcct ggccttttgc tggccttttg ctcacatgtt ctttcctgcg ttatcccctg     2520
attctgtgga taaccgtatt accgcctttg agtgagctga taccgctcgc cgcagccgaa     2580
cgaccgagcg cagcgagtca gtgagcgagg aagcggaaga gcgcccaata cgcaaaccgc     2640
ctctccccgc gcgttggccg attcattaat gcagctggca cgacaggttt cccgactgga     2700
```

```
aagcgggcag tgagcgcaac gcaattaatg tgagttagct cactcattag gcaccccagg      2760
ctttacactt tatgcttccg gctcgtatgt tgtgtggaat tgtgagcgga taacaatttc      2820
acacaggaaa cagctatgac catgattacg ccaagctatt taggtgacac tatagaatac      2880
tcaagctatg catccaacgc gttgggagct ctcccatatg gtcgacctgc aggcggccgc      2940
gaattcacta gtgattgttt gaggagcgag gcatttcttc atttcttcgt ggagaagaaa      3000
gggcacacct gcagactaaa cagccaagta agaaagtta tttatcatca tcacaatatc       3060
ctttctggcc tgtctccaag agaaagaaac ttttaaactt tttaaatttt aacttttgct      3120
tgtgctcgta tgcttacaaa agcttgcaac gaaacacagc ggaagcaagt tcagaacacg      3180
ccaatgacat ctttgctctc caaaattgaa aattgttttg tcaaatttta aaaactgatt     3240
ctgtaagaaa ccttaatttt tgcaaacaat caaaaaatcg ccgttgactg agtgtgattg     3300
aactcactcc aacgaaagcg ttagtccctc ttcctatact ttaccataat aatatccctc     3360
ttagattcca tcccgacctg ttcctactac gagcttataa accccctacgc cccaagccag   3420 gtaagagaga ctagtaaatt cttgacaatc tgactgacta tcctaaacct tctcgactac     3480
tatgcaaagg actagtcgct gtagtcccag ttgtgtgtac tatagcagta aagcgttggt     3540
gtacttaaca gtaaaacagt aaaaccaaag cccccctaaa ttccccaaac agaatgagtt     3600
gtctcagtcc gaaactttct ttgcaatgaa atacgattgg tttggaaagt tgacagtgag     3660
tgaaaagcct ttcgattgat tgatttgctt cggtcattca ttcactcatt cattcactca     3720
ttcaaattga aatgagcatg aaagtggtcg aagtggagta tctaggcgat ctacatgaac     3780
gacttcaagc agcaagagtg cgagaggtaa aaagtatgtt aaagcgttaa aagctgcaaa    3840
agctgtaaaa gtgaaagccc atctggaaac catagaaacg ttctcaattc ctcgattcct     3900
cgattcctcg tgcagacgca gaagaagact gacaaagcat cggcactggc actgacatgc    3960
gggtacgagt aggtacggac agcgagtgcc cacacagccc caagcccaca cattcattac     4020
attcattcat tgaacacatt gaacgcattg aacaatcaat cactccacat tgtcactgtc    4080
aactgatgtc aactggtaaa cttgtaactt gtattgtatt gacctcgctt ggtgcataga   4140
gtgcgtagag tgcgtagagt gcgtagccgt cgccccggag agacgctgtt gactgacaac    4200
tgtgttaagg tgtcgattac aacaaacaaa caaataaaca acaaccaaa caaacacctc     4260 ccaacacacg agctttgacg tcctcaccac ccggtttgcc ctcgcagtcg cggtcagttc    4320
agtgccacga gtgccacggg gcgtaaggaa gtttaggaag gcgtgtttcg aatcccttta    4380
cagcgcggcg ctcgcgaact gaagacgcgg agatacgcag tagtgagtgg gtggagcaag    4440
aaaagtagag ggcccccgta cgtcccggag gagagaccga ttgtggattg gactgctgga   4500
tcgtggaata ggcaagatct agctagaggt cgacggtata cagacatgat aagatacatt    4560
gatgagtttg gacaaaccac aactagaatg cagtgaaaaa aatgctttat ttgtgaaatt    4620
tgtgatgcta ttgctttatt tgtaaccatt ataagctgca ataaacaagt tggggtgggc    4680
gaagaactcc agcatgagat ccccgcgctg gaggatcatc cagccggcgt cccggaaaac    4740
gattccgaag cccaaccttt catagaaggc ggcggtggaa tcgaaatctc gtgatggcag   4800
gttgggcgtc gcttggtcgg tcatttcgcg gatctcaaaa gaactcgtcc aggaggcggt    4860
agaacgcaat cctctggctg tccggggcgg cgatgccgta gagcacgaga aagcggtcgg   4920
cccactcgcc gccaagctcc tcggcgatgt cccgcgtggc gagcgcgatg tcttggtagc    4980
ggtccgccac gcccaggcgc ccgcagtcga taaagcccga gaagcggccg ttctcgacca  5040
tgatgttggg gaggcaggcg tcgccgtgcg tgaccacgag gtcctcgccg tccggcatcc  5100
```

```
tagccttaag cctggcgaac agttccgccg gcgcgaggcc ctggtgctcc tcgtcgaggt    5160
cgtcttggtc gacgaggcca gcctccatcc gcgtgcgggc gcgttcgatc ctgtgcttcg    5220
cctggtggtc gaaggggcag gtggcggggt cgagggtgtg caggcggcgc atggcgtcgg    5280
ccatgatgga caccttctca gcgggcgcga ggtggctgct gaggaggtcc tggccgggca    5340
cttccccgag gagcagccag tcgcggccgg cttcggtgac gacgtcgagc acagcggcgc    5400
acggaacccc cgtcgtggca agccagctga ggcgggcagc ttcgtcctgg agctcgttga    5460
gggcgccgct aaggtcggtc ttgacaaaca ggaccggccg gccctgcgcg ctaaggcgga    5520
acacggccgc gtccgagcag ccgatcgtct gctgagccca gtcgtagccg aacagccgtt    5580
ccacccaagc agcgggcgag ccagcgtgaa ggccgtcctg ttcaatcatg ttggctagtg    5640
ttgcttaggt cgcttgctgc tgctggtgtt gcttgttctg cttgtcgttt ggggtctgcc    5700
cgaagtggac gcgtgacaca gcccagcgtt cgcgactttt ccagcaacca gctcgctccg    5760
cgtcagggtc actctctgct cactcccctg tctagttcgg cagaactgga gaggcaaccc    5820
gcgcttccag agggttctcc tccggaatca gttcagaatt cagaattcag aagagggaat    5880
cgcagaaccg gccgcttcgg gagttggttc gctgcaccat agcaggtggg cgatgaggcc    5940
aaccgccctg ctggctggat tctctcgggt tggcacatcg aacgaccggg acccgcgcgc    6000
gagttgtccc tgccagttgc taccagcctg ccagcgtcgg agagttatgc gctgcctgcc    6060
ggccggagag agagcgggcg tggaaagtgg cgtgtggggc gaacgcatgg ccctcccgcg    6120
tggcccgatt tcctatgcat ccgctccgct ctctctctcg gaggcaagaa gagcacacaa    6180
caacgcccgg cgggtgcacc aggcgctgcg gcagatccag atctaacttt ctgaggctct    6240
ccataaaacc ctgcacacga tctttggctt ttggctcatt cgtcaaacga acaaaatgc    6300
caggcttgtc gttggttcca actacggttg taaagttgta tggcgagtgc actcgttttt    6360
cgtcgaacca gtctggatgc ttctgcatca tggctttctt gaaggcaaca gtttccgtga    6420
aagtagactc cagggctgta taagaacctg gagcaagggt ggtcttcatg ccttgctcca    6480
tcatgtggat gacactgtga ctcacaaaat tgcatccaat ctcagacatg tacatattga    6540
ggttgtagtt ttccgggtcc gtcacgttgg agatggagat tccgctcgcc gaagcatcgc    6600
agcagtacca atgacttgag cgatccgcca cccagtgtag gtatagtcca aatcgtacaa    6660
tctcttcggg gacaggatcc ccgttgataa gtgaataagg tgcgctcgag ttgagatatt    6720
ccccaagctg gcttgccagt actacatccg tcatcttgta gttttcgtta tggtctgggt    6780
cctcgcaggt cccgttgcaa gcgcaagccg gatcacagtt gtagttaacg tattgctcac    6840
ctaacatcat atcgcctccg gcgagaggga ttggaccgct caccaatttg gagatgtgtt    6900
tagaagtgac ggttccgctt ttagggcagg tctcgccagt gaatgagat ccatcagggc     6960
caatgctagt atagcctcca acacaaagca gatccgtctc tccaaaagcc catcgtcgag    7020
cagaagcgag cgcaccctcg taaaagttgt cgtccatatt tggggccagg cccgggcaat    7080
gcgcacggta aaactcatac gacttttga agcgatacct ctgacagtca cctccttgc      7140
cacccgtgtg ctccttggcg ctctcggtta aaatggagcc attgaagtgt ccgatgtacg    7200
ggattcctaa gtgccgctgt gttcctccca gcttggtgtt tgtacggaga aaacctctca    7260
taggtggagt ccaccactcc aatcccatgt ccgcgccaca gctgtcaatt gcgcggtact    7320
gtacgaaatc aatcgcctga gaatacgcgg ccatgaagta agcgtactct gctttgaggc    7380
cctgtgccac agcaatataa tagatcgcgt aaaagtgaat gaagcctctg caggcggagg    7440
```

```
tatcgttgaa cccggttgtc atctgtggga gcagacttgc caggatgcac tttggacgcc    7500
agtcattgta cgagcactaa tcgaattccc gcggccgcca tggcggccgg gagcatgcga    7560
cgtcgggccc aattcgccc                                                  7579
```

<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49

```
gtggtcgaag tggagtatct                                                   20
```

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50

```
actcgccata caactttaca                                                   20
```

<210> SEQ ID NO 51
<211> LENGTH: 25
<212> TYPE: DNA
<213> ORGANISM: Artificial
<220> FEATURE:
<223> OTHER INFORMATION: primer

<400> SEQUENCE: 51

```
cggagctcgg agaacaacat agaag                                             25
```

<210> SEQ ID NO 52
<211> LENGTH: 23
<212> TYPE: DNA
<213> ORGANISM: Artificial
<220> FEATURE:
<223> OTHER INFORMATION: primer

<400> SEQUENCE: 52

```
gtgcaaccag gtggcaagat tgt                                               23
```

<210> SEQ ID NO 53
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 53

```
ttyytncayg tntaycayca y                                                 21
```

<210> SEQ ID NO 54
<211> LENGTH: 23
<212> TYPE: DNA
<213> ORGANISM: Artificial Sequence

```
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 54
gcrtgrtgrt anacrtgnar raa                                             23

<210> SEQ ID NO 55
<211> LENGTH: 190
<212> TYPE: DNA
<213> ORGANISM: Artificial Sequence
<220> FEATURE:
<223> OTHER INFORMATION: cDNA (DNA fragment contains elo1)

<400> SEQUENCE: 55
cgccaccatc tttgctatct ggtttatgat cgccaagtac gccccgggcg gcgacgcata    60
ctttagcgtc atcctgaact cgttcgtgca caccgtcatg tacgcgtact acttcttctc   120
gtcgcagggc ttcgggttcg tcaagccgat caagccgtac atcacctcgc tgcagatgac   180
gcagttcatg                                                           190

<210> SEQ ID NO 56
<211> LENGTH: 210
<212> TYPE: DNA
<213> ORGANISM: Artificial Sequence
<220> FEATURE:
<223> OTHER INFORMATION: cDNA (DNA fragment contains elo2)

<400> SEQUENCE: 56
ccgacgacca gcacaccgag tgggtctcgt gcgtgcgctt ctcgccctcg accaccaacc    60
cgctgatcgt gtcgtgcggc tgggacaagc tcgtcaaggt ctggaacctc tcgaactgca   120
agcttcgggc caacctcatc ggccacgacg gctacctcaa ctcggtcacc gtcagcccgg   180
acggctccct gtgcgcttcg ggcggcaagg                                    210

<210> SEQ ID NO 57
<211> LENGTH: 200
<212> TYPE: DNA
<213> ORGANISM: Artificial Sequence
<220> FEATURE:
<223> OTHER INFORMATION: cDNA (DNA fragment contains elo3)

<400> SEQUENCE: 57
aagctaacct gggcgtagtt tttcttgagg atcatcatga acgtgtcgct ccagtcgaga    60
aactttgtca ggaggtgcac gaacacgaaa aactcgatgt tcgagtcgcg cgacttgttg   120
aggccgaaag ggttgccgtt ggccaggtcg acctgcggcc agaggcccca caccatccag   180
ccgcacaccg cgatttggac                                                200

<210> SEQ ID NO 58
<211> LENGTH: 21
<212> TYPE: DNA
<213> ORGANISM: Artificial Sequence
<220> FEATURE:
<223> OTHER INFORMATION: primer

<400> SEQUENCE: 58
```
tatgatcgcc aagtacgccc c                                                    21

<210> SEQ ID NO 59
<211> LENGTH: 21
<212> TYPE: DNA
<213> ORGANISM: Artificial Sequence
<220> FEATURE:
<223> OTHER INFORMATION: primer

<400> SEQUENCE: 59
gaactgcgtc atctgcagcg a                                                    21

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
tctcgccctc gaccaccaac                                                      20

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
cggtgaccga gttgaggtag cc                                                   22

<210> SEQ ID NO 62
<211> LENGTH: 22
<212> TYPE: DNA
<213> ORGANISM: Artificial Sequence
<220> FEATURE:
<223> OTHER INFORMATION: primer

<400> SEQUENCE: 62 caacccttc ggcctcaaca ag                                                    22

<210> SEQ ID NO 63
<211> LENGTH: 26
<212> TYPE: DNA
<213> ORGANISM: Artificial Sequence
<220> FEATURE:
<223> OTHER INFORMATION: primer

<400> SEQUENCE: 63
ttcttgagga tcatcatgaa cgtgtc                                               26

<210> SEQ ID NO 64
<211> LENGTH: 1139
<212> TYPE: DNA
<213> ORGANISM: Artificial Sequence
<220> FEATURE:
<223> OTHER INFORMATION: cDNA (elo1)

<400> SEQUENCE: 64
ctaatacgac tcactatagg gcaagcagtg gtaacaacgc agagtacgcg gggaccccaa          60
acgcccgacg acaaccaaga agacagccag ccgaacaatc ggacgaagat gacgagcaac         120
atgagcgcgt ggggcgtcgc cgtcgaccag acgcagcagg tcgtcgacca gatcatgggc         180
ggcgccgagc cgtacaagct gacagaaggg cgcatgacga acgtcgagac gatgctggcg         240

```
atcgagtgcg gctacgccgc catgctgctg ttcctgaccc cgatcatgaa gcaggccgag    300
aagcccttcg agctcaagtc cttcaagctc gcccacaacc tgttcctgtt cgtcctgtcc    360
gcctacatgt gcctcgagac cgtccgccag gcctaccttg cgggctactc ggtgttcggc    420
aacgacatgg agaagggcag cgagccgcac gcgcacggca tggcccaaat cgtgtggatc    480 tttacgtgt ccaaggcgta cgagttcgtg gacacgctga tcatgatcct gtgcaaaaag    540
ttcaaccagg tctccgtcct gcacgtgtac caccacgcca ccatctttgc tatctggttt    600
atgatcgcca agtacgcccc gggcggcgac gcatacttta gcgtcatcct gaactcgttc    660
gtgcacaccg tcatgtacgc gtactacttc ttctcgtcgc agggcttcgg gttcgtcaag    720
ccgatcaagc cgtacatcac ctcgctgcag atgacgcagt tcatggcgat gctcgtgcag    780
tcgctgtacg actaccttta cccgtgcgac tacccgcagg ggctcgtcaa gctcctcggc    840
gtgtacatgc tcaccctgct tgcgctcttc ggcaactttt tcgtgcagag ctacctcaag    900
aagtcgaaca agcccaaggc caagtcggcc taagccgacc cgctcgccgg caaccgagca    960
gcacctaggc gcatctcggc ccggaaccttt tcgacctgc tgtggagcgc gcgacgcgtt   1020
tcgcgaccgt ccgcgcgttc ttgacactct ttgctctgtg tgtttcgcac ttgacaacct   1080
ggaacagaca catacacgat acaaatcatc agaacagaca aaaacaacc tcaaattat    1139

<210> SEQ ID NO 65
<211> LENGTH: 1261
<212> TYPE: DNA
<213> ORGANISM: Artificial Sequence
<220> FEATURE:
<223> OTHER INFORMATION: cDNA (elo3)

<400> SEQUENCE: 65
ctaatacgac tcactatagg gcaagcagtg gtatcaacgc agagtacgcg gggaccccga     60
acgtgtttct cccaggacgt gccgctgtcg ctcgctgatc cacccgaagc gcggtcggct    120
ggcacggtcg ctcggctgga agttgagtag tttgcttttct gttactgcgc tgctttgtaa    180
acgcgaccat ggcgacgcgc acctcgaaga gcgctccggc ggtttccaag tcggccaagg    240
ttgccgcgcc ggcgaagaag cggtcggtcg acaggagcga cggtttcttc cgcacgttca    300
acctgtgcgc cctgtacggg tctgccctcg cctatgcgta caagcacggc ccggtggaca    360
atgacggcca ggggctgtac tttcacaagt cgcccatgta cgcgttcgcc gtgtcggacg    420
tcatgacctt cggcgcgccg ctgatgtacg tgctcggtgt gatgctgctc agcaggtaca    480
tggcggacaa aaagcccctg actggcttca tcaagaccta catccagccc gtctacaacg    540
tggtccaaat cgcggtgtgc ggctggatgg tgtgggccct ctggccgcag gtcgacctgg    600
ccaacggcaa cccttcggc ctcaacaagt cgcgcgactc gaacatcgag tttttcgtgt    660
tcgtgcacct cctgacaaag tttctcgact ggagcgacac gttcatgatg atcctcaaga    720
aaaactacgc ccaggttagc tttctgcagg tgttccacca cgcaacgatc ggcatggtgt    780
ggtcgttcct tcttcagcgt ggctggggct cgggcaccgc cgcgtacggt gctttcatca    840
actcggtcac gcacgtgatc atgtactcgc actactttgc cacctcgctc aacatcaaca    900
acccgttcaa gcggtacatc acgagcttcc agctcgccca gtttgcaagc tgcatcgtgc    960
atgccctact ggtgcttgcc ttcgaggagg tgtacccgct cgagtacgct tacctgcaga   1020
tcagctacca catcatcatg ctctacctgt tcggacgccg catgaactgg agccccgagt   1080
ggtgcaccgg tgagatcgac ggccttgacg ccccaagcgc ccccaccaag tccgagtaaa   1140
```

```
cctgtttccg gctggctccc gagccatgct taccatgaat gaacctgcaa acagtctgag    1200
gtccttgtgc aaaccgctca gtgggacgtc gacgaagaaa gaaacaatgt gtactcgtcc    1260
c                                                                     1261
```

<210> SEQ ID NO 66
<211> LENGTH: 275
<212> TYPE: PRT
<213> ORGANISM: T. aureum
<220> FEATURE:
<221> NAME/KEY: misc_feature
<222> LOCATION: (275)..(275)
<223> OTHER INFORMATION: Xaa can be any naturally occurring amino acid

<400> SEQUENCE: 66

```
Met Thr Ser Asn Met Ser Ala Trp Gly Val Ala Val Asp Gln Thr Gln
1               5                   10                  15

Gln Val Val Asp Gln Ile Met Gly Gly Ala Glu Pro Tyr Lys Leu Thr
            20                  25                  30

Glu Gly Arg Met Thr Asn Val Glu Thr Met Leu Ala Ile Glu Cys Gly
        35                  40                  45

Tyr Ala Ala Met Leu Leu Phe Leu Thr Pro Ile Met Lys Gln Ala Glu
    50                  55                  60

Lys Pro Phe Glu Leu Lys Ser Phe Lys Leu Ala His Asn Leu Phe Leu
65                  70                  75                  80

Phe Val Leu Ser Ala Tyr Met Cys Leu Glu Thr Val Arg Gln Ala Tyr
                85                  90                  95

Leu Ala Gly Tyr Ser Val Phe Gly Asn Asp Met Glu Lys Gly Ser Glu
            100                 105                 110

Pro His Ala His Gly Met Ala Gln Ile Val Trp Ile Phe Tyr Val Ser
        115                 120                 125

Lys Ala Tyr Glu Phe Val Asp Thr Leu Ile Met Ile Leu Cys Lys Lys
    130                 135                 140

Phe Asn Gln Val Ser Val Leu His Val Tyr His Ala Thr Ile Phe
145                 150                 155                 160

Ala Ile Trp Phe Met Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Ser Leu Gln Met Thr Gln Phe Met Ala Met Leu Val Gln
    210                 215                 220

Ser Leu Tyr Asp Tyr Leu Tyr Pro Cys Asp Tyr Pro Gln Gly Leu Val
225                 230                 235                 240

Lys Leu Leu Gly Val Tyr Met Leu Thr Leu Leu Ala Leu Phe Gly Asn
                245                 250                 255

Phe Phe Val Gln Ser Tyr Leu Lys Ser Asn Lys Pro Lys Ala Lys
            260                 265                 270

Ser Ala Xaa
        275
```

<210> SEQ ID NO 67
<211> LENGTH: 825
<212> TYPE: DNA
<213> ORGANISM: Artificial Sequence
<220> FEATURE:
<223> OTHER INFORMATION: cDNA (T. aureum ATCC 34304 elo1)

<400> SEQUENCE: 67

```
atgacgagca acatgagcgc gtggggcgtc gccgtcgacc agacgcagca ggtcgtcgac      60
cagatcatgg cggcgccga gccgtacaag ctgacagaag gcgcatgac gaacgtcgag      120
acgatgctgg cgatcgagtg cggctacgcc gccatgctgc tgttcctgac cccgatcatg    180
aagcaggccg agaagccctt cgagctcaag tccttcaagc tcgcccacaa cctgttcctg    240
ttcgtcctgt ccgcctacat gtgcctcgag accgtccgcc aggcctacct tgcgggctac    300
tcggtgttcg gcaacgacat ggagaagggc agcgagccgc acgcgcacgg catggcccaa    360
atcgtgtgga tcttttacgt gtccaaggcg tacgagttcg tggacacgct gatcatgatc    420
ctgtgcaaaa agttcaacca ggtctccgtc ctgcacgtgt accaccacgc caccatcttt    480
gctatctggt ttatgatcgc caagtacgcc ccgggcggcg acgcatactt tagcgtcatc    540
ctgaactcgt tcgtgcacac cgtcatgtac gcgtactact tcttctcgtc gcagggcttc    600
gggttcgtca agccgatcaa gccgtacatc acctcgctgc agatgacgca gttcatggcg    660
atgctcgtgc agtcgctgta cgactacctt tacccgtgcg actacccgca ggggctcgtc    720
aagctcctcg gcgtgtacat gctcaccctg cttgcgctct tcggcaactt tttcgtgcag    780
agctacctca agaagtcgaa caagcccaag gccaagtcgg cctaa                    825
```

<210> SEQ ID NO 68
<211> LENGTH: 317
<212> TYPE: PRT
<213> ORGANISM: T. aureum
<220> FEATURE:
<221> NAME/KEY: misc_feature
<222> LOCATION: (317)..(317)
<223> OTHER INFORMATION: Xaa can be any naturally occurring amino acid

<400> SEQUENCE: 68

```
Met Ala Thr Arg Thr Ser Lys Ser Ala Pro Ala Val Ser Lys Ser Ala
1               5                   10                  15

Lys Val Ala Ala Pro Ala Lys Lys Arg Ser Val Asp Arg Ser Asp Gly
            20                  25                  30

Phe Phe Arg Thr Phe Asn Leu Cys Ala Leu Tyr Gly Ser Ala Leu Ala
        35                  40                  45

Tyr Ala Tyr Lys His Gly Pro Val Asp Asn Asp Gly Gln Gly Leu Tyr
    50                  55                  60

Phe His Lys Ser Pro Met Tyr Ala Phe Ala Val Ser Asp Val Met Thr
65                  70                  75                  80

Phe Gly Ala Pro Leu Met Tyr Val Leu Gly Val Met Leu Leu Ser Arg
                85                  90                  95

Tyr Met Ala Asp Lys Lys Pro Leu Thr Gly Phe Ile Lys Thr Tyr Ile
            100                 105                 110

Gln Pro Val Tyr Asn Val Val Gln Ile Ala Val Cys Gly Trp Met Val
        115                 120                 125

Trp Gly Leu Trp Pro Gln Val Asp Leu Ala Asn Gly Asn Pro Phe Gly
    130                 135                 140

Leu Asn Lys Ser Arg Asp Ser Asn Ile Glu Phe Val Phe Val His
145                 150                 155                 160

Leu Leu Thr Lys Phe Leu Asp Trp Ser Asp Thr Phe Met Met Ile Leu
                165                 170                 175

Lys Lys Asn Tyr Ala Gln Val Ser Phe Leu Gln Val Phe His His Ala
            180                 185                 190
```

```
Thr Ile Gly Met Val Trp Ser Phe Leu Leu Gln Arg Gly Trp Gly Ser
            195                 200                 205

Gly Thr Ala Ala Tyr Gly Ala Phe Ile Asn Ser Val Thr His Val Ile
        210                 215                 220

Met Tyr Ser His Tyr Phe Ala Thr Ser Leu Asn Ile Asn Asn Pro Phe
225                 230                 235                 240

Lys Arg Tyr Ile Thr Ser Phe Gln Leu Ala Gln Phe Ala Ser Cys Ile
                245                 250                 255

Val His Ala Leu Leu Val Leu Ala Phe Glu Glu Val Tyr Pro Leu Glu
            260                 265                 270

Tyr Ala Tyr Leu Gln Ile Ser Tyr His Ile Ile Met Leu Tyr Leu Phe
        275                 280                 285

Gly Arg Arg Met Asn Trp Ser Pro Glu Trp Cys Thr Gly Glu Ile Asp
290                 295                 300

Gly Leu Asp Ala Pro Ser Ala Pro Thr Lys Ser Glu Xaa
305                 310                 315

<210> SEQ ID NO 69
<211> LENGTH: 951
<212> TYPE: DNA
<213> ORGANISM: Artificial Sequence
<220> FEATURE:
<223> OTHER INFORMATION: cDNA (T. aureum ATCC 34304 elo3)

<400> SEQUENCE: 69
atggcgacgc gcacctcgaa gagcgctccg gcggtttcca gtcggccaa ggttgccgcg       60 ccggcgaaga agcggtcggt cgacaggagc gacggtttct tccgcacgtt caacctgtgc     120
gccctgtacg ggtctgccct cgcctatgcg tacaagcacg gcccggtgga caatgacggc     180
caggggctgt actttcacaa gtcgcccatg tacgcgttcg ccgtgtcgga cgtcatgacc     240
ttcggcgcgc cgctgatgta cgtgctcggt gtgatgctgc tcagcaggta catggcggac     300
aaaaagcccc tgactggctt catcaagacc tacatccagc ccgtctacaa cgtggtccaa     360
atcgcggtgt gcggctggat ggtgtggggc ctctggccgc aggtcgacct ggccaacggc     420
aaccctttcg gcctcaacaa gtcgcgcgac tcgaacatcg agttttcgt gttcgtgcac     480 ctcctgacaa agtttctcga ctggagcgac acgttcatga tgatcctcaa gaaaaactac     540
gcccaggtta gctttctgca ggtgttccac cacgcaacga tcggcatggt gtggtcgttc     600
cttcttcagc gtggctgggg ctcgggcacc gccgcgtacg gtgctttcat caactcggtc     660
acgcacgtga tcatgtactc gcactacttt gccacctcgc tcaacatcaa caacccgttc     720
aagcggtaca tcacgagctt ccagctcgcc cagtttgcaa gctgcatcgt gcatgcccta     780
ctggtgcttg ccttcgagga ggtgtacccg ctcgagtacg cttacctgca gatcagctac     840
cacatcatca tgctctacct gttcggacgc cgcatgaact ggagccccga gtggtgcacc     900
ggtgagatcg acggccttga cgccccaagc gcccccacca gtccgagta a              951

<210> SEQ ID NO 70
<211> LENGTH: 38
<212> TYPE: DNA
<213> ORGANISM: Artificial Sequence
<220> FEATURE:
<223> OTHER INFORMATION: primer

<400> SEQUENCE: 70
ataagcttaa aatgtctagc aacatgagcg cgtggggc                              38
```

```
<210> SEQ ID NO 71
<211> LENGTH: 28
<212> TYPE: DNA
<213> ORGANISM: Artificial Sequence
<220> FEATURE:
<223> OTHER INFORMATION: primer

<400> SEQUENCE: 71
tgtctagaac gcgcggacgg tcgcgaaa                                              28

<210> SEQ ID NO 72
<211> LENGTH: 40
<212> TYPE: DNA
<213> ORGANISM: Artificial Sequence
<220> FEATURE:
<223> OTHER INFORMATION: primer

<400> SEQUENCE: 72
taaagcttaa aatgtctacg cgcacctcga agagcgctcc                                 40

<210> SEQ ID NO 73
<211> LENGTH: 31
<212> TYPE: DNA
<213> ORGANISM: Artificial Sequence
<220> FEATURE:
<223> OTHER INFORMATION: primer

<400> SEQUENCE: 73
catctagact cggacttggt gggggcgctt g                                          31

<210> SEQ ID NO 74
<211> LENGTH: 949
<212> TYPE: DNA
<213> ORGANISM: Artificial Sequence
<220> FEATURE:
<223> OTHER INFORMATION: cDNA (TaELO1 coding region)

<400> SEQUENCE: 74
ataagcttaa aatgacgagc aacatgagcg cgtggggcgt cgccgtcgac cagacgcagc           60
aggtcgtcga ccagatcatg ggcggcgccg agccgtacaa gctgacagaa gggcgcatga         120
cgaacgtcga cgatgctgg gcgatcgagt gcggctacgc cgccatgctg ctgttcctga          180
ccccgatcat gaagcaggcc gagaagccct tcgagctcaa gtccttcaag ctcgcccaca         240
acctgttcct gttcgtcctg tccgcctaca tgtgcctcga ccgtccgc caggcctacc          300 ttgcgggcta ctcggtgttc ggcaacgaca tggagaaggg cagcgagccg cacgcgcacg         360
gcatggccca atcgtgtgg atcttttacg tgtccaaggc gtacgagttc gtggacacgc          420
tgatcatgat cctgtgcaaa aagttcaacc aggtctccgt cctgcacgtg taccaccacg         480
ccaccatctt tgctatctgg tttatgatcg ccaagtacgc cccgggcggc gacgcatact         540
ttagcgtcat cctgaactcg ttcgtgcaca ccgtcatgta cgcgtactac ttcttctcgt         600
cgcagggctt cggggttcgtc aagccgatca agccgtacat cacctcgctg cagatgacgc        660
agttcatggc gatgctcgtg cagtcgctgt acgactacct ttacccgtgc gactacccgc         720
aggggctcgt caagctcctc ggcgtgtaca tgctcaccct gcttgcgctc ttcggcaact         780
ttttcgtgca gagctacctc aagaagtcga acaagcccaa ggccaagtcg gcctaagccg         840
acccgctcgc cggcaaccga gcagcaccta ggcgcatctc ggcccggaac cttttcgacc         900
tgctgtggag cgcgcgacgc gtttcgcgac cgtccgcgcg ttctagaca                     949

<210> SEQ ID NO 75
```

```
<211> LENGTH: 967
<212> TYPE: DNA
<213> ORGANISM: Artificial Sequence
<220> FEATURE:
<223> OTHER INFORMATION: cDNA (TaELO2 coding region)

<400> SEQUENCE: 75
taaagcttaa aatggcgacg cgcacctcga agagcgctcc ggcggtttcc aagtcggcca    60
aggttgccgc gccggcgaag aagcggtcgg tcgacaggag cgacggtttc ttccgcacgt   120
tcaacctgtg cgccctgtac gggtctgccc tcgcctatgc gtacaagcac ggcccggtgg   180
acaatgacgg ccaggggctg tactttcaca gtcgcccat gtacgcgttc gccgtgtcgg    240
acgtcatgac cttcggcgcg ccgctgatgt acgtgctcgg tgtgatgctg ctcagcaggt   300
acatggcgga caaaaagccc ctgactggct tcatcaagac ctacatccag cccgtctaca   360
acgtggtcca aatcgcggtg tgcggctgga tggtgtgggg cctctggccg caggtcgacc   420
tggccaacgg caacccttc ggcctcaaca agtcgcgcga ctcgaacatc gagttttcg     480
tgttcgtgca cctcctgaca aagtttctcg actggagcga cacgttcatg atgatcctca   540
agaaaaacta cgcccaggtt agctttctgc aggtgttcca ccacgcaacg atcggcatgg   600
tgtggtcgtt ccttcttcag cgtggctggg gctcgggcac cgccgcgtac ggtgctttca   660
tcaactcggt cacgcacgtg atcatgtact cgcactactt tgccacctcg ctcaacatca   720
acaacccgtt caagcggtac atcacgagct ccagctcgc ccagtttgca agctgcatcg    780
tgcatgccct actggtgctt gccttcgagg aggtgtaccc gctcgagtac gcttacctgc   840
agatcagcta ccacatcatc atgctctacc tgttcgacg ccgcatgaac tggagccccg    900
agtggtgcac cggtgagatc gacggccttg acgccccaag cgcccccacc aagtccgagt   960
ctagatg                                                             967

<210> SEQ ID NO 76
<211> LENGTH: 1122
<212> TYPE: DNA
<213> ORGANISM: Artificial Sequence
<220> FEATURE:
<223> OTHER INFORMATION: cDNA (TaELO2 ORF upstream region)

<400> SEQUENCE: 76
cgttagaacg cgtaatacga ctcactatag ggatatcccc cgcgaggcga tggctgctcc     60
gacgacgtgg gctggcgacg tcgctcgcaa aggcgttccg caaccgcgcg ttccgctgta    120
acgagaccgt tttccctgcg ctgctgggtg gacctagcgc gtgtgtcacc tgccggcccc    180
cgttgcgtgc aaccgaattg atcgataata gaattacata caaacaact tgctggatga    240
gtacaagacc agcgtagtgt ggctgtggga cgttgaacgg agcgggtcct gtgacgcgc     300
agaaaggaac tccgcccgag gtgaaacccc gatgcgcagg actctgcggc cacagcccct    360
ccgccagtat tccactaaaa atccgccccc tttgacaaag atcgcaaccc cgtcccatca    420
actcctcaca ataggctttc cactggcgga aacgtccccg gcacaggagt gcctcccgcg    480
gttctgcgca tacggctgac cactacgcag cgcgatatcc tccatccgcg tatatatccg    540
taaacaacgg aacattctcc ctctcaacga ggcgtggttt tcgaagccat gccttctc      600
cttcctactt gccttccttc tttctttctt tctttccttc ttttgcaagc gtgcgcgaac    660
ttgaaggtac tacttacact tgacagagag agatagagac ggcaattcga ccaagtactt   720
tccacgattt tttttttttt tgtttttggt gctttcgttg gtcgtgcatg atggatggcc    780
gggattttta caattggatg cgccaggctg ccacgcatgc cgtgacgctc gctcgcggcg    840
```

```
actcatgatg cttgccagtg gcagtgcatc cagctcttcc ctctgctcgt cgtgtactca    900
ctggcgatgc tctcggcgct cgttcaaggg ccatcgatcg atcgatcgat cgatcgatcg    960
atcaatcacg tttggtggac tcggcagacc ccgaacgtgt ttctcccagg acgtgccgct   1020
gtcgctcgct gatccacccg aagcgcggtc ggctggcacg tcgctcggc tggaagttga   1080 gtagtttgct ttctgttgct gcgctgcttt gtaaacgcga cc                      1122
```

<210> SEQ ID NO 77
<211> LENGTH: 1204
<212> TYPE: DNA
<213> ORGANISM: Artificial Sequence
<220> FEATURE:
<223> OTHER INFORMATION: cDNA (TaELO2 downstream region)

<400> SEQUENCE: 77

```
acctgtttcc ggctggctcc cgagccatgc ttaccatgaa tgaacctgca acagtctga     60 ggtccttgtg caaaccgctc agtgggacgt cgacgaagaa agaaacaatg tgtactcgtc   120
ttgctctgct cccgcgccgt tttttatcgt tgttgagacc tctcgcgcag ttttgggaat   180
caaccaaaac aagagcccgg cgtcagcgtt gcttcgccc tcggctgcac tcgctcggca   240
cgcaggtata actgggtgag taccaagccc cgcatttgtc tgtccgcgat ccgcgcacgc   300
tgcgggtcag gacgacatcg cgctgcacgt cacagtgggt ccttttgac gtggctgcgg   360 cgatgaggag gcttggctcg gcttcatggc aaggcaacag actcgcttcc aggacgcgca   420
cgacgagcag cgctgctttg atcgaccttg cctgcgtcac cgcctcggct gctttgatcg   480
atcgttgtca ccggccgagt gaccgcgaac gcattgcccg cacggctcgg ctcggctcgg   540
accggaccgg ctcgccttgg cggcgcggcg cgatggcgac ccagacgcga ccggagccgc   600
gcgcggagga caaggccatg ttcatcttcg ggctcgggta cgttgggagc aggctcgcca   660
accagctggc ggaacagggg tggcgcgtcg cggggtcggt gagggagctc gggcgcgagg   720
acgactttgc cgagttcgaa aagtccaagc tgagcggcaa ggtgcaggtg ttccgactcc   780
cgcttgaggg cgaggacaac acgcccgctc gcgcgcggga gatacttagc gggtaccagc   840
acctgctgtt cacggcgcca gtggaccgcg cccggaactg tgaccccttc ttgggcgacc   900
ccgttctcgg ccccgtgatc gtcgagctag cagaggaggg ccgcatcgac tgggccggct   960
atctctcaac cacttcggtc tacggcaacc acgacgcga gtgggtggac gagaccacgc  1020
cgctcatgcc cacgctcaaa cgcggcgagc agcgcgtcat ggtggagcgc gccttcctgt  1080
acgagtcggg cctccggcc catatctttc ggctgccagg aatctacggc ccagggcgcg  1140
gcccgatatc acgaattctc tccctatagt gagtcgtatt acgcgttcta acgacaatat  1200
gtac                                                              1204
```

<210> SEQ ID NO 78
<211> LENGTH: 31
<212> TYPE: DNA
<213> ORGANISM: Artificial Sequence
<220> FEATURE:
<223> OTHER INFORMATION: primer

<400> SEQUENCE: 78

```
ctcccgggtg gacctagcgc gtgtgtcacc t                                   31
```

<210> SEQ ID NO 79
<211> LENGTH: 25
<212> TYPE: DNA

```
<213> ORGANISM: Artificial Sequence
<220> FEATURE:
<223> OTHER INFORMATION: primer

<400> SEQUENCE: 79
ggtcgcgttt acaaagcagc gcagc                                          25

<210> SEQ ID NO 80
<211> LENGTH: 52
<212> TYPE: DNA
<213> ORGANISM: Artificial Sequence
<220> FEATURE:
<223> OTHER INFORMATION: primer

<400> SEQUENCE: 80
gctgcgctgc tttgtaaacg cgaccatgat tgaacaggac ggccttcacg ct            52

<210> SEQ ID NO 81
<211> LENGTH: 52
<212> TYPE: DNA
<213> ORGANISM: Artificial Sequence
<220> FEATURE:
<223> OTHER INFORMATION: primer

<400> SEQUENCE: 81
tcgggagcca gccggaaaca ggttcaaaag aactcgtcca ggaggcggta ga            52

<210> SEQ ID NO 82
<211> LENGTH: 23
<212> TYPE: DNA
<213> ORGANISM: Artificial Sequence
<220> FEATURE:
<223> OTHER INFORMATION: primer

<400> SEQUENCE: 82
acctgtttcc ggctggctcc cga                                            23

<210> SEQ ID NO 83
<211> LENGTH: 27
<212> TYPE: DNA
<213> ORGANISM: Artificial Sequence
<220> FEATURE:
<223> OTHER INFORMATION: primer

<400> SEQUENCE: 83
atcccggggc cgagaacggg gtcgccc                                        27

<210> SEQ ID NO 84
<211> LENGTH: 2696
<212> TYPE: DNA
<213> ORGANISM: Artificial Sequence
<220> FEATURE:
<223> OTHER INFORMATION: cDNA (TaELO2 ORF upstream/Neor/ TaELO2 ORF
      downstream)

<400> SEQUENCE: 84
ctcccgggtg gacctagcgc gtgtgtcacc tgccggcccc cgttgcgtgc aaccgaattg    60
atcgataata gaattacata acaaacaact tgctggatga gtacaagacc agcgtagtgt   120
ggctgtggga cgttgaacgg agcgggtcct gtgatgcgca agaaaggaac tccgcccgag   180
gtgaaacccc gatgcgcagg actctgcggc cacagcccct ccgccagtat tccactaaaa   240
atccgccccc tttgacaaag atcgcaaccc cgtcccatca actcctcaca ataggctttc   300
cactggcgga aacgtccccg gcacaggagt gcctcccgcg ttctgcgcca tacggctgac   360
```

-continued

```
cactacgcag cgcgatatcc tccatccgcg tatatatccg taaacaacgg aacattctcc    420
ctctcaacga ggcgtggttt tcgaagccat gcctttcttc cttcctactt gccttccttc    480
tttctttctt tctttccttc ttttgcaagc gtgcgcgaac ttgaaggtac tacttacact    540
tgacagagag agatagagac ggcaattcga ccaagtactt tccacgattt tttttttttt    600
tgttttggtc gctttcgttg gtcgtgcatg atggatggcc gggattttta caattggatg    660
cgccaggctg ccacgcatgc cgtgacgctt gctcgcggcg actcatgatg cttgccagtg    720
gcagtgcatc cagctcttcc ctctgctcgt cgtgtactca ctggcgatgc tctcggcgct    780
cgttcaaggg ccatcgatcg atcgatcgat cgatcgatcg atcaatcacg tttggtggac    840
tcggcagacc ccgaacgtgt ttctcccagg acgcgccgct gtcgctcgct gatccacccg    900
aagcgcggtc ggctggcacg gtcgctcggc tggaagttga gtagtttgct ttctgttgct    960
gcgctgcttt gtaaacgcga ccatgattga acaggacggc cttcacgctg gctcgcccgc   1020
tgcttgggtg gaacgctgt  tcggctacga ctgggctcag cagacgatcg gctgctcgga   1080
cgcggccgtg ttccgcctta gcgcgcaggg ccggccggtc ctgttttgtca agaccgacct   1140
tagcggcgcc ctcaacgagc tccaggacga agctgcccgc ctcagctggc ttgccacgac   1200
gggggttccg tgcgccgctg tgctcgacgt cgtcaccgaa gccggccgcg actggctgct   1260
cctcggggaa gtgcccggcc aggacctcct cagcagccac ctcgcgcccg ctgagaaggt   1320
gtccatcatg gccgacgcca tgcgccgcct gcacaccctc gaccccgcca cctgcccctt   1380
cgaccaccag gcgaagcaca ggatcgaacg cgcccgcacg cggatggagg ctggcctcgt   1440
cgaccaagac gacctcgacg aggagcacca gggcctcgcg ccggcggaac tgttcgccag   1500
gcttaaggct aggatgccgg acggcgagga cctcgtggtc acgcacggcg acgcctgcct   1560
ccccaacatc atggtcgaga acggccgctt ctcgggcttt atcgactgcg ggcgcctggg   1620
cgtggcggac cgctaccaag acatcgcgct cgccacgcgg acatcgcccg aggagcttgg   1680
cggcgagtgg gccgaccgct ttctcgtgct ctacggcatc gccgccccgg acagccagag   1740
gattgcgttc taccgcctcc tggacgagtt cttttgaacc tgtttccggc tggctcccga   1800
gccatgctta ccatgaatga acctgcaaac agtctgaggt ccttgtgcaa accgctcagt   1860
gggacgtcga cgaagaaaga aacaatgtgt actcgtcttg ctctgctccc gcgccgtttt   1920
ttatcgttgt tgagacctct cgcgcagttt tgggaatcaa ccaaaacaag agcccggcgt   1980
cagcgtttgc ttcgccctcg gctgcactcg ctcggcacgc aggtataact gggtgagtac   2040
caagccccgc atttgtctgt ccgcgatccg cgcacgctgc gggtcaggac gacatcgcgc   2100
tgcacgtcac agtgggtccc ttttgacgtg gctgcggcga tgaggaggct tggctcggct   2160
tcatggcaag gcaacagact cgcttccggg acgcgcacga cgagcagcgc tgctttgatc   2220
gaccttgcct gcgtcaccgc ctcggctgct ttgatcgatc gttgtcaccg gccgagtgac   2280
cgcgaacgca ttgcccgcac ggctcggctc ggcccggacc ggaccggctc gccttggcgg   2340
cgcggcgcga tggcgaccca gacgcggccg gagccgcgcg cggaggacaa ggccatgttc   2400
atcttcgggc tcgggtacgt tgggagcagg ctcgccaacc agctggcgga acaggggtgg   2460
cgcgtcgcgg ggtcggtgag ggagctcggg cgcgaggacg actttgccga gttcgaaaag   2520
tccaagctga gcggcaaggt gcaggtgttc cgactcccgc ttgagggcga ggacaacacg   2580
cccgctcgcg cgcgggagat acttagcggg taccagcacc tgctgttcac ggcgccagtg   2640
gaccgcgccc ggaactgtga ccccttcttg ggcgaccccg ttctcggccc cgggat       2696
```

```
<210> SEQ ID NO 85
<211> LENGTH: 30
<212> TYPE: DNA
<213> ORGANISM: Artificial Sequence
<220> FEATURE:
<223> OTHER INFORMATION: primer

<400> SEQUENCE: 85
ggatatcccc cgcgaggcga tggctgctcc                                          30

<210> SEQ ID NO 86
<211> LENGTH: 30
<212> TYPE: DNA
<213> ORGANISM: Artificial Sequence
<220> FEATURE:
<223> OTHER INFORMATION: primer

<400> SEQUENCE: 86
tgatatcggg ccgcgccctg ggccgtagat                                          30

<210> SEQ ID NO 87
<211> LENGTH: 25
<212> TYPE: DNA
<213> ORGANISM: Artificial Sequence
<220> FEATURE:
<223> OTHER INFORMATION: primer

<400> SEQUENCE: 87
gtacgtgctc ggtgtgatgc tgctc                                               25

<210> SEQ ID NO 88
<211> LENGTH: 24
<212> TYPE: DNA
<213> ORGANISM: Artificial Sequence
<220> FEATURE:
<223> OTHER INFORMATION: primer

<400> SEQUENCE: 88
gcggcgtccg aacaggtaga gcat                                                24

<210> SEQ ID NO 89
<211> LENGTH: 35
<212> TYPE: DNA
<213> ORGANISM: Artificial Sequence
<220> FEATURE:
<223> OTHER INFORMATION: primer

<400> SEQUENCE: 89
atccgcgtat atatccgtaa acaacggaac attct                                    35

<210> SEQ ID NO 90
<211> LENGTH: 26
<212> TYPE: DNA
<213> ORGANISM: Artificial Sequence
<220> FEATURE:
<223> OTHER INFORMATION: primer

<400> SEQUENCE: 90
cttcgggtgg atcagcgagc gacagc                                              26

<210> SEQ ID NO 91
<211> LENGTH: 27
<212> TYPE: DNA
<213> ORGANISM: Artificial Sequence
<220> FEATURE:
<223> OTHER INFORMATION: primer
```

```
<400> SEQUENCE: 91
gccgcagcgc ctggtgcacc cgccggg                                          27

<210> SEQ ID NO 92
<211> LENGTH: 59
<212> TYPE: DNA
<213> ORGANISM: Artificial Sequence
<220> FEATURE:
<223> OTHER INFORMATION: primer

<400> SEQUENCE: 92
tcgcgggtga gttcaggctt tttcatgttg gctagtgttg cttaggtcgc ttgctgctg      59

<210> SEQ ID NO 93
<211> LENGTH: 57
<212> TYPE: DNA
<213> ORGANISM: Artificial Sequence
<220> FEATURE:
<223> OTHER INFORMATION: primer

<400> SEQUENCE: 93
agcgacctaa gcaacactag gccaacatga aaagcctga actcaccgcg acgtctg         57

<210> SEQ ID NO 94
<211> LENGTH: 29
<212> TYPE: DNA
<213> ORGANISM: Artificial Sequence
<220> FEATURE:
<223> OTHER INFORMATION: primer

<400> SEQUENCE: 94 ctattcctttt gccctcggac gagtgctgg                                      29

<210> SEQ ID NO 95
<211> LENGTH: 1636
<212> TYPE: DNA
<213> ORGANISM: Artificial Sequence
<220> FEATURE:
<223> OTHER INFORMATION: cDNA (T. aureum ATCC 34304 ubiruitin promoter/
      Hygr)

<400> SEQUENCE: 95
gctagccgca cgcctggtg caccccgccgg gcgttggttg tgtgtgctat ttactatgcc     60
taccgagaga gagagcggag cggatgcata ggaaatcggg ccacgcggga gggccatgcg   120
ttcgccccac acgccactta taccacgccc gctctctctc cggccggcag gcagcgcata   180
actataccga cgctggcagg cttggtagca actggcaggg acaactcgcg cgcgggtccc   240
ggtcgttcga tgtgccaacc cgagagaatc cagccagcag gcggttggc ctcatcgccc    300 acctgctatg gtgcagcgaa ccaactcccg aagcggccgg ttccgcgatt ccctcttctg   360
aattctgaat tctgaactga ttccggagga gaaccctctg gaagcgcggg ttgcctctcc   420
agttctgccg aactagacag gggagtgagc atgatgagtg accctgacgc gtgagctgag   480
ctggttgctg gaatatagtc gctgaacgct gggctgtgtc acgcgtccac ttcgggcaga   540
ccccaaacga caagcagaac aagcaacacc agcagcagca agcgacctaa gcaacactag   600
ccaacatgaa aaagcctgaa ctcaccgcga cgtctgtcga aagtttctg atcgaaaagt    660 tcgacagcgt ctccgacctg atgcagctct cggagggcga agaatctcgt gctttcagct   720
tcgatgtagg agggcgtgga tatgtcctgc gggtaaatag ctgcgccgat ggtttctaca   780
aagatcgtta tgtttatcgg cactttgcat cggccgcgct cccgattccg gaagtgcttg   840
```

```
acattgggga attcagcgag agcctgacct attgcatctc ccgccgtgca cagggtgtca    900
cgttgcaaga cctgcctgaa accgaactgc ccgctgttct gcagccggtc gcggaggcca    960
tggatgcgat cgctgcggcc gatcttagcc agacgagcgg gttcggccca ttcggaccgc   1020
aaggaatcgg tcaatacact acatggcgtg atttcatatg cgcgattgct gatccccatg   1080
tgtatcactg gcaaactgtg atggacgaca ccgtcagtgc gtccgtcgcg caggctctcg   1140
atgagctgat gctttgggcc gaggactgcc ccgaagtccg gcacctcgtg cacgcggatt   1200
tcggctccaa caatgtcctg acggacaatg gccgcataac agcggtcatt gactggagcg   1260
aggcgatgtt cggggattcc caatacgagg tcgccaacat cttcttctgg aggccgtggt   1320
tggcttgtat ggagcagcag acgcgctact tcgagcggag gcatccggag cttgcaggat   1380
cgccgcggct ccgggcgtat atgctccgca ttggtcttga ccaactctat cagagcttgg   1440
ttgacggcaa tttcgatgat gcagcttggg cgcagggtcg atgcgacgca atcgtccgat   1500
ccggagccgg gactgtcggg cgtacacaaa tcgcccgcag aagcgcggcc gtctggaccg   1560
atggctgtgt agaagtactc gccgatagtg gaaaccgacg ccccagcact cgtccgaggg   1620
caaaggaata gtctag                                                   1636
```

```
<210> SEQ ID NO 96
<211> LENGTH: 33
<212> TYPE: DNA
<213> ORGANISM: Artificial Sequence
<220> FEATURE:
<223> OTHER INFORMATION: primer

<400> SEQUENCE: 96
gtgctagccg cagcgcctgg tgcacccgcc ggg                                  33

<210> SEQ ID NO 97
<211> LENGTH: 37
<212> TYPE: DNA
<213> ORGANISM: Artificial Sequence
<220> FEATURE:
<223> OTHER INFORMATION: primer

<400> SEQUENCE: 97
gttctagact attcctttgc cctcggacga gtgctgg                              37

<210> SEQ ID NO 98
<211> LENGTH: 37
<212> TYPE: DNA
<213> ORGANISM: Artificial Sequence
<220> FEATURE:
<223> OTHER INFORMATION: primer

<400> SEQUENCE: 98
gttctagacc tgtttccggc tggctcccga gccatgc                              37

<210> SEQ ID NO 99
<211> LENGTH: 40
<212> TYPE: DNA
<213> ORGANISM: Artificial Sequence
<220> FEATURE:
<223> OTHER INFORMATION: primer

<400> SEQUENCE: 99
gtgctagcgg tcgcgtttac aaagcagcgc agcaacagaa                           40

<210> SEQ ID NO 100
<211> LENGTH: 3537
```

<212> TYPE: DNA
<213> ORGANISM: Artificial Sequence
<220> FEATURE:
<223> OTHER INFORMATION: cDNA (TaELO2 ORF upstream region/T. aureum ATCC
      34304 ubiquitin promotor/ Hygr /TaELO2 ORF downstream region)

<400> SEQUENCE: 100

```
ctcccgggtg gacctagcgc gtgtgtcacc tgccggcccc cgttgcgtgc aaccgaattg      60
atcgataata gaattacata acaaacaact tgctggatga gtacaagacc agcgtagtgt     120
ggctgtggga cgttgaacgg agcgggtcct gtgacggcgc agaaaggaac tccgcccgag     180
gtgaaacccc gatgcgcagg actctgcggc cacagcccct ccgccagtat tccactaaaa     240
atccgccccc tttgacaaag atcgcaaccc cgtcccatca actcctcaca ataggctttc     300
cactggcgga aacgtccccg gcacaggagt gcctcccgcg gttctgcgca tacggctgac     360
cactacgcag cgcgatatcc tccatccgcg tatatatccg taaacaacgg aacattctcc     420
ctctcaacga ggcgtggttt tcgaagccat gcctttcttc cttcctactt gccttccttc     480
tttctttctt tctttctttc ttttgtaagc gtgcgcgaac ttgaaggtac tacttacact     540
tgacagagag agatagagac ggcaattcga ccaagtactt tccacgattt ttttttttt     600
tgttttggtc gctttcgttg gtcgtgcatg atggatggcc gggatttta caattggatg     660
cgccaggctg ccacgcatgc cgtgacgctc gctcgcggcg actcatggtg cttgccagtg     720
gcagtgcatc cagctcttcc ctctgctcgt cgtgtactca ctggcgatgc tctcggcgct     780
cgttcaaggg ccatcgatcg atcgatcgat cgatcgatcg atcaatcacg tttggtggac     840
tcggcagacc ccgaacgtgt ttctcccagg acgtgccgct gtcgctcgct gatccacccg     900
aagcgcggtc ggctggcacg gtcgctcggc tggaagttga gtagtttgct ttctgttgct     960
gcgctgcttt gtaaacgcga ccgctagccg cagcgcctgg tgcacccgcc gggcgttggt    1020
tgtgtgtgct atttactatg cctaccgaga gagagagcgg agcggatgca taggaaatcg    1080
ggccacgcgg gagggccatg cgttcgcccc acacgccact tataccacgc ccgctctctc    1140
tccggccggc aggcagcgca taactatacc gacgctggca ggcttggtag caactggcag    1200
ggacaactcg cgcgcgggtc ccggtcgttc gatgtgccaa cccgagagaa tccagccagc    1260
agggcggttg gcctcatcgc ccacctgcta tggtgcagcg aaccaactcc cgaagcggcc    1320
ggttccgcga ttccctcttc tgaattctga attctgaact gattccggag agaaccctc    1380
tggaagcgcg ggttgcctct ccagttctgc cgaactagac aggggagtga gcatgatgag    1440
tgaccctgac gcgtgagctg agctggttgc tggaatatag tcgctgaacg ctgggctgtg    1500
tcacgcgtcc acttcgggca gaccccaaac gacaagcaga acaagcaaca ccagcagcag    1560
caagcgacct aagcaacact agccaacatg aaaaagcctg aactcaccgc gacgtctgtc    1620
gagaagtttc tgatcgaaaa gttcgacagc gtctccgacc tgatgcagct ctcggagggc    1680
gaagaatctc gtgctttcag cttcgatgta ggagggcgtg gatatgtcct gcgggtaaat    1740
agctgcgccg atggtttcta caaagatcgt tatgtttatc ggcactttgc atcggccgcg    1800
ctcccgattc cggaagtgct tgacattggg gaattcagcg agagcctgac ctattgcatc    1860
tcccgccgtg cacagggtgt cacgttgcaa gacctgcctg aaaccgaact gcccgctgtt    1920
ctgcagccgg tcgcggaggc catggatgcg atcgctgcgg ccgatcttag ccagacgagc    1980
gggttcggcc cattcggacc gcaaggaatc ggtcaataca ctacatggcg tgatttcata    2040
tgcgcgattc tgatcccca tgtgtatcac tggcaaactg tgatggacga caccgtcagt    2100
gcgtccgtcg cgcaggctct cgatgagctg atgctttggg ccgaggactg ccccgaagtc    2160
```

```
cggcacctcg tgcacgcgga tttcggctcc aacaatgtcc tgacggacaa tggccgcata    2220
acagcggtca ttgactggag cgaggcgatg ttcggggatt cccaatacga ggtcgccaac    2280
atcttcttct ggaggccgtg gttggcttgt atggagcagc agacgcgcta cttcgagcgg    2340
aggcatccgg agcttgcagg atcgccgcgg ctccgggcgt atatgctccg cattggtctt    2400
gaccaactct atcagagctt ggttgacggc aatttcgatg atgcagcttg ggcgcagggt    2460
cgatgcgacg caatcgtccg atccggagcc gggactgtcg ggcgtacaca aatcgcccgc    2520
agaagcgcgg ccgtctggac cgatggctgt gtagaagtac tcgccgatag tggaaaccga    2580
cgccccagca ctcgtccgag ggcaaaggaa tagtctagac ctgtttccgg ctggctcccg    2640
agccatgctt accatgaatg aacctgcaaa cagtctgagg tccttgtgca aaccgctcag    2700
tgggacgtcg acgaagaaag aaacaatgtg tactcgtctt gctctgctcc cgcgccgttt    2760
tttatcgttg ttgagacctc tcgcgcagtt ttgggaatca accaaaacaa gagcccggcg    2820
tcagcgtttg cttcgccctc ggctgcactc gctcggcacg caggtataac tgggtgagta    2880
ccaagccccg catttgtctg tccgcgatcc gcgcacgctg cgggtcagga cgacatcgcg    2940
ctgcacgtca cagtgggtcc cttttgacgt ggctgcggcg atgaggaggc ttggctcggc    3000
ttcatggcaa ggcaacagac tcgcttccgg gacgcgcacg acgagcagcg ctgctttgat    3060
cgaccttgcc tgcgtcaccg cctcggctgc tttgatcgat cgttgtcacc ggccgagtga    3120
ccgcgaacgc attcccgca cggctcggct cggcccggac cggaccggct cgccttggcg     3180
gcgcggcgcg atggcgaccc agacgcggcc ggagccgcgc gcggaggaca aggccatgtt    3240
catcttcggg ctcgggtacg ttgggagcag gctcgccaac cagctggcgg aacagggtg    3300 gcgcgtcgcg gggtcggtga gggagctcgg gcgcgaggac gactttgccg agttcgaaaa    3360
gtccaagctg agcggcaagg tgcaggtgtt ccgactcccg cttgagggcg aggacaacac    3420
gcccgctcgc gcgcgggaga tacttagcgg gtaccagcac ctgctgttca cggcgccagt    3480
ggaccgcgcc cggaactgtg accccttctt gggcgacccc gttctcggcc ccgggat      3537
```

<210> SEQ ID NO 101
<211> LENGTH: 30
<212> TYPE: DNA
<213> ORGANISM: Artificial Sequence
<220> FEATURE:
<223> OTHER INFORMATION: primer

<400> SEQUENCE: 101
atggcgacgc gcacctcgaa gagcgctccg                                         30

<210> SEQ ID NO 102
<211> LENGTH: 30
<212> TYPE: DNA
<213> ORGANISM: Artificial Sequence
<220> FEATURE:
<223> OTHER INFORMATION: primer

<400> SEQUENCE: 102
aggatcatca tgaacgtgtc gctccagtcg                                         30

<210> SEQ ID NO 103
<211> LENGTH: 23
<212> TYPE: DNA
<213> ORGANISM: Artificial Sequence
<220> FEATURE:
<223> OTHER INFORMATION: primer

<400> SEQUENCE: 103
cgatgaaagg tcacagaaga gtc                                           23

<210> SEQ ID NO 104
<211> LENGTH: 3181
<212> TYPE: DNA
<213> ORGANISM: Artificial Sequence
<220> FEATURE:
<223> OTHER INFORMATION: genomic DNA (T. aureum ATCC 34304 OrfA
      upstream)

<400> SEQUENCE: 104
aagcttttgc tctgcggctc tgcttgttcg aagccaacgc gcctcgcgaa gtatctgcaa    60
tctgcactcc tccggagagt aagtacgtaa gtacgtgcgt ggtgcgcgcg gattgcggtg   120
acgaaagaga gggttgggtt ggagatgctg cggcatgccg ggcgactcga gcagcatgtc   180
gccgcgagag gacctggaaa gctttcggtt tggtccgctg ccgaggcgag gctggcagag   240
tactgcgggc ggagctctcg agggaatatg ctcctcaaag acggcgtgcg cgtttgtgcc   300
cccgaatccg aatgcggaga gtcctgcgcg tttcggcccg ccgcgcgtat ccggccacgg   360
gagcgccgct gtgacgacga ggggatcaat ctgggtgcca gagtcaacgc ccagggtcgg   420
ggggatcacg ccgcgctcca ttgcaaggag aaccttgcac attcccgcaa agccggccgc   480
gacgagggtg tgtccgaagt tgcctttcgt ggacccgatc cggggcttg cgccctcaaa    540 gcaggctttg acggcttgga gctcgacggt gtcgccctgc ggcgtgccgg tggcgtggca   600
ctcgacgtac tggacgtctc ggggcggcac gccgacgagc tcgtaggtgg ctttcaagca   660
ggcctcctcg cttggctggt gcggcttgag aggaagcccg cagcctgcgt tgctcaagct   720 ggcccccaaga gcgtcccgt agatgtggtc tccgtcgcgc tcggcgtccg cgaggcgctt   780
gagcaccatc accgagccgc cctcgccggg cgtcagccct tgcgtgtccc gatgaaacgg   840
catcgagaca ccgttctcac cgactggcat cgcgtggaac gtgctaaacc cagtcaggat   900
gaagaagggc tctgggaagc acgtcgctcc gcacagcatc aagtcagcct cgcccgagag   960
gaggtggtcc tgagcgagtc gcagaacgta aagggccgag gcgcaggcgg cgtcgagcga  1020
gtagtgcagc gggccgaggc cgagctgtcc ggcgacgaag gaggctgggt cgcggtgggt  1080
cctcgggtcc ccgggcagcg ggtgaagcgc tctggttcgc gtcgaccagg gcgtttggtc  1140
cgcgaagcaa tgcttgccaa tccgcctctc agcatgggct tggtaaaggt tgagcagctc  1200
gccttgcagg ttgtccatcg ggaaggacag gcagccgctg acaatgccgc agcgcttgag  1260
ctgcgctggg tcgaacttgc cgccgtcgct gcgcctgtcc tgcgcgtctt gaagcgcagc  1320
cgcggcgagg ccgaggagca ggtcgtgctc gttgtcgact ttgggatcga tgcatccgta  1380
cctctcgttg cagaacgtat cggcgtactt tgacctctcg ggcgcatagt gctcttctcg  1440
tcgtgctgac ccgaggcgat cgtctgagat acaggcagag ttgattttgc cgttcatgag  1500
cgtgtcccag aacgcttcct tgccgcggca ccctgcatac tcgaccgcca tgcccacgac  1560
agcgatccgc gtgtcagggc atgggtccgc gcgcgccacc gagacgccct cgtcatttct  1620
cccgccctgg ttcatctctt tctgagcctt gtggcctctt gctttcgatt tcgatcggca  1680
gctccaacgc gcagctcgat ggcgattgc ttgctaaggc ggcgtgcaga caaccgctgc   1740
tcgaggttct gggcaagccg aggttcgccg cagggttcgt ggaggcactg ggatgttgtt  1800
ttgcggcagc tgcagcgctt gcggagcgag cggcgcagga cgacgttttc cgcgttcgcg  1860
cgaagctgcc tctcggctat tgtgacccgc cgccgacgct ggcagagacg tcgccgtcgg  1920

| | |
|---|---:|
| ccaccgcacc tcgagatcaa ttcgcagagg ctggcagagc cggtagcatt gcggcgtggc | 1980 |
| attgcgtgtg ccatgtgcat gtgtggcaaa caaatccagc caacctccga gtcgggcaga | 2040 |
| ccgaccgtgt gagttctcgc tgttgactga tctcttgatt gagcccaata atgatcacgg | 2100 |
| cctgagatcc ttcgcgctga gagatgcatg cgggcgctcg ttcctgggtt ggcgacccaa | 2160 |
| cggcgagtca cgtcgcccac tccgccacgc cccacacatg gccgccgatc cctcccgcca | 2220 |
| cacgaacggc gggccaagat cgcacgcctc cgtcggacga tgactgactg actgattggc | 2280 |
| tgacgacggc cgccctcgtg cgcggcgtcg ggcgtcgtcg caaaccaggc aggcaggcag | 2340 |
| gaaggaagga aggaagggcc aggccctggt gcgaaacgct ggcctgctcc gctgcaagcc | 2400 |
| aagccgcgct cgcaggtgta cttccgagtc ctcgcgatga ttaggcaagc ctgagcgagc | 2460 |
| acgtaagctg cactgcggct gttcaaccag agagagagtt ggctctcttg cgtcaaggcg | 2520 |
| gcgcgcagcc cacttgcgtc gcggctgagg gcccctggag gggaggaagg aggccggcga | 2580 |
| gcggcgagtg gcggccctca ctggcaccag gtcgcaggag gccaggcagc ccgccacgga | 2640 |
| caggaatcct cagggcgcag cagcgcacta cgtagtgcag agacgcagag cgggccggat | 2700 |
| ccgcagtgcg gtcgcgccac cccgccgcgc agctcgctcg cggacggggt ccgtggccgc | 2760 |
| gcgaaaacgg acacggtgtg ggagcggaca tgggatcgag aacgccgttc gccctgctcg | 2820 |
| cgctgccagc agcaggagcc gtccgaagga cgagcggccg gccgcctgtc ccccctccgc | 2880 |
| gcactcgaag cgcgcccggc agcgcccat tgcgtgcgcg gatggcgtct ggctggtcc | 2940 |
| ctctcgaggc gcttgctcgt gctcgccacg ccttgtccgc ctcctcgctg agcaagcgat | 3000 |
| gagctgagca cggaccgcct gcaagtgcaa gtgttcttgt gctgcagggc gccgaagaat | 3060 |
| tggattctgg cccatgatca gtttgattgg gccgaggag ggagggaggc tgggcgagtg | 3120 |
| ggcgacacca gcaagccgga ctgcgagagg ggcggggcag gatgtgagcg caggaaagtg | 3180 |
| a | 3181 |

<210> SEQ ID NO 105
<211> LENGTH: 3377
<212> TYPE: DNA
<213> ORGANISM: Artificial Sequence
<220> FEATURE:
<223> OTHER INFORMATION: genomic DNA (T. aureum ATCC 34304 OrfA upstream genomic DNA fragment)

<400> SEQUENCE: 105

| | |
|---|---:|
| gaattcgatt aatacgactc actataggga gaagcttttg ctctgcggct ctgcttgttc | 60 |
| gaagccaacg cgcctcgcga agtatctgca atctgcactc ctccggagag taagtacgta | 120 |
| agtacgtgcg tggtgcgcgc ggattgcggt gacgaaagag agggttgggt tggagatgct | 180 |
| gcggcatgcc gggcgactcg agcagcatgt cgccgcgaga ggacctggaa agctttcggt | 240 |
| ttggtccgct gccgaggcga ggctggcaga gtactgcggg cggagctctc gagggaatat | 300 |
| gctcctcaaa gacggcgtgc gcgtttgtgc ccccgaatcc gaatgcggag agtcctgcgc | 360 |
| gtttcggccc gccgcgcgta tccggccacg ggagcgccgc tgtgacgacg aggggatcaa | 420 |
| tctgggtgcc agagtcaacg cccagggtcg ggggatcac gccgcgctcc attgcaagga | 480 |
| gaaccttgca cattcccgca aagccggccg cgacgagggt gtgtccgaag ttgcctttcg | 540 |
| tggacccgat ccgggggctt gcgccctcaa agcaggcttt gacggcttgg agctcgacgg | 600 |
| tgtcgccctg cggcgtgccg gtggcgtggc actcgacgta ctggacgtct cggggcggca | 660 |
| cgccgacgag ctcgtaggtg gctttcaagc aggcctcctc gcttggctgg tgcggcttga | 720 |

```
gaggaagccc gcagcctgcg ttgctcaagc tggccccaag aagcgtcccg tagatgtggt    780
ctccgtcgcg ctcggcgtcc gcgaggcgct tgagcaccat caccgagccg ccctcgccgg    840
gcgtcagccc ttgcgtgtcc cgatgaaacg gcatcgagac accgttctca ccgactggca    900
tcgcgtggaa cgtgctaaac ccagtcagga tgaagaaggg ctctgggaag cacgtcgctc    960
cgcacagcat caagtcagcc tcgcccgaga ggaggtggtc ctgagcgagt cgcagaacgt   1020
aaagggccga ggcgcaggcg gcgtcgagcg agtagtgcag cgggccgagg ccgagctgtc   1080
cggcgacgaa ggaggctggg tcgcggtggg tcctcgggtc cccgggcagc gggtgaagcg   1140
ctctggttcg cgtcgaccag ggcgtttggt ccgcgaagca atgcttgcca atccgcctct   1200
cagcatgggc ttggtaaagg ttgagcagct cgccttgcag gttgtccatc gggaaggaca   1260
ggcagccgct gacaatgccg cagcgcttga gctgcgctgg gtcgaacttg ccgccgtcgc   1320
tgcgcctgtc ctgcgcgtct tgaagcgcag ccgcggcgag gccgaggagc aggtcgtgct   1380
cgttgtcgac tttgggatcg atgcatccgt acctctcgtt gcagaacgta tcggcgtact   1440
ttgacctctc gggcgcatag tgctcttctc gtcgtgctga cccgaggcga tcgtctgaga   1500
tacaggcaga gttgattttg ccgttcatga gcgtgtccca gaacgcttcc ttgccgcggc   1560
accctgcata ctcgaccgcc atgcccacga cagcgatccg cgtgtcaggg catgggtccg   1620
cgcgcgccac cgagacgccc tcgtcatttc tcccgccctg gttcatctct ttctgagcct   1680
tgtggcctct tgctttcgat ttcgatcggc agctccaacg cgcagctcga tggccgattg   1740
cttgctaagg cggcgtgcag acaaccgctg ctcgaggttc tgggcaagcc gaggttcgcc   1800
gcagggttcg tggaggcact gggatgttgt tttgcggcag ctgcagcgct tgcggagcga   1860
gcggcgcagg acgacgtttt ccgcgttcgc gcgaagctgc ctctcggcta ttgtgacccg   1920
ccgccgacgc tggcagagac gtcgccgtcg gccaccgcac ctcgagatca attcgcagag   1980
gctggcagag ccggtagcat tgcggcgtgg cattgcgtgt gccatgtgca tgtgtggcaa   2040
acaaatccag ccaacctccg agtcgggcag accgaccgtg tgagttctcg ctgttgactg   2100
atctcttgat tgagcccaat aatgatcacg gcctgagatc cttcgcgctg agagatgcat   2160
gcgggcgctc gttcctgggt tggcgaccca acggcgagtc acgtcgccca ctccgccacg   2220
ccccacacat ggccgccgat ccctcccgcc acacgaacgg cgggccaaga tcgcacgcct   2280
ccgtcggacg atgactgact gactgattgg ctgacgacgg ccgccctcgt gcgcggcgtc   2340
gggcgtcgtc gcaaaccagg caggcaggca ggaaggaagg aaggaagggc caggccctgg   2400
tgcgaaacgc tggcctgctc cgctgcaagc caagccgcgc tcgcaggtgt acttccgagt   2460
cctcgcgatg attaggcaag cctgagcgag cacgtaagct gcactgcggc tgttcaacca   2520
gagagagagt tggctctctt gcgtcaaggc ggcgcgcagc ccacttgcgt cgcggctgag   2580
ggcccctgga ggggaggaag gaggccggcg agcggcgagt ggcggccctc actggcacca   2640
ggtcgcagga ggccaggcag cccgccacga acaggaatcc tcagggcgca gcagcgcact   2700
acgtagtgca gagacgcaga gcgggccgga tccgcagtgc ggtcgcgcca ccccgccgcg   2760
cagctcgctc gcggacgggg tccgtggccg cgcgaaaacg gacacggtgt gggagcggac   2820
atgggatcga gaacgccgtt cgccctgctc gcgctgccag cagcaggagc cgtccgaagg   2880
acgagcggcc ggccgcctgt cccccctccg cgcactcgaa gcgcgcccgg cagcgcccca   2940
ttgcgtgcgc ggatggcgtc ttggctggtc cctctcgagg cgcttgctcg tgctcgccac   3000
gccttgtccg cctcctcgct gagcaagcga tgagctgagc acggaccgcc tgcaagtgca   3060
agtgttcttg tgctgcaggg cgccgaagaa ttggattctg gcccatgatc agtttgattg   3120
```

```
ggccgaggga gggagggagg ctgggcgagt gggcgacacc agcaagccgg actgcgagag    3180
gggcggggca ggatgtgagc gcaggaaagt gacgcaagtg catccggcca tcattgggcc    3240
atcattgggc catcattggt gttttgggcc gcgctttgcg gatcgtccgg ccgatcaggt    3300
acgaggccac gaacctacgt cgtttgccgc gctcaggctg gttggttgca cttggactct    3360
tctgtgacct ttcatcg                                                   3377
```

```
<210> SEQ ID NO 106
<211> LENGTH: 21
<212> TYPE: DNA
<213> ORGANISM: Artificial Sequence
<220> FEATURE:
<223> OTHER INFORMATION: primer

<400> SEQUENCE: 106
cagggcgagc gagtgtggtt c                                                21
```

```
<210> SEQ ID NO 107
<211> LENGTH: 1160
<212> TYPE: DNA
<213> ORGANISM: Artificial Sequence
<220> FEATURE:
<223> OTHER INFORMATION: genomic DNA (T. aureum  ATCC 34304 OrfA
      downstream)

<400> SEQUENCE: 107
tggctctcga ccaaagccga gtagagtact ctactcagta ctcttttcac ataccggcag      60
gcagtgttgc tgtgggattg gtccggggc tcttctgcac gcggcctccg tcgcgcgcag     120
aaatgccccg tcactggctg cccaggaggc agccgaatcc ctctagctag ctagctaggc    180
tagagcgtct tttccgtagt ttttcacaaa gccagtatca catggataac gaacgaaggt    240
ttcgggctcg cgctcgcagg cgttaggacg aagttgatcg ccccacgtca cttcaaacga    300
gtgaaccaag atcacgttgc atctgctcgc aagatcttct tcttccacgc cgcatcgatg    360
cgatggattt caaactcttt tcagggcttt taggtgagta tggcagcgct gtttgcgtgg    420
cagcgctgtt tgcgtggttg tactctctaa aggtgcttcc acgcatgcgc gcacaaaggg    480
gcatggcatg gttggcggcg cactctggcc ctcatttgaa gcagactatc gaagggtcca    540
gttggtactg cggcaggtcc ggcgagagca agcgcggcgg tcgctcccac tcgtccctgc    600
acagttgctg gactggcgac ggctggcgca cctgactacg agaagactcg agacgcacag    660
aggtagtcag ggacgaccga ccgcaaagca caaccgctc caaaacggcc gcaccaggca    720
gggcagtaaa ctaaaaacga atgtacctcc atcgcgcgta tctgccgagc ctcctcccac    780
gcttcggctg ggcttgattc accagtgtcc gcaagctgaa ccgaccgtct tcgatgtcat    840
gaagcttggc gcggcattag tcagacgacg cggcacgcca ggattctgtc ggtttctggg    900
aaatgggcat ctatatagct gattccctct gtcatgaggc ggccttgttc tggccctggg    960
ccgccgttcg gatgatctat gatgtcgttg tacgcataaa gcttgtcgaa aacgtcggcc   1020
atgtcttcct cagagatgta accgagcggc gcgtcgtggc gattgatgcc gatgctacaa   1080
aagccgccga gttagctcga atgtcagatg cattgcgggc tggcccgcat ggcgcgggcg   1140
cagcagcgag aggttctaga                                               1160
```

```
<210> SEQ ID NO 108
<211> LENGTH: 1204
<212> TYPE: DNA
<213> ORGANISM: Artificial Sequence
```

```
<220> FEATURE:
<223> OTHER INFORMATION: genomic DNA (T. aureum ATCC 34304 OrfA
      downstream genomic DNA fragment)

<400> SEQUENCE: 108
cagggcgagc gagtgtggtt ctgaacaagg ctctttcgtt ttgatggctc tcgaccaaag      60
ccgagtagag tactctactc agtactcttt tcacataccg gcaggcagtg ttgctgtggg     120
attggtccgg gggctcttct gcacgcggcc tccgtcgcgc gcagaaatgc cccgtcactg     180
gctgcccagg aggcagccga atccctctag ctagctagct aggctagagc gtcttttccg     240
tagtttttca caaagccagt atcacatgga taacgaacga aggtttcggg ctcgcgctcg     300
caggcgttag gacgaagttg atcgcccac gtcacttcaa acgagtgaac caagatcacg      360
ttgcatctgc tcgcaagatc ttcttcttcc acgccgcatc gatgcgatgg atttcaaact     420
cttttcaggg cttttaggtg agtatggcag cgctgtttgc gtggcagcgc tgtttgcgtg     480
gttgtactct ctaaaggtgc ttccacgcat gcgcgcacaa aggggcatgg catggttggc     540
ggcgcactct ggccctcatt tgaagcagac tatcgaaggg tccagttggt actgcggcag     600
gtccggcgag agcaagcgcg gcggtcgctc ccactcgtcc ctgcacagtt gctggactgg     660
cgacggctgg cgcacctgac tacgagaaga ctcgagacgc acagaggtag tcagggacga     720
ccgaccgcaa agcacaaacc gctccaaaac ggccgcacca ggcagggcag taaactaaaa     780
acgaatgtac ctccatcgcg cgtatctgcc gagcctcctc ccacgcttcg gctgggcttg     840
attcaccagt gtccgcaagc tgaaccgacc gtcttcgatg tcatgaagct tggcgcggca     900
ttagtcagac gacgcggcac gccaggattc tgtcggtttc tgggaaatgg gcatctatat     960
agctgattcc ctctgtcatg aggcggcctt gttctggccc tgggccgccg ttcggatgat    1020
ctatgatgtc gttgtacgca taaagcttgt cgaaaacgtc ggccatgtct tcctcagaga    1080
tgtaaccgag cggcgcgtcg tggcgattga tgccgatgct acaaaagccg ccgagttagc    1140
tcgaatgtca gatgcattgc gggctggccc gcatggcgcg ggcgcagcag cgagaggttc    1200
taga                                                                 1204

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
tgatgccgat gctacaaaag                                                  20

<210> SEQ ID NO 110
<211> LENGTH: 1488
<212> TYPE: DNA
<213> ORGANISM: Artificial Sequence
<220> FEATURE:
<223> OTHER INFORMATION: genomic DNA (T. aureum ATCC 34304 OrfA
      downstream genomic DNA fragment)

<400> SEQUENCE: 110
aagcttgtac ggtgaaaagc cctttggcgc agcccgaaac aagtcttgct tctcctgccc      60
cgtcaaactc gcaaactctg gcagcaactc ccgcacgctc tgtaccacgg cgaacccaag     120
ggcaggcacg cggtgaaacg acttgcatgc ttgcacaaca accccttgc cgacgtcgac      180
gcggtcgcct tcggagagcc caaacacagc gaacgccgga tccgcctgcg cctctgcatg     240
```

| | |
|---|---|
| cgcctctgca tgcgcctcga catgcgcctc ggcctccgtg cctgcttgcc gggccggcgg | 300 |
| ggcagcagga agtgcgtggc cgaggtccat cgcatcaaag gctcgcttcg cggcgtgaaa | 360 |
| ggcctcgagc gcctccgccg gcaagtacac cttggtcttg cacttgagca tgctcctgat | 420 |
| ccgcgcgtag aggaagacgg ccgcgcagtg gtccaggtgc ccgtgcgaca gaacacgtg | 480 |
| ctccgccctc gccgcggcct tgtccggctc gtccccgagc gacccgcagt cgaactgcaa | 540 |
| gcagacccgc gagcccaggt ccacttgcag cgccgtgccg cagccggccc tcgactgccc | 600 |
| cgtcacgcgg acgtgcgagg ccatctcccg ccgcgagcct ggagcgccag agcctcctgc | 660 |
| tgctgccgtg ccgcctcggg gggcgcgagg agggtctcgc ctgatgcagc gcgcggggcc | 720 |
| gacgcagcag cgcgggtgga ggaagactgc gctgtgggcg gcggccctcg ggctgctgct | 780 |
| cttgtggctc ctgtccgtgc gctcgttcgt gcacggcgtg gcggacaggg aggcggacgc | 840 |
| cgtcgccccg cgcgagggcc ccaggcgcc ggcgccaaag gggactggcg ggaggaatga | 900 |
| tatgcccgct gagcctgccg ctggtaggcc cgcgcacagc tcgcctcgag ggacgcccga | 960 |
| cggcaacgcg gtcgagtgct ccacgaccaa gggcccgttc cgcgtggtcc tcacgcctag | 1020 |
| cctagcgccg aacgggacca agtttttcat cgggctggtg aagcaggct atttcgacca | 1080 |
| aggcatcgcc ttctttcgcg tcaacaaggc catcacgcag ttcgggatca ccaagcgaag | 1140 |
| gccacgcgat gaggatccgt tcgtgcagtt cagaggcggg gcccagcgcg acgagaaccc | 1200 |
| tttcggtggc gtggaggatg acgaggagag tgtccatcgc aggcacatgc acccgtggcg | 1260 |
| gcgcggcacg attgcctcga taggcggctt ccactttgtt gtcacgatcc gcggggacaa | 1320 |
| aaagtaagtt cttgaatgtt gtgaagtgcg ccaactcgcg ttcggagcgg acctggaccg | 1380 |
| atattcagca atctagaacc tctcgctgct gcgcccgcgc catgcgggcc agcccgcaat | 1440 |
| gcatctgaca ttcgagctaa ctcggcggct tttgtagcat cggcatca | 1488 |

<210> SEQ ID NO 111
<211> LENGTH: 2551
<212> TYPE: DNA
<213> ORGANISM: Artificial Sequence
<220> FEATURE:
<223> OTHER INFORMATION: genomic DNA (T. aureum ATCC 34304 OrfA
      downstream genomic DNA fragment)

<400> SEQUENCE: 111

| | |
|---|---|
| tggctctcga ccaaagccga gtagagtact ctactcagta ctcttttcac ataccggcag | 60 |
| gcagtgttgc tgtgggattg gtccgggggc tcttctgcac gcggcctccg tcgcgcgcag | 120 |
| aaatgccccg tcactggctg cccaggaggc agccgaatcc ctctagctag ctagctaggc | 180 |
| tagagcgtct tttccgtagt ttttcacaaa gccagtatca catggataac gaacgaaggt | 240 |
| ttcgggctcg cgctcgcagg cgttaggacg aagttgatcg ccccacgtca cttcaaacga | 300 |
| gtgaaccaag atcacgttgc atctgctcgc aagatcttct tcttccacgc cgcatcgatg | 360 |
| cgatggattt caaactcttt tcagggcttt taggtgagta tggcagcgct gtttgcgtgg | 420 |
| cagcgctgtt tgcgtggttg tactctctaa aggtgcttcc acgcatgcgc gcacaaaggg | 480 |
| gcatggcatg gttggcggcg cactctggcc ctcatttgaa gcagactatc gaagggtcca | 540 |
| gttggtactg cggcaggtcc ggcgagagca agcgcggcgg tcgctcccac tcgtccctgc | 600 |
| acagttgctg gactggcgac ggctggcgca cctgactacg agaagactcg agacgcacag | 660 |
| aggtagtcag ggacgaccga ccgcaaagca caaccgctc caaaacgcc gcaccaggca | 720 |
| gggcagtaaa ctaaaaacga atgtacctcc atcgcgcgta tctgccgagc ctcctcccac | 780 |

```
gcttcggctg ggcttgattc accagtgtcc gcaagctgaa ccgaccgtct tcgatgtcat    840
gaagcttggc gcggcattag tcagacgacg cggcacgcca ggattctgtc ggtttctggg    900
aaatgggcat ctatatagct gattccctct gtcatgaggc ggccttgttc tggccctggg    960
ccgccgttcg gatgatctat gatgtcgttg tacgcataaa gcttgtcgaa acgtcggcc    1020 atgtcttcct cagagatgta accgagcggc gcgtcgtggc gattgatgcc gatgctacaa   1080
aagccgccga gttagctcga atgtcagatg cattgcgggc tggcccgcat ggcgcgggcg   1140
cagcagcgag aggttctaga ttgctgaata tcggtccagg tccgctccga acgcgagttg   1200
gcgcacttca caacattcaa gaacttactt tttgtccccg cggatcgtga caacaaagtg   1260
gaagccgcct atcgaggcaa tcgtgccgcg ccgccacggg tgcatgtgcc tgcgatggac   1320
actctcctcg tcatcctcca cgccaccgaa agggttctcg tcgcgctggg ccccgcctct   1380
gaactgcacg aacggatcct catcgcgtgg ccttcgcttg gtgatcccga actgcgtgat   1440
ggccttgttg acgcgaaaga aggcgatgcc ttggtcgaaa tagcctgctt ccaccagccc   1500
gatgaaaaac ttggtcccgt tcggcgctag gctaggcgtg aggaccacgc ggaacgggcc   1560
cttggtcgtg gagcactcga ccgcgttgcc gtcgggcgtc cctcgaggcg agctgtgcgc   1620
gggcctacca gcggcaggct cagcgggcat atcattcctc ccgccagtcc tctttggcgc   1680
cggcgccctg ggccctcgc gcggggcgac ggcgtccgcc tccctgtccg ccacgccgtg    1740
cacgaacgag cgcacggaca ggagccacaa gagcagcagc ccgagggccg ccgcccacag   1800
cgcagtcttc ctccacccgc gctgctgcgt cggccccgcg cgctgcatca ggcgagaccc   1860
tcctcgcgcc ccccgaggcg gcacggcagc agcaggaggc tctggcgctc caggctcgcg   1920
gcgggagatg gcctcgcacg tccgcgtgac ggggcagtcg agggccggct gcggcacggc   1980
gctgcaagtg gacctgggct cgcgggtctg cttgcagttc gactgcgggt cgctcgggga   2040
cgagccggac aaggccgcgg cgagggcgga gcacgtgttc ttgtcgcacg gcacctgga   2100 ccactgcgcg gccgtcttcc tctacgcgcg gatcaggagc atgctcaagt gcaagaccaa   2160
ggtgtacttg ccggcggagg cgctcgaggc cttttcacgcc gcgaagcgag cctttgatgc   2220
gatggacctc ggccacgcac ttcctgctgc ccgccggcc cggcaagcag gcacggaggc    2280
cgaggcgcat gtcgaggcgc atgcagaggc gcatgcagag gcgcaggcgg atccggcgtt   2340
cgctgtgttt gggctctccg aaggcgaccg cgtcgacgtc ggcaaggggg ttgttgtgca   2400
agcatgcaag tcgtttcacc gcgtgcctgc ccttgggttc gccgtggtac agagcgtgcg   2460
ggagttgctg ccagagtttg cgagtttgac ggggcaggag aagcaagact tgtttcgggc   2520
tgcgccaaag ggcttttcac cgtacaagct t                                  2551
```

<210> SEQ ID NO 112
<211> LENGTH: 1835
<212> TYPE: DNA
<213> ORGANISM: Artificial Sequence
<220> FEATURE:
<223> OTHER INFORMATION: 18S rDNA (T. aureum ATCC 34304)

<400> SEQUENCE: 112

```
cgaatattcc tggttgatcc tgccagtagt catacgctta tctcaaagat taagccatgc     60
atgtctaagt ataaaggctt atactctgaa actgcgaacg gctcattata tcagttatag    120
tttctttgat agtgtttttt ctacatggat acttgtggca aatctagaaa caatacatgc    180
gtacaggcct gactttgggg gagggctgca tttatttgac ttaagccaat accctcggg     240 gttgttttgg tgattcagaa taactgagcg aatcgcatag ctttcgggcg gcgatgaatc    300
```

```
atttcaagtt tctgccccat cagctgtcga tggtagggta taggcctacc atggctgtca    360
cgggtgacgg agaattaggg ttcgattccg gagagggagc ctgagagacg gctaccacat    420
ccaaggaagg cagcaggcgc gtaaattact caatgttgac tcgacgaagt agtgacgaga    480
attaacaatg cggagcgctc agcgttttgc aattggaatg agagcaatgt aaaagcctca    540
tcgaggatcc attggagggc aagtctggtg ccagcagccg cggtaattcc agctccaata    600
gcgtatacta aagttgttgc agttaaaaag ctcgtagttg aacctctggt agggccgacc    660
ttggcgcgcg gtgaatgccg cgtcgtttag aagcgtcgtg cccggccatc ctccccggt     720
cttttgggct gggggtcgtt tactgtaaaa aaaatagagt gttccaagca gggggtaata    780
tcccggtata tagtagtatg gaataatgag ataggacttt ggtactattt tgttggtttg    840
catgccaagg taatgattaa gagggacagt tgggggtatt cgtatttaga tgtcagaggt    900
gaaattcttg gattttcgaa agacgaacta ctgcgaaagc atttaccaag gatgttttca    960
ttaatcaaga cgaaagtta ggggatcgaa gatgattaga taccatcgta gtcttaaccg    1020
taaactatgc cgacttgcga ttgtccggcg tcgcttttag atgacctggg cagcagcaca   1080
tgagaaatca aagtctttgg gttccggggg gagtatggtc gcaaggctga aacttaaagg   1140
aattgacgga agggcaccac caggagtgga gcctgcggct taatttgact caacacggga   1200
aaacttacca ggtccggaca taggaaggat tgacagattg agagctcttt cttgattcta   1260
tgggtggtgg tgcatggccg ttcttagttg gtggagtgat ttgtctggtt aattccgtta   1320
acgaacgaga ccacagccta ctaaatagtg gccgttatgg cgacatagcg gtgaacttct   1380
tagagggaca tttcgggtat accggaagga agtttgtggc aataacaggt ctgtgatgcc   1440
cttagatgtt ctgggccgca cgcgcgctac actgatcggt tcaacgagta tttgttttt    1500
tctcattttg ggagggggca gagtccttgg ccggaaggtc tgggtaatct tttgaatgcc   1560
gatcgtgatg gggctagatt tttgcaatta ttaatctcca acgaggaatt cctagtagac   1620
gcaagtcatc agcttgcatc gattacgtcc ctgcccttg tacacaccgc ccgtcgcacc    1680
taccgattga acgatccggt gagaccttgg gattctgttg tggctgattc attttggctg   1740
cgatgggaga acttgagcaa accttatcgt ttagaggaag gtgaagtcgt aacaaggttt   1800
ccgtagtgaa cctgcaattc aaaaaaagcc gttac                              1835
```

```
<210> SEQ ID NO 113
<211> LENGTH: 30
<212> TYPE: DNA
<213> ORGANISM: Artificial Sequence
<220> FEATURE:
<223> OTHER INFORMATION: primer

<400> SEQUENCE: 113
cgaatattcc tggttgatcc tgccagtagt                                      30

<210> SEQ ID NO 114
<211> LENGTH: 46
<212> TYPE: DNA
<213> ORGANISM: Artificial Sequence
<220> FEATURE:
<223> OTHER INFORMATION: primer

<400> SEQUENCE: 114
gtaacggctt tttttgaatt gcaggttcac tacgcttgtt agaaac                    46

<210> SEQ ID NO 115
```

<211> LENGTH: 661
<212> TYPE: DNA
<213> ORGANISM: Artificial Sequence
<220> FEATURE:
<223> OTHER INFORMATION: EF1 alpha promoter (T. aureum ATCC 34304)

<400> SEQUENCE: 115

```
ggtttccgta gtgaacctgc aattcaaaaa aagccgttac tcacatcagg ccgccactca      60
tccgggcgaa agcttcgcgc attcgtcctc gtcacctcgg gtcccctgtg tcgtgacgga     120
aagcgcgacg agacgcggcc gcagcagaga gccccggggg cccgcgtcac gggggcctg      180
gcggcggtcc tccttaagcc aaaccgaggg ttagggctcc aggctgttcg gcggggtcgc     240
gggcgcggtg gacgcgcggg gccgcctagc acctcctagc gcgcgactac caggatagcc     300
cccgcgagtg cgcagggcgg tccgcggggc ggagggcggc ccagcagcgc ggcgcggcgg     360
gcgggtgcgg ctgcgtaagg tggcggcggg cgcggcggt tagtgttggt gttaggtcgc     420
ggcggggctg tgttccgggc atccgcctta cggcggtgca tactggttgg ctggaggcg     480
gtttgcgggg ttagataggc ggccaaggtg agctgcgttg ggcggataaa tccgtggagg     540
cgctcgttga cggcgcggca gagacggaac gcggagcagc acggagtagc aagcaggagt     600
agcaggagta gcaagcagcg gcaaaggaag gctagatgat tgaacaggac ggccttcacg     660
c                                                                     661
```

<210> SEQ ID NO 116
<211> LENGTH: 46
<212> TYPE: DNA
<213> ORGANISM: Artificial Sequence
<220> FEATURE:
<223> OTHER INFORMATION: primer

<400> SEQUENCE: 116

```
ggtttccgta gtgaacctgc aattcaaaaa aagccgttac tcacat                    46
```

<210> SEQ ID NO 117
<211> LENGTH: 46
<212> TYPE: DNA
<213> ORGANISM: Artificial Sequence
<220> FEATURE:
<223> OTHER INFORMATION: primer

<400> SEQUENCE: 117

```
gcgtgaaggc cgtcctgttc aatcatctag ccttcctttg ccgctg                    46
```

<210> SEQ ID NO 118
<211> LENGTH: 835
<212> TYPE: DNA
<213> ORGANISM: Artificial Sequence
<220> FEATURE:
<223> OTHER INFORMATION: Neomycin resistance gene (Neor)

<400> SEQUENCE: 118

```
catcggcaaa ggaaggctag atgattgaac aggacggcct tcacgctggc tcgcccgctg      60
cttgggtgga acggctgttc ggctacgact gggctcagca gacgatcggc tgctcggacg     120
cggccgtgtt ccgccttagc gcgcagggcc ggccggtcct gtttgtcaag accgaccta     180
gcggcgccct caacgagctc caggacgaag ctgcccgcct cagctggctt gccacgacgg     240
gggttccgtg cgccgctgtg ctcgacgtcg tcaccgaagc cggccgcgac tggctgctcc     300
tcggggaagt gccccggccag gacctcctca gcagccacct cgcgcccgct gagaaggtgt     360
ccatcatggc cgacgccatg cgccgcctgc acaccctcga ccccgccacc tgcccccttcg     420
```

```
accaccaggc gaagcacagg atcgaacgcg cccgcacgcg gatggaggct ggcctcgtcg    480
accaagacga cctcgacgag gagcaccagg gcctcgcgcc ggcggaactg ttcgccaggc    540
ttaaggctag gatgccggac ggcgaggacc tcgtggtcac gcacggcgac gcctgcctcc    600
ccaacatcat ggtcgagaac ggccgcttct cgggctttat cgactgcggg cgcctgggcg    660
tggcggaccg ctaccaagac atcgcgctcg ccacgcggga catcgccgag gagcttggcg    720
gcgagtgggc cgaccgcttt ctcgtgctct acggcatcgc cgccccggac agccaggaga    780
ttgcgttcta ccgcctcctg gacgagttct tttgagatcc gcgccggcta tgcgc         835

<210> SEQ ID NO 119
<211> LENGTH: 45
<212> TYPE: DNA
<213> ORGANISM: Artificial Sequence
<220> FEATURE:
<223> OTHER INFORMATION: primer

<400> SEQUENCE: 119
catcggcaaa ggaaggctag atgattgaac aggacggcct tcacg                     45

<210> SEQ ID NO 120
<211> LENGTH: 46
<212> TYPE: DNA
<213> ORGANISM: Artificial Sequence
<220> FEATURE:
<223> OTHER INFORMATION: primer

<400> SEQUENCE: 120
gcgcatagcc ggcgcggatc tcaaaagaac tcgtccagga ggcggt                    46

<210> SEQ ID NO 121
<211> LENGTH: 1249
<212> TYPE: DNA
<213> ORGANISM: Artificial Sequence
<220> FEATURE:
<223> OTHER INFORMATION: EF1 alpha terminator (T. aureum ATCC 34304)

<400> SEQUENCE: 121
tcctggacga gttcttttga gatccgcgcc ggctatgcgc ccgtgctcga ctgccacact     60
gcccacattg cctgcaagtt cgctgagctc cagaacaaga tggaccgccg ctcgggcaag    120
attctcgagg agaccccaa gttcatcaag tcgggtggac tctgccatgg tcaagatgta    180 tccccctccaa gcgcatgtgc gtcgagtcct tcaccgagta cccgccgctc ggccgctttg    240
ccgtgcgcga catgcgcgtc accgtcgctg tcggcgtcat caagtccgtc accaagggcg    300
acaaataaat tctacgaaag atttttttcc tcaagaagcg ccctaaagtt gacccctagc    360
agcgacgact gtgtgtgccg ttgtgagtcg agttgcgatg tcgtgcagcg cccgtcgcgt    420
cccatgctcg cgcgcgactc cgtctctgct tttcatctca agtcaagagt gggaagttcc    480
cttgctttat ctcactattt agaggtcgct cacggctgct ggttcctcgt cgcatgtagc    540
acagcctcgt ccaatcgcag cctgcaccac cccgctcgcc tgggaaaatg cgctcagcgg    600
attcgcactg gcactcctct cctcggacag gtgcgatgtg gaagcggtca catcctcggc    660
gccctcggcc acgccagcat ctgcgcaatc gctctcctcg ttctcagccg caaccgcagg    720
caggccgacg tcgtttacct cggaatccac cgagcatttc gagcccatcg cgctggcgtc    780
cacctcgatc ataccttctc catcgccgtc cgctgcggct tccgattctt ctgctgccgc    840
aaccgcgacg tcggcccccg tctcctccgt tctttccgat gccggcgcag tggccgcgcc    900
```

```
ctctgctcga accggctcgt gttcagcgtc agggcctgcg cttgagctcg ggcggctctt    960
ccgagtgatc cggccccgcg aggcaaggaa tcggcggctc tggagtgtcg gggcagccgc   1020
tctcactgcc ggtctttggc tggctgcctg tcctgcctcg cgttggcctt tgcttttgcc   1080
taggctttcg ccttggtgac ggcgtttgcc tgctgcggcg acttggcgcg gccgcggaat   1140
agcgcctcaa agtcctgctc gaggcgcccc agctctgact tgatttgcga ggtcccggtg   1200
gcatgagctc cgctgccctc gtccttacgg cccgtctttc gctgcagtg              1249

<210> SEQ ID NO 122
<211> LENGTH: 46
<212> TYPE: DNA
<213> ORGANISM: Artificial Sequence
<220> FEATURE:
<223> OTHER INFORMATION: primer

<400> SEQUENCE: 122
tcctggacga gttcttttga gatccgcgcc ggctatgcgc ccgtgc                    46

<210> SEQ ID NO 123
<211> LENGTH: 30
<212> TYPE: DNA
<213> ORGANISM: Artificial Sequence
<220> FEATURE:
<223> OTHER INFORMATION: primer

<400> SEQUENCE: 123
cactgcagcg aaagacgggc cgtaaggacg                                      30

<210> SEQ ID NO 124
<211> LENGTH: 4453
<212> TYPE: DNA
<213> ORGANISM: Artificial Sequence
<220> FEATURE:
<223> OTHER INFORMATION: fusion DNA (T. aureum ATCC 34304 18S rDNA/T.
      aureum ATCC 34304 EF1 alpha promoter/Neor/T. aureum ATCC 34304 EF1
      alpha terminator)

<400> SEQUENCE: 124
cgaatattcc tggttgatcc tgccagtagt catacgctta tctcaaagat taagccatgc     60
atgtctaagt ataaaggctt atactctgaa actgcgaacg gctcattata tcagttatag    120
tttctttgat agtgtttttt ctacatggat acttgtggca aatctagaaa caatacatgc    180
gtacaggcct gactttgggg gagggctgca tttatttgac ttaagccaat acccctcggg    240
gttgttttgg tgattcagaa taactgagcg aatcgcatag ctttcgggcg gcgatgaatc    300
atttcaagtt tctgccccat cagctgtcga tggtagggta taggcctacc atggctgtca    360
cgggtgacgg agaattaggg ttcgattccg gagagggagc tgagagacg gctaccacat    420 ccaaggaagg cagcaggcgc gtaaattact caatgttgac tcgacgaagt agtgacgaga    480
attaacaatg cggagcgctc agcgttttgc aattggaatg agagcaatgt aaaagcctca    540
tcgaggatcc attggagggc aagtctggtg ccagcagccg cggtaattcc agctccaata    600
gcgtatacta agttgttgc agttaaaaag ctcgtagttg aacctctggt agggccgacc    660
ttggcgcgcg gtgaatgccg cgtcgtttag aagcgtcgtg cccggccatc ctcccccggt    720
cttttgggct gggggtcgtt tactgtaaaa aaaatagagt gttccaagca ggggtaata    780 tcccggtata tagtagtatg gaataatgag ataggacttt ggtactattt tgttggtttg    840
catgccaagg taatgattaa gagggacagt tggggtat cgtatttaga tgtcagaggt    900
gaaattcttg gattttcgaa agacgaacta ctgcgaaagc atttaccaag gatgttttca    960
```

```
ttaatcaaga acgaaagtta ggggatcgaa gatgattaga taccatcgta gtcttaaccg    1020
taaactatgc cgacttgcga ttgtccggcg tcgcttttag atgacctggg cagcagcaca    1080
tgagaaatca aagtctttgg gttccggggg gagtatggtc gcaaggctga aacttaaagg    1140
aattgacgga agggcaccac caggagtgga gcctgcggct taatttgact caacacggga    1200
aaacttacca ggtccggaca taggaaggat tgacagattg agagctcttt cttgattcta    1260
tgggtggtgg tgcatggccg ttcttagttg gtggagtgat ttgtctggtt aattccgtta    1320
acgaacgaga ccacagccta ctaaatagtg gccgttatgg cgacatagcg gtgaacttct    1380
tagagggaca tttcgggtat accggaagga agtttgtggc aataacaggt ctgtgatgcc    1440
cttagatgtt ctgggccgca cgcgcgctac actgatcggt tcaacgagta tttgtttttt    1500
tctcattttg ggaggggca gagtccttgg ccggaaggtc tgggtaatct tttgaatgcc    1560
gatcgtgatg gggctagatt tttgcaatta ttaatctcca acgaggaatt cctagtagac    1620
gcaagtcatc agcttgcatc gattacgtcc ctgcccttgt acacaccgc ccgtcgcacc    1680 taccgattga acgatccggt gagaccttgg gattctgttg tggctgattc attttggctg    1740
cgatgggaga acttgagcaa accttatcgt ttagaggaag gtgaagtcgt aacaaggttt    1800
ccgtagtgaa cctgcaattc aaaaaaagcc gttactcaca tcaggccgcc actcatccgg    1860
gcgaaagctt cgcgcattcg tcctcgtcac ctcgggtccc ctgtgtcgtg acggaaagcg    1920
cgacgagacg cggccgcagc agagagcccc gggggcccgc gtcacggggg gcctggcggc    1980
ggtcctcctt aagccaaacc gagggttagg gctccaggct gttcggcggg gtcgcgggcg    2040
cggtggacgc gcgggccgc ctagcacctc ctagcgcgcg actaccagga tagcccccgc    2100
gagtgcgcag ggcggtccgc ggggcggagg gcggcccagc agcgcggcgc ggcgggcggg    2160
tgcggctgcg taaggtggcg gcgggcgcgg gcggttagtg ttggtgttag gtcgcggcgg    2220
ggctgtgttc cgggcatccg ccttacggcg gtgcatactg gttggctggg aggcggtttg    2280
cggggttaga taggcggcca aggtgagctg cgttgggcgg ataaatccgt ggaggcgctc    2340
gttgacggcg cggcagagac ggaacgcgga gcagacgga gtagcaagca ggagtagcag    2400
gagtagcaag catggcaaag gaaggctaga tgattgaaca ggacggcctt cacgctggct    2460
cgcccgctgc ttgggtggaa cggctgttcg gctacgactg ggctcagcag acgatcggct    2520
gctcggacgc ggccgtgttc cgccttagcg cgcaggccg gccggtcctg tttgtcaaga    2580
ccgaccttag cggcgccctc aacgagctcc aggacgaagc tgcccgcctc agctggcttg    2640
ccacgacggg ggttccgtgc gccgctgtgc tcgacgtcgt caccgaagcc ggccgcgact    2700
ggctgctcct cggggaagtg cccggccagg acctcctcag cagccacctc gcgccgctg    2760 agaaggtgtc catcatggcc gacgccatgc gccgctgca ccctcgac cccgccacct    2820 gccccttcga ccaccaggcg aagcacagga tcgaacgcgc ccgcacgcgg atggaggctg    2880
gcctcgtcga ccaagacgac ctcgacgagg agcaccaggg cctcgcgccg gcggaactgt    2940
tcgccaggct taaggctagg atgccggacg gcgaggacct cgtggtcacg cacggcgacg    3000
cctgcctccc caacatcatg gtcgagaacg gccgcttctc gggctttatc gactgcgggc    3060
gcctgggcgt ggcggaccgc taccaagaca tcgcgctcgc cacgcgggac atcgccgagg    3120
agcttggcgg cgagtgggcc gaccgctttc tcgtgctcta cggcatcgcc gccccggaca    3180
gccagaggat tgcgttctac cgcctcctgg acgagttctt ttgagatccg cgccggctat    3240
gcgcccgtgc tcgactgcca cactgcccac attgcctgca agttcgctga gctccagaac    3300
```

```
aagatggacc gccgctcggg caagattctc gaggagaccc ccaagttcat caagtcgggt    3360
ggactctgcc atggtcaaga tgtatcccct ccaagcgcat gtgcgtcgag tccttcaccg    3420
agtacccgcc gctcggccgc tttgccgtgc gcgacatgcg cgtcaccgtc gctgtcggcg    3480
tcatcaagtc cgtcaccaag ggcgacaaat aaattctacg aaagattttt ttcctcaaga    3540
agcgccctaa agttgacccc tagcagcgac gactgtgtgt gccgttgtga gtcgagttgc    3600
gatgtcgtgc agcgcccgtc gcgtcccatg ctcgcgcgcg actccgtctc tgcttttcat    3660
ctcaagtcaa gagtgggaag ttcccttgct ttatctcact atttagaggt cgctcacggc    3720
tgctggttcc tcgtcgcatg tagcacagcc tcgtccaatc gcagcctgca ccaccccgct    3780
cgcctgggaa aatgcgctca gcggattcgc actggcactc ctctcctcgg acaggtgcga    3840
tgtggaagcg gtcacatcct cggcgccctc ggccacgcca gcatctgcgc aatcgctctc    3900
ctcgttctca gccgcaaccg caggcaggcc gacgtcgttt acctcggaat ccaccgagca    3960
tttcgagccc atcgcgctgg cgtccacctc gatcatacct tctccatcgc cgtccgctgc    4020
ggcttccgat tcttctgctg ccgcaaccgc gacgtcggcc ccgtctcct ccgttctttc    4080 cgatgccggc gcagtggccg cgccctctgc tcgaaccggc tcgtgttcag cgtcagggcc    4140
tgcgcttgag ctcgggcggc tcttccgagt gatccgcccc cgccgaggcaa ggaatcggcg    4200 gctctggagt gtcggggcag ccgctctcac tgccggtctt tggctggctg cctgtcctgc    4260
ctcgcgttgg cctttgcttt tgcctaggct ttcgccttgg tgacggcgtt tgcctgctgc    4320
ggcgacttgg cgcggccgcg gaatagcgcc tcaaagtcct gctcgaggcg ccccagctct    4380
gacttgattt gcgaggtccc ggtggcatga gctccgctgc cctcgtcctt acggcccgtc    4440
tttcgctgca gtg                                                       4453
```

<210> SEQ ID NO 125
<211> LENGTH: 1218
<212> TYPE: DNA
<213> ORGANISM: Artificial Sequence
<220> FEATURE:
<223> OTHER INFORMATION: genomic DNA (T. aureum ATCC 34304 OrfA
      upstream genomic DNA fragment)

<400> SEQUENCE: 125

```
cccgaattcg gacgatgact gactgactga ttggctgacg acggccgccc tcgtgcgcgg     60
cgtcgggcgt cgtcgcaaac caggcaggca ggcaggaagg aaggaaggaa gggccaggcc    120
ctggtgcgaa acgctggcct gctccgctgc aagccaagcc gcgctcgcag gtgtacttcc    180
gagtcctcgc gatgattagg caagcctgag cgagcacgta agctgcactg cggctgttca    240
accagagaga gagttggctc tcttgcgtca aggcggcgcg cagcccactt gcgtcgcggc    300
tgagggcccc tggaggggag gaaggaggcc ggcgagcggc gagtggcggc cctcactggc    360
accaggtcgc aggaggccag gcagcccgcc acggacagga atcctcaggg cgcagcagcg    420
cactacgtag tgcagagacg cagagcgggc cggatccgca gtgcggtcgc gccacccgc    480 cgcgcagctc gctcgcggac ggggtccgtg gccgcgcgaa aacggacacg gtgtgggagc    540
ggacatggga tcgagaacgc cgttcgccct gctcgcgctg ccagcagcag gagccgtccg    600
aaggacgagc ggccggccgc ctgtcccccc tccgcgcact cgaagcgcgc ccggcagcgc    660
cccattgcgt gcgcggatgg cgtcttggct ggtccctctc gaggcgcttg ctcgtgctcg    720
ccacgccttg tccgcctcct cgctgagcaa gcgatgagct gagcacggac cgcctgcaag    780
tgcaagtgtt cttgtgctgc agggcgccga agaattggat tctggcccat gatcagtttg    840
```

```
attgggccga gggagggagg gaggctgggc gagtgggcga caccagcaag ccggactgcg      900
agaggggcgg ggcaggatgt gagcgcagga aagtgacgca agtgcatccg gccatcattg      960
ggccatcatt gggccatcat tggtgttttg ggccgcgctt tgcggatcgt ccggccgatc     1020
aggtacgagg ccacgaacct acgtcgtttg ccgcgctcag gctggttggt tgcacttgga     1080
ctcttctgtg accttcatc gtgtgcaggc aaactcgatt tgcagacccg agacacggcg     1140
aaggatccgt gctgcaaacg caagtggagt gcgtcgagag caccgccgag accaagagcc     1200
gaggcagaca agcttggg                                                    1218
```

<210> SEQ ID NO 126
<211> LENGTH: 32
<212> TYPE: DNA
<213> ORGANISM: Artificial Sequence
<220> FEATURE:
<223> OTHER INFORMATION: primer

<400> SEQUENCE: 126

```
cccgaattcg gacgatgact gactgactga tt                                      32
```

<210> SEQ ID NO 127
<211> LENGTH: 28
<212> TYPE: DNA
<213> ORGANISM: Artificial Sequence
<220> FEATURE:
<223> OTHER INFORMATION: primer

<400> SEQUENCE: 127

```
cccaagcttg tctgcctcgg ctcttggt                                           28
```

<210> SEQ ID NO 128
<211> LENGTH: 1000
<212> TYPE: DNA
<213> ORGANISM: Artificial Sequence
<220> FEATURE:
<223> OTHER INFORMATION: genomic DNA (T. aureum ATCC 34304 OrfA
      downstream genomic DNA fragment)

<400> SEQUENCE: 128

```
cccccatggt gttgctgtgg gattggtccg ggggctcttc tgcacgcggc ctccgtcgcg       60
cgcagaaatg ccccgtcact ggctgcccag gaggcagccg aatccctcta gctagctagc      120
taggctagag cgtcttttcc gtagtttttc acaaagccag tatcacatgg ataacgaacg      180
aaggtttcgg gctcgcgctc gcaggcgtta ggacgaagtt gatcgcccca cgtcacttca      240
aacgagtgaa ccaagatcac gttgcatctg ctcgcaagat cttcttcttc cacgccgcat      300
cgatgcgatg gatttcaaac tcttttcagg gcttttaggt gagtatggca gcgctgtttg      360
cgtggcagcg ctgtttgcgt ggttgtactc tctaaaggtg cttccacgca tgcgcgcaca      420
aaggggcatg gcatggttgg cggcgcactc tggccctcat ttgaagcaga ctatcgaagg      480
gtccagttgg tactgcggca ggtccggcga gagcaagcgc ggcggtcgct cccactcgtc      540
cctgcacagt tgctggactg gcgacggctg gcgcacctga ctacgagaag actcgagacg      600
cacagaggta gtcagggacg accgaccgca aagcacaaac cgctccaaaa cggccgcacc      660
aggcagggca gtaaactaaa aacgaatgta cctccatcgc gcgtatctgc cgagcctcct      720
cccacgcttc ggctgggctt gattcaccag tgtccgcaag ctgaaccgac cgtcttcgat      780
gtcatgaagc ttgcgcggc attagtcaga cgacgcggca cgccaggatt ctgtcggttt      840
ctgggaaatg ggcatctata tagctgattc cctctgtcat gaggcggcct tgttctggcc      900
```
ctgggccgcc gttcggatga tctatgatgt cgttgtacgc ataaagcttg tcgaaaacgt    960
cggccatgtc ttcctcagag atgtaaccga gccatggggg                         1000

<210> SEQ ID NO 129
<211> LENGTH: 28
<212> TYPE: DNA
<213> ORGANISM: Artificial Sequence
<220> FEATURE:
<223> OTHER INFORMATION: primer

<400> SEQUENCE: 129
cccccatggt gttgctgtgg gattggtc                                        28

<210> SEQ ID NO 130
<211> LENGTH: 30
<212> TYPE: DNA
<213> ORGANISM: Artificial Sequence
<220> FEATURE:
<223> OTHER INFORMATION: primer

<400> SEQUENCE: 130
cccccatggc tcggttacat ctctgaggaa                                      30

<210> SEQ ID NO 131
<211> LENGTH: 1632
<212> TYPE: DNA
<213> ORGANISM: Artificial Sequence
<220> FEATURE:
<223> OTHER INFORMATION: fusion DNA (T. aureum ATCC 34304 ubiqitin
      promoter/Hygr)

<400> SEQUENCE: 131
cccaagcttg ccgcagcgcc tggtgcaccc gccgggcgtt gttgtgtgct cttcttgcct     60
ccgagagaga gagcggagcg gatgcatagg aaatcgggcc acgcgggagg gccatgcgtt    120
cgccccacac gccactttcc acgcccgctc tctctccggc cggcaggcag cgcataactc    180
tccgacgctg gcaggctggt agcaactggc agggacaact cgcgcgcggg tcccggtcgt    240
tcgatgtgcc aacccgagag aatccagcca gagggcggt tggcctcatc gcccacctgc     300
tatggtgcag cgaaccaact cccgaagcgg ccggttctgc gattccctct tctgaattct    360
gaattctgaa ctgattccgg aggagaaccc tctggaagcg cgggttgcct ctccagttct    420
gccgaactag acaggggagt gagcagagag tgacccctgac gcggagcgag ctggttgctg    480
gaaaagtcgc gaacgctggg ctgtgtcacg cgtccacttc gggcagaccc caaacgacaa    540
gcagaacaag caacaccagc agcagcaagc gacctaagca acactagcca acatgaaaaa    600
gcctgaactc accgcgacgt ctgtcgagaa gtttctgatc gaaaagttcg acagcgtctc    660
cgacctgatg cagctctcgg agggcgaaga atctcgtgct ttcagcttcg atgtaggagg    720
gcgtggatat gtcctgcggg taaatagctg cgccgatggt ttctacaaag atcgttatgt    780
ttatcggcac tttgcatcgg ccgcgctccc gattccggaa gtgcttgaca ttggggaatt    840
cagcgagagc ctgacctatt gcatctcccg ccgtgcacag ggtgtcacgt tgcaagacct    900
gcctgaaacc gaactgcccg ctgttctgca gccggtcgcg gaggccatgg atgcgatcgc    960
tgcggccgat cttagccaga cgagcgggtt cggcccattc ggaccgcaag gaatcggtca   1020
atacactaca tggcgtgatt tcatatgcgc gattgctgat ccccatgtgt atcactggca   1080
aactgtgatg gacgacaccg tcagtgcgtc cgtcgcgcag gctctcgatg agctgatgct   1140
ttgggccgag gactgccccg aagtccggca cctcgtgcac gcggatttcg gctccaacaa   1200

-continued

```
tgtcctgacg gacaatggcc gcataacagc ggtcattgac tggagcgagg cgatgttcgg    1260
ggattcccaa tacgaggtcg ccaacatctt cttctggagg ccgtggttgg cttgtatgga    1320
gcagcagacg cgctacttcg agcggaggca tccggagctt gcaggatcgc cgcggctccg    1380
ggcgtatatg ctccgcattg gtcttgacca actctatcag agcttggttg acggcaattt    1440
cgatgatgca gcttgggcgc agggtcgatg cgacgcaatc gtccgatccg agccgggac     1500 tgtcgggcgt acacaaatcg cccgcagaag cgcggccgtc tggaccgatg gctgtgtaga    1560
agtactcgcc gatagtggaa accgacgccc cagcactcgt ccgagggcaa aggaatagtc    1620
gacgcatgcg gg                                                        1632
```

<210> SEQ ID NO 132
<211> LENGTH: 36
<212> TYPE: DNA
<213> ORGANISM: Artificial Sequence
<220> FEATURE:
<223> OTHER INFORMATION: primer

<400> SEQUENCE: 132

```
cccaagcttg ccgcagcgcc tggtgcaccc gccggg                              36
```

<210> SEQ ID NO 133
<211> LENGTH: 43
<212> TYPE: DNA
<213> ORGANISM: Artificial Sequence
<220> FEATURE:
<223> OTHER INFORMATION: primer

<400> SEQUENCE: 133

```
cccgcatgcg tcgactattc ctttgccctc ggacgagtgc tgg                      43
```

<210> SEQ ID NO 134
<211> LENGTH: 1000
<212> TYPE: DNA
<213> ORGANISM: Artificial Sequence
<220> FEATURE:
<223> OTHER INFORMATION: genomic DNA (T. aureum ATCC 34304 OrfA
      downstream genomic DNA fragment)

<400> SEQUENCE: 134

```
cccgtcgacg tgttgctgtg ggattggtcc gggggctctt ctgcacgcgg cctccgtcgc    60
gcgcagaaat gccccgtcac tggctgccca ggaggcagcc gaatccctct agctagctag    120
ctaggctaga gcgtcttttc cgtagttttt cacaaagcca gtatcacatg gataacgaac    180
gaaggtttcg ggctcgcgct cgcaggcgtt aggacgaagt tgatcgcccc acgtcacttc    240
aaacgagtga accaagatca cgttgcatct gctcgcaaga tcttcttctt ccacgccgca    300
tcgatgcgat ggatttcaaa ctcttttcag ggcttttagg tgagtatggc agcgctgttt    360
gcgtggcagc gctgtttgcg tggttgtact ctctaaaggt gcttccacgc atgcgcgcac    420 aaagggggcat ggcatggttg gcggcgcact ctggcccctca tttgaagcag actatcgaag    480
ggtccagttg gtactgcggc aggtccggcg agagcaagcc cggcggtcgc tcccactcgt    540
ccctgcacag ttgctggact ggcgacggct ggcgcacctg actacgagaa gactcgagac    600
gcacagaggt agtcagggac gaccgaccgc aaagcacaaa ccgctccaaa acggccgcac    660
caggcagggc agtaaactaa aaacgaatgt acctccatcg cgcgtatctg ccgagcctcc    720
tcccacgctt cggctgggct tgattcacca gtgtccgcaa gctgaaccga ccgtcttcga    780
tgtcatgaag cttggcgcgg cattagtcag acgacgcggc acgccaggat tctgtcggtt    840
```

| | | |
|---|---|---|
| tctgggaaat gggcatctat atagctgatt ccctctgtca tgaggcggcc ttgttctggc | 900 | |
| cctgggccgc cgttcggatg atctatgatg tcgttgtacg cataaagctt gtcgaaaacg | 960 | |
| tcggccatgt cttcctcaga gatgtaaccg agtcgacggg | 1000 | |

<210> SEQ ID NO 135
<211> LENGTH: 29
<212> TYPE: DNA
<213> ORGANISM: Artificial Sequence
<220> FEATURE:
<223> OTHER INFORMATION: primer

<400> SEQUENCE: 135
cccgtcgacg tgttgctgtg ggattggtc        29

<210> SEQ ID NO 136
<211> LENGTH: 29
<212> TYPE: DNA
<213> ORGANISM: Artificial Sequence
<220> FEATURE:
<223> OTHER INFORMATION: primer

<400> SEQUENCE: 136
cccgtcgact cggttacatc tctgaggaa        29

<210> SEQ ID NO 137
<211> LENGTH: 3705
<212> TYPE: DNA
<213> ORGANISM: Artificial Sequence
<220> FEATURE:
<223> OTHER INFORMATION: fusion DNA (T. aureum OrfA upstream/EF1 alpha
      promoter/Neor/T. aureum OrfA downstream)

<400> SEQUENCE: 137

| | | |
|---|---|---|
| cccccatggc tcggttacat ctctgaggaa gacatggccg acgttttcga caagctttat | 60 | |
| gcgtacaacg acatcataga tcatccgaac ggcggcccag ggccagaaca aggccgcctc | 120 | |
| atgacagagg gaatcagcta tatagatgcc catttcccag aaaccgacag aatcctggcg | 180 | |
| tgccgcgtcg tctgactaat gccgcgccaa gcttcatgac atcgaagacg gtcggttcag | 240 | |
| cttgcggaca ctggtgaatc aagcccagcc gaagcgtggg aggaggctcg gcagatacgc | 300 | |
| gcgatggagg tacattcgtt tttagtttac tgccctgcct ggtgcggccg ttttggagcg | 360 | |
| gtttgtgctt tgcggtcggt cgtccctgac tacctctgtg cgtctcgagt cttctcgtag | 420 | |
| tcaggtgcgc cagccgtcgc cagtccagca actgtgcagg gacgagtggg agcgaccgcc | 480 | |
| gcgcttgctc tcgccggacc tgccgcagta ccaactggac ccttcgatag tctgcttcaa | 540 | |
| atgagggcca gagtgcgccg ccaaccatgc catgcccctt tgtgcgcgca tgcgtggaag | 600 | |
| cacctttaga gagtacaacc acgcaaacag cgctgccacg caaacagcgc tgccatactc | 660 | |
| acctaaaagc cctgaaaaga gtttgaaatc catcgcatcg atgcggcgtg aagaagaag | 720 | |
| atcttgcgag cagatgcaac gtgatcttgg ttcactcgtt tgaagtgacg tggggcgatc | 780 | |
| aacttcgtcc taacgcctgc gagcgcgagc ccgaaacctt cgttcgttat ccatgtgata | 840 | |
| ctggcttttgt gaaaaactac ggaaaagacg ctctagccta gctagctagc tagagggatt | 900 | |
| cggctgcctc ctgggcagcc agtgacgggg catttctgcg cgcgacggag gccgcgtgca | 960 | |
| gaagagcccc cggaccaatc ccacagcaac accatggcag agtcgcccga cttgatgaac | 1020 | |
| ttgggggtct cctcgagaat cttgcccgag cggcggtcca tcttgttctg gagctcagcg | 1080 | |
| aacttgcagg caatgtgggc agtgtggcgg tcgagcacgg gcgcatagcc ggcgcggatc | 1140 | |

-continued

```
tcaaaagaac tcgtccagga ggcggtagaa cgcaatcctc tggctgtccg gggcggcgat   1200
gccgtagagc acgagaaagc ggtcggccca ctcgccgcca agctcctcgg cgatgtcccg   1260
cgtggcgagc gcgatgtctt ggtagcggtc cgccacgccc aggcgccgc agtcgataaa    1320 gcccgagaag cggccgttct cgaccatgat gttggggagg caggcgtcgc cgtgcgtgac   1380
cacgaggtcc tcgccgtccg gcatcctagc cttaagcctg gcgaacagtt ccgccggcgc   1440
gaggccctgg tgctcctcgt cgaggtcgtc ttggtcgacg aggccagcct ccatccgcgt   1500
gcgggcgcgt tcgatcctgt gcttcgcctg gtggtcgaag gggcaggtgg cggggtcgag   1560
ggtgtgcagg cggcgcatgg cgtcggccat gatggacacc ttctcagcgg gcgcgaggtg   1620
gctgctgagg aggtcctggc cgggcacttc cccgaggagc agccagtcgc ggccggcttc   1680
ggtgacgacg tcgagcacag cggcgcacgg aaccccgtc gtggcaagcc agctgaggcg    1740
ggcagcttcg tcctggagct cgttgagggc gccgctaagg tcggtcttga caaacaggac   1800
cggccggccc tgcgcgctaa ggcggaacac ggccgcgtcc gagcagccga tcgtctgctg   1860
agcccagtcg tagccgaaca gccgttccac ccaagcagcg ggcgagccag cgtgaaggcc   1920
gtcctgttca atcatctagc cttccttgc cgctgcttgc tactcctgct actcctgctt     1980
gttacttcgt gttgctccgc gttccgtctc tgccgcgccg tccacgagcg cctccacgga   2040
tttatccgcc caacgcggct caccttggcc gcctatctaa ccccgcaaac cgcctcccag   2100
ccaaccattg cgccgccgta aggcggattc ccagaacaca gccccgccgc gacctaaccc   2160
aacctaaccg cccgcgcccg ccgccaccttt acgcagccgc acccgcccgc cgcgccgcgc   2220
tgctgggccg ccctcgcccc gcagaccgcc ctgcgcgctc gcggggcta tcctggtagt    2280 cgcgcgctag gaggtgctag gcggccccgt gcttccacct cgcccgcgac cccgccgaac   2340
agcctggagc cctaaccctc ggtttggctt aaggaggact gccgccaggc cccccgtgac   2400
gcgggccccc ggggctctct gctgcggccg cgtctcgtcg cactttccgt cccgacacag   2460
gggacccgag gtgacgagga cgaatgcgcg aagcttgtct gcctcggctc ttggtctcgg   2520
cggtgctctc gacgcactcc acttgcgttt gcagcacgga tccttcgccg tgtctcgggt   2580
ctgcaaatcg agtttgcctg cacacgatga aaggtcacag aagagtccaa gtgcaaccaa   2640
ccagcctgag cgcggcaaac gacgtaggtt cgtggcctcg tacctgatcg gccggacgat   2700
ccgcaaagcg cggcccaaaa caccaatgat ggcccaatga tggcccaatg atggccggat   2760
gcacttgcgt cactttcctg cgctcacatc ctgccccgcc cctctcgcag tccggcttgc   2820
tggtgtcgcc cactcgccca gcctccctcc ctccctcggc caatcaaac tgatcatggg    2880 ccagaatcca attcttcggc gccctgcagc acaagaacac ttgcacttgc aggcggtccg   2940
tgctcagctc atcgcttgct cagcgaggag gcggacaagg cgtggcgagc acgagcaagc   3000
gcctcgagag ggaccagcca agacgccatc cgcgcacgca atggggcgct gccgggcgcg   3060
cttcgagtgc gcggagggg gacaggcggc cggccgctcg tccttcggac ggctcctgct    3120
gctggcagcg cgagcagggc gaacggcgtt ctcgatccca tgtccgctcc cacaccgtgt   3180
ccgttttcgc gcggccacgg accccgtccg cgagcgagct gcgcggcggg gtggcgcgac   3240
cgcactgcgg atccggcccg ctctgcgtct ctgcactacg tagtgcgctg ctgcgccctg   3300
aggattcctg tccgtggcgg gctgcctggc ctcctgcgac ctggtgccag tgagggccgc   3360
cactcgccgc tcgccggcct ccttcctccc ctccaggggc cctcagccgc gacgcaagtg   3420
ggctgcgcgc cgccttgacg caagagagcc aactctctct ctggttgaac agccgcagtg   3480
cagcttacgt gctcgctcag gcttgcctaa tcatcgcgag gactcggaag tacacctgcg   3540
```

```
agcgcggctt ggcttgcagc ggagcaggcc agcgtttcgc accagggcct ggcccttcct    3600
tccttccttc ctgcctgcct gcctggtttg cgacgacgcc cgacgccgcg cacgagggcg    3660
gccgtcgtca gccaatcagt cagtcagtca tcgtccgaat cggg                     3705

<210> SEQ ID NO 138
<211> LENGTH: 3826
<212> TYPE: DNA
<213> ORGANISM: Artificial Sequence
<220> FEATURE:
<223> OTHER INFORMATION: fusion DNA (T. aureum OrfA upstream/ubiquitin
      promoter/Hygr/T. aureum OrfA downstream)

<400> SEQUENCE: 138
cccccatggc tcggttacat ctctgaggaa gacatggccg acgttttcga caagctttat     60
gcgtacaacg acatcataga tcatccgaac ggcggcccag ggccagaaca aggccgcctc    120
atgacagagg gaatcagcta tatagatgcc catttcccag aaaccgacag aatcctggcg    180
tgccgcgtcg tctgactaat gccgcgccaa gcttcatgac atcgaagacg gtcggttcag    240
cttgcggaca ctggtgaatc aagcccagcc gaagcgtggg aggaggctcg gcagatacgc    300
gcgatggagg tacattcgtt tttagtttac tgccctgcct ggtgcggccg ttttggagtg    360
gtttgtgctt gcggtcggt cgtccctgac tacctctgtg cgtctcgagt cttctcgtag    420
tcaggtgcgc cagccgtcgc cagtccagca actgtgcagg gacgagtggg agcgaccgcc    480
gcgcttgctc tcgccggacc tgccgcagta ccaactggac ccttcgatag tctgcttcaa    540
atgagggcca gagtgcgccg ccaaccatgc catgcccctt tgtgcgcgca tgcgtggaag    600
cacctttaga gagtacaacc acgcaaacag cgctgccacg caaacagcgc tgccacgcaa    660
acagcgctgc catactcacc taaaagccct gaaaagagtt tgaaatccat cgcgtcgatg    720
cggcgtggaa gaagaagatc ttgcgagcag acgcaacgtg atcttggttc actcgtttga    780
agtgacgcgg gacgatcaac ttcgtcctaa cgcctgcgag cgcgagcccg aaaccttcgt    840
tcgttatcca tgtgatactg ctttgtgaa aaactacgga aaagacgcta gctagaggga    900
ttcggctgcc tccttgggca gccagtgacg gggcatttct cgcgcgacg gaggccgcgt    960 gcaaaagagc ccccggacca atcccacagc aacacgtcga ctattccttt gccctcggac   1020
gagtgctggg gcgtcggttt ccactatcgg cgagtacttc tacacagcca tcggtccaga   1080
cggccgcgct tctgcgggcg atttgtgtac gcccgacagt cccggctccg gatcggacga   1140
ttgcgtcgca tcgaccctgc gcccaagctg catcatcgaa attgccgtca accaagctct   1200
gatagagttg gtcaagacca atgcggagca tatacgcccg gagccgcggc gatcctgcaa   1260
gctccggatg cctccgctcg aagtagcgcg tctgctgctc catacaagcc aaccacggcc   1320
tccagaagaa gatgttggcg acctcgtatt gggaatcccc gaacatcgcc tcgctccagt   1380
caatgaccgc tgttatgcgg ccattgtccg tcaggacatt gttggagccg aaatccgcgt   1440
gcacgaggtg ccggacttcg gggcagtcct cggcccaaag catcagctca tcgagagcct   1500
gcgcgacgga cgcactgacg gtgtcgtcca tcacagtttg ccagtgatac acatggggat   1560
cagcaatcgc gcatatgaaa tcacgccatg tagtgtattg accgattcct tgcggtccga   1620
atgggccgaa cccgctcgtc tggctaagat cggccgcagc gatcgcatcc atggcctccg   1680
cgaccggctg cagaacagcg ggcagttcgg tttcaggcag gtcttgcaac gtgacaccct   1740
gtgcacggcg ggagatgcaa taggtcaggc tctcgctgaa ttccccaatg tcaagcactt   1800
ccggaatcgg gagcgcggcc gatgcaaagt gccgataaac ataacgatct tgtagaaac    1860
```

```
catcggcgca gctatttacc cgcaggacat atccacgccc tcctacatcg aagctgaaag    1920
cacgagattc ttcgccctcc gagagctgca tcaggtcgga cacgctgtcg aacttttcga    1980
tcagaaactt ctcgacagac gtcgcggtga gttcaggctt tttcatgttg gctagtgttg    2040
cttaggtcgc ttgctgctgc tggtgttgct tgttctgctt gtcgtttggg gtctgcccga    2100
agtggacgcg tgacacagcc cagcgttcgc gacttttcca gcaaccagct cgctcccgcg    2160
tcagggtcac tctctgctca ctcccctgtc tagttcggca gaactggaga ggcaacccgc    2220
gcttccagag ggttctcctc cggaatcagt tcagaattca gaattcagaa gagggaatcg    2280
cagaaccggc cgcttcggga gttggttcgc tgcaccatag caggtgggcg atgaggccaa    2340
ccgccctgct ggctggattc tctcgggttg gcacatcgaa cgaccgggac ccgcgcgcga    2400
gttgtccctg ccagttgcta ccagcctgcc agcgtcggag agttatgcgc tgcctgccgg    2460
ccggagagag agcgggcgtg gaaagtggcg tgtggggcga acgcatggcc ctcccgcgtg    2520
gcccgatttc ctatgcatcc gctccgctct ctctctcgga ggcaagaaga gcacaccaac    2580
aacgcccggc gggtgcacca ggcgctgcgg caagcttgtc tgcctcggct cttggtctcg    2640
gcggtgctct cgacgcactc cacttgcgtt tgcagcacgg atccttcgcc gtgtctcggg    2700
tctgcaaatc gagtttgcct gcacacgatg aaaggtcaca gaagagtcca agtgcaacca    2760
accagcctga gcgcggcaaa cgacgtaggt tcgtggcctc gtacctgatc ggccggacga    2820
tccgcaaagc gcggcccaaa acaccaatga tggcccaatg atggcccaat gatggccgga    2880
tgcacttgcg tcactttcct gcgctcacat cctgccccgc cctctcgca gtccggcttg    2940 ctggtgtcgc ccactcgccc agcctccctc cctccctcgg cccaatcaaa ctgatcatgg    3000
gccagaatcc aattcttcgg cgccctgcag cacaagaaca cttgcacttg caggcggtcc    3060
gtgctcagct catcgcttgc tcagcgagga ggcggacaag gcgtggcgag cacgagcaag    3120
cgcctcgaga gggaccagcc aagacgccat ccgcgcacgc aatggggcgc tgccgggcgc    3180
gcttcgagtg cgcggagggg ggacaggcgg ccggccgctc gtccttcgga cggctcctgc    3240
tgctggcagc gcgagcaggg cgaacggcgt tctcgatccc atgtccgctc ccacaccgtg    3300
tccgttttcg cgcggccacg gaccccgtcc gcgagcgagc tgcgcggcgg ggtggcgcga    3360
ccgcactgcg gatccggccc gctctgcgtc tctgcactac gtagtgcgct gctgcgccct    3420
gaggattcct gtccgtggcg ggctgcctgg cctcctgcga cctggtgcca gtgagggcca    3480
ccactcgccg ctcgccggcc tccttcctcc cctccagggg ccctcagccg cgacgcaagt    3540
gggctgcgcg ccgccttgac gcaagagagc caactctctc tctggttgaa cagccgcagt    3600
gcagcttacg tgctcgctca ggcttgccta atcatcgcga ggactcggaa gtacacctgc    3660
gagcgcggct tggcttgcag cggagcaggc cagcgtttcg caccagggcc tggcccttcc    3720
ttccttcctt cctgcctgcc tgcctggttt gcgacgacgc ccgacgccgc gcacgagggc    3780
ggccgtcgtc agccaatcag tcagtcagtc atcgtccgaa ttcggg                  3826
```

<210> SEQ ID NO 139
<211> LENGTH: 22
<212> TYPE: DNA
<213> ORGANISM: Artificial Sequence
<220> FEATURE:
<223> OTHER INFORMATION: primer

<400> SEQUENCE: 139

```
gaagcgtccc gtagatgtgg tc                                             22
```

```
<210> SEQ ID NO 140
<211> LENGTH: 21
<212> TYPE: DNA
<213> ORGANISM: Artificial Sequence
<220> FEATURE:
<223> OTHER INFORMATION: primer

<400> SEQUENCE: 140
gcccgagagg tcaaagtacg c                                              21

<210> SEQ ID NO 141
<211> LENGTH: 20
<212> TYPE: DNA
<213> ORGANISM: Artificial Sequence
<220> FEATURE:
<223> OTHER INFORMATION: primer

<400> SEQUENCE: 141
gcgagcccag gtccacttgc                                                20

<210> SEQ ID NO 142
<211> LENGTH: 22
<212> TYPE: DNA
<213> ORGANISM: Artificial Sequence
<220> FEATURE:
<223> OTHER INFORMATION: primer

<400> SEQUENCE: 142
cagcccgatg aaaaacttgg tc                                             22

<210> SEQ ID NO 143
<211> LENGTH: 22
<212> TYPE: DNA
<213> ORGANISM: Artificial Sequence
<220> FEATURE:
<223> OTHER INFORMATION: primer

<400> SEQUENCE: 143
gggagcgcag ggaaaacggt ct                                             22

<210> SEQ ID NO 144
<211> LENGTH: 20
<212> TYPE: DNA
<213> ORGANISM: Artificial Sequence
<220> FEATURE:
<223> OTHER INFORMATION: primer

<400> SEQUENCE: 144
ccagcccacg tcgtcggagc                                                20

<210> SEQ ID NO 145
<211> LENGTH: 2297
<212> TYPE: DNA
<213> ORGANISM: Artificial Sequence
<220> FEATURE:
<223> OTHER INFORMATION: genomic DNA (T. aureum  ATCC 34304 C20 elongase
      upstream genomic DNA fragment)

<400> SEQUENCE: 145
ggccggggca gcccgcccag cacgccgctg cgctgctttc ggtcatgcga acctggctcc     60
ccacagcaat gctgcgcggt cgctgcgcct cttgaggctc ggcgacgttg gcccggtttg    120
gggcaccctg acgttgcacg aacgtccgct gcatctcagg cgcactcgga tcgacaactg    180
tgcaaccggt cagcctttcg cggcagattg ggcacttgcc gcgctcgcgt atccgcgtgg    240
```

| | | | | |
|---|---|---|---|---|
| cgcattcttc | gcacacgcag | gcgtgccggc | agggaagcag | gagggtgttt atcgtggcgt | 300 |
| ccatgtagac | cttgcacagc | cgcggctcac | tttccctcgg | cgcagtcccg tgcccaacgt | 360 |
| cggggccggg | cgccggcgcc | ggcgagggcg | tcggttctgg | gatgggatca ggatccgccg | 420 |
| aggctgcaga | ttgctgtgcg | ggggtgccgg | ggcgcggccc | attagcaccg tcctgcggaa | 480 |
| tatccaggag | ggtgctcatc | acggaagcca | tgtccgggcg | ctggctgccg tcttcgtgcg | 540 |
| tgcaacgatc | caccaggtca | aggagcaccc | gagccacgtt | ttggcgggtg cgaaaagcgg | 600 |
| cttggtcaac | gcagcgctcc | gggtcgaagc | cgttgtcgcg | catccagtac ggaagcaggt | 660 |
| cgaggccgcg | gcggcaggga | aagcaaggcg | gcttgccgga | cacaagctcg ccgagcacga | 720 |
| cgccaaaggc | gtaaacgtcc | acggggcgat | tgtactcgac | atgggtggcg ccctccaggt | 780 |
| cggagatctc | gggcgccatg | tagccaagcg | tgcccacttg | tgtcatcgtt tgcatggtgt | 840 |
| ggagcgtggt | actggcggcc | accttggaca | cgccaaagtc | cgtccagcac agccttaggc | 900 |
| ccgcgccctt | gttcaggttg | accagagcgt | tgtcgctctt | ggatgtctct gtgcagcacg | 960 |
| ccagcagcgt | gcagcgccct | gaggccgtgc | gccgcctggt | atgccagcgc tcgcgagcg | 1020 |
| ctgccgtcca | aaagcggcgc | gctccccgaa | tcatcgcgga | gctggatggc cttcttgagc | 1080 |
| gacatttcca | tgcggggcat | gatgatcgca | aacctgccgc | cgctctgtgg ctcgagcgcg | 1140 |
| gtcgccagga | ccgtgagcac | gttctcgtgc | gttgcgctcg | ccatccgcga ggcctcagcg | 1200 |
| cgaaagtcat | cgaggacgcc | gagcgtctgc | ccgggccgcg | gtaccttgac agcgcagcgc | 1260 |
| ccgaacggcg | ccacgtccgc | ttcaaacacc | tcgccaaagg | cgccttgtcc gagcagctcg | 1320 |
| ccccagccga | agccgcgacc | actcgatctc | gggcacgcgt | gccatcgacc cttgcagcgt | 1380 |
| ggccttgcca | agtcacagtc | cagcgcgcag | ttcagtgtct | gccgcgccag gtccaccacg | 1440 |
| atcaattcat | ccgagtcggc | tgcgaactgg | acaagtgcca | tttgggtgcg ggcaacgcgc | 1500 |
| aagatcaccc | agcactggca | tgaagaccat | gaatgaatga | atgaccgtgc gcgagtgacc | 1560 |
| gaccaacacg | agtccagccg | actccttctt | cttctccttc | ttcttcttct tcttcttctc | 1620 |
| gtagcgggcg | tcaacagcat | caatcaggca | tggcggcatt | cactctgcgc gatggatggc | 1680 |
| acgagcgctg | gaggtgatga | acgcactgcc | cggattggct | ctcggtcact gtcagcacat | 1740 |
| gatgcctgtg | cttgcgcgga | gcgcgctatg | tctcgttctg | tgtcaagaca caggcgcaac | 1800 |
| tcttgatgga | ttccttgaagc | gcatgtaact | gaagtctgac | agactcggaa gtccattgtg | 1860 |
| aacaatgttg | ttccacaatt | gctccaattg | ttccgattat | tccacaattg ttgttccaat | 1920 |
| tgttccaatt | gttccgatta | ttccgattat | tccactttag | ttgttccagt tgttccgatt | 1980 |
| gttccacaat | tgttgttccg | attattccag | ttgttccagt | tgttccaatt attccaattg | 2040 |
| ttccagttcc | ttactcttga | catcggggga | ataacgggtg | tgtatttagg ggttcggcga | 2100 |
| aagcagaatg | gccgaacgta | acagcggaga | ggaacctctt | tagcggggtt tgcgtatcgg | 2160 |
| ggaaaccagg | tgttgtgctg | gcgaggagga | tccccgcga | ggcgatggct gctccgacga | 2220 |
| cgtgggctgg | cgacgtcgct | cgcaaaggcg | ttccgcaacc | gcgcgttccg ctgtaacgag | 2280 |
| accgttttcc | ctgcgct | | | | 2297 |

<210> SEQ ID NO 146
<211> LENGTH: 23
<212> TYPE: DNA
<213> ORGANISM: Artificial Sequence
<220> FEATURE:
<223> OTHER INFORMATION: primer

<400> SEQUENCE: 146
gccgctcatg cccacgctca aac                                                    23

<210> SEQ ID NO 147
<211> LENGTH: 23
<212> TYPE: DNA
<213> ORGANISM: Artificial Sequence
<220> FEATURE:
<223> OTHER INFORMATION: primer

<400> SEQUENCE: 147
ctttcggctg ccaggaatct acg                                                    23

<210> SEQ ID NO 148
<211> LENGTH: 2189
<212> TYPE: DNA
<213> ORGANISM: Artificial Sequence
<220> FEATURE:
<223> OTHER INFORMATION: genomic DNA (T. aureum ATCC 34304 OrfA
      downstream genomic DNA fragment)

<400> SEQUENCE: 148
ctttcggctg ccaggaatct acggcccagg gcgcggcccg atctcacgaa ttcgcaaggg     60
ccaggcccgc agtatcgtca aggagggcca ggtcttctcg cgggcgcacg tcgacgatat    120
caccggtgcg atccgcgctt cgctggccaa cccaaacccg ggccgcgcct acaacgtttg    180
cgacgacgag cctgcaatga accatgtcgt gacagagttt gcctgcgaac tcatggacgt    240
cccgccccg aagcgcgaag actttgacaa ggtgcgcgag accatgtcaa gcatgtcgct    300
ctccttcttc tcagagagca agcgggtctt caacaagcgg ctcaaggaag agctgcggta    360
cgcgctattg tacccgacct accgcgaagg gatcaaagcc caactggagg aggagcttgc    420
caacggctgg acgctcatcg acgcctcggg tgcttctgct ggaaccgact ccctgcctc     480
gcccaaagcg cccgccccca tcgccgcctc aagtgacgag tcgagcgggc agagcgcgac    540
agcggccgag ccggtgcgcc ggcgcaggcg ccccgagcgc aaggcgctcc cgcctgctgg    600
gccgagtggg ccgtcggtct tgcagagggt ttctcgggca atttatgggc cgttcagttg    660
gctcctcggt cgcctgtttg ggccactttc gagccgcgct gtcggcttgt ttcgcggctg    720
ggcgcactgg ctgttgcgtc tcgtggggct gcgcgcatcc gcgccgggcg cggccgtac    780
aacctgcctc cttgttgaca acggctcgct caaaccagag cctttcgcc agctgcgcgt    840
gcacgcggcg aacctcgaag agtctcttag gagcgacgcg cgtgccccac atcccgtgca    900
ggtggtggcc gtcagcgcga ggtacagcga ccgcatcgac gcctcccttc tggacggcaa    960
gcccggcgtc gccctcgccg ggttcctgag ttccttcaag gccgacgccg agtcgcagcc   1020
agcaaccagc gaggttggcc gcatcatcgc gctcccctac tttctgggcc caagcaagac   1080
ggccacgtcg tatgttgctt cccagctcgc agagcacttt ccaggagccg agcgcaccat   1140
tgccgctccg ctcgtgtcgc gggacggcgc cattgcgcag ctcctcgctg acatggtcca   1200
tgacgtcgct cgggcgcgcg cgctgcaggc cccgtacgcg gtagttctcg tcgaccacgg   1260
gtccccgagc cgagcggtca accgcgttcg gcgggccatc gctgcgcgga tgcgccgccg   1320
ccttggcccg aacgcgcgct gcgttgtcga ctgctccatg gagcgccgcg agggcgacgc   1380
tttcgccttc aacgagcctc tgctagagtc ggttttcacc aagggtggtc tcgactctgg   1440
cgacgtcatt ctcgcgatgg cattttggc gcctggtcgc cacgctggcg agggcggcga   1500
tatcgcggag atccttgacg aggctatcgc aaagtcggct ggcaagctgc gcgttcacca   1560
aacgcggttg attggtgacg tggacaggaa cggtacgcag atttgcgccc tcctcaagaa   1620

```
caggccgctt gccgcgctgt aacggcaaga gcatccacaa ttcctgacct gagcaaacca    1680
gcccacgcga gagaccgaac acgtcaagcc gatgaggcgc agaaaacaaa gaaaaaaagc    1740
aaaaagaaca aaaacccaag gcaaaatgat ggcaattttc ttggtatgga agccgatga     1800 tcgccgagtg tcgctggcta tttgctctgg tggggcatcg agctcgatga ccgaaatcca    1860
ccaattatct gcgtgtcaat catttggagc ataagacccg ggaaggcctt gagcaagcga    1920
agaaaccggc gcgtgttcac acgatagtac gagacgtcgc tctctgcgcg gatctcaatc    1980
tgagccttct tgtctccgcg gatgaaagtg ttcatgtccc gacaagggc gccgcgccca     2040 acccctcgtt tgggctgcgc gcgctactg gaaatggtga ttccgcgaaa cgtgcccgat     2100
tcgcctttct caacagggct caccgtgaca gaaccctcag cgacaagaac gatgccgtca    2160
atcttttcgc cgggcgaggc tttctgcag                                      2189
```

<210> SEQ ID NO 149
<211> LENGTH: 618
<212> TYPE: DNA
<213> ORGANISM: Artificial Sequence
<220> FEATURE:
<223> OTHER INFORMATION: genomic DNA (T. aureum ATCC 34304 ubiquitin promoter)

<400> SEQUENCE: 149

```
cccagatctg ccgcagcgcc tggtgcaccc gccgggcgtt gttggtgtgc tcttcttgcc    60
tccgagagag agagcggagc ggatgcatag gaaatcgggc cacgcgggag ggccatgcgt    120
tcgccccaca cgccactttc cacgcccgct ctctctccgg ccggcaggca gcgcataact    180
ctccgacgct ggcaggctgg tagcaactgg cagggacaac tcgcgcgcgg gtcccggtcg    240
ttcgatgtgc caacccgaga gaatccagcc agcagggcgg ttggcctcat cgcccacctg    300
ctatggtgca gcgaaccaac tcccgaagcg gccggttctg cgattccctc ttctgaattc    360
tgaattctga actgattccg gaggagaacc ctctggaagc gcgggttgcc tctccagttc    420
tgccgaacta gacaggggag tgagcagaga gtgaccctga cgcggagcga gctggttgct    480
ggaaaagtcg cgaacgctgg gctgtgtcac gcgtccactt cgggcagtcc ccaaacgaca    540
agcagaacaa gcaacaccag cagcagcaag cgacctaagc aacactagcc aacatggcca    600
agcctttgtc tcaagaag                                                  618
```

<210> SEQ ID NO 150
<211> LENGTH: 58
<212> TYPE: DNA
<213> ORGANISM: Artificial Sequence
<220> FEATURE:
<223> OTHER INFORMATION: primer

<400> SEQUENCE: 150

```
cttcttgaga caaaggcttg gccatgttgg ctagtgttgc ttaggtcgct tgctgctg      58
```

<210> SEQ ID NO 151
<211> LENGTH: 432
<212> TYPE: DNA
<213> ORGANISM: Artificial Sequence
<220> FEATURE:
<223> OTHER INFORMATION: Blasticidin resistance gene (Blar)

<400> SEQUENCE: 151

```
agcgacctaa gcaacactag ccaacatggc caagcctttg tctcaagaag aatccaccct    60
cattgaaaga gcaacggcta caatcaacag catccccatc tctgaagact acagcgtcgc    120
```

```
cagcgcagct ctctctagcg acggccgcat cttcactggt gtcaatgtat atcattttac    180
tgggggacct tgtgcagaac tcgtggtgct gggcactgct gctgctgcgg cagctggcaa    240
cctgacttgt atcgtcgcga tcggaaatga gaacaggggc atcttgagcc cctgcggacg    300
gtgccgacag gtgcttctcg atctgcatcc tgggatcaaa gccatagtga aggacagtga    360
tggacagccg acggcagttg ggattcgtga attgctgccc tctggttatg tgtgggaggg    420
ctaagatctg gg                                                        432

<210> SEQ ID NO 152
<211> LENGTH: 54
<212> TYPE: DNA
<213> ORGANISM: Artificial Sequence
<220> FEATURE:
<223> OTHER INFORMATION: primer

<400> SEQUENCE: 152
agcgacctaa gcaacactag ccaacatggc caagcctttg tctcaagaag aatc           54

<210> SEQ ID NO 153
<211> LENGTH: 38
<212> TYPE: DNA
<213> ORGANISM: Artificial Sequence
<220> FEATURE:
<223> OTHER INFORMATION: primer

<400> SEQUENCE: 153
cccagatctt agccctccca cacataacca gagggcag                             38

<210> SEQ ID NO 154
<211> LENGTH: 1000
<212> TYPE: DNA
<213> ORGANISM: Artificial Sequence
<220> FEATURE:
<223> OTHER INFORMATION: fusion DNA (T. aureum ATCC 34304 ubiquitin
      promoter/pTracer-CMV/Bsd/lacZ Blar)

<400> SEQUENCE: 154
cccagatctg ccgcagcgcc tggtgcaccc gccgggcgtt gttggtgtgc tcttcttgcc     60
tccgagagag agagcggagc ggatgcatag gaaatcgggc cacgcgggag ggccatgcgt    120
tcgccccaca cgccactttc cacgcccgct ctctctccgg ccggcaggca gcgcataact    180
ctccgacgct ggcaggctgg tagcaactgg cagggacaac tcgcgcgcgg gtcccggtcg    240
ttcgatgtgc caacccgaga gaatccagcc agcagggcgg ttggcctcat cgcccacctg    300
ctatggtgca gcgaaccaac tcccgaagcg gccggttctg cgattccctc ttctgaattc    360
tgaattctga actgattccg gaggagaacc ctctggaagc gcgggttgcc tctccagttc    420
tgccgaacta gacaggggag tgagcagaga gtgaccctga cgcggagcga gctggttgct    480
ggaaaagtcg cgaacgctgg gctgtgtcac gcgtccactt cgggcagtcc ccaaacgaca    540
agcagaacaa gcaacaccag cagcagcaag cgacctaagc aacactagcc aacatggcca    600
agcctttgtc tcaagaagaa tccaccctca ttgaaagagc aacggctaca atcaacagca    660
tccccatctc tgaagactac agcgtcgcca gcgcagctct ctctagcgac ggccgcatct    720
tcactggtgt caatgtatat catttactg ggggaccttg tgcagaactc gtggtgctgg    780
gcactgctgc tgctgcggca gctggcaacc tgacttgtat cgtcgcgatc ggaaatgaga    840
acaggggcat cttgagcccc tgcggacggt gccgacaggt gcttctcgat ctgcatcctg    900
ggatcaaagc catagtgaag gacagtgatg gacagccgac ggcagttggg attcgtgaat    960
```
tgctgccctc tggttatgtg tgggagggct aagatctggg 1000

<210> SEQ ID NO 155
<211> LENGTH: 812
<212> TYPE: DNA
<213> ORGANISM: Artificial Sequence
<220> FEATURE:
<223> OTHER INFORMATION: cDNA (T.aureum ATCC 34304 ubiquitin promoter)

<400> SEQUENCE: 155

| | | | | | |
|---|---|---|---|---|---|
| tcggtacccg | ttagaacgcg | taatacgact | cactataggg | agagtcgact | gagcacaact | 60 |
| ctgctgcgag | cgggcctcga | gagcgtttgc | ttcgagccgc | ggagcaaggg | ggatggatcg | 120 |
| ctcatgcggt | cgtgcggccc | tcggtcaccc | ggtgggtcct | gcactgacgc | atctgttctg | 180 |
| atcagacaca | cgaacgaaca | aaccgaggag | ccgcagcgcc | tggtgcaccc | gccgggcgtt | 240 |
| gttgtgtgct | cttcttgcct | ccgagagaga | gagcggagcg | gatgcatagg | aaatcgggcc | 300 |
| acgcgggagg | gccatgcgtt | tgccccacac | gccactttcc | acgcccgctc | tctctccggc | 360 |
| cggcaggcag | cgcataactc | tccgacgctg | gcaggctggt | agcaactggc | agggacaact | 420 |
| cgcgcgcggg | tcccggtcgt | tcgatgtgcc | aacccgagag | aatccagcca | gcagggcggt | 480 |
| tggcctcatc | gcccacctgc | tatggtgcag | cgaaccaact | cccgaagctg | ccggttctgc | 540 |
| gattccctct | tctgaattct | gaattctgaa | ctgattccgg | aggagaaccc | tctgaagcg | 600 |
| cgggttgcct | ctccagttct | gccgaactag | acaggggagt | gagcagagag | tgaccctgac | 660 |
| gcggagcgag | ctggttgctg | gaaaagtcgc | gaacgctggg | ctgtgtcacg | cgtccacttc | 720 |
| gggcagaccc | caaacgacaa | gcagaacaag | caacaccagc | agcagcaagc | gatctaagca | 780 |
| acactagcca | acatggtgag | caagggcgag | ga | | | 812 |

<210> SEQ ID NO 156
<211> LENGTH: 29
<212> TYPE: DNA
<213> ORGANISM: Artificial Sequence
<220> FEATURE:
<223> OTHER INFORMATION: primer

<400> SEQUENCE: 156
tcggtacccg ttagaacgcg taatacgac 29

<210> SEQ ID NO 157
<211> LENGTH: 41
<212> TYPE: DNA
<213> ORGANISM: Artificial Sequence
<220> FEATURE:
<223> OTHER INFORMATION: primer

<400> SEQUENCE: 157
tcctcgccct tgctcaccat gttggctagt gttgcttagg t 41

<210> SEQ ID NO 158
<211> LENGTH: 748
<212> TYPE: DNA
<213> ORGANISM: Artificial Sequence
<220> FEATURE:
<223> OTHER INFORMATION: Enhanced GFP gene (Enhanced GFP DNA fragment)

<400> SEQUENCE: 158

| | | | | | |
|---|---|---|---|---|---|
| acctaagcaa | cactagccaa | catggtgagc | aagggcgagg | agctgttcac | cggggtggtg | 60 |
| cccatcctgg | tcgagctgga | cggcgacgta | aacggccaca | agttcagcgt | gtccggcgag | 120 |

```
ggcgagggcg atgccaccta cggcaagctg accctgaagt tcatctgcac caccggcaag    180
ctgcccgtgc cctggcccac cctcgtgacc accctgacct acggcgtgca gtgcttcagc    240
cgctaccccg accacatgaa gcagcacgac ttcttcaagt ccgccatgcc cgaaggctac    300
gtccaggagc gcaccatctt cttcaaggac gacggcaact acaagacccg cgccgaggtg    360
aagttcgagg gcgacaccct ggtgaaccgc atcgagctga agggcatcga cttcaaggag    420
gacggcaaca tcctgggcca caagctggag tacaactaca acagccacaa cgtctatatc    480
atggccgaca agcagaagaa cggcatcaag gtgaacttca gatccgcca caacatcgag     540 gacggcagcg tgcagctcgc cgaccactac cagcagaaca cccccatcgg cgacggcccc    600
gtgctgctgc ccgacaacca ctacctgagc acccagtccg ccctgagcaa agaccccaac    660
gagaagcgcg atcacatggt cctgctggag ttcgtgaccg ccgccgggat cactctcggc    720
atggacgcca agttgaccag tgccgttc                                       748

<210> SEQ ID NO 159
<211> LENGTH: 41
<212> TYPE: DNA
<213> ORGANISM: Artificial Sequence
<220> FEATURE:
<223> OTHER INFORMATION: primer

<400> SEQUENCE: 159
acctaagcaa cactagccaa catggtgagc aagggcgagg a                         41

<210> SEQ ID NO 160
<211> LENGTH: 58
<212> TYPE: DNA
<213> ORGANISM: Artificial Sequence
<220> FEATURE:
<223> OTHER INFORMATION: primer

<400> SEQUENCE: 160
gaacggcact ggtcaacttg gcgtccatgc cgagagtgat cccggcggcg gtcacgaa       58

<210> SEQ ID NO 161
<211> LENGTH: 1519
<212> TYPE: DNA
<213> ORGANISM: Artificial Sequence
<220> FEATURE:
<223> OTHER INFORMATION: fusion DNA (T. aureum  ATCC 34304 ubiquitin
      promoter/ Enhanced GFP)

<400> SEQUENCE: 161
tcggtacccg ttagaacgcg taatacgact cactataggg agagtcgact gagcacaact    60
ctgctgcgag cgggcctcga gagcgtttgc ttcgagccgc ggagcaaggg ggatggatcg    120
ctcatgcggt cgtgcggccc tcggtcaccc ggtgggtcct gcactgacgc atctgttctg    180
atcagacaca cgaacgaaca aaccgaggag ccgcagcgcc tggtgcaccc gccgggcgtt    240
gttgtgtgct cttcttgcct ccgagagaga gagcggagcg gatgcatagg aaatcgggcc    300
acgcgggagg gccatgcgtt tgccccacac gccactttcc acgcccgctc tctctccggc    360
cggcaggcag cgcataactc tccgacgctg gcaggctggt agcaactggc agggacaact    420
cgcgcgcggg tccggtcgt tcgatgtgcc aacccgagag aatccagcca gcagggcggt     480
tggcctcatc gcccacctgc tatggtgcag cgaaccaact cccgaagctg ccggttctgc    540
gattccctct tctgaattct gaattctgaa ctgattccgg aggagaaccc tctggaagcg    600
cgggttgcct ctccagttct gccgaactag acaggggagt gagcagagag tgaccctgac    660
```

```
gcggagcgag ctggttgctg gaaaagtcgc gaacgctggg ctgtgtcacg cgtccacttc    720
gggcagaccc caaacgacaa gcagaacaag caacaccagc agcagcaagc gacctaagca    780
acactagcca acatggtgag caagggcgag gagctgttca ccggggtggt gcccatcctg    840
gtcgagctgg acggcgacgt aaacggccac aagttcagcg tgtccggcga gggcgagggc    900
gatgccacct acggcaagct gaccctgaag ttcatctgca ccaccggcaa gctgcccgtg    960
ccctggccca ccctcgtgac caccctgacc tacggcgtgc agtgcttcag ccgctacccc   1020
gaccacatga agcagcacga cttcttcaag tccgccatgc ccgaaggcta cgtccaggag   1080
cgcaccatct tcttcaagga cgacggcaac tacaagaccc gcgccgaggt gaagttcgag   1140
ggcgacaccc tggtgaaccg catcgagctg aagggcatcg acttcaagga ggacggcaac   1200
atcctggggc acaagctgga gtacaactac aacagccaca acgtctatat catggccgac   1260
aagcagaaga acggcatcaa ggtgaacttc aagatccgcc acaacatcga ggacggcagc   1320
gtgcagctcg ccgaccacta ccagcagaac ccccatcg cgacggcccc gtgctgctg   1380 cccgacaacc actacctgag cacccagtcc gccctgagca agacccccaa cgagaagcgc   1440
gatcacatgg tcctgctgga gttcgtgacc gccgccggga tcactctcgg catggacgcc   1500
aagttgacca gtgccgttc                                                1519

<210> SEQ ID NO 162
<211> LENGTH: 1319
<212> TYPE: DNA
<213> ORGANISM: Artificial Sequence
<220> FEATURE:
<223> OTHER INFORMATION: fusion DNA (T. aureum ATCC 34304 ubiquitin
      promoter/ Enhanced GFP)

<400> SEQUENCE: 162
cccagatctg ccgcagcgcc tggtgcaccc gccgggcgtt gttgtgtgct cttcttgcct     60
ccgagagaga gagcggagcg gatgcatagg aaatcgggcc acgcgggagg gccatgcgtt    120
tgccccacac gccactttcc acgcccgctc tctctccggc cggcaggcag cgcataactc    180
tccgacgctg gcaggctggt agcaactggc agggacaact cgcgcgcggg tcccggtcgt    240
tcgatgtgcc aacccgagag aatccagcca gcagggcggt tggcctcatc gcccacctgc    300
tatggtgcag cgaaccaact cccgaagctg ccggttctgc gattccctct tctgaattct    360
gaattctgaa ctgattccgg aggagaaccc tctggaagcg cgggttgcct ctccagttct    420
gccgaactag acaggggagt gagcagagag tgaccctgac gcggagcgag ctggttgctg    480
gaaaagtcgc gaacgctggg ctgtgtcacg cgtccacttc gggcagaccc caaacgacaa    540
gcagaacaag caacaccagc agcagcaagc gacctaagca acactagcca acatggtgag    600
caagggcgag gagctgttca ccggggtggt gcccatcctg gtcgagctgg acggcgacgt    660
aaacggccac aagttcagcg tgtccggcga gggcgagggc gatgccacct acggcaagct    720
gaccctgaag ttcatctgca ccaccggcaa gctgcccgtg ccctggccca ccctcgtgac    780
caccctgacc tacggcgtgc agtgcttcag ccgctacccc gaccacatga agcagcacga    840
cttcttcaag tccgccatgc ccgaaggcta cgtccaggag cgcaccatct tcttcaagga    900
cgacggcaac tacaagaccc gcgccgaggt gaagttcgag ggcgacaccc tggtgaaccg    960
catcgagctg aagggcatcg acttcaagga ggacggcaac atcctggggc acaagctgga   1020
gtacaactac aacagccaca acgtctatat catggccgac aagcagaaga acggcatcaa   1080
ggtgaacttc aagatccgcc acaacatcga ggacggcagc gtgcagctcg ccgaccacta   1140
```

```
ccagcagaac accccccatcg gcgacggccc cgtgctgctg cccgacaacc actacctgag    1200
cacccagtcc gccctgagca aagacccccaa cgagaagcgc gatcacatgg tcctgctgga    1260
gttcgtgacc gccgccggga tcactctcgg catggacgcc aagttgacca gtgccgttc     1319
```

```
<210> SEQ ID NO 163
<211> LENGTH: 408
<212> TYPE: DNA
<213> ORGANISM: Artificial Sequence
<220> FEATURE:
<223> OTHER INFORMATION: cDNA (Zeor)

<400> SEQUENCE: 163
cgccgccggg atcactctcg gcatggacgc caagttgacc agtgccgttc cggtgctcac     60
cgcgcgcgac gtcgccggag cggtcgagtt ctggaccgac cggctcgggt tctcccggga   120
cttcgtggag gacgacttcg ccggtgtggt ccggacgac gtgaccctgt tcatcagcgc    180
ggtccaggac caggtggtgc cggacaacac cctggcctgg gtgtgggtgc gcggcctgga   240
cgagctgtac gccgagtggt cggaggtcgt gtccacgaac ttccgggacg cctccggcc    300 ggccatgacc gagatcggcg agcagccgtg ggggcgggag ttcgccctgc gcgacccggc   360
cggcaactgc gtgcacttcg tggccgagga gcaggactga gatctggg               408
```

```
<210> SEQ ID NO 164
<211> LENGTH: 54
<212> TYPE: DNA
<213> ORGANISM: Artificial Sequence
<220> FEATURE:
<223> OTHER INFORMATION: primer

<400> SEQUENCE: 164
cgccgccggg atcactctcg gcatggacgc caagttgacc agtgccgttc cggt          54
```

```
<210> SEQ ID NO 165
<211> LENGTH: 38
<212> TYPE: DNA
<213> ORGANISM: Artificial Sequence
<220> FEATURE:
<223> OTHER INFORMATION: primer

<400> SEQUENCE: 165
cccagatctc agtcctgctc ctcggccacg aagtgcac                             38
```

```
<210> SEQ ID NO 166
<211> LENGTH: 1677
<212> TYPE: DNA
<213> ORGANISM: Artificial Sequence
<220> FEATURE:
<223> OTHER INFORMATION: fusion DNA (T. aureum ATCC 34304 ubiquitin
      promoter/Enhanced GFP/pcDNA3.1 Zeo(+) Zeor)

<400> SEQUENCE: 166
cccagatctg ccgcagcgcc tggtgcaccc gccgggcgtt gttgtgtgct cttcttgcct     60
ccgagagaga gagcggagcg gatgcatagg aaatcgggcc acgcgggagg gccatgcgtt   120
tgccccacac gccactttcc acgcccgctc tctctccggc cggcaggcag cgcataactc   180
tccgacgctg gcaggctggt agcaactggc agggacaact cgcgcgcggg tcccggtcgt   240
tcgatgtgcc aacccgagag aatccagcca gcagggcggt tggcctcatc gcccacctgc   300
tatggtgcag cgaaccaact cccgaagctg ccggttctgc gattcccctct tctgaattct   360 gaattctgaa ctgattccgg aggagaaccc tctggaagcg cgggttgcct ctccagttct   420
```

| | |
|---|---|
| gccgaactag acaggggagt gagcagagag tgaccctgac gcggagcgag ctggttgctg | 480 |
| gaaaagtcgc gaacgctggg ctgtgtcacg cgtccacttc gggcagaccc caaacgacaa | 540 |
| gcagaacaag caacaccagc agcagcaagc gacctaagca acactagcca acatggtgag | 600 |
| caagggcgag gagctgttca ccggggtggt gcccatcctg gtcgagctgg acggcgacgt | 660 |
| aaacggccac aagttcagcg tgtccggcga gggcgagggc gatgccacct acggcaagct | 720 |
| gaccctgaag ttcatctgca ccaccggcaa gctgcccgtg ccctggccca ccctcgtgac | 780 |
| caccctgacc tacggcgtgc agtgcttcag ccgctacccc gaccacatga agcagcacga | 840 |
| cttcttcaag tccgccatgc ccgaaggcta cgtccaggag cgcaccatct tcttcaagga | 900 |
| cgacggcaac tacaagaccc gcgccgaggt gaagttcgag ggcgacaccc tggtgaaccg | 960 |
| catcgagctg aagggcatcg acttcaagga ggacggcaac atcctggggc acaagctgga | 1020 |
| gtacaactac aacagccaca acgtctatat catggccgac aagcagaaga acggcatcaa | 1080 |
| ggtgaacttc aagatccgcc acaacatcga ggacggcagc gtgcagctcg ccgaccacta | 1140 |
| ccagcagaac accccatcg gcgacggccc cgtgctgctg cccgacaacc actacctgag | 1200 |
| cacccagtcc gccctgagca agaccccaa cgagaagcgc gatcacatgg tcctgctgga | 1260 |
| gttcgtgacc gccgccggga tcactctcgg catggacgcc aagttgacca gtgccgttcc | 1320 |
| ggtgctcacc gcgcgcgacg tcgccggagc ggtcgagttc tggaccgacc ggctcgggtt | 1380 |
| ctcccgggac ttcgtggagg acgacttcgc cggtgtggtc cggacgacg tgaccctgtt | 1440 |
| catcagcgcg gtccaggacc aggtggtgcc ggacaacacc ctggcctggg tgtgggtgcg | 1500 |
| cggcctggac gagctgtacg ccgagtggtc ggaggtcgtg tccacgaact tccgggacgc | 1560 |
| ctccgggccg gccatgaccg agatcggcga gcagccgtgg gggcgggagt tcgccctgcg | 1620 |
| cgacccggcc ggcaactgcg tgcacttcgt ggccgaggag caggactgag atctggg | 1677 |

<210> SEQ ID NO 167
<211> LENGTH: 2884
<212> TYPE: DNA
<213> ORGANISM: Artificial Sequence
<220> FEATURE:
<223> OTHER INFORMATION: genomic DNA (T. aureum ATCC 34304 C20 elongase upstream/C20 elongase/C20 elongase downstream)

<400> SEQUENCE: 167

| | |
|---|---|
| cccgaattca ctagtgattc tcccgggtgg acctagcgcg tgtgtcacct gccggccccc | 60 |
| gttgcgtgca accgaattga tcgataatag aattacataa caaacaactt gctggatgag | 120 |
| tacaagacca gcgtagtgtg gctgtgggac gttgaacgga gcgggtcctg tgatggcgca | 180 |
| gaaaggaact ccgcccgagg tgaaaccccg atgcgcagga ctctgcggcc acagcccctc | 240 |
| cgccagtatt ccactaaaaa tccgccccct ttgacaaaga tcgcaacccc gtcccatcaa | 300 |
| ctcctcacaa taggctttcc actggcggaa acgtccccgg cacaggagtg cctcccgcgg | 360 |
| ttctgcgcat acggctgacc actacgcagc gcgatatcct ccatccgcgt atatatccgt | 420 |
| aaacaacgga acattctccc tctcaacgag gcgtggtttt cgaagtcatg cctttcttcc | 480 |
| ttcctactt ccttccttct ttctttcttt ctttccttct tttgcaagcg tgcgcgaact | 540 |
| tgaaggtact acttacactt gacagagaga gatagagacg gcaattcgac caagtacttt | 600 |
| ccacgatttt tttttttttt gttttggtcg cttcgttgg tcgtgcatga tggatggccg | 660 |
| ggatttttac aattggatgc gccaggctgc cacgcatgcc gtgacgcttg ctcgcggcga | 720 |
| ctcatgatgc ttgccagtgg cagtgcatcc agctcttccc tctgctcgtc gtgtactcac | 780 |

```
tggcgatgct ctcggcgctc gttcaagggc catcgatcga tcgatcgatc gatcgatcga    840
tcaatcacgt ttggtggact cggcagaccc cgaacgtgtt tctcccagga cgcgccgctg    900
tcgctcgcta atccacccga agcgcggtcg gctggcacgg tcgctcggct ggaagttgag    960
tagtttgctt tctgttgctg cgctgctttg taaacgcgac catggcgacg cgcacctcga   1020
agagcgctcc ggcggtttcc aagtcggcca aggttgccgc gccggcgaag aagcggtcgg   1080
tcgacaggag cgacggtttc ttccgcacgt tcaacctgtg cgccctgtac gggtctgccc   1140
tcgcctatgc gtacaagcac ggcccggtgg acaatgacgg ccaggggctg tactttcaca   1200
agtcgcccat gtacgcgttc gccgtgtcgg acgtcatgac cttcggcgcg ccgctgatgt   1260
acgtgctcgg tgtgatgctg ctcagcaggt acatggcgga caaaaagccc ctgactggct   1320
tcatcaagac ctacatccag cccgtctaca acgtggtcca aatcgcggtg tgcggctgga   1380
tggtgtgggg cctctggccg caggtcgacc tggccaacgg caacccttc ggcctcaaca    1440 agtcgcgcga ctcgaacatc gagttttcg tgttcgtgca cctcctgaca aagtttctcg     1500
actggagcga cacgttcatg atgatcctca agaaaaacta cgcccaggtt agctttctgc   1560
aggtgttcca ccacgcaacg atcggcatgg tgtggtcgtt ccttcttcag cgtggctggg   1620
gctcgggcac cgccgcgtac ggtgctttca tcaactcggt cacgcacgtg atcatgtact   1680
cgcactactt tgccacctcg ctcaacatca caacccgtt caagcggtac atcacgagct    1740
tccagctcgc ccagtttgca agctgcatcg tgcatgccct actggtgctt gccttcgagg   1800
aggtgtaccc gctcgagtac gcttacctgc agatcagcta ccacatcatc atgctctacc   1860
tgttcggacg ccgcatgaac tggagccccg agtggtgcac cggtgagatc gacggccttg   1920
acgccccaag cgcccccacc aagtccgagt aaacctgttt ccggctggct cccgagccat   1980
gcttaccatg aatgaacctg caaacagtct gaggtccttg tgcaaaccgc tcagtgggac   2040
gtcgacgaag aaagaaacaa tgtgtactcg tcttgctctg ctcccgcgcc gttttttatc   2100
gttgttgaga cctctcgcgc agttttggga atcaaccaaa acaagagccc ggcgtcagcg   2160
tttgcttcgc cctcggctgc actcgctcgg cacgcaggta taactgggtg agtaccaagc   2220
cccgcatttg tctgtccgcg atccgcgcac gctgcgggtc aggacgacat cgcgctgcac   2280
gtcacagtgg gtccctttg acgtggctgc ggcgatgagg aggcttggct cggcttcatg    2340
gcaaggcaac agactcgctt ccgggacgcg cacgacgagc agcgctgctt tgatcgacct   2400
tgcctgcgtc accgcctcgg ctgctttgat cgatcgttgt caccggccga gtgaccgcga   2460
acgcattgcc cgcacggctc ggctcggccc ggaccggacc ggctcgcctt ggcggcgcgg   2520
cgcgatggcg acccagacgc ggccggagcc gcgcgcggag gacaaggcca tgttcatctt   2580
cgggctcggg tacgttggga gcaggctcgc caaccagctg gcggaacagg ggtgcgcgt    2640 cgcggggtcg gtgagggagc tcgggcgcga ggacgacttt gccgagttcg aaaagtccaa   2700
gctgagcggc aaggtgcagg tgttccgact cccgcttgag ggcgaggaca acacgcccgc   2760
tcgcgcgcgg gagatactta gcgggtacca gcacctgctg ttcacggcgc cagtggaccg   2820
cgcccggaac tgtgaccccct tcttgggcga ccccgttctc ggccccggga taatcgaatt   2880
cggg                                                                2884
```

<210> SEQ ID NO 168
<211> LENGTH: 50
<212> TYPE: DNA
<213> ORGANISM: Artificial Sequence
<220> FEATURE:
<223> OTHER INFORMATION: primer -continued

<400> SEQUENCE: 168
cccgaattca ctagtgattc tcccgggtgg acctagcgcg tgtgtcacct                50

<210> SEQ ID NO 169
<211> LENGTH: 40
<212> TYPE: DNA
<213> ORGANISM: Artificial Sequence
<220> FEATURE:
<223> OTHER INFORMATION: primer

<400> SEQUENCE: 169
cccgaattcg attatcccgg ggccgagaac ggggtcgccc                40

<210> SEQ ID NO 170
<211> LENGTH: 1939
<212> TYPE: DNA
<213> ORGANISM: Artificial Sequence
<220> FEATURE:
<223> OTHER INFORMATION: fusion DNA (T. aureum ATCC 34304 C20 elongase
      upstream/C20 elongase downstream)

<400> SEQUENCE: 170
cccgaattca ctagtgattc tcccgggtgg acctagcgcg tgtgtcacct gccggccccc     60
gttgcgtgca accgaattga tcgataatag aattacataa caaacaactt gctggatgag    120
tacaagacca gcgtagtgtg gctgtgggac gttgaacgag gcgggtcctg tgatggcgca    180
gaaaggaact ccgcccgagg tgaaaccccg atgcgcagga ctctgcggcc acagcccctc    240
cgccagtatt ccactaaaaa tccgccccct ttgacaaaga tcgcaacccc gtcccatcaa    300
ctcctcacaa taggctttcc actggcggaa acgtccccgg cacaggagtg cctcccgcgg    360
ttctgcgcat acgctgacc actacgcagc gcgatatcct ccatccgcgt atatatccgt    420
aaacaacgga acattctccc tctcaacgag gcgtggtttt cgaagtcatg cctttcttcc    480
ttcctacttt ccttccttct ttctttcttt ctttccttct tttgcaagcg tgcgcgaact    540
tgaaggtact acttacactt gacagagaga gatagagacg gcaattcgac caagtacttt    600
ccacgatttt ttttttttt gttttggtcg ctttcgttgg tcgtgcatga tggatggccg    660 ggattttac aattggatgc gccaggctgc cacgcatgcc gtgacgcttg ctcgcggcga    720
ctcatgatgc ttgccagtgg cagtgcatcc agctcttccc tctgctcgtc gtgtactcac    780
tggcgatgct ctcggcgctc gttcaagggc catcgatcga tcgatcgatc gatcgatcga    840
tcaatcacgt ttggtggact cggcagaccc cgaacgtgtt tctcccagga cgcgccgctg    900
tcgctcgcta atccacccga agcgcggtcg gctggcacgg tcgctcggct ggaagttgag    960
tagtttgctt tctgttgctg cgctgctttg taaacgcgac cagatctacc tgtttccggc   1020
tggctcccga gccatgctta ccatgaatga acctgcaaac agtctgaggt ccttgtgcaa   1080
accgctcagt gggacgtcga cgaagaaaga aacaatgtgt actcgtcttg ctctgctccc   1140
gcgccgtttt ttatcgttgt tgagacctct cgcgcagttt tgggaatcaa ccaaaacaag   1200
agcccggcgt cagcgtttgc ttcgccctcg gctgcactcg ctcggcacgc aggtataact   1260
gggtgagtac caagcccgc atttgtctgt ccgcgatccg cgcacgctgc gggtcaggac   1320
gacatcgcgc tgcacgtcac agtgggtccc ttttgacgtg gctgcggcga tgaggaggct   1380
tggctcggct tcatggcaag gcaacagact cgcttccggg acgcgcacga cgagcagcgc   1440
tgctttgatc gaccttgcct gcgtcaccgc ctcggctgct tgatcgatc gttgtcaccg   1500 gccgagtgac cgcgaacgca ttgcccgcac ggctcggctc ggcccggacc ggaccggctc   1560

```
gccttggcgg cgcggcgcga tggcgaccca gacgcggccg gagccgcgcg cggaggacaa    1620
ggccatgttc atcttcgggc tcgggtacgt tgggagcagg ctcgccaacc agctggcgga    1680
acaggggtgg cgcgtcgcgg ggtcggtgag ggagctcggg cgcgaggacg actttgccga    1740
gttcgaaaag tccaagctga gcggcaaggt gcaggtgttc cgactcccgc ttgagggcga    1800
ggacaacacg cccgctcgcg cgcgggagat acttagcggg taccagcacc tgctgttcac    1860
ggcgccagtg gaccgcgccc ggaactgtga ccccttcttg ggcgaccccg ttctcggccc    1920
cgggataatc gaattcggg                                                 1939

<210> SEQ ID NO 171
<211> LENGTH: 38
<212> TYPE: DNA
<213> ORGANISM: Artificial Sequence
<220> FEATURE:
<223> OTHER INFORMATION: primer

<400> SEQUENCE: 171
cccagatcta cctgtttccg gctggctccc gagccatg                             38

<210> SEQ ID NO 172
<211> LENGTH: 38
<212> TYPE: DNA
<213> ORGANISM: Artificial Sequence
<220> FEATURE:
<223> OTHER INFORMATION: primer

<400> SEQUENCE: 172
cccagatctg gtcgcgttta caaagcagcg cagcaaca                             38

<210> SEQ ID NO 173
<211> LENGTH: 31
<212> TYPE: DNA
<213> ORGANISM: Artificial Sequence
<220> FEATURE:
<223> OTHER INFORMATION: primer

<400> SEQUENCE: 173
ctcccgggtg gacctagcgc gtgtgtcacc t                                    31

<210> SEQ ID NO 174
<211> LENGTH: 27
<212> TYPE: DNA
<213> ORGANISM: Artificial Sequence
<220> FEATURE:
<223> OTHER INFORMATION: primer

<400> SEQUENCE: 174
atcccggggc cgagaacgcc ctcgccc                                         27

<210> SEQ ID NO 175
<211> LENGTH: 3215
<212> TYPE: DNA
<213> ORGANISM: Artificial Sequence
<220> FEATURE:
<223> OTHER INFORMATION: fusion DNA (T. aureum C20 elongase upstream/
      ubiquitin promoter/Blar/SV40 terminator/T. aureum C20 elongase
      downstream)

<400> SEQUENCE: 175
ctcccgggtg gacctagcgc gtgtgtcacc tgccggcccc cgttgcgtgc aaccgaattg     60
atcgataata gaattacata acaaacaact tgctggatga gtacaagacc agcgtagtgt    120
```

```
ggctgtggga cgttgaacgg agcgggtcct gtgatggcgc agaaaggaac tccgcccgag      180
gtgaaacccc gatgcgcagg actctgcggc cacagcccct ccgccagtat tccactaaaa      240
atccgccccc tttgacaaag atcgcaaccc cgtcccatca actcctcaca ataggctttc      300
cactggcgga aacgtcccccg gcacaggagt gcctcccgcg gttctgcgca tgcggctgac      360
cactacgcag cgcgatatcc tccatccgcg tatatatccg taaacaacgg aacattctcc      420
ctctcaacga ggcgtggttt tcgaagtcat gcctttcttc cttcctactt tccttccttc      480
tttctttctt tctttccttc ttttgcaagc gtgcgcgaac ttgaaggtac tacttacact      540
tgacagagag agatagagac ggcaattcga ccaagtactt ccacgatttt ttttttttt      600 tgttttggtc gctttcgttg gtcgtgcatg atggatggcc gggatttta caattggatg      660 cgccaggctg ccacgcatgc cgtgacgctt gctcgcggcg actcatgatg cttgccagtg      720
gcagtgcatc cagctcttcc ctctgctcgt cgtgtactca ctggcgatgc tctcggcgct      780
cgttcaaggg ccatcgatcg atcgatcgat cgatcgatcg atcaatcacg tttggtggac      840
tcggcagacc ccgaacgtgt ttctcccagg acgcgccgct gtcgctcgct aatccacccg      900
aagcgcggtc ggctggcacg gtcgctcggc tggaagttga gtagtttgct ttctgttgct      960
gcgctgcttt gtaaacgcga ccagatctgg atctgccgca gcgcctggtg cacccgccgg     1020
gcgttgttgt gtgctcttct tgcctccgag agagagagcg gagcggatgc ataggaaatc     1080
gggccacgcg ggagggccat gcgttcgccc cacacgccac tttccacgcc cgctctctct     1140
ccggccggca ggcagcgcat aactctccga cgctggcagg ctggtagcaa ctggcaggga     1200
caactcgcgc gcgggtcccg gtcgttcgat gtgccaaccc gagagaatcc agccagcagg     1260
gcggttggcc tcatcgccca cctgctatgg tgcagcgaac caactcccga agcggccggt     1320
tctgcgattc cctcttctga attctgaatt ctgaactgat tccggaggag aaccctctgg     1380
aagcgcgggt tgcctctcca gttctgccga actagacagg ggagtgagca gagagtgacc     1440
ctgacgcgga gcgagctggt tgctggaaaa gtcgcgaacg ctgggctgtg tcacgcgtcc     1500
acttcgggca gtccccaaac gacaagcaga acaagcaaca ccagcagcag caagcgacct     1560
aagcaacact agccaacatg gccaagcctt tgtctcaaga gaatccacc ctcattgaaa      1620 gagcaacggc tacaatcaac agcatcccca tctctgaaga ctacagcgtc gccagcgcag     1680
ctctctctag cgacggccgc atcttcactg gtgtcaatgt atatcatttt actggggggac     1740 cttgtgcaga actcgtggtg ctgggcactg ctgctgctgc ggcagctggc aacctgactt     1800
gtatcgtcgc gatcggaaat gagaacaggg gcatcttgag cccctgcgga cggtgccgac     1860
aggtgcttct cgatctgcat cctgggatca aagccatagt gaaggacagt gatggacagc     1920
cgacggcagt tgggattcgt gaattgctgc cctctggtta tgtgtgggag ggctaagatc     1980
cgcgaaatga ccgaccaagc gacgcccaac ctgccatcac gagatttcga ttccaccgcc     2040
gccttctatg aaaggttggg cttcggaatc gttttcgggg acgccggctg gatgatcctc     2100
cagcgcgggg atctcatgct ggagttcttc gcccacccca acttgtttat tgcagcttat     2160
aatggttaca ataaagcaa tagcatcaca aatttcacaa ataaagcatt ttttcactg      2220 cattctagtt gtggtttgtc caaactcatc aatgtatctt atcatgtctg tataccgtcg     2280
acctctagct agatctacct gtttccggct ggctcccgag ccatgcttac catgaatgaa     2340
cctgcaaaca gtcgaggtc cttgtgcaaa ccgctcagtg ggacgtcgac gaagaaagaa      2400
acaatgtgta ctcgtcttgc tctgctcccg cgccgttttt tatcgttgtt gagacctctc     2460
gcgcagtttt gggaatcaac caaaacaaga gcccggcgtc agcgtttgct tcgccctcgg     2520
```

```
ctgcactcgc tcggcacgca ggtataactg ggtgagtacc aagccccgca tttgtctgtc    2580
cgcgatccgc gcacgctgcg ggtcaggacg acatcgcgct gcacgtcaca gtgggtccct    2640
tttgacgtgg ctgcggcgat gaggaggctt ggctcggctt catggcaagg caacagactc    2700
gcttccggga cgcgcacgac gagcagcgct gctttgatcg accttgcctg cgtcaccgcc    2760
tcggctgctt tgatcgatcg ttgtcaccgg ccgagtgacc gcgaacgcat tgcccgcacg    2820
gctcggctcg gcccggaccg gaccggctcg ccttggcggc gcggcgcgat ggcgacccag    2880
acgcggccgg agccgcgcgc ggaggacaag gccatgttca tcttcgggct cgggtacgtt    2940
gggagcaggc tcgccaacca gctggcgaaa caggggtggc gcgtcgcggg gtcggtgagg    3000
gagctcgggc gcgaggacga ctttgccgag ttcgaaaagt ccaagctgag cggcaaggtg    3060
caggtgttcc aactcccgct tgagggcgag acaacacgc ccgctcgcgc gcgggagata    3120
cttagcgggt accagcacct gctgttcacg gcgccagtgg accgcgcccg gaactgtgac    3180
cccttcttgg gcgaccccgt tctcggcccc gggat    3215
```

<210> SEQ ID NO 176
<211> LENGTH: 3887
<212> TYPE: DNA
<213> ORGANISM: Artificial Sequence
<220> FEATURE:
<223> OTHER INFORMATION: fusion DNA (T. aureum C20 elongase upstream/
      ubiquitin promoter/Enhanced GFP/Zeor/SV40 terminator/T. aureum C20
      elogase downstream)

<400> SEQUENCE: 176

```
ctcccgggtg gacctagcgc gtgtgtcacc tgccggcccc cgttgcgtgc aaccgaattg      60
atcgataata gaattacata acaaacaact tgctggatga gtacaagacc agcgtagtgt     120
ggctgtggga cgttgaacgg agcgggtcct gtgatggcgc agaaaggaac tccgcccgag     180
gtgaaacccc gatgcgcagg actctgcggc cacagcccct ccgccagtat tccactaaaa     240
atccgccccc tttgacaaag atcgcaaccc cgtcccatca actcctcaca ataggctttc     300
cactggcgga aacgtccccg gcacaggagt gcctcccgcg gttctgcgca tacggctgac     360
cactacgcag cgcgatatcc tccatccgcg tatatatccg taaacaacgg aacattctcc     420
ctctcaacga ggcgtggttt tcgaagtcat gcctttcttc cttcctactt tccttccttc     480
tttctttctt tctttccttc ttttgcaagc gtgcgcgaac ttgaaggtac tacttacact     540
tgacagagag agatagagac ggcaattcga ccaagtactt ccacgatttt ttttttttt     600 tgttttggtc gctttcgttg gtcgtgcatg atggatggcc gggatttttta caattggatg     660 cgccaggctg ccacgcatgc cgtgacgctt gctcgcggcg actcatgatg cttgccagtg     720
gcagtgcatc cagctcttcc ctctgctcgt cgtgtactca ctggcgatgc tctcggcgct     780
cgttcaaggg ccatcgatcg atcgatcgat cgatcgatcg atcaatcacg tttggtggac     840
tcggcagacc ccgaacgtgt ttctcccagg acgcgccgct gtcgctcgct aatccacccg     900
aagcgcggtc ggctggcacg gtcgctcggc tggaagttga gtagtttgct ttctgttgct     960
gcgctgcttt gtaaacgcga ccagatctgc cgcagcgcct ggtgcacccg ccgggcgttg    1020
ttgtgtgctc ttcttgcctc cgagagagag agcggagcgg atgcatagga aatcgggcca    1080
cgcgggaggg ccatgcgttt gccccacacg ccactttcca cgcccgctct ctctccggcc    1140
ggcaggcagc gcataactct ccgacgctgg caggctggta gcaactggca gggacaactc    1200
gcgcgcgggt cccggtcgtt cgatgtgcca acccgagaga atccagccag cagggcggtt    1260
```

```
ggcctcatcg cccacctgct atggtgcagc gaaccaactc ccgaagctgc cggttctgcg    1320
attccctctt ctgaattctg aattctgaac tgattccgga ggagaaccct ctggaagcgc    1380
gggttgcctc tccagttctg ccgaactaga caggggagtg agcagagagt gaccctgacg    1440
cggagcgagc tggttgctgg aaaagtcgcg aacgctgggc tgtgtcacgc gtccacttcg    1500
ggcagacccc aaacgacaag cagaacaagc aacaccagca gcagcaagcg atctaagcaa    1560
cactagccaa catggtgagc aagggcgagg agctgttcac cggggtggtg cccatcctgg    1620
tcgagctgga cggcgacgta aacggccaca agttcagcgt gtccggcgag ggcgagggcg    1680
atgccaccta cggcaagctg accctgaagt tcatctgcac caccggcaag ctgcccgtgc    1740
cctggcccac cctcgtgacc accctgacct acggcgtgca gtgcttcagc cgctaccccg    1800
accacatgaa gcagcacgac ttcttcaagt ccgccatgcc cgaaggctac gtccaggagc    1860
gcaccatctt cttcaaggac gacggcaact acaagacccg cgccgaggtg aagttcgagg    1920
gcgacaccct ggtgaaccgc atcgagctga agggcatcga cttcaaggag gacggcaaca    1980
tcctggggca caagctggag tacaactaca acagccacaa cgtctatatc atggccgaca    2040
agcagaagaa cggcatcaag gtgaacttca gatccgcca caacatcgag gacggcagcg    2100
tgcagctcgc cgaccactac cagcagaaca ccccatcgg cgacggcccc gtgctgctgc    2160
ccgacaacca ctacctgagc acccagtccg ccctgagcaa agaccccaac gagaagcgcg    2220
atcacatggt cctgctggag ttcgtgaccg ccgccgggat cactctcggc atggacgcca    2280
agttgaccag tgccgttccg gtgctcaccg cgcgcgacgt cgccggagcg gtcgagttct    2340
ggaccgaccg gctcgggttc tcccgggact cgtggagga cgacttcgcc ggtgtggtcc    2400
gggacgacgt gaccctgttc atcagcgcgg tccaggacca ggtggtgccg gacaacaccc    2460
tggcctgggt gtgggtgcgc ggcctggacg agctgtacgc cgagtggtcg gaggtcgtgt    2520
ccacgaactt ccgggacgcc tccgggccgg ccatgaccga gatcggcgag cagccgtggg    2580
ggcgggagtt cgccctgcgc gacccggccg gcaactgcgt gcacttcgtg gccgaggagc    2640
aggactgaga tccgcgaaat gaccgaccaa gcgacgccca acctgccatc acgagatttc    2700
gattccaccg ccgccttcta tgaaaggttg ggcttcggaa tcgttttccg ggacgccggc    2760
tggatgatcc tccagcgcgg ggatctcatg ctggagttct tcgcccaccc caacttgttt    2820
attgcagctt ataatggtta caaataaagc aatagcatca caaatttcac aaataaagca    2880
tttttttcac tgcattctag ttgtggtttg tccaaactca tcaatgtatc ttatcatgtc    2940
tgtataccgt cgacctctag ctagatctac ctgtttccgg ctggctcccg agccatgctt    3000
accatgaatg aacctgcaaa cagtctgagg tccttgtgca aaccgctcag tgggacgtcg    3060
acgaagaaag aaacaatgtg tactcgtctt gctctgctcc cgcgccgttt tttatcgttg    3120
ttgagacctc tcgcgcagtt tgggaatca accaaaacaa gagcccggcg tcagcgtttg    3180
cttcgccctc ggctgcactc gctcggcacg caggtataac tgggtgagta ccaagccccg    3240
catttgtctg tccgcgatcc gcgcacgctg cgggtcagga cgacatcgcg ctgcacgtca    3300
cagtgggtcc cttttgacgt ggctgcggcg atgaggaggc ttggctcggc ttcatggcaa    3360
ggcaacagac tcgcttccgg gacgcgcacg acgagcagcg ctgctttgat cgaccttgcc    3420
tgcgtcaccg cctcggctgc tttgatcgat cgttgtcacc ggccgagtga ccgcgaacgc    3480 attcccgca cggctcggct cggccggac cggaccggct cgccttggcg gcgcggcgcg    3540
atggcgaccc agacgcggcc ggagccgcgc gcggaggaca aggccatgtt catcttcggg    3600
ctcgggtacg ttgggagcag gctcgccaac cagctggcgg aacaggggtg gcgcgtcgcg    3660
```

```
gggtcggtga gggagctcgg gcgcgaggac gactttgccg agttcgaaaa gtccaagctg    3720
agcggcaagg tgcaggtgtt ccgactcccg cttgagggcg aggacaacac gcccgctcgc    3780
gcgcgggaga tacttagcgg gtaccagcac ctgctgttca cggcgccagt ggaccgcgcc    3840
cggaactgtg acccctcctt gggcgacccc gttctcggcc ccgggat                 3887
```

<210> SEQ ID NO 177
<211> LENGTH: 21
<212> TYPE: DNA
<213> ORGANISM: Artificial Sequence
<220> FEATURE:
<223> OTHER INFORMATION: primer

<400> SEQUENCE: 177

```
acgtccgctt caaacacctc g                                              21
```

<210> SEQ ID NO 178
<211> LENGTH: 24
<212> TYPE: DNA
<213> ORGANISM: Artificial Sequence
<220> FEATURE:
<223> OTHER INFORMATION: primer

<400> SEQUENCE: 178

```
tcggaacaac tggaacaact aaag                                           24
```

<210> SEQ ID NO 179
<211> LENGTH: 22
<212> TYPE: DNA
<213> ORGANISM: Artificial Sequence
<220> FEATURE:
<223> OTHER INFORMATION: primer

<400> SEQUENCE: 179

```
atgtcgctct ccttcttctc ag                                             22
```

<210> SEQ ID NO 180
<211> LENGTH: 21
<212> TYPE: DNA
<213> ORGANISM: Artificial Sequence
<220> FEATURE:
<223> OTHER INFORMATION: primer

<400> SEQUENCE: 180

```
tcggctcctg gaaagtgctc t                                              21
```

<210> SEQ ID NO 181
<211> LENGTH: 23
<212> TYPE: DNA
<213> ORGANISM: Artificial Sequence
<220> FEATURE:
<223> OTHER INFORMATION: primer

<400> SEQUENCE: 181

```
ggcggagcga agtgtgaaag tta                                            23
```

<210> SEQ ID NO 182
<211> LENGTH: 24
<212> TYPE: DNA
<213> ORGANISM: Artificial Sequence
<220> FEATURE:
<223> OTHER INFORMATION: primer

<400> SEQUENCE: 182

```
gcgacagcat cttgaaatag gcag                                          24
```

<210> SEQ ID NO 183
<211> LENGTH: 2571
<212> TYPE: DNA
<213> ORGANISM: Thraustochytrium aureum

<400> SEQUENCE: 183

```
ggcggagcga agtgtgaaag ttacaaccca gttactgccc attcccggga aaagttgcgc     60
agctcacgcg gttcgctttt ctggtggcct ggcgacgttc gccgcttgcc ggatactccc    120
tcgtgccccc gcgccaggtt tgcccgctgt cgctcgagga gtggactcgc gagtcgcgac    180
agcagcagca ccaaggggga tggatcctcg ttgacagcac caagatgctc tctgcctttc    240
aggtgaaatc gatcgatcaa ttgatcaatc aagatcattg gaagcaaatg ggaagcaaat    300
gcgaaggggg aagaccctcg gtctctgctc gggaacccga cacgaggctg agggcgcgct    360
tctacaggtt gtgcagcggc cgcactgcga gcttgcgccg gccaaggcg ctcgccagaa     420 ttgctgcgtc tgccgcctcg ggatcagcca ctcggttttt cgtcatcagg gtccaccttc    480
aacctggaag tggactcggc aagtcggcag atccactccg gaattccaag atccccggtc    540
gatcggtgct ggtgcgaatt aggatggacc caggctatgt gagagtcgga gggtggcggt    600
tgtctccacc gtgacagcgc gcgtgtggtg agtaacgcga agcgcgtggt ggagaaatgg    660
ggggagattc gtaggacgcg atgcgctcgt cactgagggt gcgccggtga cgaagcttcg    720
gacccagatt ccgtcggtat ggctcgtgtt cgcacacctt caggaacccg catgacgaga    780
ccactggagt tttcaacgtc acgaagccgc tctgtgtgac gagaattggc ttgcgagtga    840
cgtgaggcgc cgagcatgtc gttggtttgc ctcttcacaa cagaatcaga cgactgggag    900
gctgcacgag gctaaggcca agggcactca ctgactcgga cgtgaagcag aagcagaagc    960
agagcgctcg acggcacgtg gcggcagacc ggcttcggga cgggcaggag acgcaaggcg   1020
cgcaacacta gggggctgga cgtggaccac tggctaagga gcgctggaaa gatgacggtc   1080
gggtttgacg aaacggtgac tatggacacg gtccgcaacc acaacatgcc ggacgacgcc   1140
tggtgcgcga tccacggcac cgtgtacgac atcaccaagt tcagcaaggt gcaccccggc   1200
ggggacatca tcatgctggc cgctggcaag gaggccacca tcctgttcga gacctaccac   1260
atcaagggcg tccggacgc ggtgctgcgc aagtacaagg tcggcaagct cccccagggc    1320
aagaagggcg aaacgagcca cgtgcccacc gggctcgact cggcctccta ctactcgtgg   1380
gacagcgagt tttacagggt gctccgcgag gcgtcgcca agaagctggc cgagcccggc    1440
ctcatgcagc gcgcgcgcat ggagctctgg gccaaggcga tcttcctcct ggcaggtttc   1500
tggggctccc tttacgccat gtgcgtgcta gacccgcacg gcggtgccat ggtagccgcc   1560
gttacgctcg gcgtgttcgc tgcctttgtc ggaacttgca tccagcacga cggcagccac   1620
ggcgccttct ccaagtcgcg attcatgaac aaggcggcgg gctggaccct cgacatgatc   1680
ggcgcgagcg cgatgacctg ggagatgcag cacgttcttg ccaccaccc gtacaccaac    1740 ctcatcgaga tggagaacgg tttggccaag gtcaagggcg ccgacgtcga cccgaagaag   1800
gtcgaccagg agagcgaccc ggacgtcttc agtacgtacc cgatgcttcg cctgcacccg   1860
tggcaccgcc agcggtttta ccacaagttc cagcacctgt acgcccgtt tatctttggg    1920 tttatgacga ttaacaaggt gatttcccag gatgtcgggg ttgtgctgcg caagcgcctg   1980
ttccagatcg acgccaactg ccggtatggc agccctggt acgtgcccg cttctggatc     2040 atgaagctcc tcaccacgct ctacatggtg gcgcttccca tgtacatgca ggggcctgct   2100
```

```
caggcttga agcttttctt catggcccac ttcacctgcg gagaggtcct cgccaccatg    2160
tttattgtca accacatcat cgagggcgtc agctacgctt ccaaggacgc ggtcaagggc    2220
gtcatggctc cgccgcgcac tgtgcacggt gtcaccccga tgcaggtgac gcaaaaggcg    2280
ctcagtgcgg ccgagtcgac caagtcggac gccgacaaga cgaccatgat ccccctcaac    2340
gactgggccg ctgtgcagtg ccagacctct gtgaactggg ctgtcgggtc gtggttttgg    2400
aaccactttt cgggcggcct caaccaccag attgagcacc actgcttccc caaaaccccc    2460
acacggtcaa cgtctacatc tcgggcatcg tcaaggagac ctgcgaagaa tacggcgtgc    2520
cgtaccaggc tgagatcagc ctcttctctg cctatttcaa gatgctgtcg c             2571
```

<210> SEQ ID NO 184
<211> LENGTH: 616
<212> TYPE: DNA
<213> ORGANISM: Thraustochytrium aureum

<400> SEQUENCE: 184

```
cgcaaggcgc gcaacactag ggggctggac gtggaccact ggctaaggag cgctggaaag     60
atgacggtcg ggtttgacga aacggtgact atggacacgg tccgcaacca caacatgccg    120
gacgacgcct ggtgcgcgat ccacggcacc gtgtacgaca tcaccaagtt cagcaaggtg    180
caccccggcg gggacatcat catgctggcc gctggcaagg aggccaccat cctgttcgag    240
acctaccaca tcaagggcgt cccggacgcg gtgctgcgca agtacaaggt cggcaagctc    300
ccccagggca agaagggcga aacgagccac gtgcccaccg gctcgactc ggcctcctac    360 tactcgtggg acagcgagtt ttacaggtg ctccgcgagc gcgtcgccaa gaagctggcc    420
gagcccggcc tcatgcagcg cgcgcgcatg gagctctggg ccaaggcgat cttcctcctg    480
gcaggtttct ggggctccct ttacgccatg tgcgtgctag acccgcacgg cggtgccatg    540
gtagccgccg ttacgctcgg cgtgttcgct gcctttgtcg gaacttgcat ccagcacgac    600
ggcagccacg gcgcct                                                   616
```

<210> SEQ ID NO 185
<211> LENGTH: 25
<212> TYPE: DNA
<213> ORGANISM: Artificial Sequence
<220> FEATURE:
<223> OTHER INFORMATION: primer

<400> SEQUENCE: 185

```
caggagatct ccaagtcgcg attca                                          25
```

<210> SEQ ID NO 186
<211> LENGTH: 26
<212> TYPE: DNA
<213> ORGANISM: Artificial Sequence
<220> FEATURE:
<223> OTHER INFORMATION: primer

<400> SEQUENCE: 186

```
cttggagatc tcctgcccgt cccgaa                                         26
```

<210> SEQ ID NO 187
<211> LENGTH: 3264
<212> TYPE: DNA
<213> ORGANISM: Artificial Sequence
<220> FEATURE:
<223> OTHER INFORMATION: fusion DNA (T. aureum delta 4 desaturase
      upstream/SV40 terminator/BlaR/ubiquitin promoter/T. aureum delta 4 desaturase)

<400> SEQUENCE: 187

| | | | | | |
|---|---|---|---|---|---|
| ggcggagcga | agtgtgaaag | ttacaaccca | gttactgccc | attcccggga | aaagttgcgc | 60 |
| agctcacgcg | gttcgctttt | ctggtggcct | ggcgacgttc | gccgcttgcc | ggatactccc | 120 |
| tcgtgccccc | gcgccaggtt | tgcccgctgt | cgctcgagga | gtggactcgc | gagtcgcgac | 180 |
| agcagcagca | ccaaggggga | tggatcctcg | ttgacagcac | caagatgctc | tctgcctttc | 240 |
| aggtgaaatc | gatcgatcaa | ttgatcaatc | aagatcattg | gaagcaaatg | ggaagcaaat | 300 |
| gcgaagggggg | aagaccctcg | gtctctgctc | gggaacccga | cacgaggctg | agggcgcgct | 360 |
| tctacaggtt | gtgcagcggc | cgcactgcga | gcttgcgccg | ggccaaggcg | ctcgccagaa | 420 |
| ttgctgcgtc | tgccgcctcg | ggatcagcca | ctcggttttt | cgtcatcagg | gtccaccttc | 480 |
| aacctggaag | tggactcggc | aagtcggcag | atccactccg | gaattccaag | atccccggtc | 540 |
| gatcggtgct | ggtgcgaatt | aggatggacc | caggctatgt | gagagtcgga | gggtggcggt | 600 |
| tgtctccacc | gtgacagcgc | gcgtgtggtg | agtaacgcga | agcgcgtggt | ggagaaatgg | 660 |
| ggggagattc | gtaggacgcg | atgcgctcgt | cactgagggt | gcgccggtga | cgaagcttcg | 720 |
| gacccagatt | ccgtcggtat | ggctcgtgtt | cgcacacctt | caggaacccg | catgacgaga | 780 |
| ccactggagt | tttcaacgtc | acgaagccgc | tctgtgtgac | gagaattggc | ttgcgagtga | 840 |
| cgtgaggcgc | cgagcatgtc | gttggtttgc | ctcttcacaa | cagaatcaga | cgactgggag | 900 |
| gctgcacgag | gctaaggcca | agggcactca | ctgactcgga | cgtgaagcag | aagcagaagc | 960 |
| agagcgctcg | acggcacgtg | gcggcagacc | ggcttcggga | cgggcaggag | atctagctag | 1020 |
| aggtcgacgg | tatacagaca | tgataagata | cattgatgag | tttggacaaa | ccacaactag | 1080 |
| aatgcagtga | aaaaaatgct | ttatttgtga | aatttgtgat | gctattgctt | tatttgtaac | 1140 |
| cattataagc | tgcaataaac | aagttgggt | gggcgaagaa | ctccagcatg | agatccccgc | 1200 |
| gctggaggat | catccagccg | gcgtcccgga | aaacgattcc | gaagcccaac | ctttcataga | 1260 |
| aggcggcggt | ggaatcgaaa | tctcgtgatg | gcaggttggg | cgtcgcttgg | tcggtcattt | 1320 |
| cgcggatctt | agccctccca | cacataacca | gagggcagca | attcacgaat | cccaactgcc | 1380 |
| gtcggctgtc | catcactgtc | cttcactatg | gctttgatcc | caggatgcag | atcgagaagc | 1440 |
| acctgtcggc | accgtccgca | ggggctcaag | atgcccctgt | tctcatttcc | gatcgcgacg | 1500 |
| atacaagtca | ggttgccagc | tgccgcagca | gcagcagtgc | ccagcaccac | gagttctgca | 1560 |
| caaggtcccc | cagtaaaatg | atatacattg | acaccagtga | agatgcggcc | gtcgctagag | 1620 |
| agagctgcgc | tggcgacgct | gtagtcttca | gagatgggga | tgctgttgat | tgtagccgtt | 1680 |
| gctcttttcaa | tgagggtgga | ttcttcttga | gacaaaggct | tggccatgtt | ggctagtgtt | 1740 |
| gcttaggtcg | cttgctgctg | ctggtgttgc | ttgttctgct | tgtcgtttgg | ggactgcccg | 1800 |
| aagtggacgc | gtgacacagc | ccagcgttcg | cgacttttcc | agcaaccagc | tcgctccgcg | 1860 |
| tcagggtcac | tctctgctca | ctcccctgtc | tagttcggca | gaactggaga | ggcaacccgc | 1920 |
| gcttccagag | ggttctcctc | cggaatcagt | tcagaattca | gaattcagaa | gagggaatcg | 1980 |
| cagaaccggc | cgcttcggga | gttggttcgc | tgcaccatag | caggtgggcg | atgaggccaa | 2040 |
| ccgccctgct | ggctggattc | tctcgggttg | gcacatcgaa | cgaccgggac | ccgcgcgcga | 2100 |
| gttgtccctg | ccagttgcta | ccagcctgcc | agcgtcggag | agttatgcgc | tgcctgccgg | 2160 |
| ccggagagag | agcgggcgtg | gaaagtgcg | tgtggggcga | acgcatgcc | ctcccgcgtg | 2220 |
| gcccgatttc | ctatgcatcc | gctccgctct | ctctctcgga | ggcaagaaga | gcacaccaac | 2280 |

```
aacgcccggc gggtgcacca ggcgctgcgg cagatccaga tctccaagtc gcgattcatg    2340
aacaaggcgg cgggctggac cctcgacatg atcggcgcga gcgcgatgac ctgggagatg    2400
cagcacgttc ttggccacca cccgtacacc aacctcatcg agatggagaa cggtttggcc    2460
aaggtcaagg gcgccgacgt cgacccgaag aaggtcgacc aggagagcga cccggacgtc    2520
ttcagtacgt acccgatgct tcgcctgcac ccgtggcacc gccagcggtt ttaccacaag    2580
ttccagcacc tgtacgcccc gtttatcttt gggtttatga cgattaacaa ggtgatttcc    2640
caggatgtcg gggttgtgct gcgcaagcgc ctgttccaga tcgacgccaa ctgccggtat    2700
ggcagcccct ggtacgtggc ccgcttctgg atcatgaagc tcctcaccac gctctacatg    2760
gtggcgcttc ccatgtacat gcaggggcct gctcagggct tgaagctttt cttcatggcc    2820
cacttcacct gcggagaggt cctcgccacc atgtttattg tcaaccacat catcgagggc    2880
gtcagctacg cttccaagga cgcggtcaag ggcgtcatgg ctccgccgcg cactgtgcac    2940
ggtgtcaccc cgatgcaggt gacgcaaaag gcgctcagtg cggccgagtc gaccaagtcg    3000
gacgccgaca agacgaccat gatcccctc aacgactggg ccgctgtgca gtgccagacc    3060
tctgtgaact gggctgtcgg gtcgtggttt tggaaccact tttcgggcgg cctcaaccac    3120
cagattgagc accactgctt ccccaaaacc cccacacggt caacgtctac atctcgggca    3180
tcgtcaagga gacctgcgaa gaatacggcg tgccgtacca ggctgagatc agcctcttct    3240
ctgcctattt caagatgctg tcgc                                          3264

<210> SEQ ID NO 188
<211> LENGTH: 3935
<212> TYPE: DNA
<213> ORGANISM: Artificial Sequence
<220> FEATURE:
<223> OTHER INFORMATION: fusion DNA (T. aureum delta 4 desaturase
      upstream/SV40 terminator /ZeoR/Enhanced GFP/ubiquitin promoter/T.
      aureum delta 4 desaturase)

<400> SEQUENCE: 188
ggcggagcga agtgtgaaag ttacaaccca gttactgccc attcccggga aaagttgcgc      60
agctcacgcg gttcgctttt ctggtggcct ggcgacgttc gccgcttgcc ggatactccc     120
tcgtgccccc gcgccaggtt tgcccgctgt cgctcgagga gtggactcgc gagtcgcgac     180
agcagcagca ccaaggggga tggatcctcg ttgacagcac caagatgctc tctgcctttc     240
aggtgaaatc gatcgatcaa ttgatcaatc aagatcattg gaagcaaatg ggaagcaaat     300
gcgaaggggg aagaccctcg gtctctgctc gggaacccga cacgaggctg agggcgcgct     360
tctacaggtt gtgcagcggc cgcactgcga gcttgcgccg ggccaaggcg ctcgccagaa     420
ttgctgcgtc tgccgcctcg ggatcagcca ctcggttttt cgtcatcagg gtccaccttc     480
aacctggaag tggactcggc aagtcggcag atccactccg gaattccaag atccccggtc     540
gatcggtgct ggtgcgaatt aggatggacc caggctatgt gagagtcgga gggtggcggt     600
tgtctccacc gtgacagcgc gcgtgtggtg agtaacgcga agcgcgtggt ggagaaatgg     660
ggggagattc gtaggacgcg atgcgctcgt cactgagggt gcgccggtga cgaagcttcg     720
gacccagatt ccgtcggtat ggctcgtgtt cgcacacctt caggaacccg catgacgaga     780
ccactggagt tttcaacgtc acgaagccgc tctgtgtgac gagaattggc ttgcgagtga     840
cgtgaggcgc cgagcatgtc gttggtttgc ctcttcacaa cagaatcaga cgactgggag     900
gctgcacgag gctaaggcca agggcactca ctgactcgga cgtgaagcag aagcagaagc     960
```

```
agagcgctcg acggcacgtg gcggcagacc ggcttcggga cgggcaggag atctagctag    1020
aggtcgacgg tatacagaca tgataagata cattgatgag tttggacaaa ccacaactag    1080
aatgcagtga aaaaaatgct ttatttgtga aatttgtgat gctattgctt tatttgtaac    1140
cattataagc tgcaataaac aagttggggt gggcgaagaa ctccagcatg agatccccgc    1200
gctggaggat catccagccg gcgtcccgga aaacgattcc gaagcccaac ctttcataga    1260
aggcggcggg ggaatcgaaa tctcgtgatg gcaggttggg cgtcgcttgg tcggtcattt    1320
cgcggatctc agtcctgctc ctcggccacg aagtgcacgc agttgccggc cgggtcgcgc    1380
agggcgaact cccgccccca cggctgctcg ccgatctcgg tcatggccgg cccggaggcg    1440
tcccggaagt tcgtggacac gacctccgac cactcggcgt acagctcgtc caggccgcgc    1500
acccacaccc aggccagggt gttgtccggc accacctggt cctggaccgc gctgatgaac    1560
agggtcacgt cgtcccggac cacaccggcg aagtcgtcct ccacgaagtc ccgggagaac    1620
ccgagccggt cggtccagaa ctcgaccgct ccggcgacgt cgcgcgcggt gagcaccgga    1680
acggcactgg tcaacttggc gtccatgccg agagtgatcc cggcggcggt cacgaactcc    1740
agcaggacca tgtgatcgcg cttctcgttg gggtctttgc tcagggcgga ctgggtgctc    1800
aggtagtggt tgtcgggcag cagcacgggg ccgtcgccga tggggggtgtt ctgctggtag    1860 tggtcggcga gctgcacgct gccgtcctcg atgttgtggc ggatcttgaa gttcaccttg    1920
atgccgttct tctgcttgtc ggccatgata tagacgttgt ggctgttgta gttgtactcc    1980
agcttgtgcc ccaggatgtt gccgtcctcc ttgaagtcga tgcccttcag ctcgatgcgg    2040
ttcaccaggt tgtcgccctc gaacttcacc tcggcgcggg tcttgtagtt gccgtcgtcc    2100
ttgaagaaga tggtgcgctc ctggacgtag ccttcgggca tggcggactt gaagaagtcg    2160
tgctgcttca tgtggtcggg gtagcggctg aagcactgca cgccgtaggt cagggtggtc    2220
acgagggtgg gccagggcac gggcagcttg ccggtggtgc agatgaactt cagggtcagc    2280
ttgccgtagg tggcatcgcc ctcgccctcg ccggacacgc tgaacttgtg gccgtttacg    2340
tcgccgtcca gctcgaccag gatgggcacc accccggtga acagctcctc gcccttgctc    2400
accatgttgg ctagtgttgc ttagatcgct tgctgctgct ggtgttgctt gttctgcttg    2460
tcgtttgggg tctgcccgaa gtggacgcgt gacacagccc agcgttcgcg acttttccag    2520
caaccagctc gctccgcgtc agggtcactc tctgctcact cccctgtcta gttcggcaga    2580
actggagagg caacccgcgc ttccagaggg ttctcctccg gaatcagttc agaattcaga    2640
attcagaaga gggaatcgca gaaccggcag cttcgggagt tggttcgctg caccatagca    2700
ggtgggcgat gaggccaacc gccctgctgg ctggattctc tcgggttggc acatcgaacg    2760
accgggaccc gcgcgcgagt tgtccctgcc agttgctacc agcctgccag cgtcggagag    2820
ttatgcgctg cctgccggcc ggagagagag cgggcgtgga aagtggcgtg tggggcaaac    2880
gcatggccct cccgcgtggc ccgatttcct atgcatccgc tccgctctct ctctcggagg    2940
caagaagagc acacaacaac gcccggcggg tgcaccaggc gctgcggcag atctccaagt    3000
cgcgattcat gaacaaggcg gcgggctgga ccctcgacat gatcggcgcg agcgcgatga    3060
cctgggagat gcagcacgtt cttggccacc acccgtacac caacctcatc gagatggaga    3120
acggtttggc caaggtcaag ggcgccgacg tcgacccgaa gaaggtcgac caggagagcg    3180
acccggacgt cttcagtacg tacccgatgc ttcgcctgca cccgtggcac cgccagcggt    3240
tttaccacaa gttccagcac ctgtacgccc cgttttatctt tgggtttatg acgattaaca    3300
aggtgatttc ccaggatgtc ggggttgtgc tgcgcaagcg cctgttccag atcgacgcca    3360
```

```
actgccggta tggcagcccc tggtacgtgg cccgcttctg gatcatgaag ctcctcacca    3420
cgctctacat ggtggcgctt cccatgtaca tgcaggggcc tgctcagggc ttgaagcttt    3480
tcttcatggc ccacttcacc tgcggagagg tcctcgccac catgtttatt gtcaaccaca    3540
tcatcgaggg cgtcagctac gcttccaagg acgcggtcaa gggcgtcatg gctccgccgc    3600
gcactgtgca cggtgtcacc ccgatgcagg tgacgcaaaa ggcgctcagt gcggccgagt    3660
cgaccaagtc ggacgccgac aagacgacca tgatccccct caacgactgg gccgctgtgc    3720
agtgccagac ctctgtgaac tgggctgtcg ggtcgtggtt ttggaaccac ttttcgggcg    3780
gcctcaacca ccagattgag caccactgct tccccaaaac ccccacacgg tcaacgtcta    3840
catctcgggc atcgtcaagg agacctgcga agaatacggc gtgccgtacc aggctgagat    3900
cagcctcttc tctgcctatt tcaagatgct gtcgc                              3935

<210> SEQ ID NO 189
<211> LENGTH: 23
<212> TYPE: DNA
<213> ORGANISM: Artificial Sequence
<220> FEATURE:
<223> OTHER INFORMATION: primer

<400> SEQUENCE: 189
aaaagaacaa gccctctcct gga                                              23

<210> SEQ ID NO 190
<211> LENGTH: 23
<212> TYPE: DNA
<213> ORGANISM: Artificial Sequence
<220> FEATURE:
<223> OTHER INFORMATION: primer

<400> SEQUENCE: 190
gaggtttgta tgttcggcgg ttt                                              23

<210> SEQ ID NO 191
<211> LENGTH: 26
<212> TYPE: DNA
<213> ORGANISM: Artificial Sequence
<220> FEATURE:
<223> OTHER INFORMATION: primer

<400> SEQUENCE: 191
tgggggacct tgtgcagaac tcgtgg                                           26

<210> SEQ ID NO 192
<211> LENGTH: 22
<212> TYPE: DNA
<213> ORGANISM: Artificial Sequence
<220> FEATURE:
<223> OTHER INFORMATION: primer

<400> SEQUENCE: 192
gacctacggc gtgcagtgct tc                                               22
```